United States Patent
Corbett et al.

(10) Patent No.: US 8,318,762 B2
(45) Date of Patent: *Nov. 27, 2012

(54) PYRAZOLOSPIROKETONE ACETYL-CoA CARBOXYLASE INHIBITORS

(75) Inventors: Jeffrey W. Corbett, Niantic, CT (US); Richard Elliott, Seattle, WA (US); Kevin Freeman-Cook, Carlsbad, CA (US); David A. Griffith, Old Saybrook, CT (US); Dennis P. Phillion, St Charles, MO (US)

(73) Assignee: Pfizer Inc., New York, NY (US)

( * ) Notice: Subject to any disclaimer, the term of this patent is extended or adjusted under 35 U.S.C. 154(b) by 106 days.

This patent is subject to a terminal disclaimer.

(21) Appl. No.: 12/934,375

(22) PCT Filed: May 18, 2009

(86) PCT No.: PCT/IB2009/005649
§ 371 (c)(1),
(2), (4) Date: Sep. 24, 2010

(87) PCT Pub. No.: WO2009/144554
PCT Pub. Date: Dec. 3, 2009

(65) Prior Publication Data
US 2011/0028390 A1    Feb. 3, 2011

Related U.S. Application Data

(60) Provisional application No. 61/056,652, filed on May 28, 2008, provisional application No. 61/058,689, filed on Jun. 4, 2008, provisional application No. 61/171,519, filed on Apr. 22, 2009.

(51) Int. Cl.
*C07D 491/107* (2006.01)
*A61K 31/436* (2006.01)
*A61K 31/438* (2006.01)

(52) U.S. Cl. .......... 514/278; 546/20

(58) Field of Classification Search .......... 546/20; 514/278
See application file for complete search history.

(56) References Cited

U.S. PATENT DOCUMENTS

| | | |
|---|---|---|
| 2008/0171761 A1 | 7/2008 | Lino et al. .......... 514/278 |
| 2009/0253725 A1 | 10/2009 | Chang et al. |
| 2010/0009982 A1 | 1/2010 | Anderson et al. |
| 2011/0111046 A1 | 5/2011 | Bagley et al. |

FOREIGN PATENT DOCUMENTS

| | | |
|---|---|---|
| EP | 1911753 | 11/2009 |
| EP | 2123652 | 11/2009 |
| JP | 2005119987 | 5/2005 |
| WO | 03072197 | 9/2003 |
| WO | 2004/002986 | 1/2004 |
| WO | 2004092179 | 10/2004 |
| WO | 2005113069 | 12/2005 |
| WO | WO 2007 011809 | 1/2007 |
| WO | WO 2007 011811 | 1/2007 |
| WO | 2007/061676 | 5/2007 |
| WO | 2007095603 | 8/2007 |
| WO | WO 2008 065508 | 6/2008 |
| WO | 2008088689 | 7/2008 |
| WO | WO 2008 102749 | 8/2008 |
| WO | 2008125945 | 10/2008 |
| WO | 2009144554 | 12/2009 |
| WO | 2009144555 | 12/2009 |
| WO | 2010002010 | 1/2010 |
| WO | 2011058473 | 5/2011 |
| WO | 2011058474 | 5/2011 |
| WO | 2012042433 | 4/2012 |

OTHER PUBLICATIONS

Database WPI Week 200537; Derwent Publications Ltd. No. 2005-359210 (XP002471702).
Abu-Elheiga, et al., PNAS, vol. 100(18), pp. 10207-10212 (2003).
Choi, et al., PNAS, vol. 104(42), pp. 16480-16485 (2007).
Oh, et al., PNAS, vol. 102(5), pp. 1384-1389 (2005).
Savage, et al., J. Clin. Invest., vol. 116(3), pp. 817-824 (2006).
Bagley, et al., "Synthesis of 7-oxo-dihydrospiro[indazole-5,4'-piperidine] Acetyl-CoA Carboxylase Inhibitors", The Journal of Organic Chemistry, vol. 77(3), pp. 1497-1506 (2012).

*Primary Examiner* — Rita Desai
(74) *Attorney, Agent, or Firm* — John A. Wichtowski; James T. Wasicak

(57) ABSTRACT

The invention provides compounds of Formula (1) or a pharmaceutically acceptable salt of said compound, wherein $R^1$, $R^2$, and $R^3$ are as described herein; pharmaceutical compositions thereof; and the use thereof in treating diseases, conditions or disorders modulated by the inhibition of acetyl-CoA carboxylase enzyme(s) in an animal.

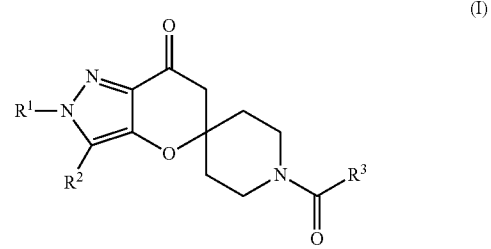

(I)

12 Claims, No Drawings

PYRAZOLOSPIROKETONE ACETYL-COA CARBOXYLASE INHIBITORS

This application is a national stage filing of PCT/IB2009/005649 filed May 18, 2009, which claims the benefit of Provisional Patent Application No. 61/056,652 filed May 28, 2008, which claims the benefit of Provisional Patent Application No. 61/058,689 filed Jun. 4, 2008, which claims the benefit of Provisional Patent Application No. 61/171,519 filed Apr. 22, 2009.

FIELD OF THE INVENTION

This invention relates to a substituted pyrazolospiroketone compound that acts as an inhibitor of acetyl-CoA carboxylases and their use in treating diseases, conditions or disorders modulated by the inhibition of acetyl-CoA carboxylase enzyme(s).

BACKGROUND OF THE INVENTION

Acetyl-CoA carboxylases (ACC) are a family of enzymes found in most species and are associated with fatty acid synthesis and metabolism through catalyzing the production of malonyl-CoA from acetyl-CoA. In mammals, two isoforms of the ACC enzyme have been identified. ACC1, which is expressed at high levels in lipogenic tissues, such as fat and the liver, controls the first committed step in the biosynthesis of long-chain fatty acids. If acetyl-CoA is not carboxylated to form malonyl-CoA, it is metabolized through the Krebs cycle. ACC2, which is a minor component of hepatic ACC but the predominant isoform in heart and skeletal muscle, catalyzes the production of malonyl-CoA at the cystolic surface of mitochondria, and regulates how much fatty acid is utilized in β-oxidation by inhibiting carnitine palmitoyl transferase. Thus, by increasing fatty acid utilization and by preventing increases in de novo fatty acid synthesis, chronic administration of an ACC inhibitor may also deplete liver and adipose tissue TG stores in obese subjects consuming a high or low-fat diet, leading to selective loss of body fat.

Studies conducted by Abu-Etheiga, et al., suggest that ACC2 plays an essential role in controlling fatty acid oxidation; therefore, ACC2 inhibition would provide a target for therapy against obesity and obesity-related diseases, such as type-2 diabetes. See, Abu-Etheiga, L., et al., "Acetyl-CoA carboxylase 2 mutant mice are protected against obesity and diabetes induced by high-fat/high-carbohydrate diets" *PNAS*, 100(18) 10207-10212 (2003). See also, Choi, C. S., et al., "Continuous fat oxidation in acetyl-CoA carboxylase 2 knockout mice increases total energy expenditure, reduces fat mass, and improves insulin sensitivity" *PNAS*, 104(42) 16480-16485 (2007). It is becoming increasingly clear that hepatic lipid accumulation causes hepatic insulin resistance and contributes to the pathogenesis of type 2 diabetes. Salvage, et al., demonstrated that ACC 1 and ACC2 are both involved in regulating fat oxidation in heptocytes while ACC1, the dominant isoform in rat liver, is the sole regulator of fatty acid synthesis. Furthermore, in their model, combined reduction of both isoforms is required to significantly lower hepatic malonyl-CoA levels, increase fat oxidation in the fed state, reduce lipid accuulmulation, and improve insultin action in vivo. Thus, showing that heptatic ACC1 and ACC2 inhibitors may be useful in the treatment of nonalcoholic fatty liver disease (NAFLD) and heptic insulin resistance. See, Savage, D. B., et al., "Reversal of diet-induced hepatic steatosis and hepatic insulin resistance by antisense oligonucleotide inhibitors of acetyl-CoA carboxylases 1 and 2" *J Clin Invest* doi: 10.1172/JCI27300. See also, Oh, W, et al., "Glucose and fat metabolism in adipose tissue of acetyl-CoA carboxylase 2 knowckout mice" *PNAS*, 102(5) 1384-1389 (2005).

Consequently, there is a need for medicaments containing ACC1 and ACC2 inhibitors to treat obesity and obesity-related diseases (such as, NAFLD and type-2 diabetes) by inhibiting fatty acid synthesis and by increasing fatty acid oxidation.

SUMMARY OF THE INVENTION

The present invention relates to compounds having the structure of Formula (1)

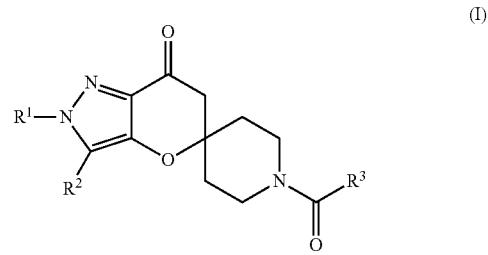

(I)

wherein $R^1$ is $(C_1-C_4)$alkyl, $(C_3-C_6)$cycloalkyl, tetrahydrofuranyl, benzyl, pyridyl, or phenyl optionally substituted 1 to 2 substituents independently selected from cyano and methoxy (preferably, $R^1$ is $(C_1-C_4)$alkyl, $(C_3-C_6)$cycloalkyl, or tetrahydrofuranyl, more preferably, ethyl, isopropyl or t-butyl, most preferably, t-butyl);

$R^2$ is hydrogen, methyl or ethyl (preferably $R^2$ is hydrogen or methyl, more preferably hydrogen);

$R^3$ is a chemical moiety selected from the group consisting of

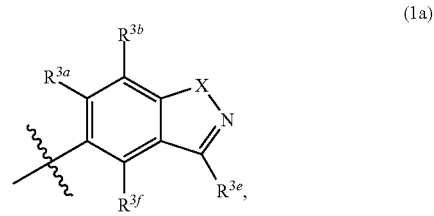

(1a)

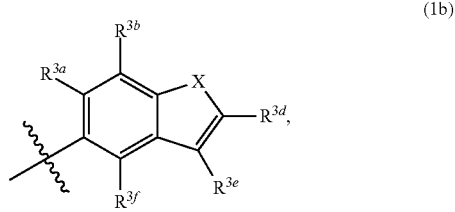

(1b)

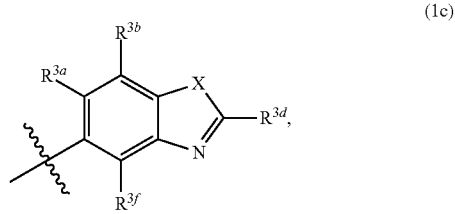

(1c)

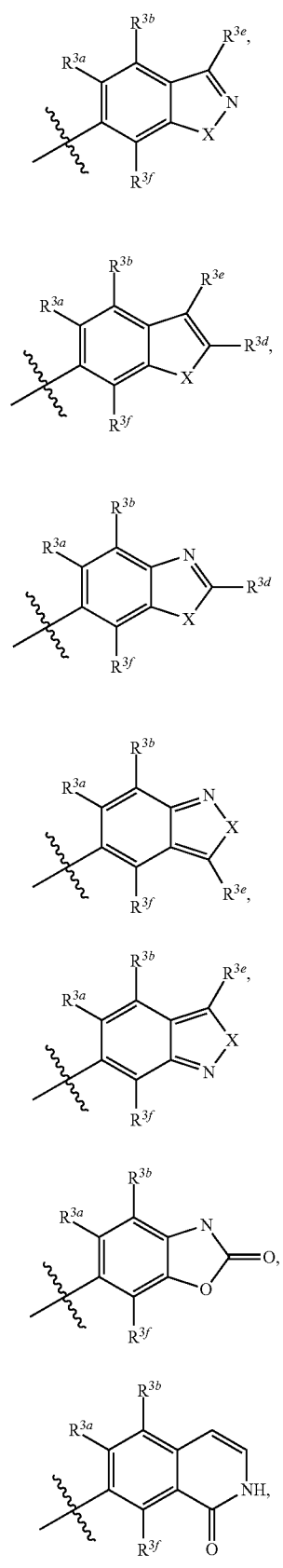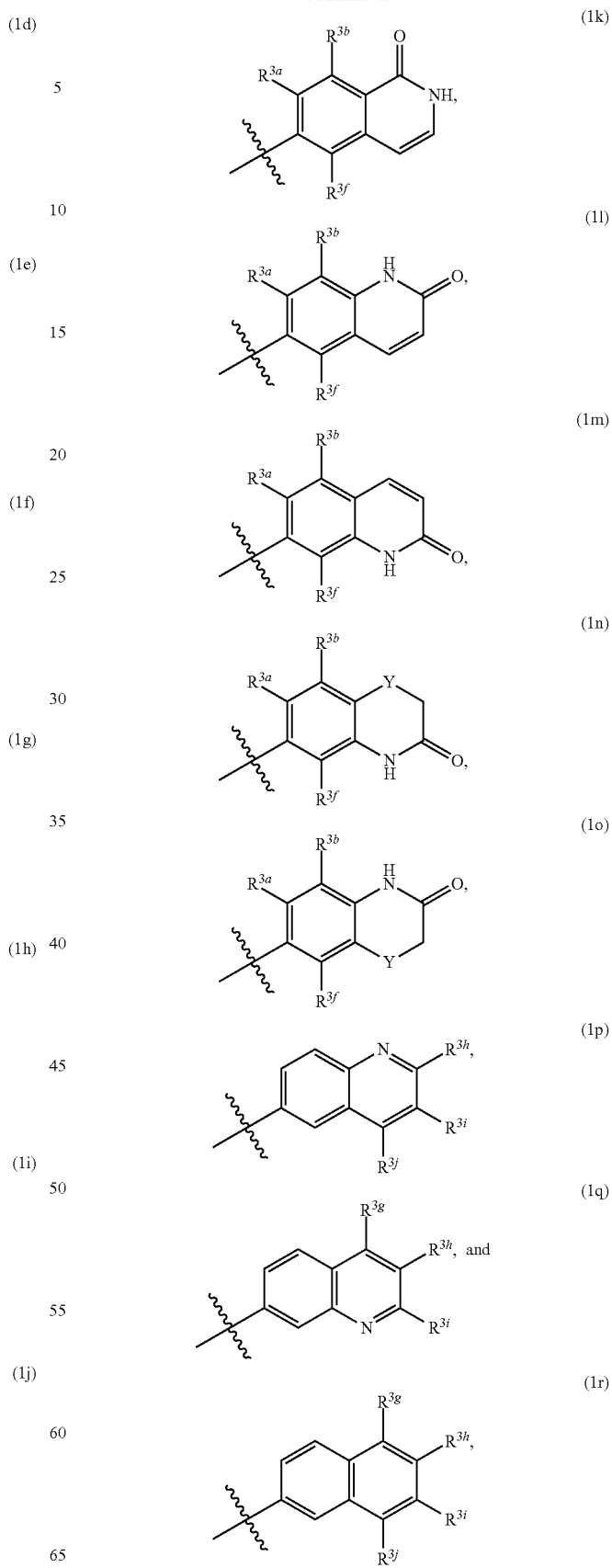

(preferably, $R^3$ is a chemical moiety of formula (1a), (1c), (1d), (1f), (1i), (1j), (1k), (1l), (1m), (1n), (1o), (1p) or (1q), more preferably, formula (1a), (1c), (1d), (1f), (1j) or (1k);

where X is O, S, or N—$R^{3c}$ (preferably, X is O or N—$R^{3c}$, more preferably, N—$R^{3c}$);

Y is $CH_2$ or O (preferably, Y is $CH_2$);

$R^{3a}$ is hydrogen or methyl ($R^{3a}$ is preferably hydrogen);

$R^{3b}$ is hydrogen, methyl, ethyl, halo, methoxy, or ethoxy ($R^{3b}$ is preferably, hydrogen, methyl methoxy, chloro or fluoro, more preferably, when $R^3$ is a chemical moiety of formula (1a), (1c), (1d), or (1f), then $R^{3b}$ is hydrogen, methyl or chloro, and when $R^3$ is a chemical moiety of formula (1b), (1e), (1g), (1h), (1i), (1j), (1k), (1m), (1n), or (1o), then $R^{3b}$ is hydrogen);

$R^{3c}$ is hydrogen, methyl, ethyl, or 3- to 6-membered cycloalkyl (preferably, $R^{3c}$ is hydrogen or methyl);

$R^{3d}$ is hydrogen, methyl, or hydroxyl (preferably, $R^{3d}$ is hydrogen);

$R^{3e}$ is hydrogen, methyl, ethyl, halo, or amino (preferably, $R^{3e}$ is hydrogen or methyl, more preferably, hydrogen);

$R^{3f}$ is hydrogen, methyl, or methoxy (preferably, $R^{3f}$ is hydrogen);

$R^{3g}$ is hydrogen, or methoxy (preferably, $R^{3g}$ is hydrogen);

$R^{3h}$ is hydrogen, methyl, methoxy, or halo (preferably, $R^{3h}$ is hydrogen);

$R^{3i}$ is hydrogen, methyl, or methoxy (preferably, $R^{3i}$ is hydrogen); or $R^{3j}$ is hydrogen, or methoxy (preferably, $R^{3j}$ is hydrogen); or a pharmaceutically acceptable salt thereof.

Another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents and/or anti-diabetic agents (described herein below).

In yet another aspect of the present invention is a method for treating a disease, condition, or disorder mediated by the inhibition of acetyl-CoA carboxylase enzyme(s) in a mammal that includes the step of administering to a mammal, preferably a human, in need of such treatment a therapeutically effective amount of a compound of the present invention, or a pharmaceutical composition thereof.

Diseases, disorders, or conditions mediated by inhibitors of acetyl-CoA carboxylases include Type II diabetes and diabetes-related diseases, such as nonalcoholic fatty liver disease (NAFLD), heptic insulin resistance, hyperglycemia, metabolic syndrome, impaired glucose tolerance, diabetic neuropathy, diabetic nephropathy, diabetic retinopathy, obesity, dyslididemia, hypertension, hyperinsulinemia, and insulin resistance syndrome. Preferred diseases, disorders, or conditions include Type II diabetes, nonalcoholic fatty liver disease (NAFLD), heptic insulin resistance, hyperglycemia, impaired glucose tolerance, obesity, and insulin resistance syndrome. More preferred are Type II diabetes, nonalcoholic fatty liver disease (NAFLD), heptic insulin resistance, hyperglycemia, and obesity. Most preferred is Type II diabetes.

A preferred emodiment is a method for treating or delaying the progression or onset of Type 2 diabetes and diabetes-related disorders in animals comprising the step of administering to an animal in need of such treatment a therapeutically effective amount of a compound of the present invention or a composition thereof.

Another preferred embodiment is a method for treating obesity and obesity-related disorders in animals comprising the step of administering to an animal in need of such treatment a therapeutically effective amount of a compound of the present invention or a composition thereof.

Yet another preferred embodiment is a method for treating nonalcoholic fatty liver disease (NAFLD) or heptic insulin resistance in animals comprising the step of administering to an animal in need of such treatment a thereapeutically effective amount of a compound of the present invention or a composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

DEFINITIONS

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the inhibition of the Acetyl-CoA carboxylases (ACC) enzyme(s) with compounds of the present invention.

The terms "mediated" or "mediating" or "mediate(s)", as used herein, unless otherwise indicated, refers to the treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by inhibiting the Acetyl-CoA carboxylases (ACC) enzyme(s).

The term "compounds of the present invention" (unless specifically identified otherwise) refer to compounds of Formula (I) and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively.

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-Pg) include for example, allyl, acetyl, silyl, benzyl, para-methoxybenzyl, trityl, and the like. The need for such protection is readily determined by one skilled in the art. For a general description of protecting groups and their use, see T. W. Greene, *Protective Groups in Organic Synthesis*, John Wiley & Sons, New York, 1991.

Scheme I outlines the general procedures one could use to provide compounds of the present invention having Formula (I).

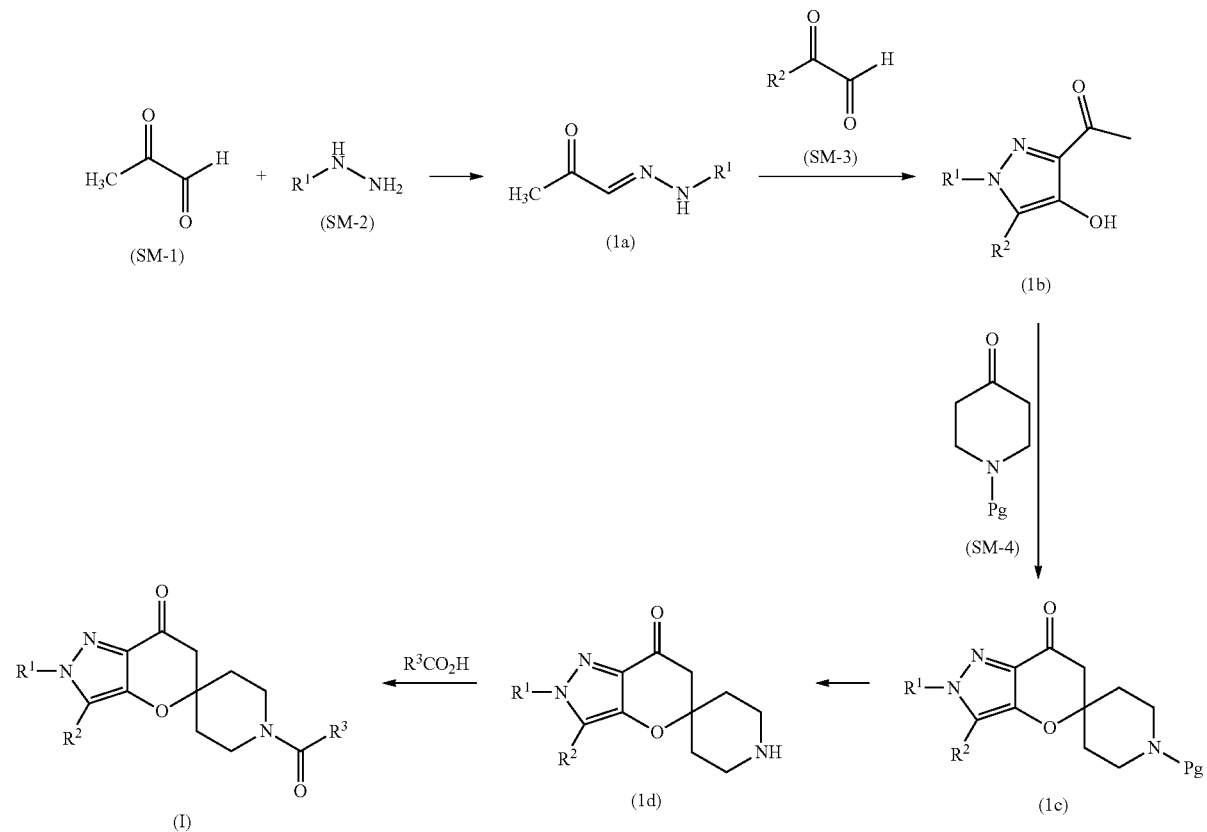

The intermediate hydrazone (1a) may be formed by treating methylglyoxal (SM-1) with the desire hydrazine (SM-2) in an acidic environment, such as acetic acid, at room temperature. Treatment of the hydrazone (1a) with the desired α-ketoaldehyde (SM-3) in refluxing aqueous acetic acid provides the 1-(4-hydroxy-1H-pyrazole-3-yl)ethanone intermediate (1b). Alternatively, the 1H-pyrazole intermediate (1b)

can also be formed directly by treating the desired α-ketoaldehyde (SM-3) with the desired hydrazine oxalate in refluxing aqueous acetic acid. The amino-protected pyrazolospiroketone intermediate (1c) may be formed by adding an amino-protected 4-piperidone (preferabley, a BOC protection group) to the 1-(4-hydroxy-1H-pyrazole-3-yl)ethanone intermediate (1b) in the presence of a an amine (preferably, pyrrolidine) at room temperature. The protecting group may then be removed to provide the pyrazolospiroketone intermediate (1d). The conditions used to remove the amino-protecting group will depend upon which protecting group was used. For example, a BOC protecting group can be removed by treatment with a strong acid (e.g., HCl). The final compound (1) may then be formed using a standard peptide coupling reaction with the desired carboxylic acid ($R^3CO_2H$). For example, The pyrazolospiroketone intermediate (1d) and carboxylic acid ($R^3CO_2H$) may be coupled by forming an activated carboxylic acid ester, such as by contacting the carboxylic acid ($R^3CO_2H$) with a peptide coupling reagent, such as O-(7-azabenzotriazol-1-yl)-N,N,N',N'-tetramethyluronium hexafluorophosphate (HATU), in the presence or absence of an activating agent, such as hydroxybenzotriazole (HOBt) and in the presence of a suitable base, such as N,N-diisopropylethylamine (DIEA) or N-methylmorpholine (NMM), in a suitable solvent such as THF and/or DMF and then contacting the activated carboxylic acid ester with the pyrazolospiroketone intermediate (1d) to form a compound of Formula (1). Alternately, compounds of Formula (1) can be formed by first converting the carboxylic acid ($R^3CO_2H$) to an acid chloride, such as by reacting with thionyl chloride, and then reacting the acid chloride with the pyrazolospiroketone intermediate (1d) to form a compound of Formula (1). Still another alternative entails treating the carboxylic acid ($R^3CO_2H$) with 2-chloro-4,6-dimethoxytriazine in the presence of a suitable base, such as N-methylmorpholine in a suitable solvent such as THF and/or DMF. To the activated ester is added a solution of pyrazolospiroketone intermediate (1d) and base, such as N-methylmorpholine, in a suitable solvent, such as THF and/or DMF.

The compounds of the present invention may be isolated and used per se or in the form of their pharmaceutically acceptable salts. In accordance with the present invention, compounds with multiple basic nitrogen atoms can form salts with varying number of equivalents ("eq.") of acid. It will be understood by practitioners that all such salts are within the scope of the present invention.

Pharmaceutically acceptable salts, as used herein in relation to compounds of the present invention, include pharmaceutically acceptable inorganic and organic salts of said compound. These salts can be prepared in situ during the final isolation and purification of a compound, or by separately reacting the compound thereof, with a suitable organic or inorganic acid and isolating the salt thus formed. Representative salts include, but are not limited to, the hydrobromide, hydrochloride, hydroiodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylammonium, dimethylammonium, trimethylammonium, triethylammonium, ethylammonium, and the like. For additional examples see, for example, Berge, et al., J. Pharm. Sci., 66, 1-19 (1977).

Certain compounds of the present invention may exist in more than one crystal form. Polymorphs of compounds of Formula (I) and salts thereof (including solvates and hydrates) form part of this invention and may be prepared by crystallization of a compound of the present invention under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of the present invention followed by gradual or fast cooling. The presence of polymorphs may be determined by solid probe nuclear magnetic resonance (NMR) spectroscopy, infrared (IR) spectroscopy, differential scanning calorimetry, powder X-ray diffraction or such other techniques.

This invention also includes isotopically-labeled compounds, which are identical to those described by Formula (1), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^2H$, $^3H$, $^{13}C$, $^{14}C$, $^{15}N$, $^{18}O$, $^{17}O$, $^{35}S$, $^{36}Cl$, $^{125}I$, $^{129}I$, and $^{18}F$ respectively. Certain isotopically-labeled compounds of the present invention, for example those into which radioactive isotopes such as $^3H$ and $^{14}C$ are incorporated, are useful in drug and/or substrate tissue distribution assays. Tritiated (i.e., $^3H$), and carbon-14 (i.e., $^{14}C$), isotopes are particularly preferred for their ease of preparation and detectability. Further, substitution with heavier isotopes such as deuterium (i.e., $^2H$), can afford certain therapeutic advantages resulting from greater metabolic stability, for example increased in vivo half-life or reduced dosage requirements and, hence, may be preferred in some circumstances. Isotopically labeled compounds of the present invention can generally be prepared by carrying out the procedures disclosed in the schemes and/or in the Examples below, by substituting a readily available isotopically labeled reagent for a non-isotopically labeled reagent.

The compounds of the present invention may contain stereogenic centers. These compounds may exist as mixtures of enantiomers or as pure enantiomers. Wherein a compound includes a stereogenic center, the compounds may be resolved into the pure enantiomers by methods known to those skilled in the art, for example by formation of diastereoisomeric salts which may be separated, for example, by crystallization; formation of stereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation.

Certain compounds of the present invention may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of Formula (1) and mixtures thereof.

Compounds of the present invention are useful for treating diseases, conditions and/or disorders modulated by the inhibition of the acetyl-CoA carboxylases enzyme(s) (in particular, ACC1 and ACC2); therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent depostion method and disintegrants" *J. Pharm. Pharmacol.*, 39, 769-773 (1987); and EP0901786 B1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of the present invention. The term "solvate" refers to a molecular complex of a compound represented by Formula (I) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by the inhibition of the acetyl-CoA carboxylases enzyme(s) in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the inhibition of acetyl-CoA carboxylases enzyme(s).

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

In yet another aspect of the present invention is the treatment of obesity comorbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology,* 7(2), (2005); and Alberti, K. G., et al., "The Metabolic Syndrome—A New Worldwide Definition," *Lancet,* 366, 1059-62 (2005). Preferably, administration of the compounds of the present invention provides a statistically significant (p<0.05) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant (p<0.05) reduction in glucose serum levels.

In yet another aspect of the invention is the treatment of nonalcoholic fatty liver disease (NAFLD) and heptic insulin resistance.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of the present invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

Suitable anti-diabetic agents include a sodium-glucose co-transporter (SGLT) inhibitor, a phosphodiesterase (PDE)-10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., Byetta™, exendin-3 and exendin-4), a protein tyrosine phosphatase-1B (PTP-1B) inhibitor (e.g., trodusquemine, hyrtiosal extract, and compounds disclosed by Zhang, S., et al., *Drug Discovery Today,* 12(9/10), 373-381 (2007)), SIRT-1 inhibitor (e.g., reservatrol), a dipeptidyl peptidease IV (DPP-IV) inhibitor (e.g., sitagliptin, vildagliptin, alogliptin and saxagliptin), an insulin secreatagogue, a fatty acid oxidation inhibitor, an A2 antagonist, a c-jun amino-terminal kinase (JNK) inhibitor, insulin, an insulin mimetic, a glycogen phosphorylase inhibitor, a VPAC2 receptor agonist and a glucokinase activator. Preferred anti-diabetic agents are metformin, a glucagon-like peptide 1 (GLP-1) agonist (e.g, Byetta™) and DPP-IV inhibitors (e.g., sitagliptin, vildagliptin, alogliptin and saxagliptin).

All of the above recited U.S. patents and publications are incorporated herein by reference.

The Examples set forth herein below are for illustrative purposes only. The compositions, methods, and various parameters reflected herein are intended only to exemplify various aspects and embodiments of the invention, and are not intended to limit the scope of the claimed invention in any way.

EXAMPLES

The compounds and intermediates described below were generally named according to the IUPAC (International Union for Pure and Applied Chemistry) recommendations on Nomenclature of Organic Chemistry and the CAS Index rules. Unless noted otherwise, all reactants were obtained commercially. All of the references cited herein below are incorporated by reference.

Flash chromatography was performed according to the method described by Still et al., J. Org. Chem., 1978, 43, 2923.

All Biotage® purifications, discussed herein, were performed using either a 40M or 40S Biotage® column containing KP-SIL silica (40-63 µM, 60 Angstroms) (Bioatge AB; Uppsala, Sweden).

All Combiflash® purifications, discussed herein, were performed using a CombiFlash® Companion system (Teledyne Isco; Lincoln, Nebr.) utilizing packed RediSep® silica columns Mass Spectra were recorded on a Waters (Waters Corp.; Milford, Mass.) Micromass Platform II spectrometer. Unless otherwise specified, mass spectra were recorded on a Waters (Milford, Mass.) Micromass Platform II spectrometer.

Proton NMR chemical shifts are given in parts per million downfield from tetramethylsilane and were recorded on a Varian Unity 400 or 500 MHz (megaHertz) spectrometer (Varian Inc.; Palo Alto, Calif.). NMR chemical shifts are given in parts per million downfield from tetramethylsilane (for proton) or fluorotrichloromethane (for fluorine).

The preparations described below were used in the synthesis of compounds exemplified in the following examples.

Key Intermediates and Starting Materials

Pyrazolospiroketone Starting Materials

Pyrazolospiroketones, which were used to prepare the exemplified compounds, were prepared using the method of one of the following Pyrazolospiroketone Preparations 1-21.

Pyrazolospiroketone Preparation 1

2'-Phenyl-2'H-spiro[piperidine-4,5'-pyrano[3,2-c]pyrazol]-7'(6'H)-one

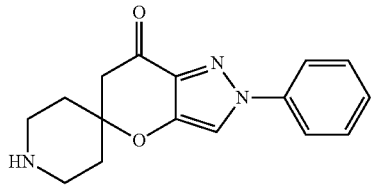

To a solution of phenylhydrazine (10.0 g, 92.5 mmol) in water (30 mL) was added acetic acid (8.8 mL) followed by the dropwise addition of pyruvaldehyde (16.7 g, 92.5 mmol) in water (400 mL) over a 15 minute period. The solution was stirred at room temperature overnight. The reaction was filtered and the resultant solid was washed with water (2×30 mL) to provide 2-oxopropanal phenylhydrazone as a yellow solid (15.2 g, 101%).

To 2-oxopropanal phenylhydrazone (5.00 g, 30.8 mmol) in acetic acid (60 mL) was added a 40% aqueous solution of glyoxal (5.9 g, 4.6 mL, 30.8 mmol) and the mixture was heated at reflux for 45 minutes. The acetic acid was removed under reduced pressure. The resultant mixture was diluted with ethyl acetate (100 mL), washed with NaHCO₃ and sat. aq. NaCl. Solids were removed by filtration, the filtrate was dried over Na₂SO₄, filtered and concentrated. The crude material was purified by CombiFlash (180 g column, 0-20 EtOAc/heptane gradient) to afford 1-(4-hydroxy-1-phenyl-1H-pyrazol-3-yl)ethanone as a yellow solid (2.70 g, 43%).

To a solution of 1-(4-hydroxy-1-phenyl-1H-pyrazol-3-yl) ethanone (2.70 g, 13.4 mmol) in methanol (25 mL) was added Boc-4-piperidone (2.66 g, 13.3 mmol) and pyrrolidine (0.95 g, 1.1 mL, 13.3 mmol). The mixture was stirred at room temperature for 6 days. The solvents were removed under reduced pressure and the crude material was purified by CombiFlash (80 g column, CH₂Cl₂-heptane (1:1)/methanol gradient) to afford tert-butyl 7'-oxo-2'-phenyl-6',7'-dihydro-1H, 2'H-spiro[piperidine-4,5'-pyrano[3,2-c]pyrazole]-1-carboxylate as a brown solid (1.33 g, 26%).

To a solution of tert-butyl 7'-oxo-2'-phenyl-6',7'-dihydro-1H,2'H-spiro[piperidine-4,5'-pyrano[3,2-c]pyrazole]-1-carboxylate (1.33 g, 3.47 mmol) was added trifluoroacetic acid (5 mL) and the mixture was stirred overnight at room temperature. The solvents were removed under reduced pressure to provide the title compound as a brown oil (0.98 g, 71%).

Pyrazolospiroketone Preparation 2

2'-Isopropyl-2'H-spiro[piperidine-4,5'-pyrano[3,2-c]pyrazol]-7'(6'H)-one

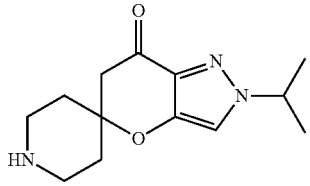

To a solution of isopropylhydrazine hydrochloride (2.0 g, 18 mmol) in water (100 mL) was added acetic acid (1.7 mL) followed by the dropwise addition of pyruvaldehyde (2.6 g, 14.5 mmol) in water. The solution was stirred at room temperature overnight. The aqueous layer was extracted with CH₂Cl₂ (4×) and the combined organic extracts were washed with sat. aq. NaHCO₃. The organic extract was dried over Na₂SO₄, filtered and concentrated to afford 2-oxopropanal isopropylhydrazone (1.3 g, 56%).

A 40% aqueous solution of gyoxal (1.47 g, 1.16 mL, 10.1 mol) was added to a solution of 2-oxopropanal isopropylhydrazone (1.3 g, 10 mmol) in water (90 mL). The mixture was heated at reflux for 2 hours, cooled to room temperature and extracted with CH₂Cl₂ (4×). The combined organic extracts were dried over Na₂SO₄, filtered and concentrated to provide 1-(4-hydroxy-1-isopropyl-1H-pyrazol-3-yl)ethanone as a yellow oil (1.40 g, 82%).

To a solution of 1-(4-hydroxy-1-isopropyl-1H-pyrazol-3-yl)ethanone (1.40 g, 8.3 mmol) in methanol (13 mL) was added pyrrolidine (0.59 g, 0.69 mL, 8.3 mmol). The mixture was stirred at room temperature for 2 hours before addition of Boc-4-piperidone (1.66 g, 8.32 mmol). The mixture was stirred at room temperature overnight. The solvents were removed under reduced pressure and the crude material was purified by CombiFlash (40 g column, 30-50% EtOAc/hexanes gradient) to afford tert-butyl 2'-isopropyl-7'-oxo-6',7'-dihydro-1H,2'H-spiro[piperidine-4,5'-pyrano[3,2-c]pyrazole]-1-carboxylate as an amber foam (1.08 g, 37%).

To a solution of tert-butyl 2'-isopropyl-7'-oxo-6',7'-dihydro-1H,2'H-spiro[piperidine-4,5'-pyrano[3,2-c]pyrazole]-1-carboxylate (1.08 g, 3.09 mmol) in dioxane (10 mL) was added 4 M HCl in dioxane (7.7 mL) and the mixture was stirred at room temperature for 30 minutes. The solvents were removed under reduced pressure and triturated with 2-methyltetrahydrofuran. The solids were filtered, washed with 2-methyltetrahydrofuran and the solids were air dried. The solids are hygroscopic and the material was taken up in CH₂Cl₂ and concentrated. The resulting solids were dried under reduced pressure to provide the title compound as a brown foam (0.53 g, 68%).

Pyrazolospiroketone Preparation 3

2'-Ethyl-3'-methyl-2'H-spiro[piperidine-4,5'-pyrano[3,2-c]pyrazol]-7'(6'H)-one

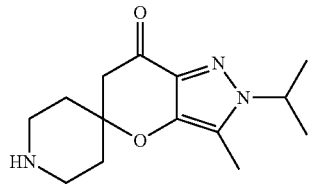

An aqueous solution of methyl glyoxal (pyruvaldehyde) (40%, 6.5 mL, 40 mmol) was added to a solution of ethylhydrazine oxalate (1 g, 6.7 mmol) and acetic acid (0.57 mL, 10 mmol) in water (11 mL), and the resulting mixture was heated at reflux for 3 hours. The reaction mixture was cooled to room temperature and extracted with EtOAc (3×). The combined organic layers were dried, filtered, and concentrated under reduced pressure. The crude product was purified by flash chromatography (silica gel) eluting with a gradient of heptane to heptane:ethyl acetate (80:20) to give 622 mg (56%) of 1-(1-ethyl-4-hydroxy-5-methyl-1H-pyrazol-3-yl)ethanone as a white solid.

To a solution of 1-(1-ethyl-4-hydroxy-5-methyl-1H-pyrazol-3-yl)ethanone (1.93 g, 11.5 mmol) in methanol (20 mL) was added pyrrolidine (0.82 g, 0.95 mL, 11.5 mmol). The mixture was stirred at room temperature for 2.5 hours before addition of Boc-4-piperidone (2.29 g, 11.5 mmol). The mixture was stirred at room temperature overnight. The solvents were removed under reduced pressure and the crude material was purified by CombiFlash (120 g column, 0-50% EtOAc/hexanes gradient) to afford tert-butyl 2'-ethyl-3'-methyl-7'-oxo-6',7'-dihydro-1H,2'H-spiro[piperidine-4,5'-pyrano[3,2-c]pyrazole]-1-carboxylate as a yellow foam (2.38 g, 59%).

To a solution of tert-butyl 2'-ethyl-3'-methyl-7'-oxo-6',7'-dihydro-1H,2'H-spiro[piperidine-4,5'-pyrano[3,2-c]pyrazole]-1-carboxylate (2.38 g, 6.81 mmol) in dioxane (17 mL) was added 4 M HCl in dioxane (17 mL) and the mixture was stirred at room temperature for 20 minutes. Solvents were removed under reduced pressure and triturated with 2-methyltetrahydrofuran and a small amount of ethanol. The solids were isolated by filtration, washed with 2-methyltetrahydrofuran and air dried to provide the title compound as a yellow solid (1.78 g, 92%).

Pyrazolospiroketone Preparation 4

2'-Ethyl-2'H-spiro[piperidine-4,5'-pyrano[3,2-c]pyrazol]-7'(6'H)-one

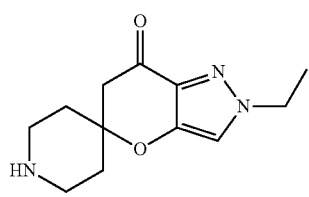

To a solution of ethylhydrazine oxalate (5.0 g, 33 mmol) in water (50 mL) was added dropwise a solution of pyruvaldehyde (4.80 g, 4.33 mL, 26.6 mmol) in water (550 mL). The solution was stirred overnight at room temperature. The aqueous layer was extracted with CH₂Cl₂ (4×). The combined organic extracts were washed with saturated aqueous NaCl, dried over Na₂SO₄, filtered and concentrated. Purify by CombiFlash (40 g column, 0-30% EtOAc/hexanes gradient) to afford 2-oxopropanal ethylhydrazone as a yellow oil (1.83 g, 48%).

A 40% aqueous solution of glyoxal (2.3 g, 1.8 mL, 16 mmol) was added to a solution of 2-oxopropanal ethylhydrazone (1.83 g, 16 mmol) in water (90 mL). The mixture was heated at reflux for 1 hour. The reaction was cooled to room temperature and extracted with CH₂Cl₂ (4×). The combined organic extracts were dried over Na₂SO₄, filtered and concentrated to afford 1-(1-ethyl-4-hydroxy-1H-pyrazol-3-yl)ethanone as a yellow oil (2.16 g, 87%).

To a solution of 1-(1-ethyl-4-hydroxy-1H-pyrazol-3-yl)ethanone (2.16 g, 14 mmol) in methanol (20 mL) was added pyrrolidine (1.0 g, 1.2 mL, 14 mmol). The mixture was stirred at room temperature for 2 hours before addition of Boc-4-piperidone (2.79 g, 14 mmol). The mixture was stirred at room temperature overnight. The solvents were removed under reduced pressure and the crude material was purified by CombiFlash (80 g column, 30-50% EtOAc/hexanes gradient) to afford tert-butyl 2'-ethyl-7'-oxo-6',7'-dihydro-1H,2'H-spiro[piperidine-4,5'-pyrano[3,2-c]pyrazole]-1-carboxylate as a yellow foam (2.39 g, 51%)

To a solution of tert-butyl 2'-ethyl-7'-oxo-6',7'-dihydro-1H,2'H-spiro[piperidine-4,5'-pyrano[3,2-c]pyrazole]-1-carboxylate (2.39 g, 7.13 mmol) in dioxane (18 mL) was added 4 M HCl in dioxane (18 mL) and the mixture was stirred at room temperature for 45 minutes. Solids precipitated out of solution and were isolated by vacuum filtration. The solids were isolated by vacuum filtration and subsequently taken up in 2-methyltetrahydrofuran and a small amount of ethanol. The solids were isolated by filtration, washed with 2-methyltetrahydrofuran and air dried to afford the title compound as a yellow solid (1.67 g, 76%).

Pyrazolospiroketone Preparation 5

2'-(3-Methoxyphenyl)-2'H-spiro[piperidine-4,5'-pyrano[3,2-c]pyrazol]-7'(6'H)-one

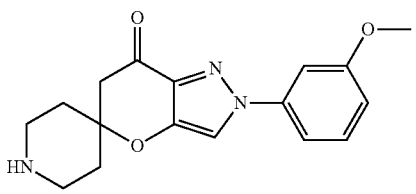

Acetic acid (1.7 mL) was added to a solution of 3-methoxyphenylhydrazine (3.0 g, 17 mmol) in water (35 mL). This mixture was then added dropwise to a solution of pyruvaldehyde (3.1 g, 2.8 mL, 17 mmol) in water (45 ml) over 15 minutes. The mixture was stirred for two days and solids were removed by filtration and washed with water to obtain 2-oxopropanal (3-methoxyphenyl)hydrazone as a black solid (1.1 g, 33%).

A mixture of 2-oxopropanal (3-methoxyphenyl)hydrazone (2.88 g, 14.5 mmol), acetic acid (20 mL) and glyoxal (6.3 g, 5.0 mL, 43 mmol) were heated at reflux overnight. The reaction was cooled to room temperature, diluted with EtOAc and washed with saturated aqueous NaCl. The black sludge was removed by decantation and the filtrate was washed with more saturated aqueous NaCl, dried over MgSO$_4$, filtered and concentrated. Purify by CombiFlash (80 g column, 0-50% heptane/EtOAc gradient) to afford 1-[4-hydroxy-1-(3-methoxyphenyl)-1H-pyrazol-3-yl]ethanone (330 mg, 10%).

To a solution of 1-[4-hydroxy-1-(3-methoxyphenyl)-1H-pyrazol-3-yl]ethanone (90 mg, 0.39 mmol) in methanol (2 mL) was added pyrrolidine (32 μL, 0.39 mmol). The mixture was stirred at room temperature for 20 minutes before addition of N-Boc-4-piperidone (77 mg, 0.39 mmol). The resulting mixture was stirred at room temperature overnight. The solvents were removed under reduced pressure and purified by CombiFlash (80 g column, 0-5% CH$_2$Cl$_2$/methanol gradient) to provide tert-butyl 2'-(3-methoxyphenyl)-7'-oxo-6',7'-dihydro-1H,2'H-spiro[piperidine-4,5'-pyrano[3,2-c]pyrazole]-1-carboxylate (66 mg, 41%).

To a solution of tert-butyl 2'-(3-methoxyphenyl)-7'-oxo-6',7'-dihydro-1H,2'H-spiro[piperidine-4,5'-pyrano[3,2-c]pyrazole]-1-carboxylate (66 mg, 0.16 mmol) in methanol (1.5 mL) was added 2 M HCl in diethyl ether (1.2 mL). The mixture was stirred at room temperature overnight. The solvents were removed under reduced pressure to provide the title compound as a hydrochloride salt (60 mg, 107%).

Pyrazolospiroketone Preparation 6

2',3'-Dimethyl-2'H-spiro[piperidine-4,5'-pyrano[3,2-c]pyrazol]-7'(6'H)-one

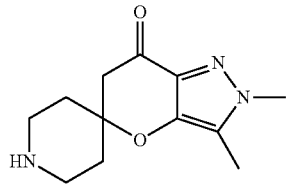

Acetic acid (4.1 mL) was slowly added to a solution of methylhydrazine (2.0 g, 2.3 mL, 43 mmol) in water (100 mL). This mixture was then added dropwise to a solution of pyruvaldehyde (6.26 g, 5.65 mL, 34.7 mmol) in water (175 mL). The resultant mixture was stirred at room temperature for 2 days. The aqueous phase was extracted with CH$_2$Cl$_2$ (4×), the combined organic extracts were washed with saturated aqueous NaCl, dried over Na$_2$SO$_4$, filtered and concentrated to provide 2-oxopropanal methylhydrazone (3.4 g, 78%).

To a 40% aqueous solution of pyruvaldehyde (5.5 mL, 34 mmol) was added a solution of 2-oxopropanal methylhydrazone (3.4 g, 34 mmol) in water (100 mL). The mixture was heated at reflux for 2 hours before cooling to room temperature. The mixture was extracted with EtOAc (4×). The combined organic extracts were dried over NaSO$_4$, filtered, concentrated and purified by CombiFlash (40 g column, 0-30% EtOAc/hexanes gradient) to provide 1-(4-hydroxy-1,5-dimethyl-1H-pyrazol-3-yl)ethanone (2.02 g, 39%).

Pyrrolidine (0.93 g, 1.1 mL, 13 mmol) was added to a solution of 1-(4-hydroxy-1,5-dimethyl-1H-pyrazol-3-yl)ethanone (2.02 g, 13 mmol) in methanol (20 mL). The mixture was stirred at room temperature for 2.5 hours before addition of N-Boc-piperidone (2.61 g, 13 mmol). The mixture was stirred at room temperature overnight before concentration to dryness. The crude material was purified by CombiFlash (120 g column, 0-50% EtOAc/hexanes gradient) to provide tert-butyl 2',3'-dimethyl-7'-oxo-6',7'-dihydro-1H,2'H-spiro[piperidine-4,5'-pyrano[3,2-c]pyrazole]-1-carboxylate (2.38 g, 54%).

To a solution of tert-butyl 2',3'-dimethyl-7'-oxo-6',7'-dihydro-1H,2'H-spiro[piperidine-4,5'-pyrano[3,2-c]pyrazole]-1-carboxylate (2.38 g, 7.10 mmol) in dioxane (17 mL) was added 4 M HCl in dioxane (17 mL). The mixture was stirred at room temperature for 20 minutes before concentrating to dryness. The residue was triturated with 2-methyltetrahydrofuran and a small amount of ethanol. The solids were isolated by filtration, washed with 2-methyltetrahydrofuran and air dried to provide the title compound as a yellow solid (1.70 g, 88%).

Pyrazolospiroketone Preparation 7

2'-Methyl-2'H-spiro[piperidine-4,5'-pyrano[3,2-c]pyrazol]-7'(6'H)-one

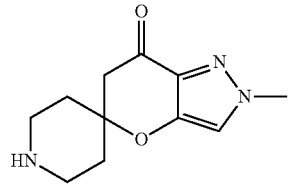

To a 40% aqueous solution of glyoxal (7.1 mL, 62 mmol) was added a solution of 2-oxopropanal methylhydrazone (6.17 g, 61.6 mmol) in water (300 mL). The mixture was heated at reflux for 1 hour before cooling to room temperature. The mixture was extracted with CH$_2$Cl$_2$ (4×). The combined organic extracts were dried over NaSO$_4$, filtered, concentrated and purified by CombiFlash (120 g column, 30-40% EtOAc/hexanes gradient) to provide 1-(4-hydroxy-1-methyl-1H-pyrazol-3-yl)ethanone (5.93 g, 69%).

Pyrrolidine (3.0 g, 3.5 mL, 42 mmol) was added to a solution of 1-(4-hydroxy-1-methyl-1H-pyrazol-3-yl)ethanone (5.93 g, 42.3 mmol) in methanol (50 mL). The mixture was stirred at room temperature for 2 hours before addition of N-Boc-piperidone (8.43 g, 42.3 mmol). The mixture was stirred at room temperature overnight before concentration to dryness. The crude material was purified by CombiFlash (120 g column, 30-50% EtOAc/hexanes gradient) to afford desired product containing unreacted starting material. This material was triturated with 30% EtOAc/hexanes, the solids were filtered and air dried to afford tert-butyl 2'-methyl-7'-oxo-6',7'-dihydro-1H,2'H-spiro[piperidine-4,5'-pyrano[3,2-c]pyrazole]-1-carboxylate (6.8 g, 50%).

A solution of tert-butyl 2'-methyl-7'-oxo-6',7'-dihydro-1H,2'H-spiro[piperidine-4,5'-pyrano[3,2-c]pyrazole]-1-carboxylate (6.83 g, 21.3 mmol) in 1:1 trifluoroacetic acid/CH$_2$Cl$_2$ (38 mL total volume) was stirred at room temperature for 15 minutes. To this was added 1 N HCl and the mixture was extracted with EtOAc. The aqueous phase was neutralized with saturated aqueous NaHCO$_3$ and extracted with CH$_2$Cl$_2$. Solids appeared in the CH$_2$Cl$_2$ extract and were isolated by vacuum filtration to afford the title compound as a white solid (2.66 g, 43%). The aqueous phase was back extracted with CHCl$_3$ (3×), dried over Na$_2$SO$_4$, filtered and concentrated to provide a second batch of title compound (1.36 g, 29%). The aqueous phase was made basic to pH 12 with 1 N NaOH and extracted with CHCl$_3$ (6×), dried over Na$_2$SO$_4$, filtered and concentrated to provide a third batch of title compound (1.56 g, 33%).

Pyrazolospiroketone Preparation 8

2'-propyl-2'H-spiro[piperidine-4,5'-pyrano[3,2-c]pyrazol]-7'(6'H)-one

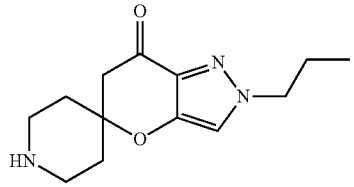

Acetic acid (2.9 mL, 50 mmol) was added to a solution of n-propylhydrazine oxalate (5.0 g, 30 mmol) in water (100 mL). This mixture was added to a solution of pyruvaldehyde (4.39 g, 3.96 mL, 24.4 mmol) in water (500 mL). The solution was stirred at room temperature overnight. The aqueous phase was extracted with $CH_2Cl_2$ (4×) and the combined organic extracts were washed with saturated aqueous $NaHCO_3$, dried over $Na_2SO_4$, filtered and concentrated to afford 2-oxopropanal propylhydrazone (3.74 g, 96%).

A 40% aqueous solution of glyoxal (4.23 g, 3.35 mL, 29.2 mmol) was added to a solution of 2-oxopropanal propylhydrazone (3.74 g, 29.2 mmol) in water (185 mL). The mixture was heated at reflux for 1 hour. The reaction was cooled to room temperature and extracted with $CH_2Cl_2$ (4×). The combined organic extracts were dried over $Na_2SO_4$, filtered and concentrated to provide 1-[4-(hydroxymethyl)-1-propyl-1H-pyrazol-3-yl]ethanone of 50% purity (3.60 g, 73%).

Pyrrolidine (1.52 g, 1.77 mL, 21.4 mmol) was added to a solution of 1-[4-(hydroxymethyl)-1-propyl-1H-pyrazol-3-yl]ethanone (3.6 g, 21 mmol) in methanol (33 mL). The mixture was stirred at room temperature for 2 hours before addition of N-Boc-piperidone (4.26 g, 21.4 mmol). The mixture was stirred at room temperature overnight before concentration to dryness. The crude material was purified by CombiFlash (80 g column, 30-50% EtOAc/hexanes gradient) to afford tert-butyl 7'-oxo-2'-propyl-6',7'-dihydro-1H,2'H-spiro[piperidine-4,5'-pyrano[3,2-c]pyrazole]-1-carboxylate (1.93 g, 26%)

To a solution of tert-butyl 7'-oxo-2'-propyl-6',7'-dihydro-1H,2'H-spiro[piperidine-4,5'-pyrano[3,2-c]pyrazole]-1-carboxylate (1.39 g, 3.98 mmol) in dioxane (10 mL) was added and stirred for 20 minutes. The mixture was concentrated and triturated with 2-methyltetrahydrofuran and a small amount of ethanol. The solid was isolated by filtration, washed with 2-methyltetrahydrofuran and dried overnight to provide the title compound (853 mg, 86%).

Pyrazolospiroketone Preparation 9

3'-Methyl-2'-(2,2,2-trifluoroethyl)-2'H-spiro[piperidine-4,5'-pyrano[3,2-c]pyrazol]-7'(6'H)-one

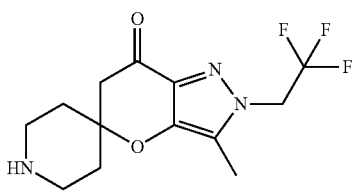

A 40% aqueous solution of methylglyoxal (33.2 g, 184 mmol) was added to a 70% aqueous solution of trifluoroethylhydrazine (10 g, 61 mmol) in water (100 mL). The resulting mixture was heated at reflux for 2.5 hours. The reaction was cooled to room temperature, extracted with EtOAc, washed with water, saturated aqueous $NaHCO_3$, dried over $Na_2SO_4$, filtered and concentrated. The crude material was purified by CombiFlash (80 g column, EtOAc/hexanes gradient) to obtain 1-[4-hydroxy-5-methyl-1-(2,2,2-trifluoroethyl)-1H-pyrazol-3-yl]ethanone (3.51 g, 25%).

To a solution of 1-[4-hydroxy-5-methyl-1-(2,2,2-trifluoroethyl)-1H-pyrazol-3-yl]ethanone (3.51 g, 15.8 mmol) in methanol (25 mL) was added N-Boc-4-piperidone (3.15 g, 15.8 mmol) followed by pyrrolidine (1.12 g, 1.32 mL, 15.8 mmol). The mixture was stirred at room temperature for 6 days. The solvents were removed under reduced pressure and purified by CombiFlash (120 g column, EtOAc/hexanes gradient) to provide tert-butyl 3'-methyl-7'-oxo-2'-(2,2,2-trifluoroethyl)-6',7'-dihydro-1H,2'H-spiro[piperidine-4,5'-pyrano[3,2-c]pyrazole]-1-carboxylate (1.22 g, 16%).

To a solution of tert-butyl 3'-methyl-7'-oxo-2'-(2,2,2-trifluoroethyl)-6',7'-dihydro-1H,2'H-spiro[piperidine-4,5'-pyrano[3,2-c]pyrazole]-1-carboxylate (1.22 g, 3.02 mmol) in $CH_2Cl_2$ (20 mL) was added trifluoroacetic acid (8 mL). The mixture was stirred at room temperature for 4 hours before concentration to obtain the hydrochloride salt of the title compound.

Pyrazolospiroketone Preparation 10

2'-Benzyl-2'H-spiro[piperidine-4,5'-pyrano[3,2-c]pyrazol]-7'(6'H)-one

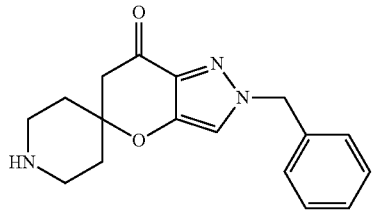

To a solution of benzylhydrazine hydrochloride (11.1 g, 57.1 mmol) in water (100 mL) was added dropwise a solution of pyruvaldehyde (10.3 g, 9.3 mL, 57.1 mmol) in water (500 mL). The mixture was stirred at room temperature overnight. The reaction mixture was diluted with $CH_2Cl_2$ (4×150 mL). The combined organic extracts were washed with saturated aqueous NaCl, dried over $Na_2SO_4$, filtered and concentrated to provide 2-oxopropanal benzylhydrazone (10.1 g, 100%).

To a 40% aqueous solution of glyoxal (8.28 g, 6.55 mL, 57.1 mmol) was added a slurry of 2-oxopropanal benzylhydrazone (10.1 g, 57.1 mmol) in water (250 mL) and methanol (25 mL). The resulting mixture was heated at reflux for 3 hours before cooling to room temperature. The mixture was extracted with EtOAc (2×100 mL) and the combined organic extracts were washed with water, saturated aqueous NaCl, dried over $Na_2SO_4$, filtered and concentrated. The crude material was purified by CombiFlash (120 g column, 0-100% EtOAc/heptane gradient) to provide 1-(1-benzyl-4-hydroxy-1H-pyrazol-3-yl)ethanone (4.07 g, 33%).

To a solution of 1-(1-benzyl-4-hydroxy-1H-pyrazol-3-yl)ethanone (4.07 g, 18.8 mmol) in methanol (50 mL) was added N-Boc-4-piperidone (3.75 g, 18.8 mmol) followed by pyrrolidine (1.34 g, 1.57 mL, 18.8 mmol). The mixture was stirred at room temperature for 6 days. The solvents were removed under reduced pressure and purified by CombiFlash (120 g column, EtOAc/hexanes gradient) to provide tert-butyl 2'-benzyl-7'-oxo-6',7'-dihydro-1H,2'H-spiro[piperidine-4,5'-pyrano[3,2-c]pyrazole]-1-carboxylate (3.02 g, 40%).

To a solution of tert-butyl 2'-benzyl-7'-oxo-6',7'-dihydro-1H,2'H-spiro[piperidine-4,5'-pyrano[3,2-c]pyrazole]-1-carboxylate (1.22 g, 3.02 mmol) in CH$_2$Cl$_2$ (6 mL) was added trifluoroacetic acid (3 mL). The mixture was stirred at room temperature overnight before concentration to obtain the trifluoroacetic acid salt of the title compound (311 mg, 100%).

Pyrazolospiroketone Preparation 11

2-Methoxy-4-(3'-methyl-7'-oxo-6',7'-dihydro-2'H-spiro[piperidine-4,5'-pyrano[3,2-c]pyrazol]-2'-yl)benzonitrile

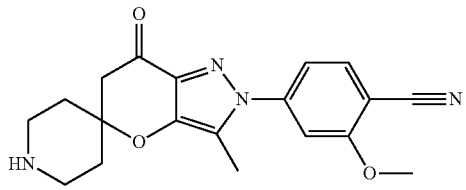

To a solution of 4-fluoro-2-methoxybenzonitrile (100 g, 0.662 mol) in ethanol (0.66 L) was added hydrazine monohydrate (331 g, 0.321 L, 6.62 mol). The mixture was heated at reflux overnight. The reaction was cooled to room temperature, diluted with water (750 mL), stirred for 1.5 hours and the resulting solids were collected by filtration. The solids were rinsed with water (2×250 mL) and air dried for 3 hours. The solids were then dried in a vacuum oven at 45° C. The material was dissolved in dioxane (2 L) and HCl gas was bubbled through for 30 minutes. The resulting solids were filtered and washed with methyl tert-butyl ether (2×1 L). The solids were air dried for 1 hour and the resulting solids were dried in a vacuum oven at 45° C. to provide -hydrazino-2-methoxybenzonitrile hydrochloride (115.6 g, 87.5%).

A mixture of 2-methoxybenzonitrile hydrochloride (1.00 g, 5.00 mmol) in acetic acid (20 mL) and methylglyoxal (1.80 g, 1.63 mL, 25.0 mmol) was heatd at reflux overnight. The mixture was cooled to room temperature and diluted with EtOAc and saturated aqueous NaCl. Solids were removed by filtration and the organic layer was washed with saturated aqueous NaCl. The organic extract was dried over MgSO$_4$, filtered and concentrated. The crude material was purified by CombiFlash (40 g column, 0-10 CH2Cl2/MeOH gradient) to afford 4-(3-acetyl-4-hydroxy-5-methyl-1H-pyrazol-1-yl)-2-methoxybenzonitrile (47 mg, 4%).

To a solution of 4-(3-acetyl-4-hydroxy-5-methyl-1H-pyrazol-1-yl)-2-methoxybenzonitrile (47 mg, 0.17 mmol) in methanol (2 mL) was added N-Boc-4-piperidone (34 mg, 0.17 mmol) followed by pyrrolidine (12 mg, 14 µL, 0.17 mmol). The mixture was stirred at room temperature overnight. The solvents were removed under reduced pressure and purified by CombiFlash to provide tert-butyl 2'-(4-cyano-3-methoxyphenyl)-3'-methyl-7'-oxo-6',7'-dihydro-1H,2'H-spiro[piperidine-4,5'-pyrano[3,2-c]pyrazole]-1-carboxylate (74 mg, 95%).

A solution of tert-butyl 2'-(4-cyano-3-methoxyphenyl)-3'-methyl-7'-oxo-6',7'-dihydro-1H,2'H-spiro[piperidine-4,5'-pyrano[3,2-c]pyrazole]-1-carboxylate (74 mg, 0.16 mmol) in methanol (1 mL) and conc. HCl (0.82 mL) was stirred at room temperature overnight. The solvents were removed under reduced pressure to afford the hydrochloride salt of the title compound (70 mg, 110%).

Pyrazolospiroketone Preparation 12

3'-Ethyl-2'-methyl-2'H-spiro[piperidine-4,5'-pyrano[3,2-c]pyrazol]-7'(6'H)-one

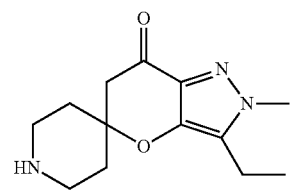

To a solution of 2-oxopropanal methylhydrazone (3.0 g, 30 mmol) in water 150 mL) was added 2-oxobutyraldehyde (4.0 g, 46 mmol). The mixture was heated at reflux for 2 hours before cooling to room temperature. The mixture was extracted with CH$_2$Cl$_2$ (4×) and the combined organic extracts were dried over Na$_2$SO$_4$, filtered and concentrated. The crude material contains 1-(5-ethyl-4-hydroxy-1-methyl-1H-pyrazol-3-yl)ethanone (2.93 g, 37%) along with unreacted 2-oxopropanal methylhydrazone and the material was used as is without further purification.

To a solution of 1-(5-ethyl-4-hydroxy-1-methyl-1H-pyrazol-3-yl)ethanone (2.93 g, 17.4 mmol) in methanol (27 mL) was added pyrrolidine (1.24 g, 1.44 mL, 17.4 mmol) and the mixture was stirred for 2 hours. To this mixture was added N-Boc-4-piperidone (3.47 g, 17.4 mmol) and the mixture was stirred at room temperature overnight. The solvents were removed under reduced pressure and purified by CombiFlash (80 g column, 30-50% EtOAc/hexanes gradient) to provide tert-butyl 3'-ethyl-2'-methyl-7'-oxo-6',7'-dihydro-1H,2'H-spiro[piperidine-4,5'-pyrano[3,2-c]pyrazole]-1-carboxylate (376 mg, 6.2%).

To a solution of tert-butyl 3'-ethyl-2'-methyl-7'-oxo-6',7'-dihydro-1H,2'H-spiro[piperidine-4,5'-pyrano[3,2-c]pyrazole]-1-carboxylate (376 mg, 1.08 mmol) in dioxane (4 mL) was added 4 M HCl in dioxane (2.7 mL). The mixture was stirred at room temperature for 30 minutes before concentration. The crude material was triturated with 2-methyltetrahydrofuran and a small amount of ethanol. The solids were collected by filtration, washed with 2-methyltetrahydrofuran and air dried to afford the hydrochloride salt of the title compound (242 mg, 90%).

Pyrazolospiroketone Preparation 13

2'-Pyridin-2-yl-2'H-spiro[piperidine-4,5'-pyrano[3,2-c]pyrazol]-7'(6'H)-one

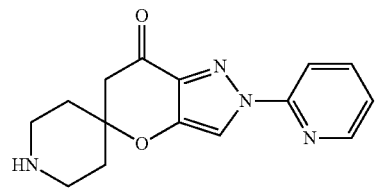

To a solution of 2-pyridylhydrazine (10.0 g, 91.6 mmol) in water (30 mL) was added acetic acid (8.7 mL). This mixture was then added to a solution of pyruvaldehyde (16.5 g, 14.9 mL, 91.6 mmol) in water (400 mL). The mixture was stirred at room temperature for 3 days. The mixture was neutralized with NaHCO$_3$ (solid) whereupon a yellow precipitate forms. The solid was isolated by filtration and then washed with water (30 mL). The solids were dried under high vacuum to afford 2-oxopropanal pyridin-2-ylhydrazone as a yellow solid (6.12 g, 41%).

A solution of 2-oxopropanal pyridin-2-ylhydrazone (6.12 g, 37.5 mmol) and glyoxal (16.3 g, 12.9 mL, 113 mmol) in water (50 mL) and methanol (10 mL) was heated at reflux overnight. The mixture was cooled to room temperature, diluted with EtOAc and sequentially washed with saturated aqueous NaHCO$_3$, saturated aqueous NaCl, dried over Na$_2$SO$_4$, filtered and concentrated. The crude material was passed over a plug of silica gel, eluting with heptane/EtOAc (1:2, 300 mL) to afford 1-(4-hydroxy-1-pyridin-2-yl-1H-pyrazol-3-yl)ethanone (199 mg, 2.6%).

To a solution of 1-(4-hydroxy-1-pyridin-2-yl-1H-pyrazol-3-yl)ethanone (199 mg, 0.98 mmol) in methanol (5 mL) was added N-Boc-4-piperidone (195 mg, 0.98 mmol) and pyrrolidine (70 µL, 0.98 mmol) and the mixture was stirred at room temperature overnight. The solvents were removed under reduced pressure, diluted with EtOAc, washed with NaHCO$_3$ (1×), saturated aqueous NaCl(3×), dried over Na$_2$SO$_4$, filtered and concentrated to provide the enamine tert-butyl 2'-pyridin-2-yl-7'-pyrrolidin-1-yl-1H,2'H-spiro[piperidine-4,5'-pyrano[3,2-c]pyrazole]-1-carboxylate (198 mg, 56%).

To a solution of tert-butyl 2'-pyridin-2-yl-7'-pyrrolidin-1-yl-1H,2'H-spiro[piperidine-4,5'-pyrano[3,2-c]pyrazole]-1-carboxylate (198 mg, 0.52 mmol) in CH$_2$Cl$_2$ (10 mL) was added trifluoroacetic acid (4 mL) and water (0.5 mL) and the mixture was stirred at room temperature overnight. The solvents were removed under reduced pressure to afford the trifluoroacetic acid salt of the title compound.

Pyrazolospiroketone Preparation 14

2'-(Tetrahydrofuran-3-yl)-2'H-spiro[piperidine-4,5'-pyrano[3,2-c]pyrazol]-7'(6'H)-one

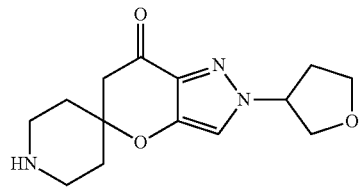

Acetic acid (1.7 mL) was slowly added to a solution of tetrahydrofuran-3-ylhydrazine hydrochloride (2.50 g, 18.0 mmol) (prepared as described by Bacon, E. R.; Singh, B.; and Lesher, G. Y. in U.S. Pat. No. 5,294,612) in water (30 mL). This mixture was then added dropwise to a solution of pyruvaldehyde (2.59 g, 2.34 mL, 14.4 mmol) in water (240 mL). The mixture was stirred overnight at room temperature. The mixture was poured into a seperatory funnel, NaCl was added and dissolved in the aqueous phase and then extracted with CH$_2$Cl$_2$ (6-times). The combined organic extracts were dried over Na$_2$SO$_4$, filtered and concentrated to provide crude material, which was purified by preadsorbing the oil on SiO$_2$ followed by chromatography (Isco, 80 g RediSep column) eluting with a 0-80% EtOAc/heptane gradient over 80 minutes. Analysis of fractions resulted in isolation of 2-oxopropanal tetrahydrofuran-3-ylhydrazone (1.19 g, 53%).

A 40% aqueous solution of glyoxal (0.83 g, 0.65 mL, 5.7 mmol) was added to 2-oxopropanal tetrahydrofuran-3-ylhydrazone (0.89 g, 5.7 mmol) in water (50 mL). The mixture was heated at reflux for 1 hour, allowed to cool to room temperature and stirred overnight. The mixture was extracted with CH$_2$Cl$_2$ (4-times), the combined organic extracts were dried over Na$_2$SO$_4$, filtered, concentrated and dried under high vacuum to give crude material. Purification was accomplished by preadsorption of the crude oil on SiO$_2$ followed by chromatography (Isco CombiFlash 100, 40 g RediSep column) eluting with a 25-55% EtOAc/heptane gradient over 40 minutes with a 10 minutes hold at 55% to provide 1-[4-hydroxy-1-(tetrahydrofuran-3-yl)-1H-pyrazol-3-yl]ethanone (1.12 g, 19%) and 1-[4-hydroxy-5-methyl-1-(tetrahydrofuran-3-yl)-1H-pyrazol-3-yl]ethanone (1.20 g, 8.4%).

To a solution of 1-[4-hydroxy-1-(tetrahydrofuran-3-yl)-1H-pyrazol-3-yl]ethanone (210 mg, 1.07 mmol) in methanol (3 mL) was added pyrrolidine (76 mg, 88 uL, 1.07 mmol). This mixture was stirred at room temperature for 2 hours before addition of N-Boc-4-piperidone (213 mg, 1.07 mmol). The mixture was stirred at room temperature overnight before concentration. Crude material was preadsorbed onto SiO$_2$ and chromatographed (Isco CombiFlash 100, 12 g RediSep column) eluting with a 10-50% EtOAc/heptane gradient over 50 minutes to afford tert-butyl 7'-oxo-2'-(tetrahydrofuran-3-yl)-6',7'-dihydro-1H,2'H-spiro[piperidine-4,5'-pyrano[3,2-c]pyrazole]-1-carboxylate (404 mg, 36%).

To a solution of tert-butyl 7'-oxo-2'-(tetrahydrofuran-3-yl)-6',7'-dihydro-1H,2'H-spiro[piperidine-4,5'-pyrano[3,2-c]pyrazole]-1-carboxylate (144 mg, 0.38 mmol) in 1,4-dioxane (2 mL) was added 4 M HCl in dioxane (0.96 mL). The mixture was stirred at room temperature for 1 hour before concentration to dryness. Triturate with diethyl ether and a small amount of ethanol. The solids were collected by vacuum filtration, washed with diethyl ether and dried under high vacuum to afford 2'-(tetrahydrofuran-3-yl)-2'H-spiro[piperidine-4,5'-pyrano[3,2-c]pyrazol]-7'(6'H)-one (49 mg, 41%).

Pyrazolospiroketone Preparation 15

3'-Methyl-2'-(tetrahydrofuran-3-yl)-2'H-spiro[piperidine-4,5'-pyrano-[3,2-c]pyrazol]-7'(6'H)-one

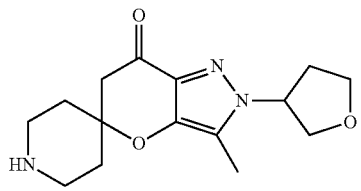

To a solution of 1-[4-hydroxy-5-methyl-1-(tetrahydrofuran-3-yl)-1H-pyrazol-3-yl]ethanone (prepared as described in Pyrazolospiroketone Preparation 14) (304 mg, 1.45 mmol) in methanol (4.5 mL) was added pyrrolidine (103 mg, 120 uL, 1.45 mmol). This mixture was stirred at room temperature for 2 hours before addition of N-Boc-4-piperidone (288 mg, 1.45 mmol). The mixture was stirred at room temperature overnight before concentration. Crude material was preadsorbed onto SiO$_2$ and chromatographed (Isco CombiFlash 100, 12 g RediSep column) eluting with a 10-50% EtOAc/heptane gradient over 50 minutes to afford tert-butyl 3'-methyl-7'-oxo-2'-(tetrahydrofuran-3-yl)-6',7'-dihydro-1H,2'H-spiro[piperidine-4,5'-pyrano[3,2-c]pyrazole]-1-carboxylate (299 mg, 53%).

To a solution of tert-butyl 3'-methyl-7'-oxo-2'-(tetrahydrofuran-3-yl)-6',7'-dihydro-1H,2'H-spiro[piperidine-4,5'-pyrano[3,2-c]pyrazole]-1-carboxylate (295 mg, 0.75 mmol) in 1,4-dioxane (4 mL) was added 4 M HCl in dioxane (1.9 mL). The mixture was stirred at room temperature for 1 hour before concentration to dryness. Triturate with diethyl ether and a small amount of ethanol. The solids were collected by vacuum filtration, washed with diethyl ether and dried under high vacuum to afford 3'-methyl-2'-(tetrahydrofuran-3-yl)-2'H-spiro[piperidine-4,5'-pyrano[3,2-c]pyrazol]-7'(6'H)-one (106 mg, 43%).

Pyrazolospiroketone Preparation 16

2'-tert-Butyl-2'H-spiro[piperidine-4,5'-pyrano[3,2-c]pyrazol]-7'(6'H)-one

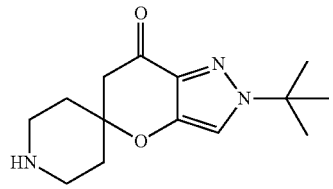

To a 200 L reactor was charged: water (72 L) and (1,1-dimethylethyl)hydrazine monohydrochloride (13.4 kg, 108 moles). Solution was agitated for 15 minutes at 23° C. (until all solids dissolved), then 2-oxo-propanal (14.8 kg, 82.1 moles) was added and held for a minimum of 4 hours. Reaction solution was extracted 2×'s MTBE (54 L). The combined organic layers were washed 2×'s 1N NaOH (32 L), 1× water (32 L), and concentrated (220 mmHg, 30° C.) to a minimum stirring volume. To the concentrate was added: water (72 L), Ethanedial (glyoxaldehyde) (27.3 kg, 188 moles) and heated reaction to 95° C., allowing residue MTBE to distill off in order to reach desired temperature. After 1.5 hours, mixture cooled to ambient temperature (over 1 hour) and was extracted 2×'s MTBE (54 L). The combined organic layers were washed 2×'s 1N NaOH (34 L). The combined aqueous layers was cooled to 5° C., acidified to pH 3 with HCl 33-40 wt/wt % in water (6 L), then extracted 2×'s MTBE (54 L). The combined organic layers were washed with water (36 L) and concentrated (200 mmHg, 30° C.) to a minimal stirring volume. To the concentrate was added: methanol (109 L), N—BOC-4-piperidone (16.7 kg, 84 moles), and pyrrolidine (1.4 L, 16 moles). Reaction was heated to 68° C. for 24 hours, cooled to 50° C., and pulled vacuum to distill to a minimum stirring volume. Removed vacuum and added ethyl acetate (45 L), distilled (atmospheric pressure) to a low stirring volume, then added MTBE (72 L). Returned solution to a gentle reflux, then added n-heptane (82 L), over 30 minutes, while cooling to ambient temperature over 3 hours. Filtered the solids through a Nutsche Filter, washed with 1:1.1 MTBE/n-heptane (50 L), and dried under vacuum at 50° C. for 12 h. Isolated 10.0 kg (27.5 moles, 33% overall) of tert-butyl 2'-tert-butyl-7'-oxo-6',7'-dihydro-2'H-spiro[piperidine-4,5'-pyrano[3,2-c]pyrazole]-1-carboxylate as a white crystalline solid.

To a 200 L reactor was charged: tert-butyl 2'-tert-butyl-7'-oxo-6',7'-dihydro-2'H-spiro[piperidine-4,5'-pyrano[3,2-c]pyrazole]-1-carboxylate (8.3 kg, 22.8 moles), ethyl acetate (89 L), and methanol (24 L). Solution was cooled to 0° C., and acetyl chloride (11.0 L, 155 moles) was added over 30 minutes. After addition, reaction was allowed to warm to ambient temperature and react for 4 hours. Heated solution in order to distill to a 41 L reaction volume, slowly refilling with ethyl acetate (~0.22 L) until an internal temperature of 72° C. was reached. Cooled to ambient temperature over 3 hours, filtered the solids through a Nutsche Filter, washed with ethyl acetate (5.3 L), and dried under vacuum at 50° C. for 12 hours. Isolated 6.6 kg (22.0 moles, 96%) of 2'-tert-butyl-2'H-spiro[piperidine-4,5'-pyrano[3,2-c]pyrazol]-7'(6'H)-one as a white crystalline solid.

Pyrazolospiroketone Preparation 17

2'-Cyclohexyl-2'H-spiro[piperidine-4,5'-pyrano[3,2-c]pyrazol]-7'(6'H)-one

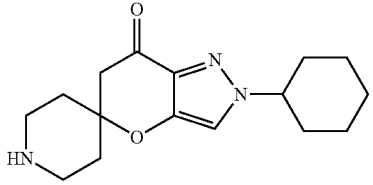

Acetic acid (3.15 mL, 54.8 mmol) was slowly added to a solution of cyclohexylhydrazine HCl in $H_2O$ (60 mL). The resulting solution was then added dropwise to a solution of pyruvaldehyde (4.78 g, 26.6 mmol) in $H_2O$ (540 mL). This solution was stirred over night at room temperature. The aqueous layer was extracted with $CH_2Cl_2$ (4×). The combined organic layers were washed with brine, dried ($Na_2SO_4$), and concentrated under reduced pressure. The crude product was then purified via flash chromatography (silica gel) eluting with a gradient of 100% hexanes to a 70:30 mixture of hexanes:ethyl acetate to deliver 2.54 g (45%) of 2-oxopropanal cyclohexyl-hydrazone as an amber oil.

A 40% aqueous solution of glyoxal (1.73 mL, 15.1 mmol) was added to 2-oxopropanal cyclohexyl-hydrazone (2.54 g, 15.1 mmol) in $H_2O$ (125 mL). The mixture was then heated at reflux. After 1 hour, the mixture was cooled to room temperature and extracted with $CH_2Cl_2$ (4×). The combined organic extracts were dried ($Na_2SO_4$) and concentrated under reduced pressure to afford 3.22 g of 1-(4-hydroxy-1-cyclohexyl-1H-pyrazol-3-yl)ethanone as a yellow oil. The crude product was then used in the next step without further purification.

Pyrrolidine (1.10 g, 15.5 mmol) was added to a solution of 1-(4-hydroxy-1-cyclohexyl-1H-pyrazol-3-yl)ethanone (3.22 g, 15.5 mmol) MeOH (25 mL). The dark red solution was stirred for 2 hours at room temperature. 1-(N-Boc)-4-piperidone (3.08 g, 15.5 mmol) was then added to the solution, and the reaction mixture was stirred at room temperature overnight. The mixture was then concentrated under reduced pressure. The crude product was then purified via flash chromatography (silica gel) eluting with a gradient of ethyl acetate:hexanes (30:70 to 50:50) to deliver a yellow. The yellow oil was then triturated with hexanes for 1 hour whereupon a white solid was afforded. The solid was filtered, washed with hexanes and air dried overnight. 372 mg (6%) of tert-butyl 2'-cyclohexyl-7'-oxo-6',7'-dihydro-1H,2'H-spiro[piperidine-4,5'-pyrano[3,2-c]pyrazole]-1-carboxylate was afforded as a white solid.

To a solution of tert-butyl 2'-cyclohexyl-7'-oxo-6',7'-dihydro-1H,2'H-spiro[piperidine-4,5'-pyrano[3,2-c]pyrazole]-1-carboxylate (372 mg, 0.955 mmol) in 1,4-dioxane (4 mL) at room temperature was added a solution of HCl (4 M in 1,4-dioxane, 2.39 mL, 9.55 mmol). The mixture was stirred at room temperature for 1 hour. The reaction mixture was concentrated to dryness and triturate for ~1 hour in 2-methyltetrahydrofuran and a small amount of EtOH. The solid was collected by vacuum filtration to afford 223 mg (80%) of the title compound as an off white solid.

Pyrazolospiroketone Preparation 18

2'-Cyclopentyl-2'H-spiro[piperidine-4,5'-pyrano[3,2-c]pyrazol]-7'(6'H)-one

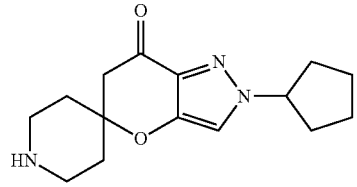

Acetic acid (1.39 mL, 24.2 mmol) was slowly added to a solution of cyclopentylhydrazine.HCl (2.0 g, 15 mmol) in H$_2$O (24 mL). The resulting solution was then added dropwise to a solution of pyruvaldehyde (40%, 1.90 mL, 11.7 mmol) in H$_2$O (200 mL). This solution was stirred over night at room temperature. The aqueous layer was extracted with CH$_2$Cl$_2$ (4×). The combined organic layers were washed with brine, dried (Na$_2$SO$_4$), and concentrated under reduced pressure. The crude product was then purified via flash chromatography (silica gel) eluting with a gradient of 100% hexanes to a 70:30 mixture of hexanes:ethyl acetate to deliver 1.53 g (68%) of 2-oxopropanal cyclopentylhydrazone as an amber oil.

A 40% aqueous solution of glyoxal (1.88 mL, 16.4 mmol) was added to 2-oxopropanal cyclopentylhydrazone (2.53 g, 16.4 mmol) in H$_2$O (125 mL). The mixture was then heated at reflux. After 1 hour, the mixture was cooled to room temperature and extracted with CH$_2$Cl$_2$ (4×). The combined organic extracts were dried (Na$_2$SO$_4$) and concentrated under reduced pressure to afford 1.68 g (53%) of 1-(4-hydroxy-1-cyclopentyl-1H-pyrazol-3-yl)ethanone as a yellow oil. The crude product was then used in the next step without further purification.

Pyrrolidine (0.615 g, 8.65 mmol) was added to a solution of 1-(4-hydroxy-1-cyclopentyl-1H-pyrazol-3-yl)ethanone (1.68 g, 8.65 mmol) MeOH (15 mL). The dark red solution was stirred for 2 hours at room temperature. 1-(N-Boc)-4-piperidone (1.72 g, 8.65 mmol) was then added to the solution, and the reaction mixture was stirred at room temperature overnight. The mixture was then concentrated under reduced pressure. The crude product was then purified via flash chromatography (silica gel) eluting with a gradient of ethyl acetate:hexanes (30:70 to 50:50) to deliver a yellow. The yellow oil was then triturated with hexanes for 1 hour whereupon a white solid was afforded. The solid was filtered, washed with hexanes and air dried overnight. 811 mg (25%) of tert-butyl 2'-cyclopentyl-7'-oxo-6',7'-dihydro-1H,2'H-spiro[piperidine-4,5'-pyrano[3,2-c]pyrazole]-1-carboxylate was afforded as a yellow solid.

To a solution of tert-butyl 2'-cyclopentyl-7'-oxo-6',7'-dihydro-1H,2'H-spiro[piperidine-4,5'-pyrano[3,2-c]pyrazole]-1-carboxylate (811 mg, 2.16 mmol) in 1,4-dioxane (9 mL) at room temperature was added a solution of HCl (4 M in 1,4-dioxane, 5.40 mL, 21.6 mmol). The mixture was stirred at room temperature for 1 hour. The reaction mixture was concentrated to dryness and triturate for ~1 hour in 2-methyltetrahydrofuran and a small amount of EtOH. The solid was collected by vacuum filtration to afford 378 mg (64%) of the title compound as an off-white solid.

Pyrazolospiroketone Preparation 19

2'-Cyclobutyl-2'H-spiro[piperidine-4,5'-pyrano[3,2-c]pyrazol]-7'(6'H)-one

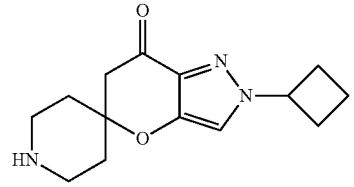

Acetic acid (2.32 mL, 40.4 mmol) was slowly added to a solution of cyclobutylhydrazine.HCl (3.0 g, 24 mmol) in H$_2$O (35 mL). The resulting solution was then added dropwise to a solution of pyruvaldehyde (40%, 3.18 mL, 19.6 mmol) in H$_2$O (300 mL). This solution was stirred overnight at room temperature. The aqueous layer was extracted with CH$_2$Cl$_2$ (4×). The combined organic layers were washed with brine, dried (Na$_2$SO$_4$), and concentrated under reduced pressure. The crude product was then purified via flash chromatography (silica gel) eluting with a gradient of 100% hexanes to a 70:30 mixture of hexanes:ethyl acetate to deliver 1.38 g (40%) of 2-oxopropanal cyclobutylhydrazone as an amber oil.

A 40% aqueous solution of glyoxal (1.13 mL, 9.84 mmol) was added to 2-oxopropanal cyclobutylhydrazone (1.38 g, 9.84 mmol) in H$_2$O (70 mL). The mixture was then heated at reflux. After 1 hour, the mixture was cooled to room temperature and extracted with CH$_2$Cl$_2$ (4×). The combined organic extracts were dried (Na$_2$SO$_4$) and concentrated under reduced pressure to afford 1.53 g (86%) of 1-(4-hydroxy-1-cyclobutyl-1H-pyrazol-3-yl)ethanone as a yellow oil. The crude product was then used in the next step without further purification.

Pyrrolidine (0.604 g, 8.49 mmol) was added to a solution of 1-(4-hydroxy-1-cyclobutyl-1H-pyrazol-3-yl)ethanone (1.53 g, 8.49 mmol) MeOH (15 mL). The dark red solution was stirred for 2 hours at room temperature. 1-(N-Boc)-4-piperidone (1.69 g, 8.49 mmol) was then added to the solution, and the reaction mixture was stirred at room temperature overnight. The mixture was then concentrated under reduced pressure. The crude product was then purified via flash chromatography (silica gel) eluting with a gradient of ethyl acetate:hexanes (30:70 to 50:50) to deliver a yellow oil. The yellow oil was then triturated with hexanes for 1 hour whereupon a white solid was afforded. The solid was filtered, washed with hexanes and air dried overnight. 812 mg (27%) of tert-butyl 2'-cyclobutyl-7'-oxo-6',7'-dihydro-1H,2'H-spiro[piperidine-4,5'-pyrano[3,2-c]pyrazole]-1-carboxylate was afforded as a yellow solid.

To a solution of tert-butyl 2'-cyclobutyl-7'-oxo-6',7'-dihydro-1H,2'H-spiro[piperidine-4,5'-pyrano[3,2-c]pyrazole]-1-carboxylate (812 mg, 2.25 mmol) in 1,4-dioxane (9 mL) at room temperature was added a solution of HCl (4 M in 1,4-dioxane, 5.62 mL, 22.5 mmol). The mixture was stirred at room temperature for 1 hour. The reaction mixture was concentrated to dryness and triturate for ~1 hour in 2-methyltetrahydrofuran and a small amount of EtOH. The solid was collected by vacuum filtration to afford 332 mg (57%) of the title compound as an off-white solid.

Pyrazolospiroketone Preparation 20

2'-Cyclopropyl-2'H-spiro[piperidine-4,5'-pyrano[3,2-c]pyrazol]-7'(6'H)-one

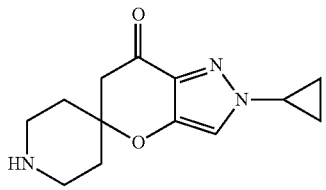

Acetic acid (1.71 mL, 29.9 mmol) was slowly added to a solution of cyclopropylhydrazine.HCl (2.5 g, 18.1 mmol) in $H_2O$ (30 mL), and was then quickly added dropwise to a solution of pyruvaldehyde (40%, 2.36 mL, 14.5 mmol) in $H_2O$ (240 mL). This solution was stirred overnight at room temperature. The aqueous layer was salted and extracted with $CH_2Cl_2$ (4×). The combined organic extracts were dried ($Na_2SO_4$) and concentrated under reduced pressure to give 1.04 g of crude product as a reddish oil. The crude product was purified via flash chromatography (silica gel) eluting with a gradient of ethyl acetate/hexanes (25:75 to 50:50) to afford 637 mg (35%) of 2-oxopropanal cyclopropylhydrazone as a yellow solid.

A 40% aqueous solution of glyoxal (0.44 mL, 3.84 mmol) was added to 2-oxopropanal cyclopropylhydrazone (485 mg, 3.84 mmol) in $H_2O$ (30 mL). The mixture was then heated at reflux. After 1 hour, the mixture was cooled to room temperature and extracted with $CH_2Cl_2$ (4×). The layers were separated, and the organic layer was set aside. Brine was added to the aqueous layer, and it was extracted with $CH_2Cl_2$ (2×). The combined organic extracts were dried ($Na_2SO_4$) and concentrated under reduced pressure. The crude product was then purified via flash chromatography (silica gel) eluting with a gradient of ethyl acetate/heptane (10:90 to 50:50) to deliver 370 mg (58%) of 1-(4-hydroxy-1-cyclopropyl-1H-pyrazol-3-yl)ethanone as a yellow oil.

Pyrrolidine (0.154 g, 2.16 mmol) was added to a solution of 1-(4-hydroxy-1-cyclopropyl-1H-pyrazol-3-yl)ethanone (360 mg, 2.17 mmol) in MeOH (3 mL). The dark red solution was stirred for 2 hours at room temperature. 1-(N-Boc)-4-piperidone (431 mg, 2.16 mmol) was then added to the solution, and the reaction mixture was stirred at room temperature overnight. An additional amount of 1-(N-Boc)-4-piperidone (50 mg) was added. The reaction mixture was stirred for an additional 4 hours. The mixture was then concentrated under reduced pressure and the resulting crude product was purified via flash chromatography (silica gel) eluting with a gradient of ethyl acetate:heptane (10:90 to 50:50) to afford 488 mg (65%) of tert-butyl 2'-cyclopropyl-7'-oxo-6',7'-dihydro-1H, 2'H-spiro[piperidine-4,5'-pyrano[3,2-c]pyrazole]-1-carboxylate.

To a solution of tert-butyl 2'-cyclopropyl-7'-oxo-6',7'-dihydro-1H,2'H-spiro[piperidine-4,5'-pyrano[3,2-c]pyrazole]-1-carboxylate (475 mg, 1.37 mmol) in 1,4-dioxane (5 mL) at room temperature was added a solution of HCl (4 M in 1,4-dioxane, 3.42 mL, 13.7 mmol). The mixture was stirred at room temperature for 1 hour. The reaction mixture was concentrated to dryness and triturated overnight in diethyl ether and a small amount of EtOH. The solid was collected by vacuum filtration, washed with $Et_2O$, and dried under high vacuum to give 360 mg (93%) of the title compound as a green solid.

Pyrazolospiroketone Preparation 21

2'-Isopropyl-3'-methyl-2'H-spiro[piperidine-4,5'-pyrano[3,2-c]pyrazol]-7'(6'H)-one

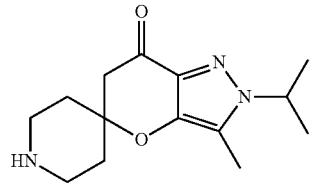

Pyruvaldehyde (40%, 7.3 g, 41 mmol) was added to a solution of ethylhydrazine oxalate (1 g, 10 mmol) and sodium bicarbonate (2.27 g, 27.0 mmol) in water (10 mL), and the resulting mixture was heated at reflux for two days. The reaction was cooled to room temperature and extracted with ethyl acetate (3×). The combined organic layers were washed with brine, dried ($Na_2SO_4$), filtered, and concentrated under reduced pressure. The crude product was purified via flash chromatography (silica gel) eluting with hexanes:ethyl acetate (80:20) to give 800 mg (30%) of 1-(1-i-propyl-4-hydroxy-5-methyl-1H-pyrazol-3-yl)ethanone as a light brown oil.

Pyrrolidine (312 mg, 4.40 mmol) was added to a solution of 1-(1-i-propyl-4-hydroxy-5-methyl-1H-pyrazol-3-yl)ethanone (800 mg, 4 mmol) in MeOH (10 mL). The dark red solution was stirred for 2 hours at room temperature. 1-(N-Boc)-4-piperidone (875 mg, 4.40 mmol) was then added to the solution, and the reaction mixture was stirred at room temperature overnight. The mixture was then concentrated under reduced pressure. The crude product was then purified via flash chromatography (silica gel) eluting with a gradient of ethyl acetate:hexanes (30:70 to 50:50) to deliver 542 mg (30%) of the tert-butyl 2'-isopropyl-3'-methyl-7'-oxo-6',7'-dihydro-1H,2'H-spiro[piperidine-4,5'-pyrano[3,2-c]pyrazole]-1-carboxylate as a yellow oil.

To a solution of tert-butyl 2'-isopropyl-3'-methyl-7'-oxo-6',7'-dihydro-1H,2'H-spiro[piperidine-4,5'-pyrano[3,2-c]pyrazole]-1-carboxylate (542 mg, 1.49 mmol) in 1,4-dioxane (5 mL) at room temperature was added a solution of HCl (4 M in 1,4-dioxane, 3.73 mL, 14.9 mmol). The mixture was stirred at room temperature for 1 hour. The reaction mixture was concentrated to dryness and triturate in 2-methyltetrahydrofuran and a small amount of EtOH. The solid was collected by vacuum filtration to afford 303 mg (77%) of the title compound as a tan solid.

Carboxylic Acid Starting Materials

The following commercially available carboxylic acids were used to prepare exemplified compounds of the present invention: 4-methoxy-7-methyl-1H-indole-2-carboxylic acid (Ambinter, Paris, France), 2-oxo-1,2,3,4-tetrahydroquinoline-6-carboxylic (Ryan Scientific, Mt. Pleasant, S.C.), 1H-indazole-5-carboxylic acid (Tyger Scientific, Inc., Ewing, N.J.), 4-ethoxy-1H-indole-2-carboxylic acid (Ryan Scientific, Mt. Pleasant, S.C.), 4-chloro-1H-indole-2-carboxylic acid (Ryan Scientific, Mt. Pleasant, S.C.), 4,6-dimethoxy-1H-indole-2-carboxylic acid (Tyger Scientific, Ewing, N.J.), 7-methoxy-1H-indole-2-carboxylic acid (Matrix Scientific, Columbia, S.C.), 4,6-dichloro-1H-indole-2-carboxylic acid (Oakwood Products, Inc, West Columbia, S.C.), 7-chloro-1H-indole-2-carboxylic acid (Aurora Fine Chemicals, Austria), 7-chloro-4-methoxy-1H-indole-2-carboxylic acid (Ambinter, Paris, France), 6,7-dimethoxy-1H-indole-2-carboxylic acid (MicroChemistry Ltd, Russia), 6-chloro-1H-indole-2-carboxylic acid (Matrix Scientific, Columbia, S.C.), 5-propoxy-1H-indole-2-carboxylic acid (Princeton BioMolecular Research, Inc., Monmouth Junction, N.J.), 6-chloro-4-fluoro-1H-indole-2-carboxylic acid (Ambinter, France), 6-ethyl-1H-indole-2-carboxylic acid (Ryan Scientific, Inc., Mt. Pleasant, S.C.), 6-fluoro-1H-indole-2-carboxylic acid (Ryan Scientific, Inc., Mt. Pleasant, S.C.), 3-ethyl-1H-indole-2-carboxylic acid (ChemBridge Corp., San Diego, Calif.), 5-methoxy-1H-indole-2-carboxylic acid (ASDI Inc., Newark, Del.), 3-fluoro-1H-indole-2-carboxylic acid (Ryan Scientific, Inc., Mt. Pleasant, S.C.), 7-(trifluoromethyl)-1H-indole-2-carboxylic acid (Matrix Scientific, Columbia, S.C.), 5-fluoro-1H-indole-2-carboxylic acid (Ryan Scientific, Inc., Mt. Pleasant, S.C.), 5-chloro-1H-indole-2-carboxylic acid (Alfa Aesar, Ward Hill, Mass.), 4,6-difluoro-1H-indole-2-carboxylic acid (Ryan Scientific, Inc., Mt. Pleasant, S.C.), indole-2-carboxylic acid (ASDI Inc., Newark, Del.), 6-methoxy-1-methyl-1H-indole-2-carboxylic acid (Matrix Scientific, Columbia, S.C.), 1-methyl-1H-indole-2-carboxylic acid (ASDI Inc., Newark, Del.), 6-methyl-1H-indole-2-carboxylic acid (Ryan Scientific, Inc., Mt. Pleasant, S.C.), 6-isopropyl-1H-indole-2-carboxylic acid (Ryan Scientific, Inc., Mt. Pleasant, S.C.), 5-ethyl-1H-indole-2-carboxylic acid (Wako Chemicals USA, Inc., Richmond, Va.), 3-(1H-pyrazol-3-yl)benzoic acid (Maybridge. Cornwall, UK), 7-methyl-1H-benzimidazole-2-carboxylic acid (Advanced Quality Scitech USA, Inc., Conshohocken, Pa.), 2-Naphthoic acid (Alfa Aesar, Ward Hill, Mass.), 5-methoxy-4,7-dimethyl-1H-indole-2-carboxylic acid (ASDI Inc., Newark, Del.), 3,6-dimethyl-1H-indole-2-carboxylic acid (ASDI Inc., Newark, Del.), 7-methyl-1H-benzimidazole-2-carboxylic acid (Advanced Quality Scitech USA, Inc., Conshohocken, Pa.), 1H-benzimidazole-6-carboxylic acid (Affinitis Pharma LLC, New Haven, Conn.), 3-(1H-pyrazol-3-yl)benzoic acid (3B Scientific Corp, Libertyville, Ill.), 2-napthoic acid (Sigma-Sigma-Aldrich, Milwaukee, Wis.), benzimidazole-5-carboxylic acid (Sigma-Aldrich, Milwaukee, Wis.), 1,3-benzoxazole-5-carboxylic acid (Bosche Scientific, LLC, New Brunswick, N.J.), 7-methyl-1H-benzimidazole-5-carboxylic acid (Chemstep, Carbon Blanc, France), 4-methyl-1H-benzimidazole-2-carboxylic acid (Chemstep, Carbon Blanc, France), 5,6-dimethoxy-1H-indole-2-carboxylic acid (3B Scientific Corporation, Libertyville, Ill.) 6-methoxy-1H-indole-2-carboxylic acid (3B Scientific Corporation, Libertyville, Ill.), 7-fluoro-1H-indole-2-carboxylic acid (Matrix Scientific, Columbia, S.C.), 4-(trifluoromethyl)-1H-indole-2-carboxylic acid (Bosche Scientific, LLC, New Brunswick, N.J.), 1-oxo-2,3,4,9-tetrahydro-1H-beta-carboline-6-carboxylic acid (J & W PharmaLab, LLC, Levittown, Pa.), 3-amino-1,2-benzisothiazole-5-carboxylic acid (Chemstep, Carbon Blanc, France), benzo[d]thiazole-6-carboxylic acid (ASDI Inc., Newark, Del.), 6-methoxy-2-naphthoic acid (Sigma-Aldrich, Milwaukee, Wis.), benzofuran-5-carboxylic acid (Apollo, Cheshire, UK), quinoline-5-carboxylic acid (Synthonix, Wake Forest, N.C.), 2-naphthoic acid (Sigma-Aldrich, Milwaukee, Wis.), 2-methylbenzo[d]thiazole-5-carboxylic acid (ASDI Inc., Newark, Del.), 7-methoxy-2-naphthoic acid (3M, St. Paul, Minn.), 2-oxo-2,3-dihydrobenzo[d]oxazole-6-carboxylic acid (ASDI Inc., Newark, Del.), 2-hydroxy-1-methyl-1H-benzo[d]imidazole-5-carboxylic acid (ASDI Inc., Newark, Del.), 1-methyl-1H-indole-6-carboxylic acid (Ryan Scientific, Inc., Mt. Pleasant, S.C.), quinoline-6-carboxylic acid (TCI America, Portland, Oreg.), 7-Quinolinecarboxylic acid (Princeton BioMolecular Research, Inc., Monmouth Junction, N.J.) and 6-chloro-3-methyl-1H-indole-2-carboxylic acid (ASDI Inc., Newark, Del.).

The following carboxylic acids (which were used to prepare compounds described in the Examples below) were prepared by previously published means: 6-fluoro-5-methoxy-1H-indole-2-carboxylic acid (U.S. Pat. No. 5,489,593, example 92); 3,7-dimethyl-1H-indole-5-carboxylic acid (Knepper, K.; Braese, S. Org. Lett. 2003, 5, 2829-2832); 3-methyl-1H-indazole-6-carboxylic acid (U.S. Pat. No. 6,303,600, example 45); 5-methoxy-4-methyl-1H-indole-2-carboxylic acid (U.S. Pat. No. 4,060,626); 6-methoxy-3-methyl-1H-indole-2-carboxylic acid (Gan, T.; et al., J. Org. Chem. 1997, 62, 9298-9304); 2-vinyl-1H-indole-2-carboxylic acid (US Patent Publication No. 2005/0026987, compound 151); 8-methyl-2-oxo-1,2-dihydroquinoline-6-carboxylic acid (analogous to J. Med. Chem., 2003, 46(14), 3033-3044); 2-oxo-1,2,3,4-tetrahydroquinoline-7-carboxylic acid (Chem. Pharm. Bull. 1986, 34(2), 682-93); 3-aminobenzo[d]isothiazole-5-carboxylic acid (J. Med. Chem. 2008, 51(5), 1231-1241); 2-methylquinoline-6-carboxylic acid (J. Med. Chem. 2002, 45(21), 4647-4654); 3-oxo-3,4-dihydro-2H-benzo[b][1,4]oxazine-7-carboxylic acid (J. Med. Chem. 2005, 48(9), 3110-3113); 5-methoxy-2-naphthoic acid (prepared by hydrolysis of ester found in Org. Lett. 2008, 10(15), 3359-3362); 3-oxo-3,4-dihydro-2H-benzo[b][1,4]oxazine-6-carboxylic acid (J. Med. Chem. 2005, 48(9), 3110-3113); and 5-fluoro-6-methoxy-1H-indole-2-carboxylic acid (PCT Publication No. WO 9109849). 3-amino-1H-indazole-5-carboxylic acid may be prepared by carbonylation of 5-bromo-1H-indazol-3-amine (Apollo, Cheshire, UK). 1-oxo-1,2-dihydroisoquinoline-6-carboxylic acid may be prepared by carbonylation of 6-bromoisoquinolin-1(2H)-one (PharmLab, Levittown, Pa.). 1-oxo-1,2-dihydroisoquinoline-7-carboxylic acid may be prepared by carbonylation of 6-bromoisoquinolin-1(2H)-one (Alfa Aesar, Ward Hill, Mass.).

The following carboxylic acid starting materials (which were used to prepare compounds described in the Examples below) were prepared as described below.

Acid Preparation 1

3-Methyl-7-methoxy-1H-indazole-5-carboxylic acid

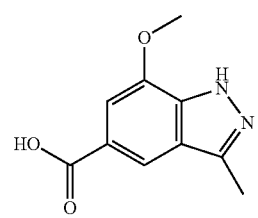

To a solution of semicarbazide.HCl (20 g, 175 mmol), acetone (11.1 g, 192 mmol) in water (400 mL), sodium acetate (21.5 g, 262 mmol) was added at room temperature and maintained for 18 hours. The reaction mixture was filtered, the obtained solid was washed with ether (2×25 mL)

and dried at 70° C. for 20 hours to afford acetone semicarbazole (15 g, 75%) as white solid. ¹H NMR (CDCl₃) δ 7.95 (br, 1H), 5.9-5.1 (br, 2H), 1.95 (s, 3H), 1.85 (s, 3H).

To cool DMF (65 mL) at 0° C., POCl₃ (39 mL) was added drop wise for 30 minutes, and maintained at 0° C. for 1 hour. To the mixture was added acetone semicarbazole (13 g, 114 mmol) portionwise at 0° C. and maintained at 70° C. for 4 hours. The mixture was poured over crushed ice (500 g), neutralized using 10% NaOH solution and extracted using ethyl acetate (3×150 mL). The combined organic layers were washed with water (2×100 mL), saturated aqueous NaCl (100 mL), dried over anhydrous Na₂SO₄ and concentrated to obtain a crude product, which was purified by column chromatography (60-120 mesh silica gel) using 2-4% methanol in chloroform as eluents to afford 3-methyl-1H-pyrazole-4-carbaldehyde (4 g, 32%) as solid. ¹H NMR (CDCl₃) δ 9.96 (s, 1H), 8.0 (s, 1H), 2.6 (s, 3H).

To a solution of 3-methyl-1H-pyrazole-4-carbaldehyde (9 g, 82 mmol) and diethyl succinate (57 g, 327 mmol) in t-butanol (50 mL), a solution of t-BuOK (37.3 g, 245 mmol) in t-butanol (40 mL) was added and the mixture was heated to 80° C. for 4 hours. The mixture was concentrated; the obtained residue was dissolved in water (50 mL), acidified (pH~2) using 6 N HCl and extracted with ethyl acetate (2×50 mL). The combined organic layers were washed with aqueous NaHCO₃ (2×50 mL). The combined aqueous layers were acidified (pH~2) and extracted with ethyl acetate (2×100 mL). The combined ethyl acetate layers were washed with saturated aqueous NaCl (25 mL), dried over anhydrous Na₂SO₄ and concentrated to afford 3-(ethoxycarbonyl)-4-(3-methyl-1H-pyrazol-4-yl)but-3-enoic acid (20 g, 100%) as gum. ¹H NMR (CDCl₃) δ 7.85 (s, 1H), 7.65 (s, 1H), 4.3 (t, 2H), 3.65 (s, 2H), 4.4 (s, 3H), 1.3 (t, 3H).

A solution of 3-(ethoxycarbonyl)-4-(3-methyl-1H-pyrazol-4-yl)but-3-enoic acid (20 g, 84 mmol) in acetic anhydride (80 mL), sodium acetate (13.8 g, 168 mmol) was added at room temperature and the mixture was heated at reflux for 4 hours. The reaction mixture was cooled to room temperature, basified (pH~9) using aqueous NaHCO₃ solution and extracted with ethyl acetate (2×100 mL). The combined organic layers were washed with water (50 mL), saturated aqueous NaCl (50 mL), dried over anhydrous Na₂SO₄ and concentrated to obtain crude product; which was purified by column chromatography (100-200 mesh silica gel) using 6-8% ethyl acetate in pet-ether as eluents to afford ethyl 3-methyl-7-hydroxy-1H-indazole-5-carboxylate (10 g, 40%) as orange solid. ¹H NMR (CDCl₃) δ 8.25 (s, 1H), 7.9 (s, 1H), 4.4 (q, 2H), 2.75 (s, 3H), 2.6 (s, 3H), 2.4 (s, 3H), 1.4 (t, 3H).

To a 0° C. solution of ethyl 3-methyl-7-hydroxy-1H-indazole-5-carboxylate (0.84 g, 3.8 mmol) in DMF (25 mL) was added 60% oil dispersion of NaH (152 mg, 3.81 mmol). After stirring for 1 hour at 0° C., a solution of iodoethane (595 mg, 0.31 mL, 3.81 mmol) in DMF (3 mL) was added. The mixture was kept at 0° C. for several hours before allowing the mixture to warm to room temperature while stirring overnight. Dilute with EtOAc, wash with saturated aqueous NaHCO₃, water, saturated aqueous NaCl and the organic extract was dried over Na₂SO₄, filtered and concentrated. The crude material was purified by CombiFlash (80 g column, 0-30% EtOAc/hexanes gradient) to provide ethyl 7-methoxy-3-methyl-1H-indazole-5-carboxylate (516 mg, 55%).

To a solution of ethyl 7-methoxy-3-methyl-1H-indazole-5-carboxylate (516 mg, 2.08 mmol) in THF (17 mL) was added 1 M LiOH (4.2 mL, 4.2 mmol) and the mixture was heated at reflux overnight. Analysis indicated the presence of small amounts of unreacted starting material; therefore, a small amount of ethanol was added to assist in solubilizing materials. Heating was continued for an additional 2 hours before concentrating to dryness. The residue was triturated with 1 N HCl, the solids were isolated by filtration, washed with water and air dried overnight to provide the title compound as an off-white solid (417 mg, 91%).

Acid Preparation 2

3-Ethyl-7-methoxy-1H-indazole-5-carboxylic acid

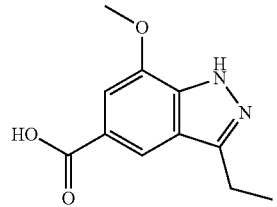

To a solution of semicarbazide HCl (61.2 g, 534 mmol), ethyl-methyl ketone (35 g, 0.49 mol) in water (525 mL), sodium acetate (79.7 g, 972 mmol) was added at room temperature and maintained for 18 hours. The reaction mixture was filtered, the obtained solid was washed with ether (2×25 mL) and dried at 70° C. for 20 hours to afford butan-2-one semicarbazone (45 g, 72%) as white solid. ¹H NMR (CDCl₃) δ 7.9 (br, 1H), 5.0-6.0 (br, 2H), 2.3 (q, 2H), 1.82 (s, 3H), 1.1 (t, 3H).

To cool DMF (50 mL) at 0° C., POCl₃ (30 mL) was added dropwise over 30 minutes, and maintained at 0° C. for 1 hour. To the mixture was added butan-2-one semicarbazone (10 g, 78 mmol) in portions at 70° C. and maintained at 70° C. for 4 hours. The mixture was poured into crushed ice (700 g), neutralized using 10% NaOH solution and extracted using ethyl acetate (3×100 mL). The combined organic layers were washed with water (2×80 mL), saturated aqueous NaCl (100 mL), dried over anhydrous Na₂SO₄ and concentrated to obtain a crude product, which was purified by column chromatography (60-120 mesh silica gel) using 3-5% methanol in chloroform as eluents to afford 3-ethyl-1H-pyrazole-4-carbaldehyde (1.5 g, 16%) as solid. ¹H NMR (CDCl₃) δ 9.95 (s, 1H), 8.0 (s, 1H), 3.0 (q, 2H), 1.35 (t, 3H).

To a solution of 3-ethyl-1H-pyrazole-4-carbaldehyde (2.2 g, 18 mmol) and diethyl succinate (12.3 g, 71.0 mmol) in t-butanol (15 mL) was added a solution of t-BuOK (8.08 g, 53.2 mmol) in t-butanol (10 mL). The mixture was heated to 80° C. for 3 hours before the mixture was concentrated. The obtained residue was dissolved in water (30 mL), acidified (pH~2) using 6 N HCl and extracted with ethyl acetate (2×30 mL). The combined organic layers were washed with aqueous NaHCO₃ (2×50 mL). The combined aqueous layers were acidified (pH~2) and extracted with ethyl acetate (2×75 mL). The combined ethyl acetate layers were washed with saturated aqueous NaCl (25 mL), dried over anhydrous Na₂SO₄ and concentrated to afford ethyl 2-[(3-ethyl-1H-pyrazol-4-yl)methylene]-4-oxopentanoate (4 g, 100%) as gum, which was taken as such into next step.

A solution of crude ethyl 2-[(3-ethyl-1H-pyrazol-4-yl)methylene]-4-oxopentanoate (4 g, 15.8 mmol) in acetic anhydride (10 mL), sodium acetate (2.6 g, 32 mmol) was added at room temperature and the mixture was heated at reflux for 4 h. The reaction mixture was cooled to room temperature, basified (pH ~9) using aqueous NaHCO₃ solution and extracted with ethyl acetate (2×50 mL). The combined organic layers were washed with water (25 mL), saturated aqueous NaCl (25 mL), dried over anhydrous Na$_2$SO$_4$ and concentrated to obtain the crude product; which was purified by column chromatography (60-120 mesh silica gel) using 2-3% ethyl acetate in pet-ether as eluents to afford ethyl 1-acetyl-7-(acetyloxy)-3-ethyl-1H-indazole-5-carboxylate (1.7 g, 34%) as brown solid. $^1$H NMR (CDCl$_3$) δ 8.44 (s, 1H), 8.24 (s, 1H), 4.58 (q, 2H), 3.2 (s, 3H), 2.9 (s, 3H), 2.58 (s, 3H), 1.6 (t, 3H).

To a solution of 1-acetyl-7-(acetyloxy)-3-ethyl-1H-indazole-5-carboxylate (4.0 g, 13 mmol) in ethanol (450 mL) was slowly added 60% NaH (0.50 g, 12.6 mmol). The mixture was stirred for 1 hour before concentration and removal of the majority of the ethanol. The residue was taken up in EtOAc and washed with saturated aqueous NaHCO$_3$. The aqueous phase was back extracted with EtOAc (2×). The combined organic extracts were washed with saturated aqueous NaCl, dried over Na$_2$SO$_4$, filtered and concentrated. The solid was triturated with CH$_2$Cl$_2$ to provide ethyl 3-ethyl-7-hydroxy-1H-indazole-5-carboxylate as an off-white solid (2.9 g, 87%).

A solution of ethyl 3-ethyl-7-hydroxy-1H-indazole-5-carboxylate (2.47 g, 10.5 mmo) in DMF (40 mL) was cooled to 0° C. To this mixture was added 60% NaH (0.42 g, 10.5 mmol) and stirred for 1 hour. To this was added a 0° C. solution of iodomethane (1.50 g, 0.66 mL, 10.5 mmol) in DMF (10 mL). The mixture was kept at 0° C. for several hours before stirring at room temperature overnight. The mixture was diluted with EtOAc, washed with a mixture of saturated aqueous NaHCO$_3$ and saturated aqueous NaCl followed by saturated aqueous NaCl. The organic extract was dried over Na$_2$SO$_4$, filtered and concentrated. Purify by CombiFlash (80 g column, 0-30% EtOAc/hexanes gradient) to provide ethyl 3-ethyl-7-methoxy-1H-indazole-5-carboxylate (2.62 g, 40%).

To a solution of 3-ethyl-7-methoxy-1H-indazole-5-carboxylate (1.05 g, 4.23 mmol) in THF (35 mL) was added 1 M LiOH (8.46 mL, 8.46 mmol) and the mixture was heated at reflux overnight. The mixture was concentrated and the residue was triturated with 1 N HCl. The precipitates were washed with water and air dried. The solids were then taken up in hot methanol, filtered, concentrated and dried overnight under high vacuum to provide the title compound as an off-white solid (849 mg, 91%).

Acid Preparation 3

7-Methoxy-1H-indazole-5-carboxylic acid

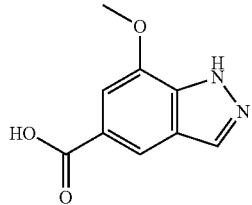

3-Bromopyrazole (50 g, 0.34 mol) was dissolved in THF (310 mL), tetrahydropyran (310 ml, 3.4 mol) and DDQ (7.7 g, 0.034 mol) were added. The reaction mixture was heated at reflux for 1 hour and evaporated. The residue was purified by chromatography (EtOAc/hexane, 1:6) to provide 4-bromo-1-(tetrahydro-2H-pyran-2-yl)-1H-pyrazole (61 g, 78%).

4-Bromo-1-(tetrahydro-2H-pyran-2-yl)-1H-pyrazole (61 g, 0.264 mol) was dissolved in THF (400 mL). Then 1.6 M n-BuLi (181 mL) was added to the solution which was at −95° C. The reaction mixture was stirred over a period of 45 minutes at the same temperature. Then DMF (22.4 mL, 0.29 mol) was added (the same temperature was maintained). The mixture was allowed to heat up to room temperature before addition of water (100 mL). The organic layer was separated, and the aqueous phase was extracted with ether (3×50 mL). The combined organic extracts were dried over Na$_2$SO$_4$, filtered and evaporated. The residue was purified by chromatography (EtOAc/hexane, 1:4) to afford 1-(tetrahydro-2H-pyran-2-yl)-1H-pyrazole-4-carbaldehyde (29 g, 57%).

A solution of t-BuOK (49 g, 0.51 mol) in t-BuOH (300 mL) was added to a mixture of 1-(tetrahydro-2H-pyran-2-yl)-1H-pyrazole-4-carbaldehyde (29 g, 0.16 mol) and diethyl succinate (121 mL, 0.72 mol). The obtained solution was heated at reflux over a period of 5 hours and poured into water (300 mL). The resulting mixture was washed with EtOAc. The aqueous layer was acidified to pH 2 and extracted with EtOAc (3×50 mL). The solvent was evaporated. The obtained oil of (3E)-3-(ethoxycarbonyl)-4-[1-(tetrahydro-2H-pyran-2-yl)-1H-pyrazol-4-yl]but-3-enoic acid (45 g) was used in the next step without additional purification.

Crude (3E)-3-(ethoxycarbonyl)-4-[1-(tetrahydro-2H-pyran-2-yl)-1H-pyrazol-4-yl]but-3-enoic acid (45 g) was mixed with acetic anhydride (500 mL) and NaOAc (12 g, 0.146 mol). The reaction mixture was heated at reflux over a period of 5 hours and evaporated. The residue was alkalized to pH 8-9 with aqueous Na$_2$CO$_3$. The product was extracted with EtOAc (5×50 mL). The combined extracts were dried and evaporated. The residue was purified by chromatography (EtOAc/hexane, 1:4) to provide ethyl 7-(acetyloxy)-1-(tetrahydro-2H-pyran-2-yl)-1H-indazole-5-carboxylate (13 g, 25%).

Ethyl 7-(acetyloxy)-1-(tetrahydro-2H-pyran-2-yl)-1H-indazole-5-carboxylate (6 g, 0.018 mol) was dissolved in EtOH (100 mL) and K$_2$CO$_3$ (7 g, 0.05 mol) was added. The reaction mixture was heated at reflux over a period of 6 hours and evaporated. The residue was treated with water (150 mL), and the product was extracted with EtOAc (3×50 mL). The combined extracts were evaporated and the residue was purified by chromatography (EtOAc/hexane, 1:4) to afford ethyl 7-hydroxy-1-(tetrahydro-2H-pyran-2-yl)-1H-indazole-5-carboxylate (4 g, 85%).

To a solution of ethyl 7-hydroxy-1-(tetrahydro-2H-pyran-2-yl)-1H-indazole-5-carboxylate (1.45 g, 5.0 mmol) in acetone (20 mL) containing K$_2$CO$_3$ (760 mg, 5.50 mmol) was added iodomethane (781 mg, 0.34 mL, 5.5 mmo). The mixture was heated at reflux under N$_2$ overnight. The mixture was cooled to room temperature, filtered, evaporated and partitioned between EtOAc and water. The aqueous phase was extracted with additional EtOAc. The combined organic extracts were washed with saturated aqueous NaCl, dried over Na$_2$SO$_4$, filtered and concentrated to provide crude product. The crude material was purified by chromatography (Isco, 0-40% EtOAc/heptane) to provide material which was dried under high vacuum overnight to afford ethyl 7-methoxy-1-(tetrahydro-2H-pyran-2-yl)-1H-indazole-5-carboxylate (1.40 g, 92%).

A mixture of ethyl 7-methoxy-1-(tetrahydro-2H-pyran-2-yl)-1H-indazole-5-carboxylate (980 mg, 4.45 mmol) in THF (10 mL), water (10 mL) and LiOH (560 mg, 13.4 mmol) was heated at 40° C. for 3 hours and then stirred at room temperature overnight. The reaction was not complete so the mixture was heated to 45° C. and heated overnight. The mixture was then concentrated to dryness, acidified to pH 6 with conc. HCl and partitioned between EtOAc and water. The resultant solids were collected by vacuum filtration, rinsed with EtOAc and dried under high vacuum to afford a white solid. The organic layer was washed with saturated aqueous NaCl, dried over MgSO$_4$, filtered and concentrated to provide an off-white solid. Both batches of white solid were combined to afford the title compound (642 mg, 75%).

Acid Preparation 4

7-Fluoro-4-methoxy-1H-indole-2-carboxylic acid

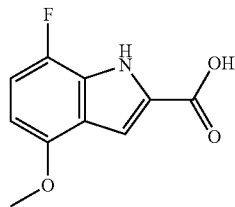

To a solution of the 2-methoxy-5-fluorobenzaldehyde (1.00 g, 6.49 mmol) and ethyl azidoacetate (14.0 g, 32.4 mmol) in EtOH (20 ml) at −20° C. (acetonitrile/dry ice) was added a solution of sodium acetate in EtOH over 20 minutes. When the addition was completed, the reaction was allowed to slowly warm to 0° C., where it was maintained for 2 hours. The suspension was then poured over a mixture of ice and solid NH$_4$Cl, stirred until all the ice had melted, and the product was collected. The crude product was dissolved in CH$_2$Cl$_2$ and MgSO$_4$ was added. The suspension was filtered through a small plug of silica gel and washed with CH$_2$Cl$_2$. Concentration provided ethyl 2-azido-3-(5-fluoro-2-methoxyphenyl)acrylate as a yellow solid which was used without further purification (1.68 g, 98%).

To xylenes (150 mL) heated at reflux was added a solution of ethyl 2-azido-3-(5-fluoro-2-methoxyphenyl)acrylate (1.50 g, 5.66 mmol) in xylenes (50 mL). The mixture was heated at reflux for 4 hours, cooled to room temperature and concentrated to ~1/5 original volume. The solution was cooled to −20° C. for 2 hours and the solids were collected by vacuum filtration. The solids were washed with cold xylenes and dried under vacuum to afford ethyl 7-fluoro-4-methoxy-1H-indole-2-carboxylate. Concentration of the mother liquor provided additional product. The solids were combined to afford the final product (0.75 g, 56%).

To a solution of ethyl 7-fluoro-4-methoxy-1H-indole-2-carboxylate (1.00 g, 4.22 mmol) in ethanol was added KOH (473 mg, 8.43 mmol). The reaction was stirred at room temperature for 12 hours, cooled to 0° C. and acidified with 1 N HCl. The mixture was extracted with EtOAc and CH$_2$Cl$_2$. The combined organic extracts were dried over Na$_2$SO$_4$, filtered and concentrated to afford the title compound (550 mg, 62%).

Acid Preparation 5

3-Methyl-1H-indazole-5-carboxylic acid

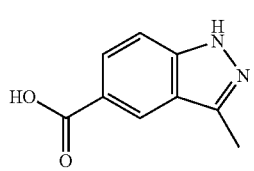

To a cooled solution of 3-bromobenzaldehyde (42.5 g, 209 mmol) in THF (300 mL) at 0° C. was added MeMgCl (17.2 g, 230 mmol) and the mixture was stirred for 2 hours. The reaction mixture was quenched with saturated NH$_4$Cl solution (100 mL) and extracted with diethyl ether (2×250 mL). The combined organic layers were washed with water (2×100 mL), saturated aqueous NaCl (100 mL), dried over anhydrous Na$_2$SO$_4$ and concentrated to give 1-(5-bromo-2-fluoro-phenyl)-ethanol (17 g, 37%) as an oil. $^1$H NMR (CDCl$_3$): δ 7.6-7.7 (d, 1H), 7.3-7.4 (m, 1H), 6.8-6.9 (t, 1H), 5.1-5.2 (m, 1H), 1.8-1.9 (br, 1H), 1.46-1.55 (d, 3H).

To a solution of 1-(5-bromo-2-fluoro-phenyl)-ethanol (37 g, 168 mmol) in CH$_2$Cl$_2$ (400 mL) and pyridinium dichromate (127 g, 337 mmol) were added molecular sieves (10 g). The mixture was stirred at room temperature for 20 hours. The mixture was filtered through diatomaceous earth, washed with CH$_2$Cl$_2$ (3×100 mL) and concentrated. The crude product was purified by column chromatography (60-120 mesh silica gel) using 10% ethyl acetate in pet-ether to afford of 1-(5-bromo-2-fluoro-phenyl)-ethanone (23 g, 63%) as pale brown oil. $^1$H NMR (CDCl$_3$): δ 7.9-8.1 (d, 1H), 7.5-7.7 (m, 1H), 6.95-7.1 (t, 1H), 2.6-2.7 (d, 3H).

A solution of 1-(5-bromo-2-fluoro-phenyl)-ethanone (10 g, 46 mmol) in hydrazine hydrate (80 mL) was heated at reflux (130° C.) for 20 hours. The reaction mixture was cooled to room temperature, excess hydrazine hydrate was removed and the crude residue was purified by column chromatography (60-120 mesh silica gel) using 10% ethyl acetate in pet-ether as eluents to obtain 5-bromo-3-methyl-1H-indazole (7.09 g, 73%) as a solid. $^1$H NMR (CDCl$_3$): δ 10.2-10.6 (br, 1H), 7.8-7.9 (s, 1H), 7.4-7.5 (d, 1H), 7.2-7.4 (d, 1H), 2.5-2.7 (s, 3H).

To a solution of 5-bromo-3-methyl-1H-indazole (10 g, 47.6 mmol) in MeOH (160 mL), PdCl$_2$.dppf (5.57 g, 7.62 mmol), NaOAc (11.7 g, 142.85 mmol) and DMF (5 mL) were added and degassed (using N$_2$ gas 3-times). The mixture was sealed, charged with CO gas (60 psi) and heated at 80° C. for 20 hours. The reaction mixture was concentrated to obtain a residue, which was diluted with water (100 mL), acidified with 10% aqueous citric acid and extracted using ethyl acetate (3×200 mL). The combined organic layers were dried over anhydrous Na$_2$SO$_4$, filtered and concentrated to afford 1H-indazole-5-carboxylic acid methyl ester (7.23 g, 80%) as a solid. $^1$H NMR (CDCl$_3$): δ 9.6-10.2 (br, 1H), 8.4-8.6 (s, 1H), 8.0-8.2 (d, 1H), 7.4-7.5 (d, 1H), 3.9-4.05 (s, 3H), 2.55-2.7 (s, 3H).

A solution of 1H-indazole-5-carboxylic acid methyl ester (8 g, 42.1 mmol), LiOH (5.05 g, 211 mmol), in methanol (100 mL) and water (35 mL) was stirred at room temperature for 20 hours. At the end of this time the reaction mixture was concentrated, the aqueous residue was acidified (pH~6) using 10% aqueous citric acid (150 mL) and filtered the solid to obtain the crude product, which was washed with water (3×30 ml) and dried well to give the title compound (7 g, 95%) as a pale brown solid. $^1$H NMR (CDCl$_3$): δ 8.5 (s, 1H), 8.0-8.1 (d, 1H), 7.45-7.55 (d, 1H), 2.5-2.66 (s, 3H),

Acid Preparation 6

3-Propyl-1H-indazole-5-carboxylic acid

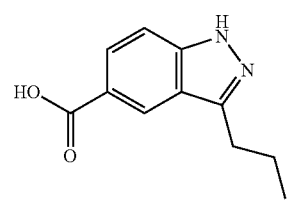

To a suspension of Mg (0.236 g, 9.83 mmol) in diethyl ether (10 mL), I₂ (1 spatula) was added n-propyl bromide (0.72 g, 0.53 mL, 5.9 mmol) at room temperature. When iodine color disappeared, the remaining n-propyl bromide in ether was added to the reaction mixture and stirred at room temperature for 10 minutes. To this Grignard reagent, 5-bromo-2-fluorobenzaldehyde (1.00 g, 4.92 mmol) in ether was added under cold conditions and stirred at room temperature for 1 hour. The reaction mixture was quenched with NH₄Cl solution and extracted with ether. The ether layer was dried over anhydrous Na₂SO₄, filtered and concentrated to afford 1-(5-bromo-2-fluoro-phenyl)-butan-1-ol (1.14 g, 92.6%). ¹H NMR (CDCl₃): δ 7.6 (m, 1H), 7.3-7.4 (m, 1H), 6.9 (t, 1H), 5.0 (brs, 1H), 2.0 (brs, 1H), 1.6-1.7 (m, 2H), 1.3-1.5 (m, 2H), 1.0 (t, 3H).

To a solution of 1-(5-bromo-2-fluoro-phenyl)-butan-1-ol (6.2 g, 25 mmol) in dry CH₂Cl₂ (60 mL) were added pyridinium dichromate (19.0 g, 50.3 mmol) and molecular sieves powder (1.24 g) at room temperature and stirred overnight. The reaction mixture was filtered through diatomaceous earth and washed with diethyl ether (200 mL). The combined CH₂Cl₂ and ether layers were dried over anhydrous Na₂SO₄, filtered and concentrated to give a crude product, which was purified by column chromatography using 5% ethyl acetate/pet-ether as eluents to afford 1-(5-bromo-2-fluorophenyl)butan-1-one (4.6 g, 75%) as a syrup. ¹H NMR (CDCl₃): δ 8.0 (m, 1H), 7.5-7.6 (m, 1H), 7.0 (t, 1H), 2.9-3.0 (m, 2H), 1.7 (q, 2H), 1.0 (t, 3H).

To 1-(5-bromo-2-fluorophenyl)butan-1-one (2.0 g, 8.1 mmol) in THF, anhydrous hydrazine (11 mL) in THF was added and heated at reflux (60-70° C.) for 5-6 hours. Xylene was added to the reaction mixture and heated at reflux for 20-24 hours. The reaction mixture was concentrated to give a crude product, which was purified by column chromatography using 15% ethyl acetate/pet-ether as eluents to afford 5-bromo-3-propyl-1H-indazole (1.02 g, 52.3%) as a solid. ¹H NMR (CDCl₃): δ 7.9 (s, 1H), 7.4 (d, 1H), 7.3 (d, 1H), 2.9 (t, 2H), 1.8 (q, 2H), 1.0 (t, 3H).

To 5-bromo-3-propyl-1H-indazole (1.00 g, 4.18 mmol) in diethyl ether (60 mL), 1.3 M t-BuLi (10.9 mL, 14.2 mmol) in pentane was added slowly at −78° C. under N₂ atm. After 1 hour, CO₂ gas was passed through the reaction mixture at −78° C. for 1 hour and allowed to slowly warm to room temperature. The reaction mixture was quenched with saturated NH₄Cl solution and the ether layer was separated. The aqueous layer was acidified with 2 N HCl and extracted with ethyl acetate to afford the title compound (350 mg, 40.8%) as an off white solid. ¹H NMR (DMSO-d₆): δ 11.8-13.0 (br, 1H), 8.4 (s, 1H), 7.9 (d, 1H), 7.5 (d, 1H), 3.0 (q, 2H), 1.8 (q, 2H), 0.9 (t, 3H). mp: 296-299° C.

Acid Preparation 7

3-Ethyl-1H-indazole-5-carboxylic acid

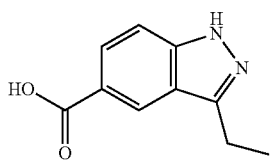

To a solution of 5-bromo-2-fluorobenzaldehyde (10 g, 49 mmol) in diethyl ether (20 mL) at 15° C., was added drop wise at 15° C. EtMgBr (7.22 g, 54.2 mmol). The mixture was stirred at room temperature for 2 hours. The reaction mixture was quenched with cold water and NH₄Cl solution. It was extracted with diethyl ether and the ether layer was washed with saturated aqueous NaCl, dried over anhydrous Na₂SO₄ and concentrated under vacuum to afford 1-(5-bromo-2-fluorophenyl)propan-1-ol (12.1 g, 98%) as a syrup. ¹H NMR (CDCl₃): δ 7.6-7.7 (m, 1H), 7.2-7.3 (m, 1H), 6.9 (t, 1H), 4.9 (brs, 1H), 1.8 (m, 2H), 1.0 (t, 3H).

To 1-(5-bromo-2-fluorophenyl)propan-1-ol (12.1 g, 64.8 mmol) in CH₂Cl₂ (100 mL) was added pyridinium dichromate (73.2 g, 194 mmol) and powdered molecular sieves. The mixture was stirred at room temperature for 16 hours. The reaction mixture was filtered through a pad of diatomaceous earth and washed with diethyl ether. The combined ether and CH₂Cl₂ layers were collected and concentrated under vacuum to afford 1-(5-bromo-2-fluorophenyl)propan-1-one (12.6 g, 98%) as a syrup. ¹H NMR (CDCl₃): δ 7.9-8.0 (m, 1H), 7.5-7.6 (m, 1H), 7.0 (t, 1H), 3.0-3.1 (m, 2H), 1.2 (t, 3H).

To 1-(5-bromo-2-fluorophenyl)propan-1-one (10 g, 43 mmol), anhydrous hydrazine (53 mL) was added and heated at reflux (70-75° C.) for 2 days. Excess hydrazine was distilled out under vacuum from the reaction mixture. To this was added xylene (60 mL) and the mixture heated to 145-150° C. for 3 days. Xylene was concentrated completely under vacuum to give a crude product, which was purified by column chromatography using 8% ethyl acetate/pet-ether as eluents to afford 5-bromo-3-ethyl-1H-indazole (4 g, 40%) as a solid. ¹H NMR (CDCl₃): δ 9.6-10.0 (br, 1H), 7.9 (s, 1H), 7.5 (d, 1H), 7.3 (d, 1H), 3.0 (q, 2H), 1.4 (t, 3H).

To a −78° C. solution of 5-bromo-3-ethyl-1H-indazole (5 g, 22 mmol) in diethyl ether (150 mL) was added t-BuLi (4.84 g, 75.6 mmol). The mixture was stirred at −78° C. for 1 hour. Dry CO₂ gas was passed through the reaction mixture at −78° C. for 1 hour and the temperature was slowly raised to room temperature for 2 hours. The reaction mixture was stirred at room temperature for 1 hour and quenched with saturated NH₄Cl solution. The ether layer was separated and concentrated to recover unreacted starting material. The pH of the aqueous layer was made acidic with 2 N HCl, which was filtered to afford the title compound (2 g, 47%) as a pale brown solid. ¹H NMR (DMSO-d₆): δ12.6-13.0 (br, 2H), 8.4 (s, 1H), 7.9 (d, 1H), 7.5 (d, 1H), 3.0 (q, 2H), 1.4 (t, 3H).

Acid Preparation 8

7-Chloro-3-methyl-1H-indazole-5-carboxylic acid

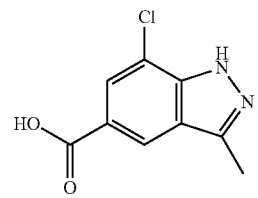

To a solution of 1-(2-amino-5-bromophenyl)ethanone (200 mg, 0.93 mmol) in CH2Cl2 (5 mL) was added N-chlorosuccinimide (125 mg, 0.93 mmol). The mixture was stirred at room temperature overnight. Analysis indicated that the reaction was incomplete; therefore, additional N-chlorosuccinimide (125 mg, 0.93 mmol) was added and the mixture was stirred at room temperature overnight. The solvents were removed under reduced pressure and the residue was purified by CombiFlash (40 g column, 0-10% EtOAc/heptane) to afford 1-(2-amino-5-bromo-3-chlorophenyl)ethanone (206 mg, 89%).

To a 0° C. solution of 1-(2-amino-5-bromo-3-chlorophenyl)ethanone (206 mg, 0.83 mmol) in 50% aqueous solution of concentrated $H_2SO_4$ was slowly added $NaNO_2$ (73 mg, 1.0 mmol). The cooling bath was removed following the addition of $NaNO_2$, stirred at room temperature for 1 hour and then recooled to 0° C. before addition of $SnCl_2.2H_2O$ (573 mg, 2.49 mmol). The mixture was stirred at 0° C. for 1 hour before dilution with water. The solids were collected by vacuum filtration to afford 5-bromo-7-chloro-3-methyl-1H-indazole (130 mg, 64%).

A microwave tube was charged with 5-bromo-7-chloro-3-methyl-1H-indazole (610 mg, 2.48 mmol), dioxane (5 mL), Hermann's catalyst (119 mg, 0.12 mmol) and a solution of sodium carbonate (790 mg, 7.46 mmol) in water (10 mL). The mixture was stirred for 20 sec, heated at 165° C. for 30 minutes in a microwave reactor at very high absorption setting. The reaction was vented before handling. The mixture was filtered through diatomaceous earth and washed with EtOAc. The filtrate was concentrated, the residue was dissolved in water and acidified to pH ~3 with conc HCl. The solids were collected by filtration and dried to afford the title compound (420 mg, 82%).

Acid Preparation 9

3-Ethyl-7-methoxy-1-methyl-1H-indazole-5-carboxylic acid

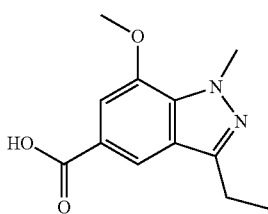

To a 0° C. solution of ethyl 3-ethyl-7-hydroxy-1H-indazole-5-carboxylate (prepared as described in Acid Preparation 2) (50 mg, 0.21 mmol) in DMF (1 mL) was added 60% NaH oil dispersion (8.5 mg, 0.21 mmol). This mixture was stirred for 30 minutes before addition of iodomethane (0.011 mL, 0.17 mmol). The reaction was kept at 0° C. for 2 hours before allowing to alowly warm to room temperature while stirring overnight. The reaction was diluted with EtOAc and saturated aqueous $NaHCO_3$. The organic phase was isolated and the aqueous phase was back extracted with EtOAc (2×). The combined organic extracts were washed with saturated aqueous NaCl, dried over $Na_2SO_4$, filtered and concentrated. The crude product was purified by CombiFlash (12 g column, 0-30% EtOAc/hexanes) to provide 3-ethyl-7-methoxy-1H-indazole-5-carboxylate (22 mg, 41%) and ethyl 3-ethyl-7-methoxy-1-methyl-1H-indazole-5-carboxylate (46 mg, 60%).

To a solution of ethyl 3-ethyl-7-methoxy-1-methyl-1H-indazole-5-carboxylate (52 mg, 0.20 mmol) in THF (1.5 mL) was added 1 M LiOH (0.36 mL, 0.36 mmol). The mixture was heated at reflux overnight. The reaction was cooled to room temperature, concentrated, triturated with 1 N HCl, the filtered solids were then washed with water and air dried to provide the title compound (46 mg, 94%).

Acid Preparation 10

7-Ethoxy-3-ethyl-1H-indazole-5-carboxylic acid

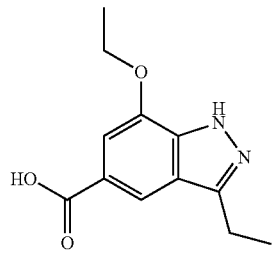

To a 0° C. solution of ethyl 3-ethyl-7-hydroxy-1H-indazole-5-carboxylate (prepared as described in Acid Preparation 2) (932 mg, 3.98 mmol) in DMF (28 mL) was added 60% NaH oil dispersion (159 mg, 3.98 mmol). This mixture was stirred at 0° C. for 1 hour before the dropwise addition of a solution of iodoethane (0.32 mL, 3.98 mmol) in DMF (3 mL). The mixture was kept at 0° C. for several hours before removal of the cooling bath and allowing the reaction to warm to room temperature while stirring overnight. The reaction was diluted with EtOAc, washed with saturated aqueous $NaHCO_3$, saturated aqueous NaCl, the organic extract was then dried over $Na_2SO_4$, filtered and concentrated. Purify by CombiFlash (80 g column, 0-30% EtOAc/hexanes) to provide ethyl 7-ethoxy-3-ethyl-1H-indazole-5-carboxylate (389 mg, 37%) and ethyl 7-ethoxy-1,3-diethyl-1H-indazole-5-carboxylate (202 mg).

To a solution of ethyl 7-ethoxy-3-ethyl-1H-indazole-5-carboxylate (389 mg, 1.48 mmol) in THF (13 mL) was added 1 M LiOH (3.0 mL, 3.0 mmol). The mixture was heated at reflux overnight. To the reaction was added trace amounts of ethanol to aid in solubilizing materials. Continue heating at reflux for an additional 2 hours. The reaction was cooled to room temperature, concentrated, triturated with 1 N HCl, the filtered solids were then washed with water and air dried to provide the title compound (347 mg, 97%).

Acid Preparation 11

1-Methyl-1H-indazole-5-carboxylic acid

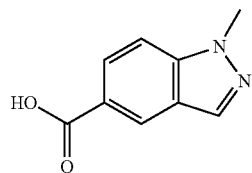

To a stirred suspension of 60% NaH oil dispersion (87 mg, 2.2 mmol) in DMF (4 mL) was added methyl 1H-indazole-5-carboxylate (264 mg, 1.50 mmol). The mixture was stirred at room temperature for 1 hour before the dropwise addition of iodomethane (0.11 mL, 1.8 mmol). The mixture was stirred at room temperature for 2 hours, concentrated and the residue was purified by Biotage chromatography (40S column, 15% acetone/heptane) to afford methyl 1-methyl-1H-indazole-5-carboxylate (107 mg, 38%).

To a solution of methyl 1-methyl-1H-indazole-5-carboxylate (107 mg, 0.56 mmol) in methanol/water (V:V 1:1, 4 mL) was added LiOH (48 mg). The solution was heated at 40° C. for 3 hours before cooling to room temperature. The mixture was diluted with water and acidified to pH 3.5-4 with KHSO$_4$. Solids precipitated and were isolated by filtration and dried under vacuum to afford the title compound as a yellow solid (70 mg, 71%).

Acid Preparation 12

2,7-Dimethyl-2H-indazole-5-carboxylic acid

To a solution of 7-methyl-1H-indazole-5-carboxylic acid (356 mg, 2.0 mmol) in DMF (6 mL) was added K$_2$CO$_3$ (0.85 g, 6.2 mmol) and iodomethane (0.45 mL, 7.2 mmol). The mixture was stirred at room temperature for 4 hours and then heated at 50° C. overnight. The reaction was cooled to room temperature, diluted with EtOAc and washed with saturated aqueous NaCl. The organic extract was concentrated and purified by Biotage chromatography (40 S column, 25-50% EtOAc/heptane) to afford methyl 1,7-dimethyl-1H-indazole-5-carboxylate (91 mg, 22%) and methyl 2,7-dimethyl-2H-indazole-5-carboxylate (141 mg, 35%).

To a solution of methyl 2,7-dimethyl-2H-indazole-5-carboxylate (140 mg, 0.69 mmol) in methanol/water (V:V 1:1, 2 mL) was added LiOH (38 mg, 1.6 mmol). The solution was heated at 50° C. for 1 hour, cooled to room temperature, concentrated and acidified to pH 2 with KHSO$_4$. The solid material was isolated by filtration to provide the title compound as a white solid (140 mg, 107%).

Acid Preparation 13

2-Methyl-2H-indazole-5-carboxylic acid

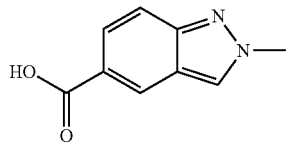

To a solution of methyl 1H-indazole-5-carboxylate (2.5 g, 14 mmol) in DMF (45 mL) was added K$_2$CO$_3$ (4.90 g, 35.5 mmol) followed by iodomethane (1.77 mL, 28.4 mmol). The mixture was stirred at room temperature for 2 hours and then heated at 50° C. overnight. The mixture was concentrated, dissolved in EtOAc and washed with saturated aqueous NaCl. The organic extract was dried over Na$_2$SO$_4$, filtered and concentrated. The crude material was purified by CombiFlash (80 g column, 25-45% EtOAc/heptane) to provide methyl 1-methyl-1H-indazole-5-carboxylate (1.07 g, 40%) and methyl 2-methyl-2H-indazole-5-carboxylate (227 mg, 8.4%).

To a solution of methyl 2-methyl-2H-indazole-5-carboxylate (210 mg, 1.10 mmol) in methanol (5 mL) was added 1.0 M LiOH (1.2 mL, 1.2 mmol). The mixture was agitated at 40° C. overnight. After cooling to room temperature, 1 N HCl (1.17 mL, 1.1 eq) was added. The solution was cooled and the solid was isolated by filtration. The solid was dried in a vacuum oven at 50° C. to provide the title compound (147 mg, 76%).

Acid Preparation 14

3-Methyl-1H-indazole-5-carboxylic acid

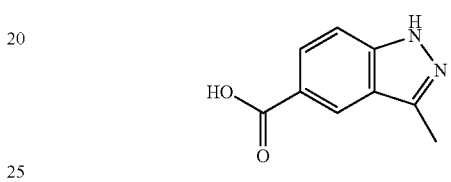

A solution of 2-fluoro-4-methoxyactophenone (2.0 g, 12 mmol) in hydrazine hydrate (30 mL) was heated at reflux for two days. The mixture was cooled to room temperature, poured into water and extracted with EtOAc (3x). The organic extracts were concentrated, dissolved in a minimal amount of CH$_2$Cl$_2$ and filtered to afford 6-methoxy-3-methyl-1H-indazole (370 mg, 19%). The filtrate was refiltered to provide additional product (250 mg, 13%).

To an ice cold solution of 6-methoxy-3-methyl-1H-indazole (620 mg, 3.82 mmol) in CH$_2$Cl$_2$ (25 mL) was added a solution of BBr$_3$ in CH$_2$Cl$_2$ (1 M, 17 mL). The ice bath was removed and the reaction was allowed to warm to room temperature and stirred overnight. The solution was carefully quenched by slowly pouring into iced saturated aqueous NaHCO$_3$. The phases were separated and the aqueous phase was extracted with EtOAc (3x). The combined organic extracts were concentrated and the crude material was purified Biotage (40S column, 45-60% acetone/heptane) to provide 3-methyl-1H-indazol-6-ol (458 mg, 81%).

A solution of 3-methyl-1H-indazol-6-ol (458 mg, 3.1 mmol) in THF (30 mL) was treated with 60% NaH oil dispersion (0.50 g, 13 mmol). After the initial effervescence, the solution was heated at 50° C. for 1 hour before cooling to room temperature. To this was added N-phenyltrifluoromethanesulphonimide (2.50 g, 7.00 mmol) and the mixture was stirred at room temperature for 2 hours before pouring into water. The aqueous phase was extracted with EtOAc (3x) and the combined organic extracts were concentrated. The crude product was purified by Biotage (40M column, 12% acetone/heptane) followed by repurification by Biotage (40S column, 10% EtOAc/heptane) to provide 3-methyl-1-[(trifluoromethyl)sulfonyl]-1H-indazol-6-yl trifluoromethanesulfonate (1.13 g, 89%).

A solution of 3-methyl-1-[(trifluoromethyl)sulfonyl]-1H-indazol-6-yl trifluoromethanesulfonate (0.61 g, 1.5 mmol) in DMF (6 mL) was flushed with CO for 5 minutes. The solution was treated with palladium acetate (68 mg, 0.30 mmol), 1,1'-bis(diphenylphosphino)ferrocene (167 mg, 0.30 mmol), triethylamine (0.33 g, 0.45 mL, 3.2 mmol) and methanol (4 mL). The mixture was stirred at room temperature under CO (1 atm). The solution was poured into water and extracted with EtOAc (3×). The combined organic extracts were concentrated and purified by Biotage (40S column, 8% EtOAc/heptane) to provide methyl 3-methyl-1-[(trifluoromethyl)sulfonyl]-1H-indazole-6-carboxylate (330 mg, 69%).

To a solution of methyl 3-methyl-1-[(trifluoromethyl)sulfonyl]-1H-indazole-6-carboxylate (590 mg, 1.83 mmol) in methanol/water (3:1, 72 mL) was added $K_2CO_3$ (1.01 g, 7.31 mmol) and the mixture was heated at reflux for 2 hours. The reaction was cooled to room temperature and the methanol was removed under reduced pressure. The aqueous solution was acidified to pH 3-3.5 with $KHSO_4$. The solid was isolated by filtration, dissolved in EtOAc and washed with water. The organic layer was dried over $Na_2SO_4$, filtered and concentrated to provide the title compound (259 mg, 80%).

Acid Preparation 15

3-Methyl-1H-pyrazolo[3,4-b]pyridine-5-carboxylic acid

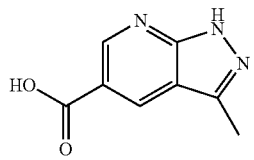

A solution of 2-bromomalonaldehyde (4.0 g, 30 mmol) and methyl-1H-pyrazol-5-amine (2.57 g, 26.5 mmol) in acetic acid (40 mL) was heated to 116° C. for 2.5 hours. The reaction was then stirred at room temperature for 2 days. The solution was concentrated and the residue was taken up in methanol, filtered through diatomaceous earth and concentrated. Purify by silica gel chromatography (2-5% $CH_2Cl_2$/methanol) to afford 5-bromo-3-methyl-1H-pyrazolo[3,4-b]pyridine (515 mg, 9%).

A microwave tube was charged with 5-bromo-3-methyl-1H-pyrazolo[3,4-b]pyridine (515 mg, 2.43 mmol), dioxane (2 mL), Hermann's catalyst (72.1 mg, 0.12 mmol) and a solution of sodium carbonate (772 mg, 7.29 mmol) in water (5 mL). The mixture was stirred for 20 sec, heated at 165° C. for 15 minutes in a microwave reactor at very high absorption setting. The reaction was vented before handling. The mixture was diluted with EtOAc and stirred for 5 minutes before filtering through diatomaceous earth to provide the title compound (124 mg, 29%).

Acid Preparation 16

3,7-Dimethyl-1H-indole-5-carboxylic acid

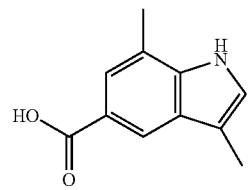

4-Bromo-2-methylaniline (2.00 g, 10.8 mmol) was dissolved in conc. HCl (10 mL) and heated to 80° C. for 30 minutes. The reaction was then cooled to 5° C. and a solution of $NaNO_2$ (781 mg, 10.8 mmol) in water (4 mL) was added over 10 minutes. The resulting mixture was stirred at 5° C. for 30 minutes before addition of $SnCl_2$ (15.3 g, 80.6 mmol) in conc. HCl (8 mL) over 10 minutes. The mixture was stirred at room temperature for 45 minutes before addition of 50% aqueous NaOH. The resulting precipitate was isolated by filtration and the filtrate was extracted with $CH_2Cl_2$. The combined organic phases were dried over $MgSO_4$, filtered and concentrated to provide (4-bromo-2-methylphenyl)hydrazine (1.08 g, 50%).

To a suspenstion of (4-bromo-2-methylphenyl)hydrazine (1.44 g, 7.16 mmol) in ethanol (10 mL) was added propionaldehyde (0.68 mL, 9.3 mmol). The solution became clear and the mixture was stirred at room temperature for 45 minutes. The solvents were removed and anhydrous $ZnCl_2$ (1.07 g, 7.88 mmol) was added and the mixture was heated at 170° C. for 30 minutes. The mixture was cooled to room temperature, diluted with 10% HCl, extracted with $CH_2Cl_2$ and the organic extract was dried over $MgSO_4$. After filtration and concentration, the residue was purified by CombiFlash (0-10% EtOAc/heptane) to provide 5-bromo-3,7-dimethyl-1H-indole (317 mg, 20%).

A microwave tube was charged with 5-bromo-3,7-dimethyl-1H-indole (317 mg, 1.42 mmol), dioxane (3 mL), Hermann's catalyst (42.1 mg, 0.07 mmol) and a solution of sodium carbonate (450 mg, 4.24 mmol) in water (6 mL). The mixture was stirred for 20 sec, heated at 165° C. for 15 minutes in a microwave reactor at very high absorption setting. The reaction was vented before handling. The mixture was filtered through diatomaceous earth and washed with EtOAc. The filtrate was concentrated and the residue was dissolved in water. The solution was acidified to pH 3 and the solid was collected to afford the title compound (250 mg, 93%).

Acid Preparation 17

7-Chloro-3-ethyl-1H-indazole-5-carboxylic acid

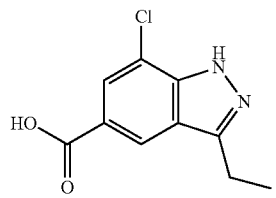

A three-necked round bottom flask under $N_2$ was charged with $AlCl_3$ (775 mg, 5.81 mmol), then add 5.00 mL of toluene. The slurry was cooled to −10° C. and 4-bromoaniline (1.0 g, 5.81 mmol) was added in one portion. To this was added $BCl_3$ (6.4 mL of 1.0 M solution in xylene) to the mixture at −10° C. slowly, and the mixture was purged with $N_2$ until no more smoke appeared. Propioitrile (1.88 mL, 25.6 mmol) was added and the temperature was allowed to raise to no great than 45° C. The reaction was heated at 63° C. for 10 minutes and maintained at 63° C. for 5 minutes to give a homogeneous solution. Another 4.0 mL of toluene was added into another three-necked flask, and heated to reflux under $N_2$. The solution from previous flask was added to the toluene at reflux over 10 minutes. The mixture was heated to reflux for an additional 4 hours, while continuing to purge the reaction with $N_2$. Toluene would be lost during this process, added more toluene to the mixture if necessary. The reaction was cooled to room temperature and 10 mL of water was added under efficient stirring for ~30 minutes. The mixture was heated to 55° C. and stirred for 15 minutes before allowing separation into two layers. The organic phase was washed with water, dried over MgSO$_4$, filtered, and concentrated to give a crude solid. The residue was purified though column chromatography (0-50% EtOAc/Heptane gradient) to afford 1-(2-amino-5-bromophenyl)-propan-1-one as a yellow solid (144.0 mg, 10.9%).

1-(2-Amino-5-bromo-phenyl)-propan-1-one (144.0 mg, 0.63 mmol) was dissolved in CH$_2$Cl$_2$ (10.0 mL), and N-chlorosuccinimide (168.0 mg, 1.26 mmol) was added to this solution. The resulting mixture was stirred at 45° C. overnight. The reaction was cooled to room temperature and concentrated. The residue was purified through column chromatography to afford 1-(2-amino-5-bromo-3-chloro-phenyl)-propan-1-one as a solid (130.0 mg, 76.1%).

1-(2-Amino-5-bromo-3-chloro-phenyl)-propan-1-one (130.0 mg, 0.50 mmol) dissolved in aqueous 50% H$_2$SO$_4$ (2.5 mL) and NaNO$_2$ (43.1 mg, 0.59 mmol) was slowly added to this mixture at 0° C. The mixture was then stirred at room temperature for 1 hour. SnCl$_2$ 2H$_2$O (342.0 mg, 1.48 mmol) was then added, and the mixture was stirred at 0° C. for 1 hour, and then diluted with water. White solid appeared and was collected by filtration and dried to afford 5-bromo-7-chloro-3-ethyl-1H-indazole as a solid (127.0 mg, 98.8%).

To a microwave tube were added 5-bromo-7-chloro-3-ethyl-1H-indazole (127.0 mg, 0.49 mmol) dissolved in dioxane (1.0 mL). The Hermann's catalyst ((trans-Bis(acetato)bis[o-(di-o-tolylphosphino)benzyl]dipalladium(II))) (23.0 mg, 0.024 mmol) and molybdenum hexacarbonyl (64.4 mg, 0.244 mmol) were added followed by a solution of sodium carbonate (156 mg, 1.47 mmol) in water (2.0 mL). Separation occurs within the vessel. The mixture was stirred for 20 seconds and then the mixture was heated to 165° C. for 15 minutes under mircrowave irradiation with the absorption setting at very high. The reaction was stopped and the vessel was vented before handling. The mixture was filtered and washed with EtOAc. The filtrate was concentrated and the residue was re-dissolved with water. The solution was then acidified to pH ~3. The solid was collected and dried to afford 7-chloro-3-ethyl-1H-indazole-5-carboxylic acid as a solid (95.0 mg, 86.4%).

Acid Preparation 18

2,4-Dimethyl-1H-benzimidazole-6-carboxylic acid

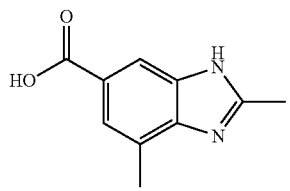

To a solution of 5-bromo-3-methylbenzene-1,2-diamine (201 mg, 1.00 mmol) in EtOH (15 mL) was added 5 N HCl (4 mL). The mixture was heated at reflux before addition of 2,4-pentanedione (200 mg, 0.21 mL, 2.0 mmol). Heating was continued for 45 minutes before analysis indicated the reaction was complete. The reaction was cooled to room temperature, neutralized with saturated aqueous NaHCO$_3$ and extracted with CHCl$_3$. The organic layer was washed with saturated aqueous NaCl, dried over MgSO$_4$, filtered, concentrated and dried to afford 6-bromo-2,4-dimethyl-1H-benzimidazole (217 mg, 96%).

To a solution of 6-bromo-2,4-dimethyl-1H-benzimidazole (200 mg, 0.90 mmol) in degassed dioxane (2 mL) was added ((trans-bis(acetato)bis[o-(di-o-tolylphosphino)benzyl]dipalladium(II))) (30 mg, 0.05 mmol), molybdenum hexacarbonyl (120 mg, 0.45 mmol) and a solution of Na$_2$CO$_3$ (283 mg, 2.67 mmol) in degassed water (2.4 ml). The mixture was stirred for 20 seconds and then heated at 165° C. for 15 minutes in a microwave reactor with absorption set at very high for 20 minutes. The reaction vessel was vented and filtered through diatomaceous earth. The solution was extracted with EtOAc and the aqueous phase was back extracted with additional EtOAc (2×). The combined organic extracts were set aside. Water (5 mL) was added to the aqueous extract which was then acidified with 0.5 M HCl to pH 3. The resulting solids were air dried to provide the title compound (97 mg, 57%).

Acid Preparation 19

4-Methyl-1H-benzimidazole-6-carboxylic Acid

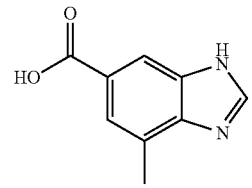

To a solution of 5-bromo-3-methylbenzene-1,2-diamine (2.02 g, 10 mmol) was added water (10 mL) followed by formic acid (1.16 mL, 30 mmol). The mixture was stirred at 100° C. for 6 hours before cooling to room temperature. A solid precipitated from the solution and was allowed to sit at room temperature for 2 days. To this mixture was then added 1 N KOH (35 mL) and the solids were isolated by vacuum filtration. The solids were air dried and recrystallized from CHCl$_3$ (70 mL) to provide 6-bromo-4-methyl-1H-benzimidazole (0.82 mg, 39%). Additional batches of product were obtained from the CHCl$_3$ mother liquors (1.01 g, 48%).

To a solution of 6-bromo-4-dimethyl-1H-benzimidazole (100 mg, 0.47 mmol) in degassed dioxane (2 mL) was added ((trans-bis(acetato)bis[o-(di-o-tolylphosphino)benzyl]dipalladium(II))) (16 mg, 0.03 mmol), molybdenum hexacarbonyl (64 mg, 0.24 mmol) and a solution of Na$_2$CO$_3$ (150 mg, 1.42 mmol) in degassed water (2.4 ml). The mixture was stirred for 20 seconds and then heated at 165° C. for 15 minutes in a microwave reactor with absorption set at very high for 20 minutes. The reaction vessel was vented and filtered through a SPE cartridge. The aqueous solution was extracted with EtOAc (3×). The organic extracts were combined and concentrated. The residue was dissolved in water and acidified to pH 3 and stored in a refrigerator overnight. To the aqueous material was added water (3 mL) and pH 3. A solid precipitated from solution and was isolated by filtration. The solids were washed with water, air dried to provide product (44 mg, 53%). Upon sitting, solids precipitated from the mother liquors to afford additional product (34 mg, 41%).

Acid Preparation 20

7-Ethyl-3-methyl-1H-indazole-5-carboxylic Acid

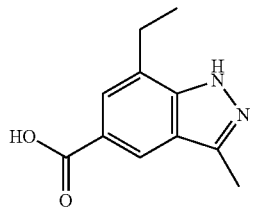

To a solution of 7-ethyl-1H-indazole-5-carboxylic acid (500 mg, 2.63 mmol) in MeOH (15 mL) was added conc. $H_2SO_4$ (0.25 mL). The mixture was heated at reflux overnight. The solvent was removed under reduced pressure to afford a tan solid that was purified by flash chromatography (40 g column) using 15-30% EtOAc/heptane to afford methyl 7-ethyl-1H-indazole-5-carboxylate (252 mg, 47%).

To a solution of methyl 7-ethyl-1H-indazole-5-carboxylate (252 mg, 1.23 mmol) in DMF (10 mL) was added $K_2CO_3$ (550 mg, 3.98 mmol) and $I_2$ (370 mg, 1.46 mmol). The mixture was stirred at room temperature overnight. To this was then added 5% $NaHSO_3$ (10 mL) followed by 1:1 EtOAc/THF (50 mL). The organic layer was isolated, dried over $Na_2SO_4$, filtered and concentrated. The solid was suspended in $CH_2Cl_2$, collected by filtration and dried to provide methyl 7-ethyl-3-iodo-1H-indazole-5-carboxylic acid (298 mg, 73%).

To a degassed solution of methyl 7-ethyl-3-iodo-1H-indazole-5-carboxylic acid (100 mg, 0.30 mmol) in DME (2.5 mL) was added degassed boroxine solution (50%, 0.28 mL) followed by palladium tetrakistriphenylphosphine (3.5 mg, 0.003 mmol) and 2 M $Na_2CO_3$ (0.57 mL). The mixture was heated in a microwave reactor (very high absorption setting) at 125° C. for 10 minutes and then at 165° C. for 10 minutes. The reaction was extracted with EtOAc and washed with saturated aqueous NaCl. The organic extract was reduced and the crude material was purified by silica gel chromatography (40 g column) using 0-40% EtOAc/heptane to afford methyl 7-ethyl-3-methyl-1H-indazole-5-carboxylic acid (18 mg, 27%).

To a solution of methyl 7-ethyl-3-methyl-1H-indazole-5-carboxylic acid (240 mg, 1.10 mmol) in EtOH (13 mL) was added 1 M LiOH (2.2 mL). The mixture was heated overnight at reflux and cooled to room temperature. The solvents were removed under reduced pressure and the resultant material was suspended in 1 N HCl. The solids were isolated by vacuum filtration, washed with water, dried at 45° C. under vacuum to afford the title compound (154 mg, 69%) containing ~10% of des-methyl material.

Acid Preparation 21

3-Chloro-1H-indazole-5-carboxylic Acid

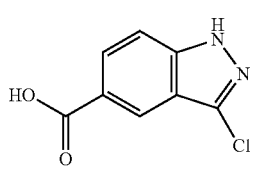

To a suspension of 1H-indazole-5-carboxylic acid (155 mg, 0.96 mmol) in $CH_3CN$ (8 mL) was added N-chlorosuccinimide (142 mg, 1.06 mmol). The mixture was heated at reflux overnight before concentration. The solid was suspended in water and aqueous sodium thiosulfate solution, acidified with 1 N HCl and the solids were isolated by filtration. The solids were then washed with water and dried under vacuum at 50° C. to provide the title compound as an off-white solid (157 mg, 84%).

Acid Preparation 22

3-Chloro-7-methyl-1H-indazole-5-carboxylic Acid

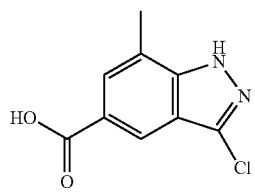

To a suspension of 7-methyl-1H-indazole-5-carboxylic acid (180 mg, 1.01 mmol) in $CH_3CN$ (10 mL) was added N-chlorosuccinimide (150 mg, 1.12 mmol). The mixture was heated at reflux overnight before concentration. The solid was suspended in water and aqueous sodium thiosulfate solution, acidified with 1 N HCl and the solids were isolated by filtration. The solids were then washed with water and dried to provide the title compound as a tan solid (208 mg, 98%).

Acid Preparation 23

7-Ethoxy-1H-indazole-5-carboxylic Acid

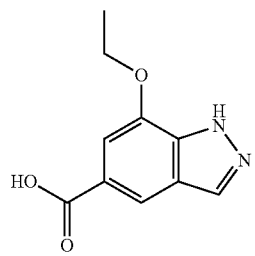

A solution of 7-hydroxy-1H-indazole-5-carboxylic acid (1.08 g, 6.06 mmol) in EtOH (50 mL) containing conc. $H_2SO_4$ (0.34 mL) was heated at reflux overnight. The mixture was diluted with EtOAc and washed with saturated aqueous $NaHCO_3$. The aqueous phase was back extracted with EtOAc (3×). The combined organic extracts were washed with saturated aqueous NaCl, dried over $Na_2SO_4$, filtered and concentrated to afford ethyl 7-hydroxy-1H-indazole-5-carboxylate (918 mg, 73%).

To a solution of ethyl 7-hydroxy-1H-indazole-5-carboxylate (918 mg, 4.45 mmol) in DMF (35 mL) at 0° C. was added 60% oil dispersion of NaH (178 mg, 4.45 mmol). The mixture was aged for 1 hour at 0° C. before dropwise addition of a solution of iodoethane (694 mg, 0.36 mL, 4.45 mmol) in DMF (15 mL). The mixture was aged at 0° C. for several hours before removal of the ice bath. The reaction was allowed to warm to room temperature and aged overnight. The mixture was diluted with EtOAc, washed with water, saturated aqueous NaCl, dried over $Na_2SO_4$, filtered concentrated. Purify by silica gel chromatography (40 g column) eluting with 0-30% EtOAc/hexanes gradient to afford ethyl 7-ethoxy-1H-indazole-5-carboxylate (400 mg, 38%).

To a solution of ethyl 7-ethoxy-1H-indazole-5-carboxylate (400 mg, 1.71 mmol) was added 1 M LiOH (3.4 mL). The mixture was heated at reflux overnight. The reaction was concentrated to dryness and the solids were triturated with 1 N HCl. The solids were washed with water and air dried to afford the title compound as an off-white solid (350 mg, 99%).

Acid Preparation 24

7-Methoxy-3-methyl-1H-indazole-5-carboxylic Acid

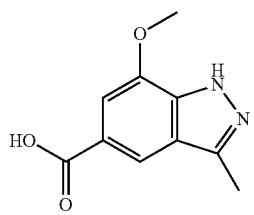

To a solution of ethyl 7-hydroxy-3-methyl-1H-indazole-5-carboxylate (Anti-Cancer Drug Design 1997, 12, 555) in DMF (25 mL) at 0° C. was added 60% oil dispersion of NaH (152 mg, 3.81 mmol). The mixture was stirred for 1 hour before the dropwise addition of a solution of iodomethane (0.54 g, 0.24 mL, 3.8 mmol) in DMF (3 mL). The mixture was kept at 0° C. for several hours before allowing the mixture to warm to room temperature and stirred overnight. The reaction was diluted with EtOAc, saturated aqueous $NaHCO_3$, water and saturated aqueous NaCl. The organic extract was dried over $Na_2SO_4$, filtered and concentrated. The material was purified by silica gel chromatography (80 g column) eluting with a 0-30% EtOAc/hexanes gradient to provide ethyl 7-methoxy-3-methyl-1H-indazole-5-carboxylate (294 mg, 33%).

To a solution of ethyl 7-methoxy-3-methyl-1H-indazole-5-carboxylate (294 mg, 1.26 mmol) in EtOH (11 mL) was added 1 M LiOH (2.5 mL). The mixture was heated at reflux for 4 hours, cooled to room temperature and concentrated. The crude material was triturated with 1 N HCl, the solids were isolated by filtration and washed with water. The solid was air dried overnight to provide the title compound (235 mg, 91%).

Acid Preparation 25

7-methyl-1H-indazole-5-carboxylic acid

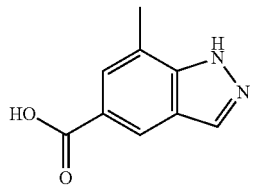

To a solution of 5-bromo-7-methylindazole, (purchased from PharmaLab, Morrisville, Pa.) (2.00 g, 9.47 mmol) in anhydrous THF (50 mL) was added NaH (570 mg, 14.25 mmol; 60% suspension in mineral oil) at room temperature. After 20 minutes the mixture was cooled to −78° C. and sec-butyllithium (1.4 M in cyclohexane, 17 mL; 23.8 mmol) was added drop wise and the resulting mixture was stirred for 4 hours. Dry $CO_2$ was then bubbled through the reaction mixture for 1 hour while allowing warming to room temperature. It was then stirred at room temperature overnight. 1 N HCl was added and the solution extracted with EtOAc. The organic layer was washed with saturated aqueous NaCl, dried ($MgSO_4$), then filtered and concentrated. The residue was re-dissolved in MeOH, filtered, then concentrated to provide the product as a brown solid (1.445 g, 86.6%). $^1$H NMR (DMSO-$d_6$) δ 8.23 (s, 1H), 8.17 (s, 1H), 7.65 (s, 1H), 2.46 (s, 3H). LC/MS ES+ 177 (MH+).

Acid Preparation 26

7-ethyl-1H-indazole-5-carboxylic acid

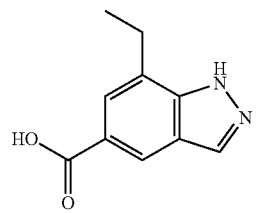

To a solution of 2-ethyl-6-methylaniline (2.03 g, 15 mmol) in DMF (50 mL) at 0° C. was added N-bromosuccinimide (2.66 g, 14.9 mmol). The mixture was stirred at room temperature for 10 minutes before addition to saturated aqueous NaCl. The mixture was extracted with EtOAc, the organic phase was washed with sat aqueous NaCl (2×), concentrated and the crude material was purified by Biotage chromatography (40M, 15% EtOAc/heptane) to provide 4-bromo-2-ethyl-6-methylbenzenamine as a red brown liquid (3.21 g, 100%).

A solution of 4-bromo-2-ethyl-6-methylbenzenamine (3.21 g, 15 mmol) in acetic acid (50 mL) was stirred for 3 hours before addition of a 2 M solution of sodium nitrite (11 mL, 22.5 mmol). The resulting mixture was stirred overnight at room temperature. The solution was concentrated and the solid was dissolved in EtOAc and washed with saturated aqueous NaCl (3×). The organic extract was dried over Na2SO4, filtered and concentrated. the crude material was purified by Biotage chromatography (40M, 15-30% EtOAc/heptane) to provide 5-bromo-7-ethyl-1H-indazole (1.11 g, 33%) and 5-bromo-3,7-dimethyl-1H-indazole (0.84 g, 25%).

To a solution of 5-bromo-7-ethyl-1H-indazole (225 mg, 1.00 mmol) in dioxane (1.5 mL), hexacarbonylmolybdenum (132 mg, 0.50 mmol), Herrmann's catalyst (trans-Bis(acetato)bis[o-(di-o-tolylphosphino)benzyl]dipalladium) (46.9 mg, 0.05 mmol) and a solution of sodium carbonate (318 mg, 3.00 mmol) in water (2 mL). The suspension was sealed and irradiated in a microwave at 165° C. for 15 minutes (high absorption setting). The vial was vented, filtered through diatomaceous earth, washed with EtOAc and concentrated to provide the title compound (140 mg, 74%).

Acid Preparation 27

7-chloro-1H-indazole-5-carboxylic acid

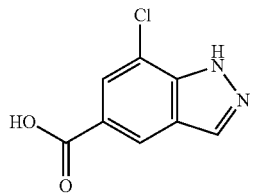

To a solution of 4-amino-3-chloro-5-methylbenzonitrile (3.00 g, 18.0 mmol) in CHCl₃ (50 mL) was added acetic anhydride (3.9 mL, 41.4 mmol). The mixture was stirred at room temperature overnight and then heated at reflux for 5 hours. The reaction mixture was cooled to room temperature and potassium acetate (530 mg, 5.40 mmol) and isoamyl nitrite (5.28 mL, 39.6 mmol) were added. The mixture was heated at reflux for 3 days. The reaction mixture was washed with saturated aqueous NaHCO₃, dried over Na₂SO₄ and concentrated. To this was added methanol followed by water (25 mL) and 38% HCl (25 mL). The mixture was stirred at room temperature overnight. The reaction mixture was concentrated and the pH was adjusted to about 7. The solids were isolated by filtration and then washed with water (2×30 mL) and heptane (2×30 mL). Purify by Biotage chromatography (CH₂Cl₂-heptane (1:1)/MeOH gradient to afford 7-chloro-1H-indazole-5-carbonitrile was isolated as a white solid (585 mg, 18%).

To a solution of 7-chloro-1H-indazole-5-carbonitrile (250 mg, 1.41 mmol) in ethanol/water (3:1 ration, 15 mL) was added potassium hydroxide (395 mg, 7.04 mmol) and the mixture was heated at reflux. After 3 houra, the majority of the ethanol was allowed to distill off, additional potassium hydroxide (614 mg) was added and heating was continued for overnight. The reaction mixture was cooled to room temperature, washed with Et₂O (3×20 mL) and the organic extract was acidified with 1 N HCl. The resultant precipitate was isolated by vacuum filtration, washed with water (about 15 mL) and heptane (about 15 mL), dried at room temperature/ 0.5 mmHg to provide the title compound (221 mg, 79.7%).

Acid Preparation 28

3,7-dimethyl-1H-indazole-5-carboxylic acid

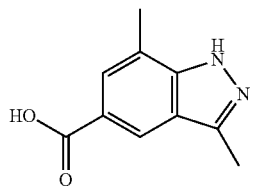

To a reaction vessel containing a re-purified solution of 5-bromo-3,7-dimethyl-1H-indazole (prepared as described for Acid Preparation 26, 285 mg, 1.27 mmol) in dioxane (1.3 mL) was added hexacarbonylmolybdenum (264 mg, 1.0 mmol), Herrmann's catalyst (93 mg, 0.1 mmol) and a solution of Na₂CO₃ in water (636 mg in 2 mL water). The suspension was heated in a microwave at 165° C. for 15 minutes (high absorption). The vial was vented, acidified with 1 N HCl (to pH 2). The reaction mixture was filtered through diatomaceous earth, washed with EtOAc and the organic layer was washed with saturated aqueous NaCl (3×). The organic extract was concentrated to yield the title compound as a pink solid (65 mg, 17%).

Acid Preparation 29

2-oxo-1,2,3,4-tetrahydroquinoline-6-carboxylic acid

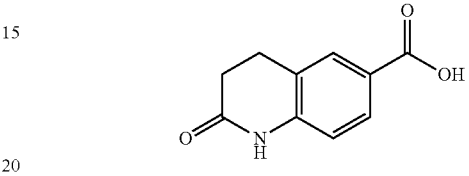

(analogous to *J of Med Chem*, 46(14), 3033-3044; 2003)

Step 1:
6-(2-chloroacetyl)-3,4-dihydroquinolin-2(1H)-one

To a 10 L, 4-neck flask, fitted with a mechanical stirrer and under N₂, AlCl₃ (408 g, 3.06 mol) and dry CH₂Cl₂ (2.7 L, 18 vol) was added. Chloroacetylchloride (89 mL, 1.22 mol) was then added from an addition funnel gradually over 15 minutes at room temperature. The resulting mostly clear solution was maintained at that temp for 30 minutes and turned into a muddy mixture. A solution of 3,4-dihydroquinolin-2(1H)-one (150 g, 1.02 mol) and CH₂Cl₂ (0.3 L, 2 vol) was added, over 1.5 hours, at such a rate as to keep the internal temperature below 30° C. The resulting brown mixture was stirred at that temp for 2 hours, then heated at 40° C. for an additional 2 hours, and then left to stir overnight at room temperature. The reaction mixture was cooled in an ice bath and connected to an HCl gas trap. Ice-cold H₂O (total 3 L) was then added, over 1.5 hours, at such a rate as to keep the internal temperature below 30° C. The resulting mixture was stirred at room temperature for 1 hour and then heated at 40-50° C. to remove the CH₂Cl₂. To this mixture, THF (1 L) was added and the mixture was stirred at room temperature overnight. The solids were collected by filtration. The yellow cake was washed with H₂O (500 mL), THF (200 mL) and hexane (1 L×2) and it was dried in a vacuum oven (@50° C., 1 day) to afford 6-(2-chloroacetyl)-3,4-dihydroquinolin-2(1H)-one (221 g, 97%). ¹H NMR (270 MHz, d-DMSO) δ 10.48 (s, 1 H), 7.86-7.77 (m, 2 H), 6.96 (d, J=8.2 Hz, 1 H), 5.08 (s, 2 H), 2.96 (t, J=7.6 Hz, 2 H), 2.51 (t, J=7.6 Hz, 2 H)

Step 2:
2-oxo-1,2,3,4-tetrahydroquinoline-6-carboxylic acid 6-(2-chloroacetyl)-3,4-dihydroquinolin-2(1H)-one (50.0 g, 0.22 mol) was added to 190 ml pyridine. The mixture was heated for 2.5 hours at 90° C. then cooled to room temperature. The pyridinium salt was collected by filtration and the filtercake washed with ethanol. Solid was dried on a vacuum oven overnight. The dry salt was added to 630 mL 0.5M aqueous sodium hydroxide and heated at 80° C. for 1 hour. The reaction was cooled to room temperature and acidified with 12N HCl (30 mL) and the solids collected by filtration. The collected solids were stirred with 2:1 water/DMF and filtered to collect the product as a pale yellow solid. The collected solid was dried on a vacuum oven overnight to yield 38.77 g (92%) of 2-oxo-1,2,3,4-tetrahydroquinoline-6-carboxylic acid as a pale yellow solid. $^1$H NMR (300 MHz, d-DMSO) δ 12.63 (br, 1 H), 10.40 (s, 1 H), 7.75-7.72 (m, 2 H), 6.92 (d, J=8.1 Hz, 1 H), 2.96-2.91 (m, 2 H), 2.51-2.46 (m, 2 H).

Acid Preparation 30

3,7-dimethylindole-5-carboxylic acid

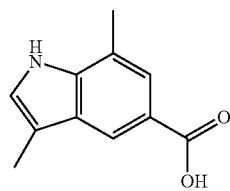

4-bromo-2-methylaniline (2.0 g) was dissolved in conc. HCl (10 mL) and heated to 80° C. for 30 minutes. The reaction was cooled to 5° C. and a solution of sodium nitrite (781.0 mg in 4.0 mL of water) was added over 10 minutes. The resulting mixture was then stirred at 5° C. for 30 minutes. A solution of tin(II)chloride (15.3 g in 8 mL of concentrated HCl) was added over 10 minutes, and the resulting solution was stirred at room temperature for 45 minutes. The reaction was made basic with 50% NaOH solution and a white precipitate formed. The solid was filtered and the filtrate extracted with dichloromethane. The organic extract was dried over magnesium sulfate, filtered and concentrated to yield 1.08 g (50%) of 1-(4-bromo-2-methylphenyl)hydrazine as a white solid. LC-MS @ 201.1 (M+1)

200 mg of 1-(4-bromo-2-methylphenyl)hydrazine was suspended in 10.0 mL EtOH propionaldehyde (678 μL) was added. The reaction became clear after the addition of propionaldehyde. The resulting solution was then stirred at room temperature for 45 minutes. The reaction was concentrated and zinc(II)chloride (1070.0 mg) was added and the mixture was heated at 170° C. for 30 minutes. The melting mixture was then cooled to room temperature, and diluted with 10% HCl solution. The solution was then extracted with dichloromethane, dried over magnesium sulfate, filtered and concentrated. The residue was flash chromatographed (0-10% EtOAc/Haptanes gradient) to obtain 317.0 mg of 5-bromo-3, 7-dimethyl-1H-indole. LC-MS @ 222.1 (M−1)

A 25 mL microwave reaction tube was charged with 317 mg 5-bromo-3,7-dimethyl-1H-indole dissolved in 3 L dioxane. 42 mg trans-Bis(acetato)bis[o-(di-o-tolylphosphino)benzyl]dipalladium(II) and 187 mg molybdenum hexacarbonyl were added followed by 450 mg sodium carbonate dissolved in 6 mL water. The vial was sealed and heated in a microwave reactor for 20 minutes at 165° C. The reaction was cooled and then filtered through celite, and the filtercake washed with EtOAc. The filtrate was concentrated and the resultant oil was redissolved with water. The solution was acidified to pH 3 and the precipitate collected by filtration to yield 250.0 mg (93%) of 3,7-dimethylindole-5-carboxylic acid. LC-MS @ 188.1 (M−1)

Acid Preparation 31 benzo[d]isothiazole-5-carboxylic acid

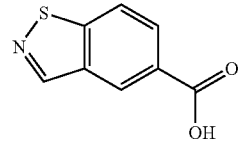

To a solution of 5-bromo-2-fluorobenzaldehyde (4.06 g) in 2-propanol (20.0 mL) was added 2-methyl-2-propanethiol (2.26 mL) and K$_2$CO$_3$ (3.04 g) and heated overnight. The reaction mixture was cooled to room temperature, poured into 50.0 mL water and extracted with dichloromethane. The organic phase was washed with brine, dried over magnesium sulfate, filtered and concentrated. The residue was flash chromatographed (3% EtOAc/Haptanes) to obtain 1.97 g (36%) of 5-bromo-2-(tert-butylthio)benzaldehyde as a clear oil. $^1$H NMR (500 MHz, CDCl3) δ ppm 1.30 (s, 9 H) 7.51 (d, J=8.05 Hz, 1 H) 7.70 (dd, J=8.29, 2.20 Hz, 1 H) 8.12 (d, J=2.20 Hz, 1 H) 10.70 (s, 1 H).

Hydroylamine hydrochloride (1.5 g) was dissolved in 25 mL water and treated with 10.8 mL 2N aqueous sodium hydroxide. This solution was added dropwise to a solution of 5-bromo-2-(tert-butylthio)benzaldehyde (1.97 g) in 25 mL ethanol at room temperature over 20 minutes. The mixture was heated at reflux for 2 hours then cooled to room temperature. The reaction mixture was poured into water (150.0 mL) and extracted with EtOAc. The organic layer was washed with saturated aqueous ammonium chloride, saturated aqueous sodium bicarbonate, brine, and dried over magnesium sulfate. The organic phase was filtered and concentrated. The residue was treated with polyphosphoric acid, (105.0 g) and heated at 100° C. for 2 hours. The reaction mixture was then poured into ice water (400.0 mL), neutralized with 5N aqueous NaOH under ice cooling, and then extracted with EtOAc. The organic layer was washed with brine dried over magnesium sulfate, filtered and concentrated. The residue was flash chromatographed (3% EtOAc/Haptanes) to obtain 1.51 g (98%) of 5-bromobenzo[d]isothiazole as a white solid. $^1$H NMR (400 MHz, CDCl3) δδ ppm 7.61 (dd, J=8.58, 1.76 Hz, 1 H) 7.83 (d, J=8.58 Hz, 1 H) 8.20 (d, J=1.37 Hz, 1 H) 8.84 (s, 1 H), LC-MS @ 214.0, 216.0 (M+2).

To a solution of 1.51 g of 5-bromobenzo[d]isothiazole and 825.0 mg of 1,1'-cis(diphenylphosphino)ferrocene]dichloropalladium(II) in 35 mL methanol in a small Parr bottle was added sodium acetate (1.74 g) and DMF (543 μL). The mixture was degassed several times with nitrogen, then shaken under an atmosphere of CO (40 psi) at 50 degrees for 18 hours. The solution was filtered and concentrated. The residue was flash chromatographed (0-20% EtOAc/Haptanes gradient) to yield 61.0 mg (5%) of methyl benzo[d]isothiazole-5-carboxylate as a white solid. $^1$H NMR (400 MHz, CD3OD) δ ppm 3.96 (s, 3 H) 8.17 (d, J=0.98 Hz, 2 H) 8.84 (s, 1 H) 9.08 (s, 1 H); LC-MS @ 194.1 (M+1).

61 mg of methyl benzo[d]isothiazole-5-carboxylate was dissolved in 1.26 mL methanol and treated with 1.26 mL 10% aqueous sodium hydroxide. The mixture was stirred 18 h at room temperature. The reaction mixture was concentrated, and then diluted with water. Acidified to pH ~3 and collected the precipitate by filtration. The filtercake was washed with water. The solid was then dried under high vacuum to yield 48 mg of benzo[d]isothiazole-5-carboxylic acid as a white solid. $^1$H NMR (400 MHz, DMSO-d6) δδ ppm 8.08 (dd, J=8.49, 1.46 Hz, 1 H) 8.31 (d, J=8.58 Hz, 1 H) 8.79 (s, 1 H) 9.24 (d, J=0.78 Hz, 1 H).

Acid Preparation 32

7-methylbenzo[d]isothiazole-5-carboxylic acid

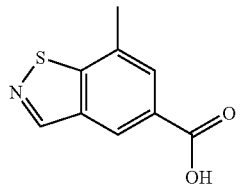

To a stirred solution of 5-bromo-2-fluoro-1,3-dimethylbenzene (5.0 g, 25 mmol) in carbon tetrachloride (100.0 mL) was added N-bromosuccinimide (4.11 g, 23.1 mmol) and benzoyl peroxide (100.0 mg, 0.017 mmol). The reaction was heated at reflux for 7 hours. The reaction was filtered and the filtrate washed with 2N HCl, saturated aqueous sodium bicarbonate, water and brine. The organic phase was dried over sodium sulfate, filtered and concentrated. The residue was flash chromatographed (5% EtoAc/Haptanes) to obtain 6.56 g of 5-bromo-1-(bromomethyl)-2-fluoro-3-methylbenzene as an oil product. $^1$H NMR (400 MHz, CDCl3) δ ppm 2.22-2.36 (s, 3 H) 4.42 (d, J=0.98 Hz, 2 H) 7.21-7.37 (m, 2 H)

To a stirred solution of 5-bromo-1-(bromomethyl)-2-fluoro-3-methylbenzene (6.56 g, 23.3 mmol) in acetone (150.0 mL) was added sodium bicarbonate (2.44 g, 29.1 mmol) and water (250.0 mL). The reaction was refluxed overnight. The reaction was cooled to room temperature and extracted 3× with ethyl acetate. The organic extracts were combined and washed with brine, dried over sodium sulfate and concentrated. The resultant oil was flash chromatographed (80 g silica, 5-10% ethyl acetate/hexanes gradient) to yield 2.5 g of (5-bromo-2-fluoro-3-methylphenyl)methanol as a white solid.

To a stirred suspension of pyridinium chlorochromate (3.77 g, 17.1 mmol) and silica gel in 25 ml dichloromethane was added a solution of (5-bromo-2-fluoro-3-methylphenyl)methanol in 25 mL dichloromethane. The reaction was stirred for 30 minutes at room temperature. Added additional silica gel and concentrated to adsorb reaction products onto the silica gel. Flash chromatographed (80 g silica, 5-10% ethyl acetate/hexanes gradient) to yield 2.1 g of 5-bromo-2-fluoro-3-methylbenzaldehyde as a white solid. $^1$H NMR (400 MHz, CDCl3) δ ppm 2.31 (d, J=2.15 Hz, 3 H) 7.42-7.63 (m, 1 H) 7.77 (dd, J=5.46, 2.34 Hz, 1 H) 10.27 (s, 1 H).

The synthesis of 7-methylbenzo[d]isothiazole-5-carboxylic acid was completed analogous to the carbonylation method described in Acid Preparation 31.

Acid Preparation 33

6-bromo-4-fluoro-1H-benzo[d]imidazole

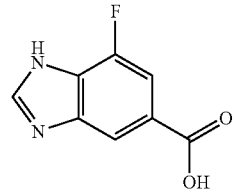

5-bromo-3-fluorobenzene-1,2-diamine (0.2 g, 0.975 mmol) was mixed with 1 ml water followed by formic acid (0.1 mL, 3 mmol). The dark brown mixture was stirred at 100° C. for 6 hours. The reaction was cooled to room temperature and treated with 3 mL 1 N KOH (cold) and the precipitated solids were collected by filtration and air dried overnight to yield 162 mg of 6-bromo-4-fluoro-1H-benzo[d]imidazole as a light pink solid. LC/MS @ 215 (M+H).

The synthesis of 6-bromo-4-fluoro-1H-benzo[d]imidazole was completed analogous to the carbonylation method described in Acid Preparation 31.

Acid Preparation 34

7-methoxy-2-methylbenzo[d]oxazole-5-carboxylic acid

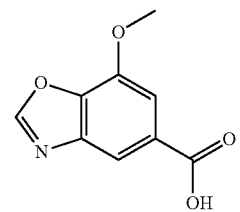

To a vigorously stirred suspension of 4-hydroxy-3-methoxy-5-nitrobenzaldehyde (47.0 g, 238 mmol) in EtOAc (450 mL) at room temperature, anhydrous aluminum chloride (38.1 g, 286 mmol) was added in one portion. Then pyridine (77 mL, 954 mmol) was added dropwise at 45-50° C. for 30 minutes. The reaction mixture was refluxed for 2 hours and allowed to cool down to 60° C. The reaction mixture was carefully poured into ice/concentrated HCl mixture (265 mL). After stirring at 50° C. for 1 hour, the reaction mixture was cooled to 0° C. The formed precipitate was separated by filtration, washed with water, and vacuum-dried to afford 3,4-dihydroxy-5-nitrobenzaldehyde (29.4 g, 161 mmol, 67.3% yield).

A solution of sodium chlorite (47.6 g, 526 mmol) in water (350 mL) was added dropwise to a solution of 3,4-dihydroxy-5-nitrobenzaldehyde (68.8 g, 376 mmol) and sodium dihydrogen phosphate (45.1 g, 376 mmol) in DMSO/H$_2$O mixture (375 mL/150 mL) at room temperature for 1.5 hours. The reaction mixture was stirred at room temperature for 1 hour and poured into a separatory funnel containing a 5% solution NaHCO$_3$ (500 mL). The product was extracted with dichloromethane (3×100 mL). The water layer was acidified with concentrated HCl to pH~1 and extracted with ether (3×250 mL). The combined organic layers were washed with brine (200 mL), dried over Na$_2$SO$_4$, and evaporated to afford 3,4-dihydroxy-5-nitrobenzoic acid (70.3 g, 353 mmol, 94% yield).

Thionyl chloride (6.07 mL, 83 mmol) was added dropwise to a stirred solution of 3,4-dihydroxy-5-nitrobenzoic acid (14.4 g, 72.3 mmol) in MeOH (70 mL) at room temperature for 1 hour. The reaction mixture was refluxed for 3 hours and concentrated with the use of a rotary evaporator. The residue was recrystallized from water and vacuum-dried to afford ester methyl 3,4-dihydroxy-5-nitrobenzoate (11.0 g, 51.6 mmol, 71.4% yield).

To a stirred solution of methyl 3,4-dihydroxy-5-nitrobenzoate (11.9 g, 55.8 mmol) in EtOH (200 mL), 4M HCl in dioxane (13.96 mL, 55.8 mmol) and 10% palladium on carbon (4.0 g, 3.76 mmol) were added. The reaction mixture was hydrogenated at atmospheric pressure of $H_2$ for 3 hours (TLC-monitoring). The resulting mixture was filtered and concentrated with the use of a rotary evaporator. The residue was triturated with ether (100 mL). The precipitate was filtered off and vacuum-dried to afford methyl 3-amino-4,5-dihydroxybenzoate hydrochloride (12.0 g, 54.6 mmol, 98% yield).

To stirred triethyl orthoacetate (35.0 mL, 190 mmol), 3-amino-4,5-dihydroxybenzoate hydrochloride (6.00 g, 27.3 mmol) was added. The stirred suspension was refluxed for 20 minutes and cooled to room temperature. The reaction mixture was poured into hexane (200 mL). The formed precipitate was separated by filtration and vacuum-dried to afford benzoxazole methyl 7-hydroxy-2-methyl-1,3-benzoxazole-5-carboxylate (4.98 g, 24.04 mmol, 88% yield). $^1$H NMR (400 MHz, DMSO-d6): δ 10.74 (br. s, 1H), 7.66 (d, J=1.4 Hz, 1H), 7.43 (d, J=1.4 Hz, 1H), 3.85 (s, 3H), 2.62 (s, 3H).

Methyl 7-methoxy-2-methyl-1,3-benzoxazole-5-carboxylate (365 mg) was dissolved in 16 mL ethanol and 3.3 mL of 1 M lithium hydroxide was added. Reaction was heated at 60° C. overnight. Volatiles were removed under vacuum and the residue dissolved in water and acidified with 1 M HCl to pH3. Collected the tan solid by filtration and washed with water. Air dried to yield 221 mg (65%) of 7-hydroxy-2-methyl-1,3-benzoxazole-5-carboxylic acid LC/MS=208 (M+H).

To methyl 7-hydroxy-2-methyl-1,3-benzoxazole-5-carboxylate (400 mg, 2.07 mmol) in DMF (10 mL) was added ground potassium carbonate (570 mg, 4.14 mmol) and methyl iodide (0.142 mL, 2.28 mmol). The reaction was stirred overnight at room temperature. The reaction was diluted with ethyl acetate and washed with water. Organic phase was dried over sodium sulfate, filtered and concentrated to yield 368 mg (73%) of methyl 7-methoxy-2-methyl-1,3-benzoxazole-5-carboxylate as an off white solid. LC/MS=222 (M+H).

Acid Preparation 35

7-Methoxy-2-methylbenzo[d]oxazole-5-carboxylic Acid

The synthesis of 7-methoxy-2-methylbenzo[d]oxazole-5-carboxylic acid may be completed using the hydrolysis method described in Acid Preparation 31.

EXAMPLES

The compounds of Formula (1) exemplified in Tables 1-25 below were prepared by one of the following methods using the appropriate carboxylic acids and spirocyclic ketones:

Method A: To a flask was added the appropriate amine or amine hydrochloride (1 equivalent), DMF, DMSO or $CH_2Cl_2$ (about 0.1 M), carboxylic acid, N,N-diisopropylethylamine (DIEA) (4-6 equivalents) or triethylamine (TEA) (4-6 equivalents) and 2-(7-aza-1H-benzotriazole-1-yl)-1,1,3,3-tetramethyluronium hexafluorophosphate (HATU) (1-1.3 equivalents) or 1-ethyl-3-(3'-dimethylaminopropyl)carbodiimide (EDCI) (1 equivalent) with or without N-Hydroxybenzotriazole (HOBt) (1 equivalent). The mixture was stirred at room temperature until the reaction was complete as determined by LC/MS. The mixture was diluted with ethyl acetate or $CH_2Cl_2$ and washed with either saturated aqueous $NaHCO_3$ (2×) or aqueous NaOH (0.5 M solution) and then saturated aqueous NaCl. The organic extract was dried over $MgSO_4$, filtered and concentrated. The crude material was purified by liquid chromatography to afford product.

Method B: A mixture of carboxylic acid (1 equivalent), 2-chloro-4,6-dimethoxy-1,3,5-triazine (1 equivalent) and N-methylmorpholine (NMM) (1 equivalent) in DMF and/or THF was stirred at room temperature for 1 hour before addition of the amine (1 equivalent) as well as additional NMM (1 equivalent). The resultant mixture was stirred overnight at room temperature. The solution was diluted with EtOAc and washed with saturated aqueous $NH_4Cl$. The layers were separated and the aqueous layers were washed with EtOAc. The combined organic extract was dried over $MgSO_4$, filtered and concentrated under reduced pressure. The crude material was purified by chromatography.

Method C: To the carboxylic acid (1.5 equivalents) in $CH_2Cl_2$ (0.1 M) was added N-(3-dimethylaminopropyl)-N'-ethylcarbodiimide (1.5 equivalents) and hydroxybenzotriazole (1.5 eq). After stirring for approximately 5 minutes, a solution of the amine (1 equivalent) in $CH_2Cl_2$ (0.1 M) and triethylamine (1.5 equivalents) was added. The mixture was stirred at room temperature until the reaction was complete as determined by LC/MS. The reaction was washed with water, saturated aqueous $NaHCO_3$, saturated aqueous NaCl, dried over $Na_2SO_4$, filtered and concentrated. The crude material was purified by liquid chromatography to afford product.

Method D: To reaction vials containing the carboxylic acid (125 umol) was added DMF (0.5 mL) and 2-chloro-4,6-dimethoxy-1,3,5-triazine (125 umol) in THF (0.5 mL) followed by NMM (2 equivalents). The vials were sonicated and vortexed to insure solubilization of materials. The vials were shaken at room temperature for 1.75 hours after which time was added a suspension of the amine salt (1 equivalent) in 3:1 DMF/THF followed by NMM. The mixture was shaken at room temperature overnight. The solvents were removed under reduced pressure. To the residue was added EtOAc (2.5 mL) and saturated aqueous $NH_4Cl$ (1 mL). The vials were vortexed and centrifuged. The organic phase was transferred into pre-weighed vials, solvents were then removed under reduced pressure. Samples were purified by HPLC using a Waters system equipped with a Symmetry C8 4.6×50 mm 3.5 um particle size column.

High Performance Liquid Chromatography (HPLC) Analytical Conditions:

Method LC-1: Column: Waters ACQUITY Ultra Performance LC® BEH $C_{18}$ column, 2.1×30 mm, 1.7 μm, 0.05% TFA 95/5 to 5/95 water/acetonitrile, flow rate: 1.3 mL/minute, run time: 1.1 minutes.

Method LC-2: Column: Waters XTerra® $C_{18}$ 4.6×50 mm, 3.5 μm column. Solvents A and B are Water w/0.1% TFA and acetonitrile w/0.1% TFA, respectively. 9 minute total method time with 5% B to 95% B over 5.83 minutes. Mass spectral data were acquired from 180-850 amu in electrospray positive mode. Flow rate 2.0 mL/minute.

Method LC-3: Column: HALO® $C_{18}$ 3.0×30 mm, 2.7 μm HPLC column. Solvents A and B are Water w/0.05% TFA and acetonitrile w/0.05% TFA, respectively. 2.5 minute total method time with 5% B to 95% B over 2.30 minutes and then a hold at 95% B for 0.2 minute. Mass spectral data were acquired from 160-650 amu in electrospray positive mode. Flow rate 1.5 mL/minute.

TABLE 1

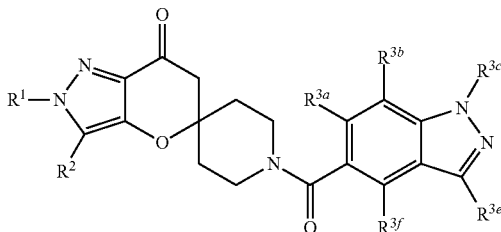

| Ex. | Method | R¹ | R² | R³ᵃ | R³ᵇ | R³ᶜ | R³ᵉ | R³ᶠ |
|---|---|---|---|---|---|---|---|---|
| 1.001 | B | CH₂CH₃ | CH₃ | H | CH₃ | H | CH₃ | H |
| | | ¹H NMR (400 MHz, METHANOL-d₄) δ ppm 1.16(t, J = 7.06 Hz, 1 H) 1.38(t, J = 7.27 Hz, 1 H) 1.77(br. s., 1 H) 2.27(s, 1 H) 2.45-2.62(m, 2 H) 2.73(br. s., 1 H) 3.39-3.58(m, 1 H) 3.66(br. s., 1 H) 4.04-4.22(m, 1H) 4.43(br. s., 1 H) 4.89(s, 2 H) 7.21(s, 1 H) 7.65(s, 1 H), MS ES+ m/z 422 (MH+), HPLC (Method LC-1) Retention time = 0.38 minutes. | | | | | | |
| 1.002 | B | CH(CH₃)₂ | H | H | CH₃ | H | CH₃ | H |
| | | ¹H NMR (400 MHz, METHANOL-d₄) δ ppm 1.10-1.20(m, 1 H) 1.38-1.51(m, 2 H) 2.50-2.57(m, 6 H) 2.70-2.79(m, 2 H) 3.42-3.52(m, 2 H) 4.45-4.55(m, 1 H) 7.20(s, 1 H) 7.49(s, 1 H) 7.65(s, 1 H), MS ES+ m/z 422 (MH+), HPLC (Method LC-1) Retention time = 0.46 minutes. | | | | | | |
| 1.003 | B | CH₂CH₃ | H | H | CH₃ | H | CH₃ | H |
| | | ¹H NMR (400 MHz, METHANOL-d₄) δ ppm 1.44(t, J = 7.27 Hz, 3 H) 1.78(br. s., 2 H) 2.06(br. s., 3 H) 2.54(s, 3 H) 2.54(s, 3 H) 2.75(s, 2 H) 4.17(q, J = 7.27 Hz, 2 H) 7.20, 1 H) 7.46(s, 1 H) 7.64(s, 1 H), MS ES+ m/z 408 (MH+), HPLC (Method LC-1) Retention time (s = 0.34 minutes. | | | | | | |
| 1.004 | B | CH₂CH₂CH₃ | H | H | CH₃ | H | CH₃ | H |
| | | ¹H NMR (400 MHz, METHANOL-d₄) δ ppm 0.89(t, J = 7.48 Hz, 3 H) 2.54(d, J = 2.49 Hz, 6 H) 2.76(s, 3 H) 4.09(t, J = 7.06 Hz, 2 H) 7.20(s, 1 H) 7.46(s, 1 H) 7.65(s, 1 H), MS ES+ m/z 422 (MH+), HPLC (Method LC-1) Retention time = 0.38 minutes. | | | | | | |
| 1.005 | B | CH₃ | CH₃ | H | CH₃ | H | CH₃ | H |
| | | ¹H NMR (400 MHz, METHANOL-d₄) δ ppm 1.63-1.90(m, 2 H) 1.90-2.22(m, 2 H) 2.25(s, 3 H) 2.54(d, J= 2.49 Hz, 6 H) 2.73(s, 2 H) 3.46(br. s., 1 H) 3.64(br. s., 1 H) 3.79(s, 3 H) 4.43(br. s., 1 H) 7.21(s, 1 H) 7.65(s, 1 H), MS ES+ m/z 408 (MH+), HPLC (Method LC-1) Retention time = 0.36 minutes. | | | | | | |
| 1.006 | B | CH₃ | H | H | CH₃ | H | CH₃ | H |
| | | ¹H NMR (400 MHz, CHLOROFORM-d) δ ppm 2.62(s, 3 H) 2.57(s, 3 H) 2.69(s, 2 H) 3.92(s, 4 H) 7.09(s, 1 H) 7.19(s, 1 H) 7.59(s, 1 H), MS ES+ m/z 394 (MH+), HPLC (Method LC-1) Retention time = 0.32 minutes. | | | | | | |
| 1.007 | B | CH₃ | CH₂CH₃ | H | CH₃ | H | CH₃ | H |
| | | ¹H NMR (500 MHz, TFA δ ppm 1.60(t, J = 7.68 Hz, 3 H) 2.81(s, 3 H) 3.05(s, 3 H) 3.06-3.13(m, 2 H) 3.25(s, 2 H) 4.32(s, 3 H) 7.82(s, 1 H) 8.20(s, 1 H), MS ES+ m/z 422 (MH+), HPLC (Method LC-1) Retention time = 0.36 minutes. | | | | | | |
| 1.008 | B | cyclohexyl-C(CH₃)- | | H | H | CH₃ | H | CH₃ | H |
| | | ¹H NMR (400 MHz, METHANOL-d₄) δ ppm 1.21-1.55 (complex, 4 H) 1.66-2.26 (complex, 14 H) 2.56(s, 3 H) 2.56(s, 3 H) 2.77(s, 2 H) 4.06-4.23(m, 1 H) 7.22(s, 1 H) 7.51(s, 1 H) 7.67(s, 1 H), MS ES+ m/z 462(MH+), HPLC (Method LC-1) Retention time = 0.45 minutes. | | | | | | |
| 1.009 | B | cyclopentyl-C(CH₃)- | | H | H | CH₃ | H | CH₃ | H |
| | | ¹H NMR (400 MHz, METHANOL-d₄) δ ppm 1.60-2.24 (complex, 14 H) 2.54(s, 3 H) 2.54(s, 3 H) 2.75(s, 2 H) 4.61-4.74(m, 1 H) 7.20(s, 1 H) 7.48(s, 1 H) 7.64(s, 1 H), MS ES+ m/z 448 (MH+), HPLC (Method LC-1) Retention time = 0.42 minutes. | | | | | | |
| 1.010 | B | cyclobutyl-C(CH₃)- | | H | H | CH₃ | H | CH₃ | H |
| | | ¹H NMR (400 MHz, METHANOL-d₄) δ ppm 1.68-1.93 (complex, 5 H) 1.96-2.25 (complex, 3 H) 2.37-2.48 (complex, 3 H) 2.54(s, 3 H) 2.54(s, 3 H) 2.76 (s, 2 H) 4.76-4.86(m, 1 H) 7.20(s, 1 H) 7.51(s, 1 H) 7.64(s, 1 H), MS ES+ m/z 434 (MH+), HPLC (Method LC-1) Retention time = 0.41 minutes. | | | | | | |

TABLE 1-continued

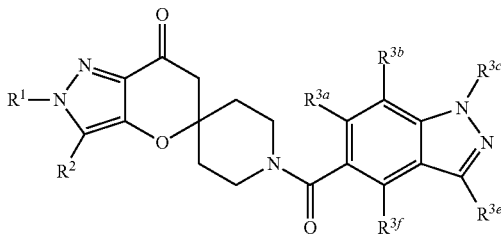

| Ex. | Method | R¹ | R² | R³ᵃ | R³ᵇ | R³ᶜ | R³ᵉ | R³ᶠ |
|---|---|---|---|---|---|---|---|---|
| 1.011 | B | C(CH₃)₃ | CH₃ | H | CH₃ | H | CH₃ | H |
| | | ¹H NMR (400 MHz, METHANOL-d₄) δ ppm 1.62(s, 9 H) 1.78(s, 2 H) 2.43(s, 3 H) 2.54(d, J = 2.91 Hz, 6 H) 2.72(s, 2 H) 7.21(s, 1 H) 7.66(s, 1 H), MS ES+ m/z 450(MH+), HPLC (Method LC-1) Retention time = 0.4 minutes. | | | | | | |
| 1.012 | B | C(CH₃)₃ | H | H | CH₃ | H | CH₃ | H |
| | | ¹H NMR (500 MHz, METHANOL-d₄) δ ppm 1.58(s, 9 H) 2.56(s, 3 H) 2.56(s, 3 H) 2.77(br. s., 2 H) 7.22(s, 1 H) 7.61(s, 1 H) 7.67(s, 1 H), MS ES+ m/z 436 (MH+), HPLC (Method LC-1) Retention time = 0.41 minutes. | | | | | | |
| 1.013 | B | CH(CH₃)₂ | CH₃ | H | CH₃ | H | CH₃ | H |
| | | ¹H NMR (400 MHz, METHANOL-d₄) δ ppm 1.34-1.51(m, 6 H) 1.61-2.37(m, 7 H) 2.54(d, J = 2.15 Hz, 6 H) 2.66-2.82(m, 2 H) 3.05-3.90(m, 4 H) 4.49-4.72 (m, 1 H) 7.21(s, 1 H) 7.65(s, 1 H), MS ES+ m/z 436 (MH+), HPLC (Method LC-1) Retention time = 0.40 minutes. | | | | | | |
| 1.014 | B | cyclopropyl-CH< | CH₃ | H | CH₃ | H | CH₃ | H |
| | | ¹H NMR (500 MHz, METHANOL-d4) δ ppm 1.10(dd, J = 7.32, 1.46 Hz, 2 H) 1.16-1.20(m, 2 H) 2.38(s, 3 H) 2.56-2.59(m, 6 H) 2.76(br. s., 2 H) 3.58-3.62(m, 1 H) 7.24(s, 1 H) 7.68(s, 1 H), MS ES+ m/z 434 (MH+), HPLC (Method LC-1) Retention time = 0.38 minutes. | | | | | | |
| 1.015 | A | tetrahydrofuran-3-yl | CH₃ | H | CH₃ | H | CH₃ | H |
| | | ¹H NMR (400 MHz, CHLOROFORM-d) δ ppm 1.25(br.s., 2 H) 1.67(br. s., 2 H) 2.12(br. s., 2 H) 2.27(s, 3 H) 2.30-2.42(m, 2 H) 2.52(s, 3 H) 2.57(s, 3 H) 2.69(s, 2 H) 3.38(br. s., 2 H) 3.78(s, 1 H) 3.90-4.03(m, 1 H) 4.09-4.20(m, 2 H) 4.80-4.90(m, 1 H) 7.20(s, 1 H) 7.60(s, 1 H), MS ES+ m/z 464 (MH+), HPLC (Method LC-1) Retention time = 0.35 minutes. | | | | | | |
| 1.016 | A | tetrahydrofuran-3-yl | H | H | CH₃ | H | CH₃ | H |
| | | ¹H NMR (400 MHz, CHLOROFORM-d) δ ppm 1.40(t, J = 7.22 Hz, 2 H) 2.03(br. s., 2 H) 2.34(br. s., 1 H) 2.41-2.50(m, 1 H) 2.52(s, 3 H) 2.56(s, 3 H) 2.70(s, 2 H) 3.04-3.17(m, 1 H) 3.37(br. s., 2 H) 3.78(s, 1 H) 3.85-3.95(m, 1 H) 3.97-4.04(m, 1 H) 4.03-4.16(m, 2 H) 4.97(br. s., 2 H) 7.19(s, 2 H) 7.21(s, 1 H) 7.59(s, 1 H), MS ES+ m/z 450 (MH+), HPLC (Method LC-1) Retention time = 0.33 minutes. | | | | | | |
| 1.017 | B | CH(CH₃)₂ | H | H | CH₃ | H | CH₂CH₃ | H |
| | | ¹H NMR (400 MHz, METHANOL-d₄) δ ppm 1.36(t, J = 7.48 Hz, 2 H) 1.43(d, J = 6.65 Hz, 1 H) 1.47(d, J = 6.65 Hz, 2 H) 2.27(s, 1 H) 2.54(s, 2 H) 2.70-2.79 (m, 1 H) 2.99(q, J = 7.62 Hz, 2 H) 3.43-3.52(m, 1 H) 4.44-4.56(m, 1 H) 7.20 (s, 1 H) 7.49(s, 1 H) 7.68(s, 1 H), MS ES+ m/z 436 (MH+), HPLC (Method LC-1) Retention time = 0.40 minutes. | | | | | | |
| 1.018 | B | CH₂CH₃ | CH₃ | H | OCH₂CH₃ | H | CH₂CH₃ | H |
| | | ¹H NMR (500 MHz, METHANOL-d₄) δ ppm 1.29-1.55(m, 5 H) 2.30(s, 3 H) 2.58(s, 3 H) 2.77(br. s., 2 H) 2.92-3.11(m, 2 H) 4.17(q, J = 7.32 Hzz, 2 H) 7.24 (s, 1 H) 7.72(s, 1 H), MS ES+ m/z 452 (MH+), HPLC (Method LC-1) Retention time = 0.39 minutes. | | | | | | |
| 1.019 | B | CH₂CH₃ | H | H | CH₃ | H | CH₂CH₃ | H |
| | | ¹H NMR (500 MHz, METHANOL-d₄) δ ppm 1.39(t, J = 7.56 Hz, 3 H) 1.47(t, J = 7.32 Hz, 3 H) 2.57(s, 3 H) 2.79(br. s., 1 H) 3.02(q, J = 7.56 Hz, 2 H) 4.20(q, J = 7.16 Hz, 2 H) 7.23(s, 1 H) 7.49(s, 1 H) 7.71(s, 1 H), MS ES+ m/z 422 (MH+), HPLC (Method LC-1) Retention time = 0.36 minutes. | | | | | | |

TABLE 1-continued

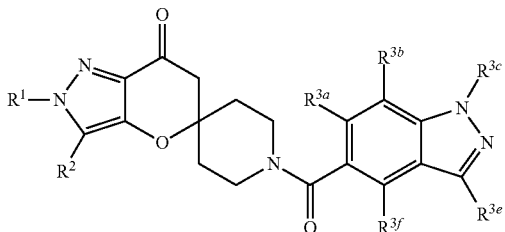

| Ex. | Method | R¹ | R² | R$^{3a}$ | R$^{3b}$ | R$^{3c}$ | R$^{3e}$ | R$^{3f}$ |
|---|---|---|---|---|---|---|---|---|
| 1.020 | A | C(CH$_3$)$_3$ | H | H | CH$_3$ | H | CH$_2$CH$_3$ | H |

$^1$H NMR (400 MHz, DMSO-d$_6$) δ ppm 1.26(t, J = 7.48 Hz, 3 H) 1.47(s, 9 H) 2.71 (s, 2 H) 2.89(q, J = 7.62 Hz, 2 H) 7.11(s, 1 H) 7.59(s, 1 H) 7.76(s, 1 H) 12.85 (s, 1 H), MS ES+ m/z 450 (MH+), HPLC (Method LC-1) Retention time = 0.44 minutes.

| 1.021 | A | 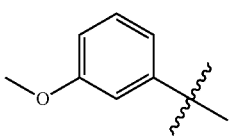 | H | H | CH$_3$ | H | H | H |

$^1$H NMR (400 MHz, METHANOL-d$_4$) δ ppm 2.58(br. s., 2H) 2.86(br. s., 1 H) 3.81-3.88(m, 2 H) 6.92-6.97(m, 1 H) 7.03-7.09(m, 1 H) 7.23(br. s. 1 H) 7.32-7.42(m, 2 H) 7.72(s, 1 H) 8.10(s, 1H), MS ES+ m/z 472 (MH+), HPLC (Method LC-1) Retention time = 0.41 minutes.

| 1.022 | B | CH(CH$_3$)$_2$ | H | H | CH$_3$ | H | H | H |

$^1$H NMR (400 MHz, METHANOL-d$_4$) δ ppm 1.22(t, J = 7.27 Hz, 1 H) 1.43(d, J = 6.65 Hz, 2 H) 1.47(d, J = 7.06 Hz, 3 H) 1.99(s, 1 H) 2.27(s, 1 H) 2.58(s, 4 H) 2.71-2.79(m, 2 H) 4.46-4.55(m, 1 H) 4.56-4.63(m, 1 H) 7.22(s, 1 H) 7.49 (s, 1 H) 7.71(s, 1 H) 8.10(s, 1 H), MS ES+ m/z 408 (MH+), HPLC (Method LC-1) Retention time = 0.36 minutes.

| 1.023 | B | CH$_2$CH$_3$ | CH$_3$ | H | CH$_3$ | H | H | H |

$^1$H NMR (400 MHz, METHANOL-d$_4$) δ ppm 1.38(t, J = 7.27 Hz, 3 H) 1.77(br. s., 2 H) 2.27(s, 3 H) 2.58(s, 3 H) 2.73(s, 2 H) 4.14(q, J = 7.34 Hz, 2 H) 7.23(s, 1 H) 7.71(s, 1 H) 8.10(s, 1 H), MS ES+ m/z 408 (MH+), HPLC (Method LC-1) Retention time = 0.37 minutes.

| 1.024 | A | 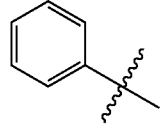 | H | H | CH$_3$ | H | H | H |

MS m/z ES⁺ 442 (MH⁺), HPLC (Method LC-1) Retention time = 0.41 minutes.

| 1.025 | B | CH$_2$CH$_3$ | H | H | CH$_3$ | H | H | H |

$^1$H NMR (400 MHz, METHANOL-d$_4$) δ ppm 1.44(t, J = 7.27 Hz, 3 H) 2.53-2.63 (m, 4 H) 2.75(s, 3 H) 4.05-4.25(m, 4 H) 7.22(s, 1 H) 7.46(s, 1 H) 7.71(s, 1 H) 8.10(s, 1 H), MS ES+ m/z 394 (MH+), HPLC (Method LC-1) Retention time = 0.32 minutes.

| 1.026 | A | CH$_2$CF$_3$ | CH$_3$ | H | CH$_3$ | H | H | H |

$^1$H NMR (400 MHz, METHANOL-d$_4$) δ ppm 2.31(s, 4 H) 2.58(s, 4 H) 2.79(s, 2 H) 4.96(q, J = 8.44 Hz, 2 H) 7.22(s, 1 H) 7.71(s, 1 H) 8.10(s, 1 H), MS ES+ m/z 462 (MH+), HPLC (Method LC-1) Retention time = 0.38 minues

| 1.027 | B | CH$_2$CH$_2$CH$_3$ | H | H | CH$_3$ | H | H | H |

$^1$H NMR (400 MHz, METHANOL-d$_4$) δ ppm 0.89(t, J = 7.27 Hz, 3 H) 1.62-1.97 (m, 5 H) 2.58(s, 3 H) 2.66-2.87(m, 2 H) 4.09(t, J = 7.06 Hz, 2 H) 7.22(s, 1 H) 7.45(s, 1 H) 7.71(s, 1 H) 8.10(s, 1 H), MS ES+ m/z 408 (MH+), HPLC (Method LC-1) Retention time = 0.36 minutes.

| 1.028 | A | 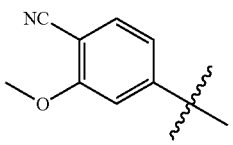 | CH$_3$ | H | CH$_3$ | H | H | H |

MS(ACPI) m/z AP⁺ 511 (M+ H)⁺; AP⁻ 509 (M − H)⁻, HPLC (Method LC-1) Retention time = 0.41 minutes.

| 1.029 | A | CH$_3$ | H | H | CH$_3$ | H | H | H |

$^1$H NMR (400 MHz, DMSO-d$_6$) δ ppm 1.65-1.74(m, 2 H) 2.50(s, 3 H) 2.71(s, 2 H) 3.83(s, 3 H) 7.14(s, 1 H) 7.56(s, 1 H) 7.62(s, 1 H) 8.09(d, J = 1.61 Hz, 1 H) 13.28(s, 1 H), MS ES+ m/z 380 (MH+), HPLC (Method LC-1) Retention time = 0.29 minutes.

TABLE 1-continued

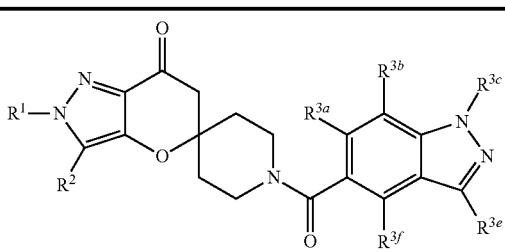

| Ex. | Method | R$^1$ | R$^2$ | R$^{3a}$ | R$^{3b}$ | R$^{3c}$ | R$^{3e}$ | R$^{3f}$ |
|---|---|---|---|---|---|---|---|---|
| 1.030 | A | CH$_3$ | CH$_3$ | H | CH$_3$ | H | H | H |

$^1$H NMR (400 MHz, CHLOROFORM-d) δ ppm 2.22(s, 3 H) 2.56(s, 3 H) 2.67(s, 2 H) 3.82(s, 3 H) 7.23(s, 1 H) 7.66(s, 1 H) 8.11(s, 1 H), MS ES+ m/z 394 (MH+), HPLC (Method LC-1) Retention time = 0.32 minutes.

| 1.031 | A | 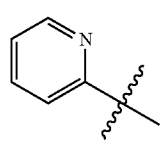 | | H | H | CH$_3$ | H | H | H |
|---|---|---|---|---|---|---|---|---|

MS(ACPI) m/z 443 (M + H)$^+$, HPLC (Method LC-1) Retention time = 0.61 minutes.

| 1.032 | A | 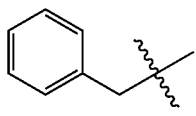 | | H | H | CH$_3$ | H | H | H |
|---|---|---|---|---|---|---|---|---|

$^1$H NMR (400 MHz, CHLOROFORM-d) δ ppm 2.65(s, 3 H) 2.70(s, 2 H) 7.03(s, 1 H) 7.26-7.37(m, 5 H) 7.69(s, 1 H) 8.22(s, 1 H), MS ES+ m/z 456 (MH+), HPLC (Method LC-1) Retention time = 0.40 minutes.

| 1.033 | A | 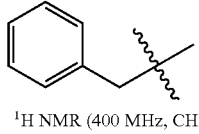 | CH$_3$ | H | CH$_3$ | H | H | H |
|---|---|---|---|---|---|---|---|---|

$^1$H NMR (400 MHz, CHLOROFORM-d) δ ppm 2.12(s, 3 H) 2.59(s, 3 H) 2.70(s, 2 H) 7.15-7.20(m, 2 H) 7.25-7.26(m, 1 H) 7.26-7.35(m, 3 H) 7.66(s, 1 H) 8.13(s, 1 H), MS ES+ m/z 470 (MH+), HPLC (Method LC-1) Retention time = 0.42 minutes.

| 1.034 | A | 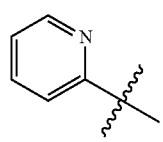 | CH$_3$ | H | CH$_3$ | H | H | H |
|---|---|---|---|---|---|---|---|---|

$^1$H NMR (400 MHz, CHLOROFORM-d) δ ppm 2.61(s, 3 H) 2.64(s, 3 H) 7.28(s, 2 H) 7.69(s, 1 H) 7.79-7.86(m, 1 H) 8.00(d, J = 8.31 Hz, 1 H) 8.15(s, 1 H) 8.45 (d, J = 4.98 Hz, 1 H), MS ES+ m/z 457 (MH+), HPLC (Method LC-1) Retention time = 0.61 minutes.

| 1.035 | B | CH$_3$ | CH$_2$CH$_3$ | H | CH$_3$ | H | H | H |
|---|---|---|---|---|---|---|---|---|

$^1$H NMR (400 MHz, METHANOL-d$_4$) δ ppm 1.16(t, J = 7.06 Hz, 2 H) 1.28(t, J = 7.69 Hz, 3 H) 1.63-2.34(m, 3 H) 2.47-2.66(m, 3 H) 2.73(q, J = 7.62 Hz, 4 H) 3.47(q, J = 7.06 Hz, 2 H) 3.75-3.93(m, 3 H) 4.46(br. s., 2 H) 7.23(s, 1 H) 7.72(s, 1 H) 8.03-8.18(m, 1 H), MS ES+ m/z 408 (M+), HPLC (Method LC-1) Retention time = 0.34 minutes.

| 1.036 | A | 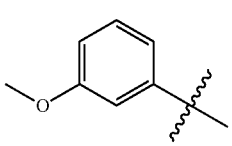 | CH$_3$ | H | CH$_3$ | H | H | H |
|---|---|---|---|---|---|---|---|---|

$^1$H NMR (400 MHz, METHANOL-d$_4$) δ ppm 2.29-2.31(m, 3 H) 2.57-2.60(m, 3 H) 2.83(s, 2 H) 3.83(s, 3H) 7.05-7.08(m, 3 H) 7.24(s, 1 H) 7.40-7.47(m, 1 H) 7.73(s, 1 H) 8.11(s, 1 H), MS ES+ m/z 486 (MH+), HPLC (Method LC-1) Retention time = 0.42 minutes.

TABLE 1-continued

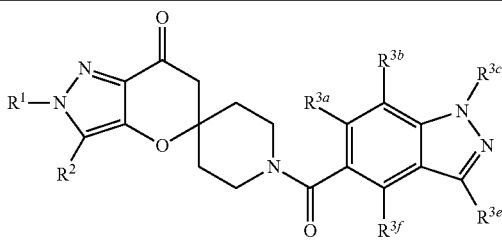

| Ex. | Method | R¹ | R² | R³ᵃ | R³ᵇ | R³ᶜ | R³ᵉ | R³ᶠ |
|---|---|---|---|---|---|---|---|---|
| 1.037 | B | cyclohexyl-C(CH₃)₂- | H | H | CH₃ | H | H | H |

¹H NMR (400 MHz, METHANOL-d₄) δ ppm 1.58(s, 9 H) 1.77(br. s., 2 H) 2.12 (br. s., 2 H) 2.60(s, 3 H) 2.77(s, 2 H) 7.24(s, 1 H) 7.61(s, 1 H) 7.73(s, 1 H) 8.12(s, 1 H), MS ES+ m/z 448 (MH+), HPLC (Method LC-1) Retention time = 0.44 minutes.

| 1.038 | B | cyclopentyl-C(CH₃)₂- | H | H | CH₃ | H | H | H |

¹H NMR (400 MHz, METHANOL-d₄) δ ppm 1.66-2.29 (complex, 14 H) 2.58(s, 3 H) 2.77(s, 2 H) 4.63-4.79(m, 1 H) 7.24(s, 1 H) 7.51(s, 1 H) 7.73(s, 1 H) 8.12(s, 1 H), MS ES+ m/z 434 (MH+), HPLC (Method LC-1) Retention time = 0.41 minutes.

| 1.039 | B | cyclobutyl-C(CH₃)₂- | H | H | CH₃ | H | H | H |

¹H NMR (400 MHz, METHANOL-d₄) δ ppm 1.68-1.96 (complex, 5 H) 1.99-2.30(complex, 3 H) 2.40-2.50(complex, 2 H), 2.51-2.57(complex, 2 H) 2.60 (s, 3 H) 2.78(s, 2 H) 4.77-4.87(m, 1 H) 7.24(s, 1 H) 7.53(s, 1 H) 7.73(s, 1 H) 8.12(s, 1 H), MS ES+ m/z 420 (MH+), HPLC (Method LC-1) Retention time = 0.39 minutes.

| 1.040 | B | CH(CH₃)₂ | CH₃ | H | CH₃ | H | H | H |

¹H NMR (400 MHz, METHANOL-d₄) δ ppm 1.43(d, J = 6.65 Hz, 6 H) 1.77(s, 1 H) 2.27(s, 3 H) 2.58(s, 3 H) 2.73(s, 2 H) 4.54-4.63(m, 1 H) 7.23(s, 1 H) 7.71 (s, 1 H) 8.10(s, 1 H), MS ES+ m/z 422 (MH+), HPLC (Method LC-1) Retention time = 0.39 minutes.

| 1.041 | A | tetrahydrofuran-3-yl | CH₃ | H | CH₃ | H | H | H |

¹H NMR (400 MHz, CHLOROFORM-d) δ ppm 1.18-1.32(m, 2 H) 1.67(br. s., 2 H) 2.03(br. s., 2 H) 2.27(s, 3 H) 2.30-2.42(m, 2 H) 2.52(s, 3 H) 2.57(s, 3H) 2.69(s, 2 H) 3.38(br. s., 2 H) 3.78(s, 1 H) 3.97(br. s., 2 H) 4.07-4.21(m, 2 H) 4.80-4.91(m, 1 H) 7.20(s, 1 H) 7.60(s, 1 H), MS ES+ m/z 450 (MH+), HPLC (Method LC-1) Retention time = 0.34 minutes.

| 1.042 | B | C(CH₃)₃ | H | H | CH₃ | H | H | H |

¹H NMR (400 MHz, METHANOL-d₄) δ ppm 1.57(s, 9 H) 2.58(s, 3 H) 2.75(s, 2 H) 7.22(s, 1 H) 7.59(s, 1 H) 7.71(s, 1 H) 8.10(s, 1 H), MS ES+ m/z 422 (MH+), HPLC (Method LC-1) Retention time = 0.39 minutes.

| 1.043 | B | C(CH₃)₃ | CH₃ | H | CH₃ | H | H | H |

¹H NMR (400 MHz, METHANOL-d₄) δ ppm 1.62(s, 9 H) 1.78(s, 2 H) 2.43(s, 3 H) 2.58(s, 3 H) 2.72(s, 2 H) 7.22(s, 1 H) 7.71(s, 1 H) ,8.10(s, 1 H), MS ES+ m/z 436 (MH+), HPLC (Method LC-1) Retention time = 0.43 minutes.

| 1.044 | B | CH(CH₃)₂ | H | H | OCH₃ | H | CH₂CH₃ | H |

¹H NMR (400 MHz, METHANOL-d₄) δ ppm 1.35(t, J = 7.69 Hz, 3 H) 1.40-1.45 (m, 2 H) 1.47(d, J = 6.65 Hz, 4 H) 2.72-2.79(m ,2 H) 2.97(q, J = 7.62 Hz, 2 H) 3.47(q, J = 7.06 Hz, 1 H) 3.97-4.02(m, 3 H) 4.44-4.55(m, 1 H) 4.88(s, 3H) 6.84(s, 1H) 7.40(s, 1 H) 7.49(s, 1 H), MS ES+ m/z 452 (MH+), HPLC (Method LC-1) Retention time = 0.38 minutes.

| 1.045 | B | CH₂CH₃ | CH₃ | H | OCH₃ | H | CH₂CH₃ | H |

¹H NMR (400 MHz, METHANOL-d₄) δ ppm 1.29-1.46(m, 6 H) 2.19-2.36(m, 3 H) 2.74(s, 2 H) 2.97(q, J = 7.62 Hz, 2 H) 4.00(s, 3 H) 4.14(q, J = 7.48 Hz, 2 H) 6.85(s, 1 H) 7.41(s, 1 H), MS ES+ m/z 452 (MH+), HPLC (Method LC-1) Retention time = 0.38 minutes TABLE 1-continued

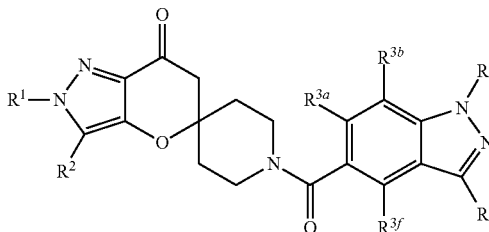

| Ex. | Method | R$^1$ | R$^2$ | R$^{3a}$ | R$^{3b}$ | R$^{3c}$ | R$^{3e}$ | R$^{3f}$ |
|---|---|---|---|---|---|---|---|---|
| 1.046 | B | CH$_2$CH$_3$ | H | H | OCH$_3$ | H | CH$_2$CH$_3$ | H |
| | | $^1$H NMR (400 MHz, METHANOL-d$_4$) δ ppm 1.35(t, J = 7.48 Hz, 3 H) 1.44(t, J = 7.48 Hz, 3 H) 1.80(br. s. , 3 H) 2.76(s, 3 H) 2.96(q, J = 7.62 Hz, 3 H) 4.00(s, 3 H), MS ES+ m/z 438 (MH+), HPLC (Method LC-1) Retention time = 0.36 minutes. | | | | | | | |
| 1.047 | B | C(CH$_3$)$_3$ | H | H | OCH$_3$ | H | CH$_2$CH$_3$ | H |
| | | $^1$H NMR (400 MHz, METHANOL-d$_4$) δ ppm 1.37(t, J = 7.69 Hz, 3 H) 1.58(s, 9 H) 1.82(br. s., 2 H) 2.01(br. s., 3 H) 2.77(s, 2 H) 2.98(q, J = 7.69 Hz, 2 H) 4.02(s, 3 H) 6.86(s, 1 H) 7.42(s, 1 H) 7.60(s, 1 H), MS ES+ m/z 466 (MH+), HPLC (Method LC-1) Retention time = 0.43 minutes. | | | | | | | |
| 1.048 | B | 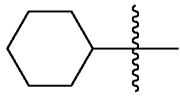 | H | H | OCH$_3$ | H | CH$_2$CH$_3$ | H |
| | | $^1$H NMR (400 MHz, METHANOL-d$_4$) δ ppm 1.23-1.32(m, 1 H) 1.36(t, J = 7.69 Hz, 3 H) 1.39-1.53(m, 2 H) .162-2.30(m, 14 H) 2.77(s, 2 H) 2.98(q, J = 7.69 Hz, 2 H) 4.01(s, 3 H) 4.08-4.20(m, 1 H) 6.85(s, 1 H) 7.42(s, 1 H) 7.50(s, 1 H), MS ES+ m/z 492 (MH+), HPLC (Method LC-1) Retention time = 0.47 minutes. | | | | | | | |
| 1.049 | B | 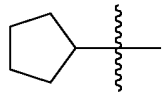 | H | H | OCH$_3$ | H | CH$_2$CH$_3$ | H |
| | | $^1$H NMR (400 MHz, METHANOL-d$_4$) δ ppm 1.35(t, J = 7.69 Hz, 3 H) 1.63-2.24 (m, 13 H) 2.75(s, 2 H) 2.96(q, J = 7.69 Hz, 2 H) 4.00(s, 3H) 4.62-4.75(m, 1 H) 6.84(s, 1 H) 7.40(s, 1 H) 7.48(s, 1 H), MS ES+ m/z 478 (MH+), hPLC (Method LC-1) Retention time = 0.44 minutes. | | | | | | | |
| 1.050 | B | 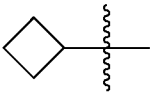 | H | H | OCH$_3$ | H | CH$_2$CH$_3$ | H |
| | | $^1$H NMR (400 MHz, METHANOl-d$_4$) δ ppm 1.36(t, J = 7.69 Hz, 3 H) 1.73-1.94 (complex, 5 H) 2.01(s, 3 H) 2.39-2.50( complex, 2 H) 2.49-2.62(complex, 2 H) 2.78(s, 2 H) 2.98(q, J = 7.69 Hz, 2 H) 4.01(s, 3 H) 4.77-4.86(m, 1 H) 6.86 (s, 1 H) 7.42(s, 1 H) 7.53(s, 1 H), MS ES+ m/z 464 (MH+), HPLC (Method LC-1) Retention time = 0.42 minutes. | | | | | | | |
| 1.051 | B | CH(CH$_3$)$_2$ | H | H | OCH$_3$ | H | H | H |
| | | $^1$H NMR (400 MHz, METHANOL-d$_4$) δ ppm 1.37-1.51(m, 6 H) 1.79(br. s., 3 H) 2.70-2.80(m, 3 H) 4.02(s, 3 H) 6.86(s, 1 H) 7.43(s, 1 H) 7.49(s, 1 H) 8.05(s, 1 H), MS ES+ m/z 424 (MH+), HPLC (Method LC-1) Retention time = 0.35 minutes. | | | | | | | |
| 1.052 | B | CH$_2$CH$_3$ | CH$_3$ | H | OCH$_3$ | H | H | H |
| | | $^1$H NMR (400 MHz, METHANOL-d$_4$) δ ppm 1.38(t, J = 7.27 Hz, 3 H) 1.79(br. s., 4 H) 2.21-2.35(m, 3 H) 2.74(s, 3H) 4.14(q, J = 7.48 Hz, 3 H) 6.86 (s, 2 H) 7.44 (s, 2 H) 8.05(s, 2 H), MS ES+ m/z 424 (MH+), HPLC (Method LC-1) Retention time = 0.34 minutes. | | | | | | | |
| 1.053 | B | CH$_2$CH$_3$ | H | H | OCH$_3$ | H | H | H |
| | | $^1$H NMR (400 MHz, METHANOL-d$_4$) δ ppm 1.44(t, J = 7.27 Hz, 3 H) 1.70-1.90 (m, 2 H) 1.91-2.25(m, 2 H) 2.76(s, 2 H) 3.36-3.79(m, 2 H) 4.02(s, 3 H) 4.17 (q, J = 7.20 Hz, 2 H) 6.86(s, 1 H) 7.43(s, 1 H) 7.46(s, 1 H) 8.05(s, 1 H), MS ES+ m/z 410 (MH+), HPLC (Method LC-1) Retention time = 0.32 minutes. | | | | | | | |
| 1.054 | B | C(CH$_3$)$_3$ | CH$_3$ | H | OCH$_3$ | H | H | H |
| | | $^1$H NMR (400 MHz, METHANOL-d$_4$) δ ppm 1.62(s, 9 H) 1.78(s, 2 H) 2.43(s, 3 H) 2.73(s, 2 H) 4.02(s, 3 H) 6.86(s, 1 H) 7.44(s, 1 H) 8.05(s, 1 H), MS ES+ m/z 452 (MH+), HPLC (Method LC-1) Retention time = 0.42 minutes. | | | | | | | |
| 1.055 | B | CH(CH$_3$)$_2$ | CH$_3$ | H | OCH$_3$ | H | H | H |
| | | $^1$H NMR (400 MHz, METHANOL-d$_4$) δ ppm 1.43(d, J = 6.23 Hz, 6 H) 1.79(s, 2 H) 2.27(s, 3 H) 2.74(s, 2 H) 4.02(s, 3H) 4.55-4.63(m, 1 H) 6.86(s, 1 H) 7.43 (s, 1 H) 8.05(s, 1 H), MS ES+ m/z 438 (MH+), HPLC (Method LC-1) Retention time = 0.39 minutes. | | | | | | | |

TABLE 1-continued

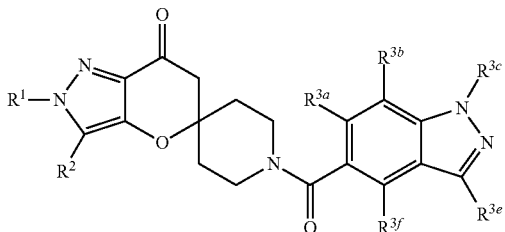

| Ex. | Method | R$^1$ | R$^2$ | R$^{3a}$ | R$^{3b}$ | R$^{3c}$ | R$^{3e}$ | R$^{3f}$ |
|---|---|---|---|---|---|---|---|---|
| 1.056 | B | CH$_2$CH$_3$ | CH$_3$ | H | CH$_2$CH$_3$ | H | H | H |
| | | $^1$H NMR (400 MHz, METHANOL-d$_4$) δ ppm 1.24-1.46(m, 6 H) 1.78(br. s., 3 H) 2.27(s, 4 H) 2.74(s, 3H) 2.97(q, J = 7.48 Hz, 3 H) 4.14(q, J = 7.48 Hz, 3 H) 7.25 (s, 2 H) 7.72(s, 2 H) 8.11(s, 1 H), MS ES+ m/z 422 (MH+), HPLC (Method LC-1) Retention time = 0.39 minutes. | | | | | | | |
| 1.057 | B | CH$_2$CH$_3$ | H | H | CH$_2$CH$_3$ | H | H | H |
| | | $^1$H NMR (400 MHz, METHANOL-d$_4$) δ ppm 1.30-1.39(m, 3 H) 1.44(t, J = 7.27 Hz, 3 H) 2.76(s, 3 H) 2.97(q, J = 7.48 Hz, 3 H) 4.17(q, J = 0 7.34 Hz, 3 H) 7.25(s, 1 H) 7.46(s, 1 H) 7.72(s, 1 H) 8.11(s, 1 H), MS ES+ m/z 408 (MH+), HPLC (Method LC-1) Retention time = 0.34 minutes. | | | | | | | |
| 1.058 | B | CH$_3$ | CH$_3$ | H | CH$_2$CH$_3$ | H | H | H |
| | | $^1$H NMR (400 MHz, METHANOL-d$_4$) δ ppm 1.35(t, J = 7.48 Hz, 3 H) 2.25(s, 3 H) 2.73(s, 2 H) 2.97(q, J = 7.48 Hz, 2 H) 3.81(s, 3 H) 7.25(s, 1 H) 7.72(s, 1 H) 8.11(s, 1 H), MS ES+ m/z 408 (MH+), HPLC (Method LC-1) Retention time = 0.35 minutes. | | | | | | | |
| 1.059 | B | CH$_3$ | H | H | CH$_2$CH$_3$ | H | H | H |
| | | $^1$H NMR (400 MHz, METHANOL-d$_4$) δ ppm 1.35(t, J = 7.69 Hz, 3 H) 1.79(s, 2 H) 1.94-2.26(m, 2 H) 2.75(s, 2 H) 2.97(q, 2 H) 3.89(s, 3 H) 7.24(s, 1 H) 7.41(s, 1 H) 7.72(s, 1 H) 8.11(s, 1 H), MS ES+ m/z 394 (MH+), HPLC (Method LC-1) Retention time = 0.31 minutes. | | | | | | | |
| 1.060 | A | C(CH$_3$)$_3$ | H | H | CH$_2$CH$_3$ | H | H | H |
| | | $^1$H NMR (400 MHz, DMSO-d$_6$) δ ppm 1.26(t, J = 7.48 Hz, 3 H) 1.47(s, 9 H) 2.71 (s, 2 H) 2.85-2.93(m, 2 H) 7.16(s, 1 H) 7.64(s, 1 H) 7.77(s, 1 H) 8.09(s, 1 H) 13.31(s, 1 H), MS ES+ m/z 436 (MH+), HPLC (Method LC-1) Retention time = 0.37 minutes. | | | | | | | |
| 1.061 | B | CH$_2$CH$_3$ | CH$_3$ | H | Cl | H | H | H |
| | | $^1$H NMR (400 MHz, METHANOL-d$_4$) δ ppm 1.38(t, J = 7.27 Hz, 3 H) 1.78(br. s., 3 H) 2.14-2.36(m, 5 H) 2.73(s, 3 H) 4.14(q, J = 7.48 Hz, 3 H) 7.51(s, 1 H) 7.85 (s, 1 H) 8.20(s, 1 H), MS ES+ m/z 428 (MH+), HPLC (Method LC-1) Retention time = 0.37 minutes. | | | | | | | |
| 1.062 | B | CH$_2$CH$_3$ | H | H | Cl | H | H | H |
| | | $^1$H NMR (400 MHz, METHANOL-d$_4$) δ ppm 1.42(t, 3 H) 1.65-1.92(m, 2 H) 1.91-2.26(m, 2 H) 2.64(s, 2 H) 2.67-2.84(m, 2 H) 3.39-3.76(m, 2 H) 4.16 q, 2 H) 4.43(br. s., 1 H) 7.46(s, 1 H) 7.50(s, 1 H) 7.84(s, 1 H) 8.19(s, 1 H), MS ES+ m/z 414 (MH+), HPLC (Method LC-1) Retention time = 0.35 minutes. | | | | | | | |
| 1.063 | B | CH$_3$ | CH$_3$ | H | Cl | H | H | H |
| | | $^1$H NMR (400 MHz, METHANOL-d$_4$) δ ppm 1.16(t, J = 7.06 Hz, 3 H) 1.78(s, 2 H) 2.25(s, 3 H) 2.73(s, 2 H) 3.81(s, 3 H) 7.51(s, 1 H) 7.85(s, 1 H) 8.20(s, 1 H), MS ES+ m/z 414 (MH+), HPLC (Method LC-1) Retention time = 0.32 minutes. | | | | | | | |
| 1.064 | A | CH$_3$ | H | H | Cl | H | H | H |
| | | $^1$H NMR (400 MHz, DMSO-d$_6$) δ ppm 1.67-1.79(m, 2 H) 2.04(s, 2 H) 2.70(s, 2 H) 3.83(s, 3H) 7.46(s, 1 H) 7.57(s, 1 H) 7.81(s, 1 H) 8.24(s, 1 H), MS ES+ m/z 400 (MH+), HPLC (Method LC-1) Retention time = 0.30 minutes. | | | | | | | |
| 1.065 | B | C(CH$_3$)$_3$ | H | H | Cl | H | H | H |
| | | $^1$H NMR (400 MHz, DMSO-d$_6$) δ ppm 1.51(s, 9 H) 1.76(br. s., 2 H) 1.95(br. s., 2 H) 7.50(s, 1 H) 7.80(s, 1 H) 7.85(d, J = 0.98 Hz, 1 H) 8.27(s, 2 H) 13.79(br. s., 1 H), MS ES+ m/z 442 (MH+), HPLC (Method LC-1) Retention time = 0.49 minutes. | | | | | | | |
| 1.066 | B | CH(CH$_3$)$_2$ | H | H | Cl | H | H | H |
| | | $^1$H NMR (400 MHz, METHANOL-d$_4$) δ ppm 1.47(d, J = 7.06 Hz, 6 H) 1.80(br. s., 2 H) 2.75(s, 2 H) 4.47-4.53(m, 1 H) 7.49(s, 1 H) 7.50(s, 1 H) 7.85(s, 1 H) 8.20(s, 1 H), MS ES+ m/z 428 (MH+), HPLC (Method LC-1) Retention time = 0.38 minutes. | | | | | | | |
| 1.067 | B | CH(CH$_3$)$_2$ | H | H | H | H | H | H |
| | | $^1$H NMR (400 MHz, METHANOL-d$_4$) δ ppm 1.39-1.51(m, 6 H) 1.79(br. s., 3 H) 2.67-2.80(m, 3H) 7.45(dd, J = 8.72, 1.66 Hz, 1 H) 7.49(s, 1H) 7.60(d, J = 8.72 Hz, 1 H) 7.90(s, 1 H) 8.12(s, 1 H), MS ES+ m/z 394 (MH+), HPLC (Method LC-1) retention time = 0.33 minutes. | | | | | | | |
| 1.068 | B | CH$_2$CH$_3$ | CH$_3$ | H | H | H | H | H |
| | | $^1$H NMR (400 MHz, METHANOL-d$_4$) δ ppm 1.38(t, J = 7.27 Hz, 3 H) 1.63-1.91 (m, 2 H) 1.91-2.24(m, 2 H) 2.27(s, 3H) 2.74(s, 2 H) 3.41-3.57(m, 1 H) 3.67 (br. s., 1 H) 4.14(q, J = 7.06 Hz, 2 H) 4.46(br. s., 1 H) 7.46(d, J = 8.72 Hz, 1 H) 7.60(d, J = 8.31 Hz, 1 H) 7.91(s, 1 H) 8.12(s, 1 H), MS ES+ m/z 394 (MH+), HPLC (Method LC-1) Retention time = 0.33 minutes. | | | | | | | |

TABLE 1-continued

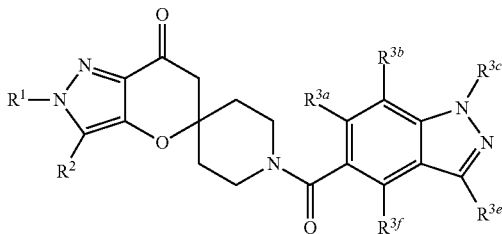

| Ex. | Method | R[1] | R[2] | R[3a] | R[3b] | R[3c] | R[3e] | R[3f] |
|---|---|---|---|---|---|---|---|---|
| 1.069 | B | CH$_2$CH$_3$ | H | H | H | H | H | H |
| | | $^1$H NMR (400 MHz, METHANOL-d$_4$) δ ppm 1.44(t, J = 7.27 Hz, 3 H) 2.76(s, 2 H) 4.11-4.21(m, 2H) 7.43-7.48(m, 2 H)7. 60(d, J = 8.31 Hz, 1 H) 7.90(s, 1 H) 8.12(s, 1 H), MS ES+ m/z 380 (MH+), HPLC (Method LC-1) Retention time = 0.32 minutes. | | | | | | | |
| 1.070 | B | CH$_3$ | CH$_3$ | H | H | H | H | H |
| | | $^1$H NMR (400 MHz, METHANOL-d$_4$) δ ppm 1.35-2.38(m, 5 H) 2.73(s, 2 H) 3.37-3.75(m, 4 H) 3.81(s, 3 H) 4.44(br. s., 2 H) 5.48(s, 1 H) 7.46(d, J = 8.72 Hz, 1 H) 7.60(d, J = 8.72 Hz, 1 H) 7.91(s, 1 H) 8.12(s, 1 H), MS ES+ m/z 380 (MH+), HPLC (Method LC-1) Retention time = 0.31 minutes. | | | | | | | |
| 1.071 | B | CH$_3$ | H | H | H | H | H | H |
| | | $^1$H NMR (400 MHz, CHLOROFORM-d) δ ppm 1.58(br. s., 2 H) 1.92-2.28(m, 2 H) 2.70(s, 2 H) 3.14-3.56(m, 2 H) 3.93(s, 3H) 4.11(q, J = 7.20 Hz, 2 H) 7.09 (s, 1 H) 7.37-7.58(m, 2 H) 7.84(s, 1 H) 8.11(s, 1 H), MS ES+ m/z 366 (MH+), HPLC (Method LC-1) Retention time = 0.28 minutes. | | | | | | | |
| 1.072 | B | C(CH$_3$)$_3$ | CH$_3$ | H | H | H | H | H |
| | | $^1$H NMR (400 MHz, METHANOL-d$_4$) δ ppm 1.62(s, 9 H) 1.78(s, 2 H) 2.43(s, 3 H) 2.72(s, 2 H) 7.46(d, J = 8.72 Hz, 1 H) 7.60(d, J = 8.72 Hz, 1 H) 7.91(s, 1H) 8.12(s, 1 H), MS ES+ m/z 422 (MH+), HPLC (Method LC-1) Retention time = 0.41 minutes. | | | | | | | |
| 1.073 | B | CH(CH$_3$)$_2$ | CH$_3$ | H | H | H | H | H |
| | | $^1$H NMR (400 MHz, METHANOL-d$_4$) δ ppm 1.43(d, J = 6.65 Hz, 6 H) 1.78(s, 2 H) 2.27(s, 3 H) 2.73(s, 2 H) 4.54-4.63(m, 1 H) 7.46(d, J = 9.97 Hz, 1 H) 7.60 (d, J = 8.72 Hz, 1 H) 7.91(s, 1 H) 8.12(s, 1 H), MS ES+ m/z 408 (MH+), HPLC (Method LC-1) Retention time = 0.37 minutes. | | | | | | | |
| 1.074 | B | C(CH$_3$)$_3$ | H | H | H | H | H | H |
| | | $^1$H NMR (500 MHz, DMSO-d$_6$) δ ppm 13.26(q H, br. s.), 8.14(1 H, s), 7.86(1 H, s), 7.81(1 H, s), 7.58(1 H, d, J = 8.54 Hz), 7.40(1 H, br. s.), 3.18(2 H, br.s.), 2.75(2 H, s), 1.99(2 H, s), 1.88(2 H, br. s.), 1.74(2 H, t), 1.51(9 H, s), MS ES+ m/z 408 (MH+), HPLC (Method LC-1) Retention time = 0.38 minutes. | | | | | | | |
| 1.075 | B | CH(CH$_3$)$_2$ | H | H | OCH$_3$ | H | CH$_3$ | H |
| | | $^1$H NMR (400 MHz, METHANOL-d$_4$) δ ppm 1.39-1.51(m, 6 H) 1.80(br. s. , 3 H) 2.52(s, 3 H) 2.69-2.80(m, 2 H) 4.00(s, 3H) 6.85(s, 1 H) 7.37(s, 1H) 7.49(s, 1 H), MS ES+ m/z 438 (MH+), HPLC (Method LC-1) Retention time = 0.37 minutes. | | | | | | | |
| 1.076 | B | C(CH$_3$)$_3$ | H | H | OCH$_3$ | H | CH$_3$ | H |
| | | $^1$H NMR (400 MHz, METHANOl-d$_4$) δ ppm 1.59(s, 9 H) 1.83(br. s., 3 H) 2.16 (br. s., 3 H) 2.54(s, 3 H) 2.77(s, 2 H) 4.02(s, 3 H) 6.86(s, 1 H) 7.39(s, 1H) 7.60(s, 1 H), MS ES+ m/z 452 (MH+), HPLC (Method LC-1) Retention time = 0.41 minutes. | | | | | | | |
| 1.077 | B | CH$_2$CH$_3$ | CH$_3$ | H | OCH$_3$ | H | CH$_3$ | H |
| | | $^1$H NMR (400 MHz, METHANOl-d$_4$) δ ppm 1.38(t, J = 7.27 Hz, 3 H) 1.79(s, 2 H) 2.27(s, 3 H) 2.52(s, 3 H) 2.74(s, 2 H) 4.00(s, 3H) 4.14(q, J = 7.27 Hz, 2 H) 6.85(s, 1 H) 7.38(s, 1 H), MS ES+ m/z 438 (MH+), HPLC (Method LC-1) Retention time = 0.37 minutes. | | | | | | | |
| 1.078 | B | CH(CH$_3$)$_2$ | CH$_3$ | H | OCH$_3$ | H | CH$_3$ | H |
| | | $^1$H NMR (400 MHz, METHANOL-d$_4$) δ ppm 1.43(d, J = 6.65 Hz, 6 H) 1.79(br. s., 2 H) 2.27(s, 3 H) 2.52(s, 3 H) 2.74(s, 2 H) 4.00(s, 3 H) 4.52-4.65(m, 1 H) 6.85(s, 1 H) 7.38(s, 1 H), MS ES+ m/z 452 (MH+), HPLC (Method LC-1) Retention time = 0.39 minutes. | | | | | | | |
| 1.079 | B | CH$_2$CH$_3$ | H | H | OCH$_3$ | H | CH$_3$ | H |
| | | $^1$H NMR (400 MHz, METHANOL-d$_4$) δ ppm 1.46(t, J = 7.48 Hz, 3 H) 1.81(br. s., 2 H) 2.16(br. s., 3 H) 2.54(s, 3H) 2.78(s, 2 H) 4.02(s, 3 H) 4.19(q, J = .06 Hz, 2 H) 6.87(s, 1 H) 7.39(s, 1 H) 7.48(s, 1 H), MS ES+ m/z 424 (MH+), HPLC (Method LC-1) Retention time = 0.35 minutes. | | | | | | | |
| 1.080 | B | CH$_2$CH$_3$ | CH$_3$ | H | H | H | CH$_3$ | H |
| | | $^1$H NMR (400 MHz, CDCl$_3$) δ ppm 0.65-0.97(m, 1 H) 0.97-1.44(m, 1 H) 1.96-2.38(m, 1 H) 2.67-2.87(m, 1 H) 3.06(t, J = 7.06 Hz, 1 H) 3.38(br. s., 2 H) 3.72(t, J = 6.64 Hz, 2 H) 6.02(br. s., 1 H) 7.28-7.41(m, 1 H) 7.40-7.54(m, 2 H) 7.66(s, 1 H) 7.73(d, J = 7.48 Hz, 1 H) 9.92(s, 1 H), MS ES+ m/z 408 (MH+), HPLC (Method LC-1) Retention time = 0.33 minutes. | | | | | | | |
| 1.081 | B | CH(CH$_3$)$_2$ | H | H | H | H | CH$_3$ | H |
| | | $^1$H NMR (400 MHz, CD$_3$OD) δ ppm 1.39-1.50(m, 2 H) 2.56(s, 1 H), 2.69-2.81 (m, 1 H) 3.29(d, J = 1.66 Hz, 3 H) 4.87(s, 2 H) 7.40-7.47(m, 1 H) 7.47-7.54 (m, 1 H) 7.84(s, 1 H), MS ES+ m/z 408 (MH+), HPLC (Method LC-1) Retention time = 0.35 minutes. | | | | | | | |

TABLE 1-continued

| Ex. | Method | R[1] | R[2] | R[3a] | R[3b] | R[3c] | R[3e] | R[3f] |
|---|---|---|---|---|---|---|---|---|
| 1.082 | B | CH$_2$CH$_2$CH$_3$ | H | H | H | H | CH$_3$ | H |
| | | $^1$H NMR (400 MHz, METHANOL-d$_4$) δ ppm 0.89(t, J = 7.48 Hz, 3 H) 1.69-1.91 (m, 6 H) 2.56(s, 3 H) 2.76(s, 3 H) 4.09(t, J = 7.06 Hz, 3 H) 7.40-7.45(m, 1 H) 7.46(s, 1 H) 7.49-7.54(m, 1 H) 7.84(s, 1 H), MS ES+ m/z 408 (MH+), HPLC (Method LC-1) Retention time = 0.37 minutes. | | | | | | |
| 1.083 | B | CH$_2$CH$_3$ | H | H | H | H | CH$_3$ | H |
| | | $^1$H NMR (400 MHz, METHANOL-d$_4$) δ ppm 1.43(t, 3 H) 1.69-1.92(m, 2H) 1.91-2.25(m, 2 H) 2.56(s, 3 H) 2.76(s, 2 H) 3.47(d, J = 7.06 Hz, 1 H) 3.68(br. s., 1 H) 4.17(q, J = 7.06 Hz, 2 H) 4.45(br. s., 1 H) 7.36-7.39(m, 2 H) 7.51(d, 1 H) 7.84(s, 1 H), MS ES+ m/z 394 (MH+), HPLC (Method LC-1) Retention time = 0.33 minutes. | | | | | | |
| 1.084 | B | CH$_3$ | CH$_3$ | H | H | H | CH$_3$ | H |
| | | $^1$H NMR (400 MHz, METHANOL-d$_4$) δ ppm 1.17(q, J = 7.06 Hz, 2 H) 1.67-2.33 (m, 5 H) 2.49-2.63(m, 3 H) 2.73(s, 2 H) 3.37-3.62(m, 2 H) 3.74-3.87(m, 3 H) 4.50(s, 2 H) 7.38-7.60(m, 2 H) 7.75-7.91(m, 1 H), MS ES+ m/z 394 (MH+), HPLC (Method LC-1) Retention time = 0.34 minutes. | | | | | | |
| 1.085 | B | CH$_3$ | H | H | H | H | CH$_3$ | H |
| | | $^1$H NMR (400 MHz, CHLOROFORM-d) δ ppm 1.19(t, J = 6.85 Hz, 2 H) 2.18(d, J = 42.79 Hz, 2 H) 2.58(s, 3 H) 2.70(s, 2 H) 3.18-3.61(m, 2 H) 3.93(s, 3H) 7.25(s, 2 H) 7.33-7.52(m, 1 H) 7.79(s, 1 H), MS ES+ m/z 380 (MH+), HPLC (Method LC-1) Retention time = 0.30 minutes. | | | | | | |
| 1.086 | B | C(CH$_3$)$_3$ | H | H | H | H | CH$_3$ | H |
| | | $^1$H NMR (400 MHz, METHANOL-d$_4$) δ ppm 1.59(s, 9 H) 1.81(br. s., 3 H) 2.01 (br. s., 3 H) 2.59(s, 3 H) 2.77(s, 2 H) 7.45(d, J = 8.7 Hz, 1 H) 7.53(d, J = 8.7 Hz, 1 H) 7.60(s, 1 H) 7.86(s, 1 H), MS ES+ m/z 422 (MH+), HPLC (Method LC-1) Retention time = 0.40 minutes. | | | | | | |
| 1.087 | B | cyclohexyl-CH(CH$_3$)- | | H | H | H | H | CH$_3$ | H |
| | | $^1$H NMR (400 MHz, METHANOL-d$_4$) δ ppm 1.21-1.55(m, 4 H) 1.59-2.25(m, 14 H) 2.55(s, 3 H) 2.77(s, 2 H) 4.07-4.25(m, 1 H) 7.45(dd, J = 8.3, 1.2 Hz, 1 H) 7.51(s, 1 H) 7.53(d, J = 8.3 Hz, 1 H) 7.86(s, 1 H), MS ES+ m/z 448 (MH+), HPLC (Method LC-1) Retention time = 0.44 minutes. | | | | | | |
| 1.088 | B | cyclopentyl-CH(CH$_3$)- | | H | H | H | H | CH$_3$ | H |
| | | $^1$H NMR (400 MHz, METHANOL-d$_4$) δ ppm 1.64-2.27(m, 15 H) 2.57(s, 3 H) 2.77(s, 2H) 4.64-4.77(m, 1 H) 7.43-7.47(dd, J = 8.8, 1.7 Hz, 1 H) 7.50(d, J = 8.8 Hz, 1 H) 7.86(d, J = 1.7 Hz, 1 H), MS ES+ m/z 434 (MH+), HPLC (Method LC-1) Retention time = 0.41 minutes. | | | | | | |
| 1.089 | B | cyclobutyl-CH(CH$_3$)- | | H | H | H | H | CH$_3$ | H |
| | | $^1$H NMR (400 MHz, METHANOL-d$_4$) δ ppm 1.74-1.93(complex, 5 H) 2.39-2.56(complex, 5 H) 2.58(s, 3 H) 2.78(s, 2 H) 4.77-4.88(m, 1 H) 7.45(d, J = 8.7 Hz, 1 H) 7.53(s, 1 H), 7.53(d, J = 8.7 Hz, 1 H) 7.51-7.57(m, 2 H) 7.86 (s, 1 H), MS ES+ m/z 420 (MH+), HPLC (Method LC-1) Retention time = 0.39 minutes. | | | | | | |
| 1.090 | B | C(CH$_3$)$_3$ | CH$_3$ | H | H | H | CH$_3$ | H |
| | | $^1$H NMR (400 MHz, METHANOL-d$_4$) δ ppm 1.62(s, 9 H) 1.78(s, 2 H) 2.43(s, 3 H) 2.56(s, 3 H) 2.72(s, 2 H) 7.44(d, 1 H) 7.51(d, 2 H) 7.85(s, 1 H), MS ES+ m/z 436 (MH+), HPLC (Method LC-1) Retention time = 0.42 minutes. | | | | | | |
| 1.091 | B | CH(CH$_3$)$_2$ | CH$_3$ | H | H | H | CH$_3$ | H |
| | | $^1$H NMR (400 MHz, METHANOL-d$_4$) δ ppm 1.43(d, J = 6.65 Hz, 6 H) 1.78(s, 2 H) 2.27(s, 3 H) 2.56(s, 3 H) 2.73(s, 2 H) 4.54-4.62(m, 1 H) 7.44(d, 1 H) 7.52 (d, 1 H) 7.85(s, 1 H), MS ES+ m/z 422 (MH+), HPLC (Method LC-1) Retention time = 0.39 minutes. | | | | | | |

TABLE 1-continued

| Ex. | Method | R¹ | R² | $R^{3a}$ | $R^{3b}$ | $R^{3c}$ | $R^{3e}$ | $R^{3f}$ |
|---|---|---|---|---|---|---|---|---|
| 1.092 | B | CH₂CH₃ | CH₃ | H | H | H | CH₂CH₃ | H |
| | | ¹H NMR (400 MHz, METHANOL-d₄) δ ppm 1.30-1.42(m, 6 H) 1.79(br. s., 3 H) 2.27(s, 3 H) 2.74(s, 3 H) 3.00(q, J = 7.48 Hz, 2 H) 4.14(q, J = 7.48 Hz, 2 H) 7.41-7.46(m, 1 H) 7.49-7.55(m, 1 H) 7.88(s, 1 H), MS ES+ m/z 422 (MH+), HPLC (Method LC-1) Retention time = 0.39 mintes. | | | | | | | |
| 1.093 | B | CH₂CH₃ | H | H | H | H | CH₂CH₃ | H |
| | | ¹H NMR (400 MHz, METHANOL-d₄) δ ppm 1.37(t, J = 7.48 Hz, 3 H) 1.44(t, J = 7.27 Hz, 3 H) 1.80(br. s., 3 H) 2.76(s, 3 H) 3.00(q, J = 7.62 Hz, 2 H) 4.17(q, J = 7.48 Hz, 2 H) 7.39-7.45(m, 1 H) 7.46(s, 1 H) 7.49-7.55(m, 1 H) 7.87(s, 1 H), MS ES+ m/z 408 (MH+), HPLC (Method LC-1) Retention time = 0.34 minutes. | | | | | | | |
| 1.094 | B | CH₃ | CH₃ | H | H | H | CH₂CH₃ | H |
| | | ¹H NMR (400 MHz, METHANOL-d₄) δ ppm 1.37(t, J = 7.69 Hz, 3 H) 2.25(s, 3 H) 2.73(s, 2 H) 3.00(q, J = 7.62 Hz, 2 H) 3.81(s, 3 H) 7.43(d, 1 H) 7.52(d, 1 H) 7.88(s, 1 H), MS ES+ m/z 408 (MH+), HPLC (Method LC-1) Retention time = 0.37 minutes. | | | | | | | |
| 1.095 | B | CH₃ | H | H | H | H | CH₂CH₃ | H |
| | | ¹H NMR (400 MHz, METHANOL-d₄) δ ppm 1.37(t, J = 7.48 Hz, 3 H) 2.75(s, 2 H) 3.00(q, J = 7.62 Hz, 2 H) 3.89(s, 3 H) 7.39-7.46(m, 2 H) 7.52(d, 1 H) 7.87(s, 1 H), MS ES+ m/z 294 (MH+), HPLC (Method LC-1) Retention time = 0.31 minutes. | | | | | | | |
| 1.096 | B | C(CH₃)₃ | H | H | H | H | CH₂CH₃ | H |
| | | ¹H NMR (400 MHz, DMSO-d₆) δ ppm 1.31(t, J = 7.61 Hz, 3 H) 1.51(d, 9 H) 1.74 (br. s., 2 H) 1.95(br. s., 2 H) 2.72-2.78(m, 2 H) 2.86-2.99(m, 2 H) 7.36(dd, J = 8.49, 1.27 Hz, 1 H) 7.48(d, J = 8.49 Hz, 1 H) 7.79(s, 1 H) 7.82(s, 1 H) 12.79 (s, 1 ), MS ES+ m/z 436 (MH+), HPLC (Method LC-1) Retention time = 0.49 minutes. | | | | | | | |
| 1.097 | B | CH₂CH₃ | CH₃ | H | H | H | (CH₂)₂CH₃ | H |
| | | ¹H NMR (400 MHz, METHANOL-d₄) δ ppm 0.97(t, J =7.27 Hz, 3 H) 1.38(t, J = 7.27 Hz, 3 H) 1.73-1.90(m, 4 H) 2.27(s, 3 H) 2.74(s, 2 H) 2.96(t, J = 7.48 Hz, 2 H) 4.14(q, J = 7.48 Hz, 2 H) 7.39-7.47(m, 1 H) 7.49-7.55(m, 1 H) 7.87 (s, 1 H), MS ES+ m/z 436 (MH+), HPLC (Method LC-1) Retention time = 0.42 minutes. | | | | | | | |
| 1.098 | B | CH₃ | CH₃ | H | H | H | (CH₂)₂CH₃ | H |
| | | ¹H NMR (400 MHz, METHANOL-d₄) δ ppm 0.97(t, J = 7.48 Hz, 3 H) 1.72-1.87 (m, 4 H) 2.25(s, 3 H) 2.73(s, 2 H) 2.96(t, J = 7.27 Hz, 2 H) 3.81(s, 3 H) 7.41-7.46(m, 1 H) 7.50-7.54(m, 1 H) 7.87(s, 1 H), MS ES+ m/z 422 (MH+), HPLC (Method LC-1) Retention time = 0.39 minutes. | | | | | | | |
| 1.099 | A | CH₂CH₃ | H | H | OCH₃ | CH₃ | CH₂CH₃ | H |
| | | ¹H NMR (400 MHz, METHANOL-d₄) δ ppm 1.26-1.37(m, 3 H) 1.39-1.53(m, 3 H) 1.79(br. s., 3 H) 2.66-2.82(m, 3H) 2.92(q, J = 7.48 Hz, 3 H) 3.29(s, 3 H) 3.99(s, 3 H) 4.07-4.24(m, 4 H) 4.88(s, 3 H) 6.84(s, 1 H) 7.36(s, 1 H) 7.46(s, 1 H), MS ES+ m/z 452 (MH+), HPLC (Method LC-1) Retention time = 0.43 minutes. | | | | | | | |
| 1.100 | A | CH₂CH₃ | H | H | CH₂CH₃ | H | CH₃ | H |
| | | ¹H NMR (500 MHz, DMSO-d₆) δ ppm 1.25-1.29(m, 3 H) 1.37(t, J = 7.32 Hz, 3 H) 2.75(s, 2 H) 2.85-2.90(m, 2 H) 4.14(q, J = 7.32 Hz, 2 H) 7.16(s, 1 H) 7.61 (s, 1 H) 7.66(s, 1 H), MS ES+ m/z 422 (MH+), HPLC (Method LC-1) Retention time = 0.37 minutes. | | | | | | | |
| 1.101 | A | CH₂CH₃ | H | H | Cl | H | CH₂CH₃ | H |
| | | ¹H NMR (400 MHz, METHANOL-d₄) δ ppm 1.23-1.51(m, 6 H) 1.69-2.17(m, 4 H) 2.64(s, 2 H) 2.75(s, 2 H) 2.90(s, 2 H) 2.94-3.07(m, 2 H) 4.17(q, J = 7.22 Hz, 2 H) 7.39-7.52(m, 2 H) 7.81(d, J = 1.17 Hz, 1 H), MS ES+ m/z 442 (MH+), HPLC (Method LC-1) Retention time = 0.39 minutes. | | | | | | | |
| 1.102 | A | CH(CH₃)₂ | H | H | Cl | H | CH₃ | H |
| | | ¹H NMR (500 MHz, METHANOL-d₄) δ ppm 1.50(d, J = 6.59 Hz, 6 H) 2.60(s, 3 H) 2.79(s, 2 H) 4.51-4.57(m, 1 H) 7.52(d, J = 1.22 Hz, 1 H) 7.52(s, 1 H) 7.82 (d, J = 1.22 Hz, 1 H), MS ES+ m/z 442 (MH+), HPLC (Method LC-1) Retention time = 0.39 minutes. | | | | | | | |
| 1.103 | A | C(CH₃)₃ | H | H | H | H | Cl | H |
| | | ¹H NMR (500 MHz, METHANOL-d₄) δ ppm 1.60(s, 9 H) 2.79(br. S., 2 H) 7.54 (dd, J = 8.78, 1.46 Hz, 1 H) 7.60-7.64(m, 2 H) 7.81(s, 1 H), MS ES+ m/z 442 (MH+), HPLC (Method LC-1) Retention time = 0.46 minutes. | | | | | | | |

TABLE 1-continued

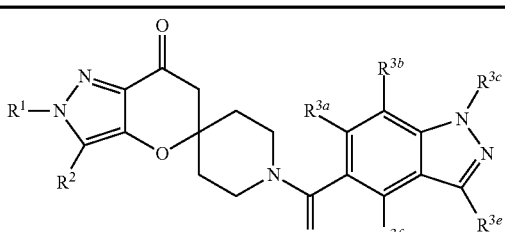

| Ex. | Method | R¹ | R² | R$^{3a}$ | R$^{3b}$ | R$^{3c}$ | R$^{3e}$ | R$^{3f}$ |
|---|---|---|---|---|---|---|---|---|
| 1.104 | A | CH(CH$_3$)$_2$ | H | H | CH$_3$ | H | Cl | H |
| | | $^1$H NMR (500 MHz, METHANOL-d$_4$) δ ppm 1.50(d, J = 6.59 Hz, 6 H) 2.59(s, 3 H) 2.79(br. S., 2 H) 4.52-4.57(m, 1 H) 7.30-7.32(m, 1 H) 7.52(s, 1 H) 7.62 (s, 1 H), MS ES+ m/z 442 (MH+), HPLC (Method LC-1) Retention time = 0.41 minutes. | | | | | | |
| 1.105 | A | C(CH$_3$)$_3$ | H | H | CH$_3$ | H | Cl | H |
| | | $^1$H NMR (500 MHz, METHANOL-d$_4$) δ ppm 1.60(s, 9 H) 2.59(s, 3 H) 2.79(br. S., 2 H) 7.31(d, J = 1.46 Hz, 1 H) 7.62(s, 2 H), MS ES+ m/z 456 (MH+), HPLC (Method LC-1) Retention time = 0.44 minutes. | | | | | | |
| 1.106 | A | 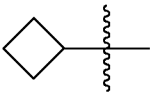 | H | H | CH$_3$ | H | Cl | H |
| | | $^1$H NMR (500 MHz, METHANOL-d$_4$) δ ppm 2.55(d, J = 1.95 Hz, 2 H) 2.57(d, J = 2.68 Hz, 2 H) 2.59(s, 3 H) 2.80(br. S., 2 H) 4.85(s, 1 H) 7.31(s, 1 H) 7.55 (s, 1 H) 7.62(s, 1 H), MS ES+ m/z 454 (MH+), HPLC (Method LC-1) Retention time = 0.43 minutes. | | | | | | |
| 1.107 | A | 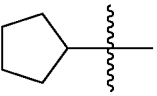 | H | H | CH$_3$ | H | Cl | H |
| | | $^1$H NMR (500 MHz, METHANOL-d$_4$) δ ppm 1.71-1.76(m, 3 H) 1.87-1.92(m, 3 H) 1.99-2.06(m, 3 H) 2.18(dd, J = 13.42, 5.37 Hz, 3 H) 2.59(s, 3 H) 2.79(br. S., 2 H) 4.72(s, 1 H) 7.31(s, 1 H) 7.52(s, 1 H) 7.62(s, 1 H), MS ES+ m/z 468 (MH+), HPLC (Method LC-1) Retention time = 0.46 minutes. | | | | | | |
| 1.108 | A | CH$_2$CH$_3$ | H | H | CH$_3$ | H | Cl | H |
| | | $^1$H NMR (500 MHz, METHANOL-d$_4$) δ ppm 1.47(t, J = 7.32 Hz, 3 H) 2.59(s, 3H) 2.79(br. S., 2 H) 4.21(q, J = 7.32 Hz, 2 H) 7.31(d, J = 1.46 Hz, 1 H) 7.50(s, 1 H) 7.62(s, 1 H), MS ES+ m/z 428 (MH+), HPLC (Method LC-1) Retention time = 0.38 minutes. | | | | | | |
| 1.109 | A | CH$_2$CH$_2$CH$_3$ | H | H | CH$_3$ | H | Cl | H |
| | | $^1$H NMR (500 MHz, METHANOL-d$_4$) δ ppm 0.92(t, J = 7.44 Hz, 3 H) 1.87-1.92 (m, 2 H) 2.59(s, 3H) 2.79(br. S., 2 H) 4.13(t, J = 7.07 Hz, 2 H) 7.31(d, J = 1.46 Hz, 1 H) 7.49(s, 1 H) 7.62(s, 1 H), MS ES+ m/z 442 (MH+), HPLC (Method LC-1) Retention time = 0.41 minutes. | | | | | | |
| 1.110 | B | C(CH$_3$)$_3$ | H | H | Cl | H | H | CH$_3$ |
| | | $^1$H NMR (500 MHz, DMSO-d$_6$) δ ppm 1.51(s, 9 H) 1.68-1.82(br. S., 2 H) 2.04 (br. S., 2 H) 2.74(s, 3 H) 7.48(d, J = 0.98 Hz, 1 H) 7.76-7.82(m, 2 H) 13.37(s, 1 H), MS ES+ m/z 456 (MH+), HPLC (Method LC-1) Retention time = 0.42 minutes. | | | | | | |
| 1.111 | A | CH$_2$CH$_3$ | CH$_3$ | H | Cl | H | CH$_3$ | H |
| | | MS(APCI) AP+ m/z 442 (MH+), HPLC (Method LC-1) Retention time = 0.37 minutes. | | | | | | |
| 1.112 | A | CH$_2$CH$_3$ | CH$_3$ | H | H | CH$_3$ | H | H |
| | | $^1$H NMR (400 MHz, METHANOL-d$_4$) δ ppm 1.38(t, J = 7.27 Hz, 3 H) 1.78(s, 2 H) 2.26(s, 3 H) 2.73(s, 2 H) 4.08(s, 3 H) 4.14(q, J = 7.48 Hz, 2 H) 7.48(d, J = 8.72 Hz, 1 H) 7.62(:d, J = 8.72 Hz, 1 H) 7.88(s, 1 H) 8.07(s, 1 H), MS ES+ m/z 408 (MH+), HPLC (Method LC-1) Retention time = 0.35 minutes. | | | | | | |
| 1.113 | A | CH$_2$CH$_3$ | CH$_3$ | H | CH$_2$CH$_3$ | H | CH$_3$ | H |
| | | $^1$H NMR (500 MHz, DMSO-d6) δ ppm 1.24-1.34(m, 6 H) 2.23(s, 3 H) 2.71(s, 2 H) 2.85-2.91(m, 2 H) 4.10(d, J = 7.32 Hz, 2 H) 7.16(d, J = 0.98 Hz, 1 H) 7.61 (s, 1 H), ES+ m/z 436 (MH+), HPLC (Method LC-1) Retention time = 0.39 minutes. | | | | | | |
| 1.114 | A | CH$_2$CH$_3$ | CH$_3$ | H | CH$_3$ | H | Cl | H |
| | | $^1$H NMR (500 MHz, METHANOL-d$_4$) δ ppm 1.41(t, J = 7.20 Hz, 3 H) 2.30(s, 3H) 2.59(s, 3H) 2.77(br. S., 2 H) 4.17(d, J = 7.32 Hz, 2 H) 7.32(s, 1 H) 7.63(s, 1 H), MS ES+ m/z 442 (MH+), HPLC (Method LC-1) Retention time = 0.40 minutes. | | | | | | |

TABLE 1-continued

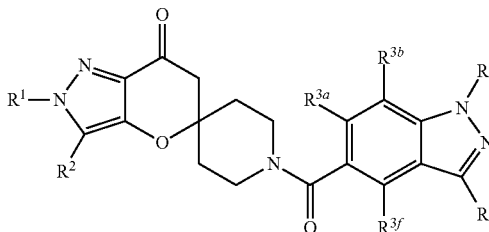

| Ex. | Method | R$^1$ | R$^2$ | R$^{3a}$ | R$^{3b}$ | R$^{3c}$ | R$^{3e}$ | R$^{3f}$ |
|---|---|---|---|---|---|---|---|---|
| 1.115 | A | CH$_2$CH$_3$ | H | H | OCH$_2$CH$_3$ | H | CH$_3$ | H |

$^1$H NMR (400 Mhz, METHANOL-d$_4$) δ ppm 1.16(none, 1 H) 1.35(t, J = 7.48 Hz, 3 H) 1.44(t, J = 7.27 Hz, 3 H) 1.50(t, J = 7.06 Hz, 3 H) 1.80(br. s., 2 H) 2.76(s, 2 H) 2.96(q, J = 7.48 Hz, 2 H) 3.47(q, J = 7.06 Hz, 2 H) .407-4.32(m, 4 H) 4.89(s, 3 H) 6.82(s, 1 H) 7.39(s, 1 H) 7.46(s, 1 H), MS ES+ m/z 438 (MH+), HPLC (Method LC-1) Retention time = 0.36 minutes.

| 1.116 | B | C(CH$_3$)$_3$ | H | H | OCH$_2$CH$_3$ | H | CH$_3$ | H |

$^1$H NMR (400 MHz, METHANOL-d$_4$) δ ppm 1.52(t, J = 7.06 Hz, 3 H) 1.58(s, 9 H) 1.78(br. S., 2 H) 2.16(br. S., 2 H) 2.54(s, 3 H) 2.77(s, 2 H) 4.26(q, J = 7.06 Hz, 2 H) 6.84(s, 1 H) 7.37(s, 1 H), 7.60(s, 1 H), MS ES+ m/z 466 (MH+), HPLC (Method LC-1) Retention time = 0.43 minutes.

| 1.117 | B | C(CH$_3$)$_3$ | H | H | OCH$_2$CH$_3$ | H | CH$_2$CH$_3$ | H |

$^1$H NMR (400 MHz, METHANOL-d$_4$) δ ppm 1.37(t, J = 7.48 Hz, 3 H) 1.52(t, J = 7.06 Hz, 3 H) 1.58(s, 9 H) 1.81(br. S., 2 H) 2.12(br. S., 2 H) 2.77(s, 2 H) 2.98(q, J = 7.48 Hz, 2 H) 4.27(q, J = 7.06 Hz, 2 H) 6.84(s, 1 H) 7.41(s, 1H) 7.60 (s, 1 H), MS ES+ m/z 480 (MH+), HPLC (Method LC-1) Retention time = 0.46 minutes.

| 1.118 | B | CH$_2$CH$_3$ | CH$_3$ | H | OCH$_2$CH$_3$ | H | CH$_3$ | H |

$^1$H NMR (400 MHz, METHANOL-d$_4$) δ ppm 1.38(t, J = 7.27 Hz, 3 H) 1.50(t, J = 7.06 Hz, 3 H) 1.79(s, 2 H) 2.27(s, 3H) 2.52(s, 3 H) 2.74(s, 2 H) 4.14(q, J = 7.27 Hz, 2 H) 4.24(q, J = 7.06 Hz, 2 H) 6.83(s, 1 H) 7.36(s, 1 H), MS ES+ m/z 452 (MH+), HPLC (Method LC-1) Retention time = 0.47 minutes.

| 1.119 | B | CH$_2$CH$_3$ | CH$_3$ | H | OCH$_2$CH$_3$ | H | CH$_2$CH$_3$ | H |

$^1$H NMR (400 MHz, METHANOL-d$_4$) δ ppm 1.31-1.41(m, 6 H) 1.50(t, J = 6.85 Hz, 3 H) 1.78(s, 2 H) 2.27(s, 3H) 2.74(s, 2 H) 2.96(q, J = 7.75 Hz, 2 H) 4.14 (q, J = 7.06 Hz, 2 H) 4.25(q, J = 7.06 Hz, 2 H) 6.83(s, 1 H) 7.39(s, 1 H), MS ES+ m/z 466 (MH+), HPLC (Method LC-1) Retention time = 0.49 minutes.

| 1.120 | B | CH(CH$_3$)$_2$ | H | H | OCH$_2$CH$_3$ | H | CH$_3$ | H |

$^1$H NMR (400 MHz, METHANOL-d$_4$) δ ppm 1.44-1.53(m, 9 H) 1.79(br. S., 2 H) 2.52(s, 3 H) 2.76(s, 2 H) 4.24(q, J = 7.06 Hz, 2 H) 4.45-4.55(m, 1 H) 6.83 (s, 1 H) 7.35(s, 1 H) 7.49(s, 1 H), MS ES+ m/z 452 (MH+), HPLC (Method LC-1) Retention time = 0.40 minutes.

| 1.121 | B | CH(CH$_3$)$_2$ | H | H | OCH$_2$CH$_3$ | H | CH$_2$CH$_3$ | H |

$^1$H NMR (400 MHz, METHANOL-d$_4$) δ ppm 1.35(t, J = 7.69 Hz, 3 H) 1.43-1.54 (m, 9 H) 1.79(br. S., 2 H) 2.76(s, 2 H) 2.96(q, J = 7.48 Hz, 2 H) 4.24(q, J = 7.06 Hz, 2 H) 4.37-4.57(m, 1 H) 6.82(s, 1 H) 7.39(s, 1 H) 7.49(s, 1 H), MS ES+ m/z 466 (MH+), HPLC (Method LC-1) Retention time = 0.42 minutes.

| 1.122 | B | CH(CH$_3$)$_2$ | CH$_3$ | H | OCH$_2$CH$_3$ | H | H | H |

$^1$H NMR (400 MHz, METHANOL-d$_4$) δ ppm 1.43(d, J = 6.65 Hz, 6 H) 1.52(t, J = 7.06 Hz, 3 H) 1.78(br. S., 2 H) 2.27(s, 3 H) 2.73(s, 2 H) 4.26(q, J = 7.06 Hz, 2 H) 4.52-4.65(m, 1 H), 6.84(s, 1 H) 7.42(s, 1 H) 8.05(s, 1H), MS ES+ m/z 452 (MH+), HPLC (Method LC-1) Retention time = 0.41 minutes.

| 1.23 | B | CH(CH$_3$)$_2$ | H | H | OCH$_2$CH$_3$ | H | H | H |

$^1$H NMR (400 MHz, METHANOL-d$_4$) δ ppm 1.42-1.56(m, 9 H) 1.79(br. S., 2 H) 2.75(s, 2 H) 4.26(q, J = 6.92 Hz, 2 H) 4.43-4.58(m ,1 H) 6.84(s, 1 H) 7.41 (s, 1 H) 7.49(s, 1 H) 8.05(s, 1 H), MS ES+ m/z 438 (MH+), HPLC (Method LC-1) Retention time = 0.38 minutes.

| 1.124 | B | CH$_3$ | CH$_3$ | H | H | CH$_3$ | H | H |

MS ES+ m/z 394 (MH+), HPLC (Method LC-1) Retention time = 0.32 minutes.

| 1.125 | B | CH$_3$CH$_2$ | CH$_3$ | H | CH$_3$ | H | CH$_3$CH$_2$ | H |

MS ES+ m/z 436 (MH+), HPLC (Method LC-1) Retention time = 0.39 minutes.

| 1.126 | B | 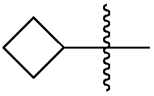 | CH$_3$ | H | CH$_3$ | H | CH$_3$ | H |

MS ES+ m/z 448 (MH+), HPLC (Method LC-1) Retention time = 0.43 minutes.

| 1.127 | B | 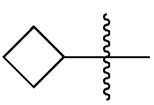 | CH$_3$ | H | OCH$_3$ | H | H | H |

MS ES+ m/z 450 (MH+), HPLC (Method LC-1) Retention time = 0.41 minutes.

TABLE 1-continued

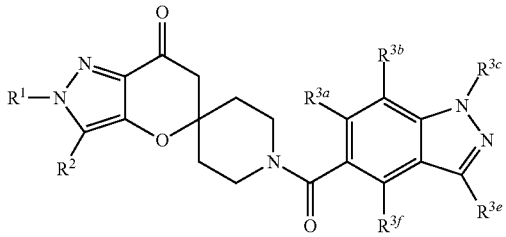

| Ex. | Method | R$^1$ | R$^2$ | R$^{3a}$ | R$^{3b}$ | R$^{3c}$ | R$^{3e}$ | R$^{3f}$ |
|---|---|---|---|---|---|---|---|---|
| 1.128 | B | 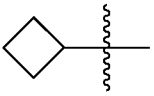 | CH$_3$ | H | CH$_3$ | H | H | H |
| | | MS ES+ m/z 434 (MH+), HPLC (Method LC-1) Retention time = 0.42 minutes. | | | | | | |
| 1.129 | B | CH$_2$CH(CH$_3$)$_2$ | CH$_3$ | H | CH$_3$ | H | CH$_3$ | H |
| | | MS ES+ m/z 450 (MH+), HPLC (Method LC-1) Retention time = 0.44 minutes. | | | | | | |
| 1.130 | B | CH$_2$CH(CH$_3$)$_2$ | CH$_3$ | H | CH$_3$ | H | H | H |
| | | MS ES+ m/z 436 (MH+), HPLC (Method LC-1) Retention time = 0.42 minutes. | | | | | | |
| 1.131 | B | CH$_2$CH(CH$_3$)$_2$ | CH$_3$ | H | OCH$_3$ | H | H | H |
| | | MS ES+ m/z 452 (MH+), HPLC (Method LC-1) Retention time = 0.41 minutes. | | | | | | |
| 1.132 | B | CH$_2$CH(CH$_3$)$_2$ | CH$_3$ | H | OCH$_3$ | H | CH$_3$ | H |
| | | MS ES+ m/z 466 (MH+), HPLC (Method LC-1) Retention time = 0.43 minutes. | | | | | | |
| 1.133 | B | CH(CH$_3$)$_2$ | CH$_3$ | H | Cl | H | H | H |
| | | MS ES+ m/z 442 (MH+), HPLC (Method LC-1) Retention time = 0.40 minutes. | | | | | | |
| 1.134 | B | CH$_2$CH(CH$_3$)$_2$ | H | H | CH$_3$ | H | CH$_3$ | H |
| | | MS ES+ m/z 436 (MH+), HPLC (Method LC-1) Retention time = 0.41 minutes. | | | | | | |
| 1.135 | B | CH$_2$CH(CH$_3$)$_2$ | H | H | CH$_3$ | H | H | H |
| | | MS ES+ m/z 422 (MH+), HPLC (Method LC-1) Retention time = 0.40 minutes. | | | | | | |
| 1.136 | B | CH(CH$_3$)CH$_2$CH$_3$ | CH$_3$ | H | CH$_3$ | H | CH$_3$ | H |
| | | MS ES+ m/z 450 (MH+), HPLC (Method LC-1) Retention time = 0.43 minutes. | | | | | | |
| 1.137 | B | CH(CH$_3$)CH$_2$CH$_3$ | CH$_3$ | H | CH$_3$ | H | H | H |
| | | MS ES+ m/z 436 (MH+), HPLC (Method LC-1) Retention time = 0.42 minutes. | | | | | | |
| 1.138 | B | CH(CH$_3$)CH$_2$CH$_3$ | CH$_3$ | H | H | H | CH$_3$ | H |
| | | MS ES+ m/z 436 (MH+), HPLC (Method LC-1) Retention time = 0.42 minutes. | | | | | | |
| 1.139 | B | CH(CH$_3$)CH$_2$CH$_3$ | CH$_3$ | H | H | H | H | H |
| | | MS ES+ m/z 422 (MH+), HPLC (Method LC-1) Retention time = 0.40 minutes. | | | | | | |
| 1.140 | B | CH(CH$_3$)CH$_2$CH$_3$ | H | H | CH$_3$ | H | CH$_3$ | H |
| | | MS ES+ m/z 436 (MH+), HPLC (Method LC-1) Retention time = 0.41 minutes. | | | | | | |
| 1.041 | B | CH(CH$_3$)CH$_2$CH$_3$ | H | H | H | H | CH$_3$ | H |
| | | MS ES+ m/z 422 (MH+), HPLC (Method LC-1) Retention time = 0.40 minutes. | | | | | | |
| 1.042 | B | CH(CH$_3$)CH$_2$CH$_3$ | H | H | H | H | H | H |
| | | MS ES+ m/z 408 (MH+), HPLC (Method LC-1) Retention time = 0.38 minutes. | | | | | | |
| 1.143 | A | 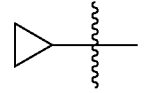 | H | H | CH$_3$ | H | CH$_3$ | H |
| | | MS ES+ m/z 420 (MH+), HPLC (Method LC-1) Retention time = 0.37 minutes. | | | | | | |
| 1.144 | A | 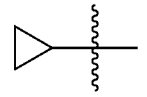 | H | H | CH$_3$ | H | H | H |
| | | MS ES+ m/z 406 (MH+), HPLC (Method LC-1) Retention time = 0.35 minutes. | | | | | | |
| 1.145 | B | C(CH$_3$)$_3$ | H | H | H | CH$_3$ | H | H |
| | | MS ES+ m/z 422 (MH+), HPLC (Method LC-1) Retention time = 0.42 minutes. | | | | | | |
| 1.146 | A | C(CH$_3$)$_3$ | H | H | H | H | H | CH$_3$ |
| | | MS ES+ m/z 422 (MH+), HPLC (Method LC-1) Retention time = 0.52 minutes. | | | | | | |
| 1.147 | A | C(CH$_3$)$_3$ | CH$_3$ | H | H | H | H | H |
| | | MS ES+ m/z 422 (MH+), HPLC (Method LC-1) Retention time = 0.52 minutes. | | | | | | |

TABLE 2

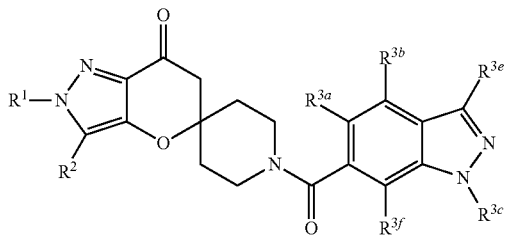

| Ex. | Method | R$^1$ | R$^2$ | R$^{3a}$ | R$^{3b}$ | R$^{3c}$ | R$^{3e}$ | R$^{3f}$ |
|---|---|---|---|---|---|---|---|---|
| 2.001 | A | CH$_2$CH$_3$ | CH$_3$ | H | H | CH$_3$ | H | H |

$^1$H NMR (400 MHz, METHANOL-d$_4$) δ ppm 1.31-1.45 (m, 6 H) 1.81 (br. s., 2 H) 1.99 (br. s., 1 H) 2.17 (m, 1 H) 2.23-2.30 (m, 2 H) 2.48-2.63 (m, 2 H) 2.73 (d, J = 4.57 Hz, 2 H) 3.29 (s, 3 H) 3.38-3.67 (m, 2 H) 4.14 (q, J = 7.20 Hz, 2 H) 4.35-4.54 (m, 1 H) 4.88 (s, 2 H) 7.15 (d, J = 8.31 Hz, 1 H) 7.52 (s, 1 H) 7.78 (d, J = 8.31 Hz, 1 H), MS ES+ m/z 408 (MH+), HPLC (Method LC-1) Retention time = 0.37 minutes.

| 2.002 | A | (phenyl-CH-) | | H | H | H | H | CH$_3$ | H |

$^1$H NMR (500 MHz, DMSO-d$_6$) δ ppm 1.69-1.88 (m, 2 H) 1.94 (br. S., 1 H) 2.01-2.17 (m, 2 H) 2.88 (s, 2 H) 3.11-3.29 (m, 2 H) 3.41-3.60 (m, 1 H) 4.30 (br. S., 1 H) 7.09 (d, J = 8.29 Hz, 1 H) 7.41 (t, J = 7.52 Hz, 1 H) 7.43-7.60 (m, 4 H) 7.76 (d, J = 7.78 Hz, 1 H) 7.87 (d, J = 7.78 Hz, 2 H) 8.47 (s, 1 H), MS ES+ m/z 442 (MH+), HPLC (Method LC-1) Retention time = 0.45 minutes.

| 2.003 | A | CH$_2$CH$_3$ | H | H | H | CH$_3$ | H | H |

$^1$H NMR (400 MHz, METHANOL-d$_4$) δ ppm 1.42 (t, J = 7.34 Hz, 3 H) 1.63-1.91 (m, 2 H) 1.92-2.08 (m, 1 H) 2.11-2.24 (m, 1 H) 2.55 (s, 3 H) 2.63-2.85 (m, 2 H) 3.38-3.53 (m, 1 H) 3.53-3.68 (m, 1 H) 4.17 (q, J = 7.34 Hz, 2 H) 4.45 (br. S., 1 H) 7.14 (d, J = 8.31 Hz, 1 H) 7.46 (s, 1 H) 7.52 (s, 1 H) 7.78 (d, J = 8.31 Hz, 1 H), MS ES+ m/z 394 (MH+), HPLC (Method LC-1) Retention time = 0..35 minutes.

| 2.004 | B | CH$_2$CH$_3$ | CH$_3$ | H | CH$_3$ | H | H | H |

$^1$H NMR (500 MHz, METHANOL-d$_4$) δ ppm 1.41 (t, J = 7.20 Hz, 3 H) 1.85 (br. S., 2 H) 2.01 (br. S., 2 H) 2.15-2.27 (m, 2 H) 2.30 (s, 3 H) 2.77 (d, J = 7.56 Hz, 2 H) 3.41-3.70 (m, 2 H) 4.17 (q, J = 7.32 Hz, 3 H) 7.22 (dd, J = 8.29, 1.22 Hz, 1 H) 7.69 (s, 1 H) 7.86 (d, J = 8.78 Hz, 1 H) 8.07 (s, 1 H), MS ES+ m/z 408 (MH+), HPLC (Method LC-1) Retention time = 0.38 minutes.

| 2.005 | A | CH(CH$_3$)$_2$ | H | H | H | H | CH$_3$ | H |

$^1$H NMR (400 MHz, METHANOL-d$_4$) δ ppm 1.47 (d, J = 6.64 Hz, 6 H) 1.61-2.27 (m, 4 H) 2.55 (s, 3 H) 2.75 (d, J = 3.71 Hz, 2 H) 3.32-3.66 (m, 2 H) 4.33-4.60 (m, 4 H) 7.14 (dd, J = 8.30, 1.07 Hz, 1 H) 7.39-7.57 (m, 2 H) 7.72-7.87 (m, 1 H), MS ES+ m/z 408 (MH+), HPLC (Method LC-1) Retention time = 0.37 minutes.

| 2.006 | A | CH(CH$_3$)$_2$ | H | H | H | Cl | H | H |

$^1$H NMR (400 MHz, METHANOL-d$_4$) δ ppm 1.49 (d, J = 6.64 Hz, 6 H) 1.81 (br. s., 2 H) 2.04 (br. s., 2 H) 2.77 (s, 2 H) 4.47-4.61 (m, 1 H) 7.23 (s, 1 H) 7.50 (s, 1 H) 7.57 (s, 1 H) 8.16 (s, 1 H), MS ES+ m/z 428 (MH+), HPLC (Method LC-1) Retention time = 0.41 minutes.

| 2.007 | A | CH(CH$_3$)$_2$ | H | H | H | CH$_3$ | CH$_2$CH$_3$ | H |

$^1$H NMR (400 MHz, METHANOL-d$_4$) δ ppm 1.37 (t, J = 7.6 Hz, 3 H) 1.48 (d, J = 6.7 Hz, 6 H) 1.80 (br. s., 2 H) 2.29 (br. s., 3 H) 2.70-2.82 (m, 2 H) 2.99 (q, J = 7.6 Hz, 2 H) 4.02 (s, 3 H) 4.43-4.62 (m, 1 H) 7.12-7.19 (m, 1 H) 7.50 (s, 1 H) 7.55-7.59 (m, 1 H) 7.82 (dd, J = 8.20, 0.78 Hz, 1 H), MS ES+ m/z 436 (MH+), HPLC (Method LC-1) Retention time = 0.44 minutes.

| 2.008 | A | CH$_2$CH$_3$ | H | H | H | CH$_3$ | CH$_2$CH$_3$ | H |

$^1$H NMR (400 MHz, CHLOROFORM-d) δ ppm 1.38 (t, J = 7.48 Hz, 3 H) 1.50 (t, J = 7.27 Hz, 3 H) 2.69 (s, 2 H) 2.97 (q, 2 H) 4.00 (s, 3 H) 4.17 (q, 2 H) 7.06 (d, J = 8.31 Hz, 1 H) 7.10 (s, 1 H) 7.42 (s, 1 H) 7.68 (d, J = 8.72 Hz, 1 H), MS ES+ m/z 422 (MH+), HPLC (Method LC-1) Retention time = 0.41 minutes.

| 2.009 | A | C(CH$_3$)$_3$ | H | H | H | Cl | H | H |

MS ES+ m/z 442 (MH+), HPLC (Method LC-1) Retention time = 0.44 minutes.

| 2.010 | A | C(CH$_3$)$_3$ | H | H | H | H | CH$_3$ | H |

MS ES+ m/z 422 (MH+), HPLC (Method LC-1) Retention time = 0.41 minutes.

| 2.011 | A | CH$_2$CH$_3$ | CH$_3$ | H | H | H | H | H |

MS ES+ m/z 394 (MH+), HPLC (Method LC-1) Retention time = 0.33 minutes.

| 2.012 | B | C(CH$_3$)$_3$ | H | H | H | H | H | H |

MS ES+ m/z 408 (MH+), HPLC (Method LC-1) Retention time = 0.38 minutes.

| 2.013 | A | C(CH$_3$)$_3$ | H | H | H | CH$_3$ | H | H |

MS ES+ m/z 422 (MH+), HPLC (Method LC-1) Retention time = 0.55 minutes.

TABLE 2-continued

| Ex. | Method | R¹ | R² | R³ᵃ | R³ᵇ | R³ᶜ | R³ᵉ | R³ᶠ |
|---|---|---|---|---|---|---|---|---|
| 2.014 | C | C(CH₃)₃ | H | H | F | H | H | H |

$^1$H NMR (400 MHz, DMSO-d6) δ ppm 1.47 (s, 9 H) 1.63-2.07 (m, 4 H) 2.69 (s, 2 H) 3.00-3.20 (m, 2 H) 4.22 (br. s., 1 H) 6.91 (d, 1 H) 7.39 (s, 1 H) 7.75 (s, 1 H) 8.21 (s, 1 H) 13.60 (s, 1 H), MS ES+ m/z 426 (MH+), HPLC (Method LC-1) Retention time = 0.43 minutes.

| 2.015 | C | CH(CH₃)₂ | H | H | F | H | H | H |

$^1$H NMR (400 MHz, DMSO-d6) δ ppm 1.37 (s, 6 H) 1.63-2.08 (m, 4 H) 2.71 (s, 2 H) 3.04-3.20 (m, 2 H) 4.20 (br. s., 1 H) 4.37-4.56 (m, 1 H) 6.90 (d, 1 H) 7.41 (s, 1 H) 7.67 (s, 1 H) 8.20 (s, 1 H) 13.57 (s, 1 H), MS ES+ m/z 412 (MH+), HPLC (Method LC-1) Retention time = 0.40 minutes.

| 2.016 | C | CH₂CH₃ | CH₃ | H | F | H | H | H |

$^1$H NMR (400 MHz, DMSO-d6) δ ppm 1.30 (t, 3 H) 1.54-2.05 (m, 4 H) 2.17 (s, 3 H) 2.64 (s, 2 H) 3.11 (br. s., 1 H) 4.05 (q, 2 H) 4.25 (s, 1 H) 6.76-7.01 (m, 1 H) 7.38 (s, 1 H) 8.20 (s, 1 H) 13.57 (s, 1 H), MS ES+ m/z 412 (MH+), HPLC (Method LC-1) Retention time = 0.39 minutes.

| 2.017 | C | C(CH₃)₃ | H | H | H | H | H | F |

$^1$H NMR (400 MHz, DMSO-d6) δ ppm 1.47 (s, 9 H) 1.57-2.08 (m, 4 H) 2.72 (s, 2 H) 3.04-3.23 (m, 2 H) 4.21-4.37 (m, 1 H) 6.94-7.10 (m, 1 H) 7.63 (d, 1 H) 7.78 (s, 1 H) 8.18 (s, 1 H) 13.78 (s, 1 H), MS ES+ m/z 426 (MH+), HPLC (Method LC-1) Retention time = 0.39 minutes.

| 2.018 | A | C(CH₃)₃ | H | H | CH₃ | H | H | H |

$^1$H NMR (400 MHz, METHANOL-d4) δ ppm 1.47-1.66 (m, 9 H) 1.96 (Br. s., 2 H) 2.21 (br. s., 2 H) 2.50 (s, 3 H) 2.75 (d, J = 4.49 Hz, 2 H) 3.47 (br. s., 2 H) 4.50 (br. s., 2 H) 7.05 (s, 1 H) 7.42 (s, 1 H) 7.54-7.62 (m, 1 H) 7.98 (s, 1 H), MS ES+ m/z 422 (MH+), HPLC (Method LC-1) Retention time = 0.42 minutes.

| 2.019 | A | CH(CH₃)₂ | H | H | CH₃ | H | H | H |

$^1$H NMR (400 MHz METHANOL-d4) δ ppm 1.42-1.50 (m, 6 H) 1.96 (br. s., 2 H) 2.20 (br. s., 2 H) 2.49 (s, 3 H) 2.76 (d, J = 4.49 Hz, 2 H) 3.47 (br. s., 2 H) 4.37-4.59 (m, 3 H) 7.05 (s, 1 H) 7.41 (s, 1 H) 7.49 (s, 1 H) 7.98 (s, 1 H), MS ES+ m/z 408 (MH+), HPLC (Method LC-1) Retention time = 0.39 minutes.

| 2.020 | A | C(CH₃)₃ | H | H | H | H | H | OCH₃ |

$^1$H NMR (400 MHz, METHANOL-d4) δ ppm 1.49-1.65 (m, 9 H) 1.93 (d, J = 166.23 Hz, 6 H) 2.75 (s, 2 H) 3.47 (br. s., 2 H) 3.91-4.11 (m, 3 H) 6.87 (d, J = 7.80 Hz, 1 H) 7.18 (d, J = 7.80 Hz, 1 H) 7.59 (s, 1 H) 8.01 (s, 1 H), MS ES+ m/z 438 (MH+), HPLC (Method LC-1) Retention time = 0.41 minutes.

| 2.021 | A | CH₂CH₃ | CH₃ | H | H | H | H | OCH₃ |

$^1$H NMR (400 MHz, METHANOL-d4) δ ppm 1.38 (t, J = 7.32 Hz, 3 H) 1.60-2.18 (m, 4 H) 2.21-2.33 (m, 3 H) 2.74 (s, 2 H) 3.45 (d, J = 12.10 Hz, 2 H) 4.03 (s, 3 H) 4.14 (q, J = 7.35 Hz, 2 H) 6.87 (d, J = 7.80 Hz, 1 H) 7.19 (d, J = 7.80 Hz, 1 H) 8.03 (s, 1 H), MS ES+ m/z 424 (MH+), HPLC (Method LC-1) Retention time = 0.37 minutes.

| 2.022 | A | CH(CH₃)₂ | H | H | H | H | H | OCH₃ |

$^1$H NMR (400 MHz, METHANOL-d4) δ ppm 1.40-1.55 (m, 6 H) 1.57-2.31 (m, 4 H) 2.75 (s, 2 H) 3.34-3.53 (m, 2 H) 4.03 (s, 3 H) 4.32-4.60 (m, 3 H) 6.86 (d, J = 7.80 Hz, 1 H) 7.18 (d, J = 7.80 Hz, 1 H) 7.49 (s, 1 H) 8.01 (s, 1 H), MS ES+ m/z 424 (MH+), HPLC (Method LC-1) Retention time = 0.38 minutes.

| 2.023 | B | C(CH₃)₃ | H | H | OCH₃ | H | H | H |

MS ES+ m/z 438 (MH+), HPLC (Method LC-1) Retention time = 0.41 minutes.

| 2.024 | B | CH₂CH₃ | H | H | H | H | CH₃ | H |

MS ES+ m/z 394 (MH+), HPLC (Method LC-1) Retention time = 0.34 minutes.

| 2.025 | B | CH₂CH₃ | CH₃ | H | H | H | CH₃ | H |

MS ES+ m/z 408 (MH+), HPLC (Method LC-1) Retention time = 0.37 minutes.

TABLE 3

[Structure: spiro compound with pyrazolone-pyranone fused ring linked through spiropiperidine N–C(=O) to a benzimidazole bearing R³ᵃ, R³ᵇ, R³ᶜ, R³ᵈ, R³ᶠ substituents; pyrazole bears R¹ and R².]

| Ex. | Method | R¹ | R² | R³ᵃ | R³ᵇ | R³ᶜ | R³ᵈ | R³ᶠ |
|---|---|---|---|---|---|---|---|---|
| 3.001 | B | CH(CH₃)₂ | H | H | CH₃ | H | CH₃ | H |

¹H NMR (500 MHz, METHANOL-d₄) δ ppm 1.50 (d, J = 6.59 Hz, 6 H) 2.57 (s, 3 H) 2.61 (s, 3 H) 2.78 (br. s., 2 H) 4.51-4.57 (m, 1 H) 7.09 (s, 1 H) 7.41 (s, 1 H) 7.52 (s, 1 H), MS ES+ m/z 422 (MH+), HPLC (Method LC-1) Retention time = 0.30 minutes.

| 3.002 | B | CH₂CH₃ | CH₃ | H | CH₃ | H | CH₃ | H |

¹H NMR (500 MHz, METHANOL-d₄) δ ppm 1.41 (t, J = 7.32 Hz, 3 H) 2.30 (s, 3 H) 2.57 (s, 3 H) 2.61 (s, 3 H) 2.76 (br. s., 2 H) 4.17 (q, J = 7.32 Hz, 2 H) 7.10 (s, 1 H) 7.42 (br. s., 1 H), MS ES+ m/z 422 (MH+), HPLC (Method LC-1) Retention time = 0.29 minutes.

| 3.003 | B | C(CH₃)₃ | H | H | CH₃ | H | CH₃ | H |

¹H NMR (400 MHz, METHANOL-d₄) δ ppm 1.57 (s, 9 H) 2.54 (s, 3 H) 2.57 (s, 3 H) 2.75 (br. s., 2 H) 7.06 (s, 1 H) 7.38 (br. s., 1 H) 7.58 (s, 1 H), MS ES+ m/z 436 (MH+), HPLC (Method LC-1) Retention time = 0.33 minutes.

| 3.004 | B | CH₂CH₃ | H | H | CH₃ | H | CH₃ | H |

¹H NMR (400 MHz, METHANOL-d₄) δ ppm 1.47 (t, J = 7.32 Hz, 3 H) 2.57 (s, 3 H) 2.61 (s, 3 H) 2.78 (br. s., 2 H) 4.20 (q, J = 7.32 Hz, 2 H) 7.09 (s, 1 H) 7.41 (s, 1 H) 7.49 (s, 1 H), MS ES+ m/z 408 (MH+), HPLC (Method LC-1) Retention time = 0.28 minutes.

| 3.005 | A | CH₂CH₃ | CH₃ | H | CH₃ | H | H | H |

¹H NMR (500 MHz, METHANOL-d₄) δ ppm 2.43-2.50 (m, 2 H) 2.54-2.60 (m, 2 H) 2.60-2.65 (m, 3 H) 4.80-4.89 (m, 1 H) 7.16 (br. s., 1 H) 7.53-7.55 (m, 2 H) 8.27 (s, 1 H), MS ES+ m/z 408 (MH+), HPLC (Method LC-1) Retention time = 0.41 minutes.

| 3.006 | A | cyclobutyl-C(CH₃)- (structure) | | H | H | CH₃ | H | H | H |

¹H NMR (500 MHz, METHANOL-d₄) δ ppm 2.43-2.50 (m, 2 H) 2.54-2.60 (m, 2 H) 2.60-2.65 (m, 3 H) 4.80-4.89 (m, 1 H) 7.16 (br. s., 1 H) 7.53-7.55 (m, 2 H) 8.27 (s, 1 H), MS ES+ m/z 420 (MH+), HPLC (Method LC-1) Retention time = 0.42 minutes.

| 3.007 | A | CH(CH₃)₂ | H | H | CH₃ | H | H | H |

¹H NMR (500 MHz, METHANOL-d₄) δ ppm 1.50 (d, J = 6.59 Hz, 6 H) 2.63 (br. s., 3 H) 2.78 (br. s., 2 H) 4.51-4.57 (m, 1 H) 7.16 (br. s., 1 H) 7.51-7.53 (m, 2 H), MS ES+ m/z 408 (MH+), HPLC (Method LC-1) Retention time = 0.42 minutes

| 3.008 | A | C(CH₃)₃ | H | H | CH₃ | H | H | H |

¹H NMR (500 MHz, METHANOL-d₄) δ ppm 1.50 (d, J = 6.59 Hz, 6 H) 2.60 (s, 3 H) 2.79 (s, 2 H) 4.51-4.57 (m, 1 H) 7.52 (d, J = 1.22 Hz, 1 H) 7.52 (s, 1 H) 7.82 (d, J = 1.22 Hz, 1 H), MS ES+ m/z 422 (MH+), HPLC (Method LC-1) Retention time = 0.32 minutes.

| 3.009 | C | CH(CH₃)₂ | H | H | CH₃ | CH₃ | H | H |

¹H NMR (500 MHz, METHANOL-d4) δ ppm 1.50 (d, J = 6.83 Hz, 6 H) 2.64 (s, 3 H) 2.78 (br. s., 2 H) 3.93 (s, 3 H) 4.51-4.57 (m, 1 H) 7.17 (s, 1 H) 7.49-7.52 (m, 2 H) 8.22 (s, 1 H), MS ES+ m/z 422 (MH+), HPLC (Method LC-1) Retention time = 0.29 minutes.

| 3.010 | C | C(CH₃)₃ | H | H | H | H | H | H |

¹H NMR (500 MHz, METHANOL-d4) δ ppm 1.58-1.61 (m, 9 H) 2.79 (d, J = 3.90 Hz, 2 H) 7.38 (dd, J = 8.29, 1.46 Hz, 1 H) 7.62 (s, 1 H) 7.74 (s, 2 H) 8.31 (s, 1 H), MS ES+ m/z 408 (MH+), HPLC (Method LC-1) Retention time = 0.31 minutes.

| 3.011 | C | C(CH₃)₃ | H | H | H | H | CH₃ | H |

¹H NMR (500 MHz, METHANOL-d4) δ ppm 1.60 (s, 9 H) 2.60 (s, 3 H) 2.78 (d, J = 1.95 Hz, 2 H) 7.31 (d, 1 H) 7.50-7.63 (m, 3 H), MS ES+ m/z 422 (MH+), HPLC (Method LC-1) Retention time = 0.31 minutes.

| 3.012 | C | CH(CH₃)₂ | H | H | H | H | CH₃ | H |

¹H NMR (500 MHz, METHANOL-d4) δ ppm 1.50 (d, J = 6.83 Hz, 6 H) 2.60 (s, 3 H) 2.78 (br. s., 2 H) 4.53 (d, J = 6.59 Hz, 1 H) 7.31 (s, 1 H) 7.53 (s, 1 H), MS ES+ m/z 408 (MH+), HPLC (Method LC-1) Retention time = 0.28 minutes.

TABLE 3-continued

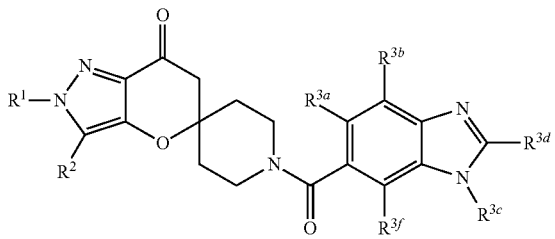

| Ex. | Method | R¹ | R² | R³ᵃ | R³ᵇ | R³ᶜ | R³ᵈ | R³ᶠ |
|---|---|---|---|---|---|---|---|---|
| 3.013 | C | CH₂CH₃ | CH₃ | H | H | H | CH₃ | H |

¹H NMR (400 MHz, METHANOL-d4) δ ppm 1.38 (t, J = 7.27 Hz, 3 H) 2.27 (s, 3 H) 2.57 (s, 3 H) 2.73 (br. s., 2 H) 4.14 (q, J = 7.48 Hz, 2 H) 7.27 (d, J = 8.72 Hz, 1 H) 7.57 (br. s., 2 H), MS ES+ m/z 408 (MH+), HPLC (Method LC-1) Retention time = 0.27 minutes.

| 3.014 | C | C(CH₃)₃ | H | H | H | H | CH₃ | H |

¹H NMR (500 MHz, METHANOL-d4) δ ppm 1.60 (s, 9 H) 2.78 (br. s., 2 H) 3.96 (s, 3 H) 7.39 (d, 1 H) 7.62 (s, 1 H) 7.70-7.77 (m, 2 H) 8.26 (s, 1 H), MS ES+ m/z 422 (MH+), HPLC (Method LC-1) Retention time = 0.31 minutes.

| 3.015 | C | CH(CH₃)₂ | H | H | H | H | CH₃ | H |

¹H NMR (500 MHz, METHANOL-d4) δ ppm 1.50 (d, J = 6.83 Hz, 6 H) 2.79 (br. s., 2 H) 3.95 (s, 3 H) 4.50-4.57 (m, 1 H) 7.39 (d, 1 H) 7.53 (s, 1 H) 7.71 (s, 1 H) 7.74 (d, 1 H) 8.26 (s, 1 H), MS ES+ m/z 408 (MH+), HPLC (Method LC-1) Retention time = 0.28 minutes.

| 3.016 | C | CH₂CH₃ | CH₃ | H | H | H | CH₃ | H |

¹H NMR (500 MHz, METHANOL-d4) δ ppm 1.41 (t, J = 7.07 Hz, 3 H) 2.30 (s, 3 H) 2.78 (br. s., 2 H) 3.96 (s, 3 H) 4.17 (q, 2 H) 7.40 (d, 1 H) 7.72 (s, 1 H) 7.75 (d, J = 8.54 Hz, 1 H) 8.26 (s, 1 H), MS ES+ m/z 408 (MH+), HPLC (Method LC-1) Retention time = 0.28 minutes.

| 3.017 | C | CH(CH₃)₂ | CH₃ | H | CH₃ | H | H | H |

¹H NMR (500 MHz, METHANOL-d4) δ ppm 1.46 (d, J = 6.59 Hz, 6 H) 2.30 (s, 3 H) 2.61 (br. s., 3 H) 2.76 (br. s., 2 H) 4.56-4.65 (m, 1 H) 7.17 (br. s., 1 H) 8.27 (s, 1 H), MS ES+ m/z 422 (MH+), HPLC (Method LC-1) Retention time = 0.31 minutes.

| 3.018 | C | CH₂CH₃ | CH₃ | H | F | H | CH₃ | H |

¹H NMR (500 MHz, METHANOL-d4) δ ppm 1.41 (t, J = 7.20 Hz, 3 H) 2.30 (s, 3 H) 2.61 (s, 3 H) 2.76 (s, 2 H) 4.17 (q, J = 7.40 Hz, 2 H) 7.07 (br. s., 1 H) 7.37 (br. s., 1 H), MS ES+ m/z 426 (MH+), HPLC (Method LC-1) Retention time = 0.29 minutes.

| 3.019 | C | C(CH₃)₃ | H | H | F | H | CH₃ | H |

MS ES+ m/z 440 (MH+), HPLC (Method LC-1) Retention time = 0.32 minutes.

| 3.020 | C | CH₂CH₃ | CH₃ | H | F | H | H | H |

¹H NMR (400 MHz, METHANOL-d4) δ ppm 1.38 (t, J = 7.06 Hz, 3 H) 2.27 (s, 3 H) 2.74 (s, 2H) 4.14 (q, J = 7.20 Hz, 2 H) 7.11 (br. s., 1 H) 7.47 (br. s., 1 H) 8.29 (s, 1 H), MS ES+ m/z 412 (MH+), HPLC (Method LC-1) Retention time = 0.29 minutes.

| 3.021 | C | CH(CH₃)₂ | H | H | F | H | H | H |

¹H NMR (500 MHz, METHANOL-d4) δ ppm 1.50 (d, J = 6.59 Hz, 6 H) 2.78 (br. s., 2 H) 4.49-4.57 (m, 1 H) 7.13 (br. s., 1 H) 7.51 (s, 2 H) 8.32 (s, 1 H), MS ES+ m/z 412 (MH+), HPLC (Method LC-1) Retention time = 0.30 minutes.

| 3.022 | C | C(CH₃)₃ | H | H | F | H | H | H |

¹H NMR (500 MHz, METHANOL-d4) δ ppm 1.60 (s, 9 H) 2.78 (br. s., 2 H) 7.13 (br. s., 1 H) 7.50 (br. s., 1 H) 7.61 (s, 1 H) 8.32 (s, 1 H), MS ES+ m/z 426 (MH+), HPLC (Method LC-1) Retention time = 0.34 minutes.

| 3.023 | C | C(CH₃)₃ | H | H | CH₃ | CH₃ | H | H |

¹H NMR (500 MHz, METHANOL-d4) δ ppm 1.60 (s, 9 H) 2.64 (s, 3 H) 2.78 (br. s., 2 H) 3.93 (s, 3 H) 7.17 (s, 1 H) 7.50 (s, 1 H) 7.61 (s, 1 H) 8.22 (s, 1 H), MS ES+ m/z 436 (MH+), HPLC (Method LC-1) Retention time = 0.33 minutes.

| 3.024 | C | CH(CH₃)₂ | H | H | F | H | CH₃ | H |

¹H NMR (500 MHz, METHANOL-d4) δ ppm 1.50 (d, J = 6.59 Hz, 6 H) 2.61 (s, 3 H) 2.78 (s, 2 H) 7.07 (br. s., 1 H) 7.36 (br. s., 1 H) 7.51 (s, 1 H), MS ES+ m/z 426 (MH+), HPLC (Method LC-1) Retention time = 0.29 minutes.

| 3.025 | C | CH₂CH₃ | CH₃ | H | CH₃ | CH₃ | H | H |

¹H NMR (500 MHz, METHANOL-d4) δ ppm 1.41 (t, J = 7.32 Hz, 3 H) 2.30 (s, 3 H) 2.64 (s, 3 H) 2.77 (br. s., 2 H) 3.93 (s, 3 H) 4.17 (q, J = 7.16 Hz, 2 H) 7.18 (s, 1 H) 7.51 (s, 1 H) 8.22 (s, 1 H), MS ES+ m/z 422 (MH+), HPLC (Method LC-1) Retention time = 0.29 minutes.

| 3.026 | A | CH₂CH₃ | CH₃ | H | H | H | H | H |

MS ES+ m/z 394 (MH+), HPLC (Method LC-1) Retention time = 0.26 minutes.

| 3.027 | C | C(CH₃)₃ | H | H | H | CH₃ | CH₃ | H |

MS ES+ m/z 436 (MH+), HPLC (Method LC-1) Retention time = 0.33 minutes.

TABLE 4

| Ex. | Method | R¹ | R² | R³ᵃ | R³ᵇ | R³ᶜ | R³ᵈ | R³ᵉ | R³ᶠ |
|---|---|---|---|---|---|---|---|---|---|
| 4.001 | A | CH₂CH₃ | CH₃ | H | CH₃ | H | H | CH₃ | H |

$^1$H NMR (400 MHz, METHANOL-d₄) δ ppm 1.37 (t, J = 7.32 Hz, 3 H) 2.25 (s, 3 H) 2.28 (s, 3 H) 2.47 (s, 3 H) 2.73 (br. s., 2 H) 4.13 (q, J = 7.32 Hz, 2 H) 6.96 (s, 1 H) 7.05 (s, 1 H) 7.44 (s, 1 H), MS ES⁺ m/z 421 (MH⁺), HPLC (Method LC-1) Retention time = 2.2 minutes

TABLE 5

| Ex. | Method | R¹ | R² | R³ᵃ | R³ᵇ | R³ᶜ | R³ᵉ | R³ᶠ |
|---|---|---|---|---|---|---|---|---|
| 5.001 | A | CH(CH₃)₂ | H | H | H | CH₃ | H | H |

$^1$H NMR (400 MHz, METHANOL-d₄) δ ppm 1.49 (d, J = 6.83 Hz, 6 H) 1.80 (br. s., 2 H) 2.13 (br. s., 2 H) 2.77 (s, 6 H) 4.24 (s, 4 H) 4.47-4.59 (m, 1 H) 7.10 (dd, J = 8.49, 1.27 Hz, 1 H) 7.50 (s, 1 H) 7.68 (d, J =1.27 Hz, 1 H) 7.79 (dd, J = 8.49, 0.98 Hz, 1 H) 8.26 (s, 1 H), MS ES+ m/z 394 (MH+), HPLC (Method LC-1) Retention time = 0.33 minutes.

| Ex. | Method | R¹ | R² | R³ᵃ | R³ᵇ | R³ᶜ | R³ᵉ | R³ᶠ |
|---|---|---|---|---|---|---|---|---|
| 5.002 | A | CH(CH₃)₂ | H | H | H | H | CH₃ | H |

MS ES+ m/z 408 (MH+), HPLC (Method LC-1) Retention time = 0.36 minutes.

TABLE 6

| Ex. | Method | R¹ | R² | R³ᵍ | R³ʰ | R³ⁱ | R³ʲ |
|---|---|---|---|---|---|---|---|
| 6.001 | B | CH₃CH₂ | CH₃ | H | H | OCH₃ | H |
| 6.002 | B | CH₃CH₂ | CH₃ | H | H | CH₃ | H |
| 6.003 | B | C(CH₃)₃ | H | H | H | OCH₃ | H |
| 6.004 | B | C(CH₃)₃ | H | H | OCH₃ | H | H |
| 6.005 | B | C(CH₃)₃ | H | H | H | CH₃ | H |
| 6.006 | B | C(CH₃)₃ | H | H | OCH₃ | H | H |
| 6.007 | B | CH₃CH₂ | CH₃ | H | H | H | H |
| 6.008 | B | CH₃CH₂ | CH₃ | H | H | H | OCH₃ |

6.001: MS ES+ m/z 434.2 (MH+), HPLC (Method LC-2) Retention time = 3.54 minutes.
6.002: MS ES+ m/z 418.6 (MH+), HPLC (Method LC-2) Retention time = 3.64 minutes.
6.003: MS ES+ m/z 448.2 (MH+), HPLC (Method LC-2) Retention time = 3.81 minutes.
6.004: MS ES+ m/z 448.2 (MH+), HPLC (Method LC-2) Retention time = 3.80 minutes.
6.005: MS ES+ m/z 432.2 (MH+), HPLC (Method LC-2) Retention time = 3.91 minutes.
6.006: MS ES+ m/z 448.2 (MH+), HPLC (Method LC-2) Retention time = 3.93 minutes.
6.007: MS ES+ m/z 404 (MH+), HPLC (Method LC-1) Retention time = 0.48 minutes.
6.008: MS ES+ m/z 434 (MH+), HPLC (Method LC-1) Retention time = 0.49 minutes.

TABLE 7

| Ex. | Method | R¹ | R² | R³ᵃ | R³ᵇ | R³ᵉ | R³ᶠ |
|---|---|---|---|---|---|---|---|
| 7.001 | A | CH(CH₂)₂ | H | H | H | NH₂ | H |
| | MS ES+ m/z 426 (MH+), HPLC (Method LC-1) Retention time = 0.30 minutes. | | | | | | |
| 7.002 | A | C(CH₃)₃ | H | H | H | NH₂ | H |
| | MS ES+ m/z 440 (MH+), HPLC (Method LC-1) Retention time = 0.33 minutes. | | | | | | |
| 7.003 | A | CH₂CH₃ | CH₃ | H | H | NH₂ | H |
| | MS ES+ m/z 426 (MH+), HPLC (Method LC-1) Retention time = 0.29 minutes. | | | | | | |
| 7.004 | A | C(CH₃)₃ | H | H | H | H | H |
| | ¹H NMR (400 MHz, METHANOL-d4) δ ppm 1.46-1.65 (m, 9 H) 1.65-2.29 (m, 4 H) 2.76 (d, J = 2.34 Hz, 2 H) 3.42-3.73 (m, 2 H) 4.47 (br. s., 2 H) 7.58 (s, 1 H) 7.63 (dd, J = 8.39, 1.56 Hz, 1 H) 8.17 (d, J = 8.39 Hz, 1 H) 8.25 (s, 1 H) 9.03 (d, J = 0.78 Hz, 1 H), MS ES+ m/z 425 (MH+), HPLC (Method LC-1) Retention time = 0.44 minutes. | | | | | | |
| 7.005 | A | CH₂CH₃ | CH₃ | H | H | H | H |
| | ¹H NMR (400 MHz, METHANOL-d4) δ ppm 1.38 (t, J = 7.22 Hz, 3 H) 1.60-2.13 (m, 4 H) 2.27 (s, 3 H) 2.74 (d, J = 2.34 Hz, 2 H) 3.57 (br. s., 2 H) 4.14 (q, J = 7.28 Hz, 2 H) 4.47 (br. s., 2 H) 7.63 (dd, J = 8.39, 1.37 Hz, 1 H) 8.17 (d, J = 8.39 Hz, 1 H) 8.25 (s, 1 H) 9.03 (s, 1 H), MS ES+ m/z 411 (MH+), HPLC (Method LC-1) Retention time = 0.40 minutes. | | | | | | |
| 7.006 | A | CH(CH₂)₂ | H | H | H | H | H |
| | ¹H NMR (400 MHz, DMSO-d6) δ ppm 1.28-1.50 (m, 6 H) 1.60-2.27 (m, 6 H) 2.72 (s, 2 H) 2.92-3.65 (m, 2 H) 4.38-4.57 (m, 1 H) 7.52-7.74 (m, 2 H) 8.10-8.42 (m, 2 H) 9.14 (d, J = 0.78 Hz, 1 H), MS ES+ m/z 411 (MH+), HPLC Retention time = 0.42 minutes. | | | | | | |
| 7.007 | A | C(CH₃)₃ | H | H | H | CH₃ | H |
| | ¹H NMR (400 MHz, METHANOL-d4) δ ppm 1.57 (s, 9 H) 1.68-2.33 (m, 4 H) 2.64 (s, 3 H) 2.76 (d, J = 4.68 Hz, 2 H) 3.47 (br. s., 2 H) 4.47 (br. s., 2 H) 7.43 (s, 1 H) 7.59 (s, 1 H) 8.08 (s, 1 H) 9.05 (s, 1 H), MS ES+ m/z 439 (MH+), HPLC (Method LC-1) Retention time = 0.49 minutes. | | | | | | |
| 7.008 | A | CH₂CH₃ | CH₃ | H | H | CH₃ | H |
| | ¹H NMR (400 MHz, METHANOL-d4) δ ppm 1.38 (t, J = 7.22 Hz, 3 H) 1.89 (d, J = 82.92 Hz, 4 H) 2.27 (s, 3 H) 2.64 (s, 3 H) 2.74 (d, J = 5.07 Hz, 2 H) 3.44-3.66 (m, 2 H) 4.14 (q, J = 7.28 Hz, 2 H) 4.47 (br. s., 2 H) 7.43 (s, 1 H) 8.08 (s, 1 H) 9.05 (s, 1 H), MS ES+ m/z 425 (MH+), HPLC (Method LC-1) Retention time = 0.45 minutes. | | | | | | |
| 7.009 | A | CH(CH₂)₂ | H | H | H | CH₃ | H |
| | ¹H NMR (400 MHz, METHANOL-d4) δ ppm 1.41-1.50 (m, 6 H) 1.66-2.29 (m, 4 H) 2.57-2.66 (m, 3 H) 2.76 (d, J = 4.88 Hz, 2 H) 3.40-3.71 (m, 2 H) 4.40-4.64 (m, 3 H) 7.43 (s, 1 H) 7.49 (s, 1 H) 8.08 (s, 1 H) 9.05 (s, 1 H), MS ES+ m/z 425 (MH+), HPLC (Method LC-1) Retention time = 0.46 minutes. | | | | | | |

TABLE 8

| Ex. | Method | R¹ | R² | R³ᵃ | R³ᵇ | R³ᶜ | R³ᵈ | R³ᶠ |
|---|---|---|---|---|---|---|---|---|
| 8.001 | A | C(CH₃)₃ | H | H | CH₃ | CH₃ | H | H |
| | ¹H NMR (500 MHz, METHANOL-d4) δ ppm 1.60 (s, 9 H) 2.82 (s, 5 H) 4.15 (s, 3 H) 7.13 (s, 1 H) 7.61 (s, 2 H) 8.12 (s, 1 H), MS ES+ m/z 436 (MH+), HPLC (Method LC-1) Retention time = 0.33 minutes. | | | | | | | |
| 8.002 | A | CH(CH₃)₂ | H | H | CH₃ | CH₃ | H | H |
| | ¹H NMR (500 MHz, METHANOL-d4) δ ppm 1.50 (d, J = 6.59 Hz, 6 H) 2.82 (s, 5 H) 4.15 (s, 3 H) 4.50-4.57 (m, 1 H) 7.13 (s, 1 H) 7.52 (s, 2 H) 8.12 (s, 1 H), MS ES+ m/z 422 (MH+), HPLC (Method LC-1) Retention time = 0.30 minutes. | | | | | | | |

TABLE 8-continued

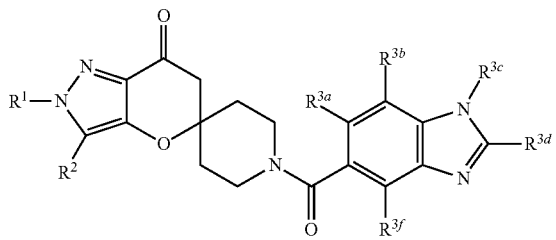

| Ex. | Method | $R^1$ | $R^2$ | $R^{3a}$ | $R^{3b}$ | $R^{3c}$ | $R^{3d}$ | $R^{3f}$ |
|---|---|---|---|---|---|---|---|---|
| 8.003 | A | $CH_2CH_3$ | $CH_3$ | H | $CH_3$ | $CH_3$ | H | H |
| | $^1$H NMR (500 MHz, METHANOL-d4) δ ppm 1.41 (t, J = 7.32 Hz, 3 H) 2.30 (s, 3 H) 2.75-2.83 (m, 5 H) 4.14-4.20 (m, 5 H) 7.14 (s, 1 H) 7.57 (s, 1 H) 8.13 (s, 1 H), MS ES+ m/z 422 (MH+), HPLC (Method LC-1) Retention time = 0.29 minutes. | | | | | | | |
| 8.004 | B | $CH_2CH_3$ | $CH_3$ | H | H | $CH_2CH_3$ | $CH_3$ | H |
| | MS ES+ m/z 436 (MH+), HPLC (Method LC-1) Retention time = 0.31 minutes. | | | | | | | |
| 8.005 | B | $CH_2CH_3$ | $CH_3$ | H | H | $CH_3$ | H | H |
| | MS ES+ m/z 408 (MH+), HPLC (Method LC-1) Retention time = 0.29 minutes. | | | | | | | |
| 8.006 | B | $CH_2CH_3$ | $CH_3$ | H | H | $CH_3$ | $CH_3$ | H |
| | MS ES+ m/z 422 (MH+), HPLC (Method LC-1) Retention time = 0.29 minutes. | | | | | | | |
| 8.007 | B | $C(CH_3)_3$ | H | H | H | $CH_3$ | H | H |
| | MS ES+ m/z 422 (MH+), HPLC (Method LC-1) Retention time = 0.33 minutes. | | | | | | | |
| 8.008 | B | $C(CH_3)_3$ | H | H | H | $CH_2CH_3$ | $CH_3$ | H |
| | MS ES+ m/z 450 (MH+), HPLC (Method LC-1) Retention time = 0.35 minutes. | | | | | | | |
| 8.009 | B | $C(CH_3)_3$ | H | H | H | $CH_3$ | $CH_3$ | H |
| | MS ES+ m/z 436 (MH+), HPLC (Method LC-1) Retention time = 0.34 minutes. | | | | | | | |
| 8.010 | B | $C(CH_3)_3$ | H | H | H | $CH_3$ | OH | H |
| | MS ES+ m/z 438.2 (MH+), HPLC (Method LC-2) Retention time = 2.83 minutes. | | | | | | | |
| 8.011 | B | $CH_2CH_3$ | $CH_3$ | H | H | $CH_3$ | OH | H |
| | MS ES+ m/z 424 (MH+), HPLC (Method LC-1) Retention time = 0.35 minutes. | | | | | | | |

TABLE 9

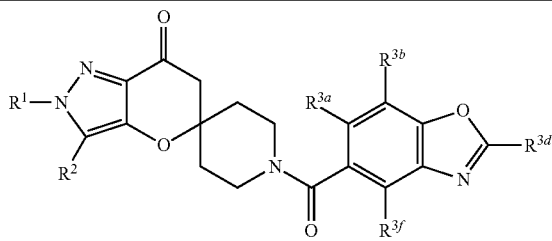

| Ex. | Method | $R^1$ | $R^2$ | $R^{3a}$ | $R^{3b}$ | $R^{3d}$ | $R^{3f}$ |
|---|---|---|---|---|---|---|---|
| 9.001 | B | $CH(CH_2)_2$ | H | H | H | H | H |
| | $^1$H NMR (500 MHz, DMSO-d6) δ ppm 1.40 (d, J = 6.59 Hz, 6 H) 1.70-1.81 (m, 2 H) 1.88 (br. s., 1 H) 2.02 (br. s., 1 H) 2.74 (s, 2 H) 3.15 (br. s., 1 H) 4.27 (br. s., 1 H) 4.43-4.56 (m, 1 H) 7.49 (dd, J = 8.42, 1.59 Hz, 1 H) 7.71 (s, 1 H) 7.82-7.88 (m, 2 H) 8.85 (s, 1 H), MS ES+ m/z 395 (MH+), HPLC (Method LC-1) Retention time = 0.36 minutes. | | | | | | | |
| 9.002 | B | $C(CH_3)_3$ | H | H | H | H | H |
| | MS ES+ m/z 409 (MH+), HPLC (Method LC-1) Retention time = 0.40 minutes. | | | | | | | |
| 9.003 | A | $C(CH_3)_3$ | H | H | $OCH_3$ | $CH_3$ | H |
| | $^1$H NMR (500 MHz, METHANOL-d4) δ ppm 1.60 (s, 9 H) 2.66 (s, 3 H) 2.78 (br. s., 2 H) 4.05 (s, 3 H) 7.03 (s, 1 H) 7.28 (s, 1 H) 7.61 (s, 1 H), MS ES+ m/z 453 (MH+), HPLC (Method LC-1) Retention time = 0.44 minutes. | | | | | | | |
| 9.004 | A | $CH(CH_2)_2$ | H | H | $OCH_3$ | $CH_3$ | H |
| | $^1$H NMR (500 MHz, METHANOL-d4) δ ppm 1.50 (d, J = 6.59 Hz, 6 H) 2.66 (s, 3 H) 2.78 (br. s., 2 H) 4.05 (s, 3 H) 4.50-4.57 (m, 1 H) 7.03 (d, J = 1.22 Hz, 1 H) 7.28 (d, J = 1.22 Hz, 1 H) 7.51 (s, 1 H), MS ES+ m/z 439 (MH+), HPLC (Method LC-1) Retention time = 0.40 minutes. | | | | | | | |
| 9.005 | A | $CH_2CH_3$ | $CH_3$ | H | $OCH_3$ | $CH_3$ | H |
| | $^1$H NMR (500 MHz, METHANOL-d4) δ ppm 1.41 (t, J = 7.32 Hz, 3 H) 2.29 (s, 3 H) 2.66 (s, 3 H) 2.76 (d, J = 2.68 Hz, 2 H) 4.05 (s, 3 H) 4.17 (q, J = 7.16 Hz, 2 H) 7.03 (d, J = 1.22 Hz, 1 H) 7.29 (d, J = 1.46 Hz, 1 H), MS ES+ m/z 439 (MH+), HPLC (Method LC-1) Retention time = 0.39 minutes. | | | | | | | |

TABLE 10

| Ex. | Method | R¹ | R² | R³ᵃ | R³ᵇ | R³ᵈ | R³ᶠ |
|---|---|---|---|---|---|---|---|
| 10.001 | A | $CH_2CH_3$ | $CH_3$ | H | H | H | H |
| | MS ES+ m/z 411 (MH+), HPLC (Method LC-1) Retention time = 0.36 minutes. | | | | | | |
| 10.002 | A | $C(CH_3)_3$ | H | H | H | H | H |
| | MS ES+ m/z 425 (MH+), HPLC (Method LC-1) Retention time = 0.41 minutes. | | | | | | |

TABLE 11

| Ex. | Method | R¹ | R² | R³ᵃ | R³ᵇ | R³ᶠ |
|---|---|---|---|---|---|---|
| 11.001 | A | $CH_2CH_3$ | $CH_3$ | H | $CH_3$ | H |
| | MS ES+ m/z 435 (MH+), HPLC (Method LC-1) Retention time = 0.35 minutes. | | | | | |
| 11.002 | A | $C(CH_3)_3$ | H | H | $CH_3$ | H |
| | MS ES+ m/z 449 (MH+), HPLC (Method LC-1) Retention time = 0.39 minutes. | | | | | |

TABLE 12

| Ex. | Method | R¹ | R² | R³ᵃ | R³ᵇ | R³ᶜ | R³ᶠ | Y |
|---|---|---|---|---|---|---|---|---|
| 12.001 | B | $CH_2CH_3$ | $CH_3$ | H | H | $CH_3$ | H | $CH_2$ |
| | MS ES+ m/z 437 (MH+), HPLC (Method LC-1) Retention time = 0.38 minutes. | | | | | | | |
| 12.002 | B | $CH_2CH_3$ | $CH_3$ | H | H | H | H | $CH_2$ |
| | MS ES+ m/z 423 (MH+), HPLC (Method LC-1) Retention time = 0.37 minutes. | | | | | | | |
| 12.003 | B | $C(CH_3)_3$ | H | H | H | $CH_3$ | H | $CH_2$ |
| | MS ES+ m/z 451 (MH+), HPLC (Method LC-1) Retention time = 0.43 minutes. | | | | | | | |
| 12.004 | B | $C(CH_3)_3$ | H | H | H | H | H | $CH_2$ |
| | ¹H NMR (500 MHz, DMSO-d6) δ ppm 1.51 (s, 9 H) 1.65-1.75 (br m, 2 H) 1.85-2.05 (br m, 2 H) 2.45 (t, 3 H) 2.74 (s, 2 H) 2.89 (t, 2 H) 6.88 (s, 1 H), 6.95 (d, 1 H) 7.21 (d, 1 H) 7.80 (s, 1 H) 10.18 (s, 1 H), MS ES+ m/z 437 (MH+), HPLC (Method LC-1) Retention time = 0.39 minutes. | | | | | | | |
| 12.005 | B | $C(CH_3)_3$ | H | H | H | H | H | O |
| | MS ES+ m/z 439.2 (MH+), HPLC (Method LC-2) Retention time = 2.91 minutes. | | | | | | | |

TABLE 13

| Ex. | Method | R¹ | R² | R³ᵃ | R³ᵇ | R³ᶠ | Y |
|---|---|---|---|---|---|---|---|
| 13.001 | B | $CH_2CH_3$ | $CH_3$ | H | H | H | $CH_2$ |
| | MS ES+ m/z 423 (MH+), HPLC (Method LC-1) Retention time = 0.35 minutes. | | | | | | |
| 13.002 | B | $CH_2CH_3$ | $CH_3$ | H | H | H | O |
| | MS ES+ m/z 425 (MH+), HPLC (Method LC-1) Retention time = 0.35 minutes. | | | | | | |
| 13.003 | B | $C(CH_3)_3$ | H | H | H | H | O |
| | MS ES+ m/z 439 (MH+), HPLC (Method LC-1) Retention time = 0.39 minutes. | | | | | | |
| 13.004 | B | $C(CH_3)_3$ | H | H | H | H | $CH_2$ |
| | MS ES+ m/z 437 (MH+), HPLC (Method LC-1) Retention time = 0.39 minutes. | | | | | | |

TABLE 14

| Ex. | Method | R¹ | R² | R³ᵃ | R³ᵈ | R³ᶠ |
|---|---|---|---|---|---|---|
| 14.001 | B | $C(CH_3)_3$ | H | H | $CH_3$ | H |
| | ¹H NMR (500 MHz, DMSO-d6) δ ppm 1.51 (s, 9 H) 1.63-1.73 (br m, 2 H) 1.75-2.05 (br m, 2 H) 2.74 (s, 2 H) 2.82 (s, 3 H) 7.42 (d, 1 H), 7.80 (s, 1 H) 7.92 (s, 1 H) 8.12 (d, 1 H), MS ES+ m/z 439 (MH+), HPLC (Method LC-1) Retention time = 0.45 minutes. | | | | | |
| 14.002 | B | $CH_2CH_3$ | $CH_3$ | H | $CH_3$ | H |
| | MS ES+ m/z 425 (MH+), HPLC (Method LC-1) Retention time = 0.42 minutes. | | | | | |

TABLE 15

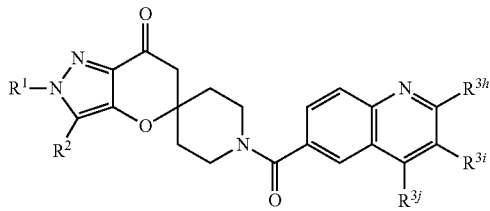

| Ex. | Method | R¹ | R² | $R^{3h}$ | $R^{3i}$ | $R^{3j}$ |
|---|---|---|---|---|---|---|
| 15.001 | B | C(CH$_3$)$_3$ | H | CH$_3$ | H | H |
| | MS ES+ m/z 433.2 (MH+), HPLC (Method LC-2) | | | | | |
| | Retention time = 2.47 minutes. | | | | | |
| 15.002 | B | C(CH$_3$)$_3$ | H | H | H | H |
| | MS ES+ m/z 419.2 (MH+), HPLC (Method LC-2) | | | | | |
| | Retention time = 2.44 minutes. | | | | | |
| 15.003 | B | CH$_2$CH$_3$ | CH$_3$ | H | H | H |
| | MS ES+ m/z 405.2 (MH+), HPLC (Method LC-3) | | | | | |
| | Retention time = 1.04 minutes. | | | | | |

TABLE 16

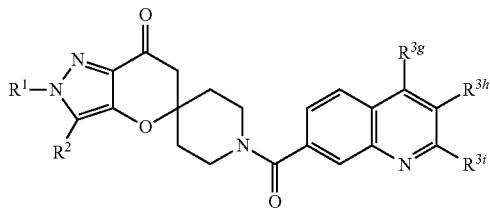

| Ex. | Method | R¹ | R² | $R^{3g}$ | $R^{3h}$ | $R^{3i}$ |
|---|---|---|---|---|---|---|
| 16.001 | B | C(CH$_3$)$_3$ | H | H | H | H |
| | MS ES+ m/z 419.2 (MH+), HPLC (Method LC-2) | | | | | |
| | Retention time = 2.46 minutes. | | | | | |
| 16.002 | B | CH$_2$CH$_3$ | CH$_3$ | H | H | H |
| | MS ES+ m/z 405.2 (MH+), HPLC (Method LC-2) | | | | | |
| | Retention time = 2.24 minutes. | | | | | |

TABLE 17

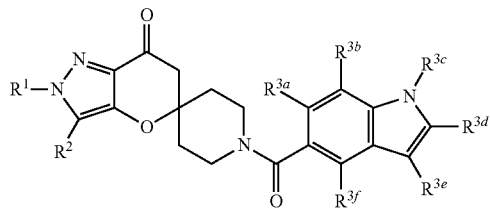

| Ex. | Method | R¹ | R² | $R^{3a}$ | $R^{3b}$ | $R^{3c}$ | $R^{3d}$ | $R^{3ef}$ | $R^{3f}$ |
|---|---|---|---|---|---|---|---|---|---|
| 17.001 | B | C(CH$_3$)$_3$ | H | H | H | H | H | H | H |
| | MS ES+ m/z 408.2 (MH+), HPLC (Method LC-2) | | | | | | | | |
| | Retention time = 3.44 minutes. | | | | | | | | |
| 17.002 | B | CH$_2$CH$_3$ | CH$_3$ | H | H | CH$_3$ | H | H | H |
| | MS ES+ m/z 394.2 (MH+), HPLC (Method LC-2) | | | | | | | | |
| | Retention time = 3.18 minutes. | | | | | | | | |

TABLE 18

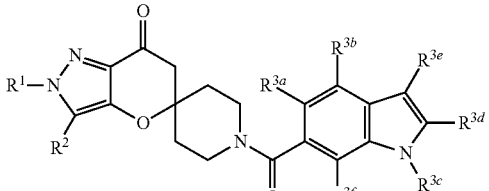

| Ex. | Method | R¹ | R² | $R^{3a}$ | $R^{3b}$ | $R^{3c}$ | $R^{3d}$ | $R^{3ef}$ | $R^{3f}$ |
|---|---|---|---|---|---|---|---|---|---|
| 18.001 | B | C(CH$_3$)$_3$ | H | H | H | H | H | H | H |
| | MS ES+ m/z 421.2 (MH+), HPLC (Method LC-2) | | | | | | | | |
| | Retention time = 3.58 minutes. | | | | | | | | |
| 18.002 | B | CH$_2$CH$_3$ | CH$_3$ | H | H | CH$_3$ | H | H | H |
| | MS ES+ m/z 407.1 (MH+), HPLC (Method LC-3) | | | | | | | | |
| | Retention time = 1.48 minutes. | | | | | | | | |

TABLE 19

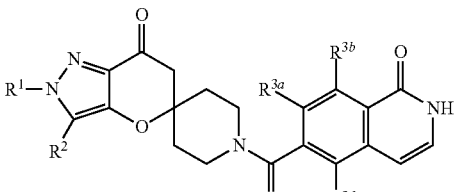

| Ex. | Method | R¹ | R² | $R^{3a}$ | $R^{3b}$ | $R^{3f}$ |
|---|---|---|---|---|---|---|
| 19.001 | A | C(CH$_3$)$_3$ | H | H | H | H |
| | MS ES+ m/z 435 (MH+), HPLC (Method LC-1) | | | | | |
| | Retention time = 0.49 minutes. | | | | | |

TABLE 20

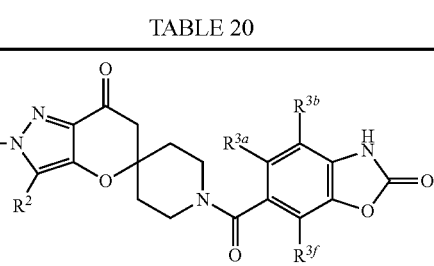

| Ex. | Method | R¹ | R² | $R^{3a}$ | $R^{3b}$ | $R^{3f}$ |
|---|---|---|---|---|---|---|
| 20.001 | A | C(CH$_3$)$_3$ | H | H | H | H |
| | MS ES+ m/z 425 (MH+), HPLC (Method LC-1) | | | | | |
| | Retention time = 0.50 minutes. | | | | | |

TABLE 21

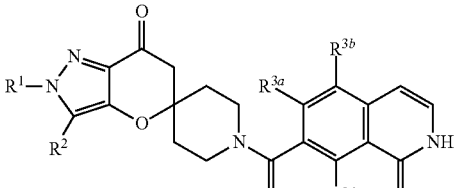

| Ex. | Method | R¹ | R² | $R^{3a}$ | $R^{3b}$ | $R^{3f}$ |
|---|---|---|---|---|---|---|
| 21.001 | A | C(CH$_3$)$_3$ | H | H | H | H |
| | MS ES+ m/z 435 (MH+), HPLC (Method LC-1) | | | | | |
| | Retention time = 0.50 minutes. | | | | | |

TABLE 22

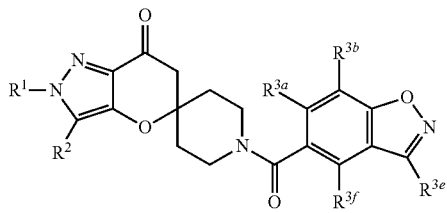

| Ex. | Method | R¹ | R² | R³ᵃ | R³ᵇ | R³ᵉ | R³ᶠ |
|---|---|---|---|---|---|---|---|
| 22.001 | A | CH(CH$_3$)$_2$ | H | H | H | H | H |

¹H NMR (500 MHz, METHANOL-d4) δ ppm 1.24-1.38 (m, 6 H) 1.51 (d, J = 6.83 Hz, 2 H) 1.69-1.86 (m, 2 H) 2.13 (br. s., 2 H) 2.67 (s, 2 H) 2.76 (s, 2 H) 4.42-4.62 (m, 1 H) 7.00 (d, J = 8.78 Hz, 1 H) 7.44-7.58 (m, 3 H) 7.66 (d, J = 1.71 Hz, 1 H), MS ES+ m/z 395 (MH+), HPLC (Method LC-1) Retention time = 0.35 minutes.

| 22.002 | A | C(CH$_3$)$_3$ | H | H | H | H | H |

¹H NMR (400 MHz, METHANOL-d4) δ ppm 1.46-1.65 (m, 9 H) 1.74 (d, J = 13.29 Hz, 4 H) 2.07 (d, J = 57.33 Hz, 4 H) 2.68-2.78 (m, 2 H) 7.00 (d, J = 8.72 Hz, 1 H) 7.48-7.61 (m, 3 H) 7.65 (s, 1 H), MS ES+ m/z 409 (MH+), HPLC (Method LC-1) Retention time = 0.39 minutes.

| 22.003 | A | CH$_2$CH$_3$ | CH$_3$ | H | H | H | H |

¹H NMR (500 MHz, METHANOL-d4) δ ppm 1.24-1.36 (m, 3 H) 1.66-1.86 (m, 2 H) 2.10 (d, J = 8.05 Hz, 2 H) 2.22-2.34 (m, 3 H) 2.67 (s, 2 H) 2.69-2.77 (m, 2 H) 3.22 (q, J = 7.32 Hz, 4 H) 4.17 (q, J = 7.32 Hz, 1 H) 6.99 (d, J = 8.54 Hz, 1 H) 7.55 (dd, J = 8.66, 1.83 Hz, 1 H) 7.66 (s, 1 H), MS ES+ m/z 395 (MH+), HPLC (Method LC-1) Retention time = 0.35 minutes.

TABLE 23

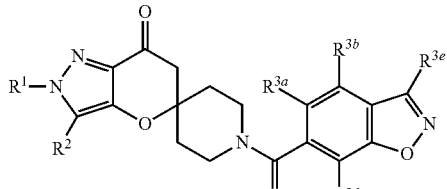

| Ex. | Method | R¹ | R² | R³ᵃ | R³ᵇ | R³ᵉ | R³ᶠ |
|---|---|---|---|---|---|---|---|
| 23.001 | A | C(CH$_3$)$_2$ | H | H | H | CH$_3$ | H |

¹H NMR (400 MHz, DMSO-d6) δ ppm 1.36 (d, J = 6.83 Hz, 6 H) 1.53-2.11(m, 4 H) 2.50-2.81 (m, 5 H) 2.90-3.56 (m, 4 H) 4.34-4.57 (m, 1 H) 7.33(dd, J = 8.10, 1.27 Hz, 1 H) 7.58-7.78 (m, 3 H), MS ES+ m/z 409 (MH+), HPLC (Method LC-1) Retention time = 0.38 minutes.

| 23.002 | A | C(CH$_3$)$_3$ | H | H | H | CH$_3$ | H |

¹H NMR (400 MHz, DMSO-d6) δ ppm 1.38-1.54 (m, 9 H) 1.59-2.08 (m, 4 H) 2.54-2.63 (m, 3 H) 2.63-2.77 (m, 2 H) 3.00-3.42 (m, 2 H) 7.33 (dd, J = 8.10, 1.46 Hz, 1 H) 7.61-7.72 (m, 2 H) 7.75 (s, 1 H), MS ES+ m/z 423 (MH+), HPLC (Method LC-1) Retention time = 0.41 minutes.

| 23.003 | A | CH$_2$CH$_3$ | CH$_3$ | H | H | CH$_3$ | H |

¹H NMR (400 MHz, DMSO-d6) δ ppm, 1.28 (t, J = 7.22 Hz, 3 H) 1.53-2.03 (m, 4 H) 2.11-2.28 (m, 3 H) 2.50-2.75 (m, 5 H) 2.95-3.53 (m, 4 H) 4.06 (q, J = 7.22 Hz, 2 H) 7.33 (dd, J = 8.20, 1.17 Hz, 1 H) 7.55-7.80 (m, 2 H), MS ES+ m/z 409 (MH+), HPLC (Method LC-1) Retention time = 0.37 minutes.

TABLE 23-continued

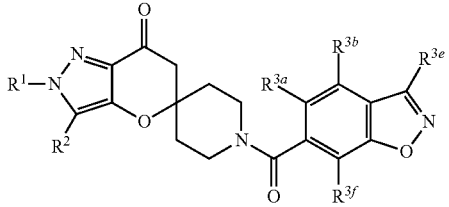

| Ex. | Method | R¹ | R² | R³ᵃ | R³ᵇ | R³ᵉ | R³ᶠ |
|---|---|---|---|---|---|---|---|
| 23.004 | A | CH(CH$_3$)$_2$ | H | H | H | H | H |

¹H NMR (400 MHz, DMSO-d6) δ ppm 1.37 (t, J = 7.13 Hz, 6 H) 1.53-2.06 (m, 4 H) 2.58-2.74 (m, 2 H) 3.18 (d, J = 103.48 Hz, 4 H) 4.37-4.56 (m, 1 H) 6.53 (d, J = 1.37 Hz, 1 H) 6.67 (d, J = 7.81 Hz, 1 H) 6.77 (s, 1 H) 7.50 (d, J = 7.81 Hz, 1 H) 7.57-7.68 (m, 1 H), MS ES+ m/z 395 (MH+), HPLC (Method LC-1) Retention time = 0.37 minutes.

| 23.005 | A | C(CH$_3$)$_3$ | H | H | H | H | H |

¹H NMR (400 MHz, DMSO-d6) δ ppm, 1.36-1.54 (m, 9 H) 1.52-2.12 (m, 4 H) 2.60-2.89 (m, 3 H) 2.87-3.63 (m, 2 H) 4.14 (br. s.,1 H) 6.54 (s, 1 H) 6.78-6.95 (m, 2 H) 7.54-7.67 (m, 1 H) 7.68-7.83 (m, 1 H), MS ES+ m/z 409 (MH+), HPLC (Method LC-1) Retention time = 0.40 minutes.

TABLE 24

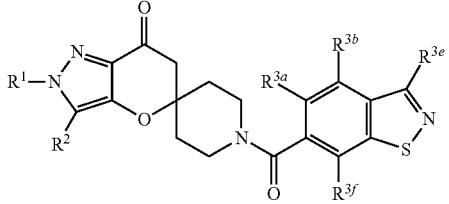

| Ex. | Method | R¹ | R² | R³ᵃ | R³ᵇ | R³ᵉ | R³ᶠ |
|---|---|---|---|---|---|---|---|
| 24.001 | A | C(CH$_3$)$_3$ | H | H | H | H | H |

¹H NMR (500 MHz, DMSO-d6) ppm 1.43-1.55 (m, 9 H) 1.64-2.21 (m, 4 H) 2.75 (s, 2 H) 2.98-3.53 (m, 2 H) 4.28 (br. s., 2 H) 7.53 (dd, J = 8.17, 1.10 Hz, 1 H) 8.05-8.42 (m, 2 H) 9.18 (s, 1 H), MS ES+ m/z 425 (MH+), HPLC (Method LC-1) Retention time = 0.44 minutes.

| 24.002 | A | CH(CH$_3$)$_2$ | H | H | H | H | H |

¹H NMR (400 MHz, DMSO-d6) δ ppm 1.38 (d, J = 6.64 Hz, 6 H) 1.89 (d, J = 126.67 Hz, 4 H) 2.59-2.80 (m, 2 H) 3.03-3.59 (m, 2 H) 4.24 (br. s., 2 H) 4.40-4.57 (m, 1 H) 7.50 (d, J = 7.89 Hz, 1 H) 7.68 (s, 1 H) 8.07-8.41 (m, 2 H) 9.16 (s, 1 H), MS ES+ m/z 411 (MH+), HPLC (Method LC-1) Retention time = 0.42 minutes.

| 24.003 | A | CH$_2$CH$_3$ | CH$_3$ | H | H | H | H |

¹H NMR (500 MHz, DMSO-d6) δ ppm 1.32 (t, J = 7.32 Hz, 3 H) 1.63-1.82 (m, 3 H) 1.78-2.16 (m, 2 H) 2.22 (s, 2 H) 2.71 (s, 2 H) 3.03-3.50 (m, 2 H) 4.10 (q, J = 7.32 Hz, 2 H) 4.30 (br. s., 2 H) 7.53 (dd, J = 8.17, 1.10 Hz, 1 H) 8.12-8.38 (m, 2 H) 9.18 (s, 1 H), MS ES+ m/z 411 (MH+), HPLC (Method LC-1) Retention time = 0.40 minutes.

TABLE 25

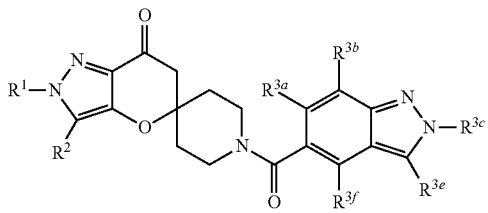

| Ex. | Method | R¹ | R² | R³ᵃ | R³ᵇ | R³ᶜ | R³ᵉ | R³ᶠ |
|---|---|---|---|---|---|---|---|---|
| 25.001 | B | CH₂CH₃ | CH₃ | H | CH₃ | CH₃ | H | H |
| | ¹H NMR (400 MHz, DMSO-d6) δ ppm 1.38 (t, 3 H) 2.26 (s, 3 H) 2.57 (s, 3 H) 2.73 (s, 2 H) 4.14 (q, 2 H) 4.22 (s, 3 H) 7.08 (s, 1 H) 7.63 (s, 1 H) 8.25 (s 2 H), MS ES+ m/z 422 (MH+), HPLC (Method LC-1) Retention time = 0.34 minutes | | | | | | | |
| 25.002 | B | CH₃ | CH₃ | H | CH₃ | CH₃ | H | H |
| | ¹H NMR (400 MHz, DMSO-d6) δ ppm 2.25 (s, 3 H) 2.58 (s, 3 H) 2.73 (s, 2 H) 3.91 (s, 3 H) 4.22 (s, 3 H) 7.19 (s, 1 H) 7.63 (s, 1 H) 8.26 (s 2 H), MS ES+ m/z 408 (MH+), HPLC (Method LC-1) Retention time = 0.32 minutes. | | | | | | | |
| 25.003 | B | CH₃ | CH₃ | H | H | CH₃ | CH₃ | H |
| | ¹H NMR (400 MHz, DMSO-d6) δ ppm 2.57 (s, 3 H) 2.75 (s, 2 H) 3.89 (s, 3 H) 4.22 (s, 3 H) 7.17 (s, 1 H) 7.41 (s, 1 H) 7.63 (s, 1 H) 8.26 (s 2 H), MS ES+ m/z 394 (MH+), HPLC (Method LC-1) Retention time = 0.30 minutes. | | | | | | | |
| 25.004 | B | CH₂CH₃ | CH₃ | H | H | CH₃ | H | H |
| | ¹H NMR (400 MHz, DMSO-d6) δ ppm 1.38 (t, 3 H) 2.26 (s, 3 H) 2.73 (s, 2 H) 4.13 (q, 2 H) 4.22 (s, 3 H) 7.33 (d, 1 H) 7.64 (d, 1 H) 7.83 (s, 2 H) 8.28 (s, 2 H), MS ES+ m/z 408 (MH+), HPLC (Method LC-1) Retention time = 0.32 minutes. | | | | | | | |
| 25.005 | B | CH₃ | CH₃ | H | H | CH₃ | H | H |
| | ¹H NMR (400 MHz, DMSO-d6) δ ppm 2.24 (s, 3 H) 2.73 (s, 2 H) 3.81 (s, 3 H) 4.22 (s, 3 H) 7.33 (d, 1 H) 7.64 (d, 1 H) 7.83 (s, 2 H) 8.29 (s, 2 H), MS MS ES+ m/z 394 (MH+), HPLC (Method LC-1) Retention time = 0.30 minutes. | | | | | | | |

Pharmacological Data

Biological Protocols

The utility of the compound of present invention, in the treatment of diseases (such as are detailed herein) in animals, particularly mammals (e.g., humans) may be demonstrated by the activity thereof in conventional assays known to one of ordinary skill in the relevant art, including the in vitro and in vivo assays described below. Such assays also provide a means whereby the activities of the compound of the present invention can be compared with the activities of other known compounds.

Direct Inhibition of the Activities of ACC1 and ACC2

The ACC inhibitory activity of the compound of the present invention was demonstrated by methods based on standard procedures. For example direct inhibition of ACC activity, for the compound of Formula (1) was determined using preparations of rat liver ACC and recombinant human ACC2.

[1] Preparation of rat liver ACC. Rat liver ACC was obtained from rat liver based upon standard procedures such as those described by Thampy and Wakil (J. Biol. Chem. 260: 6318-6323; 1985) using the following method.

Male CD rats weighing 150-200 g were fasted for 18-24 hours and then fed a high sucrose diet (AIN-76A rodent diet; Cat # D10001, Research Diets Inc., New Brunswick, N.J.), for 3 days at which time they were sacrificed by $CO_2$ asphyxiation. The livers were removed, rinsed in ice-cold phosphate-buffered saline (PBS), and homogenized in 5 volumes of homogenization buffer (50 mM potassium phosphate, pH 7.5, 10 mM EDTA, 10 mM 2-mercaptoethanol, 2 mM benzamidine, 0.2 mM phenylmethylsulfonylfluoride (PMSF), 5 mg/L each leupeptin, aprotinin, and antitrypsin) in a Waring® blender for 1 minute at 4° C. All subsequent operations were carried out at 4° C. The homogenate has made 3% with respect to polyethylene glycol (PEG) by the addition of 50% PEG solution and centrifuged at 20,000×g for 15 minutes. The resulting supernatant was adjusted to 5% PEG with the addition of 50% PEG solution and stirred for 5 minutes. The pellet (contains ACC activity) was collected by centrifugation at 20,000×g for 20 minutes, rinsed with ice-cold doubly distilled water to remove excess PEG and re-suspended in one-fourth the original homogenate volume with homogenization buffer. Ammonium sulfate (200 g/liter) was slowly added with stirring. After 45 minutes the enzyme is collected by centrifugation for 30 minutes at 20,000×g, re-suspended in 10 mL of 50 mM HEPES, pH7.5, 0.1 mM DTT, 1.0 mM EDTA, and 10% glycerol and desalted on a Sephadex™ G-25 column (2.5 cm×50 cm) (Pharmacia, Piscataway N.J. now GE Healthcare) equilibrated with the same buffer. The desalted enzyme preparation was stored in aliquots at −70° C. Immediately prior to use, frozen rat liver ACC aliquots were thawed, diluted to 500 µg/mL in buffer containing 50 mM HEPES, pH7.5, 10 mM $MgCl_2$, 10 mM tripotassium citrate, 2.0 mM dithiothreitol (DTT), and 0.75 mg/mL fatty acid-free bovine serum albumin (BSA) and pre-incubated at 37° C. for 30 minutes.

[2] Measurement of rat liver ACC inhibition. For measurement of ACC activity and assessment of ACC inhibition, test compounds were dissolved in dimethylsulfoxide (DMSO) and 1 µL aliquots were added to a clear bottom, 96-well plates (Perkin-Elmer PN#1450-514). Control wells contain 1 µL of DMSO alone or 1 µL of high inhibition compound. The enzyme obtained from rat liver as described above was activated in Enzyme buffer at 37° C. for 30 minutes prior to addition to compound plate. All wells receive 75 µL of activated enzyme (1.33×) in a buffer containing 50 mM HEPES, pH7.5, 7.5 mM $MgCl_2$ 7.5 mM tripotassium citrate, 2 mM DTT, 50 mg/mL BSA. The activated enzyme was pre-incubated with the cmpd for 10 minute prior to initiating the reaction through the addition of 25 µL of substrate solution containing 50 mM HEPES, pH7.5, 7.5 mM $MgCl_2$ 7.5 mM tripotassium citrate, 2 mM DTT, 50 mg/mL BSA, 120 µM acetyl-CoA, 8.0 mM ATP, 38.4 mM $KHCO_3$, and 1.6 mM NaH[$^{14}$C]$O_3$ (100 µCi/µL). The final substrate concentrations in the reaction were 30 µM Acetyl-CoA, 9.6 mM KHCO3, 0.4 mM NaH[$^{14}$C]O3, and 2 mM ATP. The reaction was terminated after 10 mins by the addition of 25 µL 3N HCl and the plates were dried at 50° C. for a minimum 20 hrs. 30 µL of water was added to the dried plate and mixed for 5 minutes. 95 µL of Optiphase Supermix liquid scintillation fluid (Perkin Elmer, Waltham, Mass.) was added and the plates are mixed for 20 minutes. Incorporation of $^{14}$C into MCoA was measured using a Wallac Trilux 1450 Microbeta LSC luminescence counter.

[3] Measurement of human ACC2 inhibition. Human ACC2 inhibition was measured using purified recombinant human ACC2 (hrACC2). Briefly, a full length Cytomax clone of ACC2 was purchased from Cambridge Bioscience Limited and was sequenced and subcloned into PcDNA5 FRT TO-TOPO (Invitrogen, Carlsbad, Calif.). The ACC2 was expressed in CHO cells by tetracycline induction and harvested in 5 liters of DMEM/F12 with glutamine, biotin, hygromycin and blasticidin with 1 μg/mL tetracycline (Invitrogen, Carlsbad, Calif.). The conditioned medium containing ACC2 was then applied to a Softlink Soft Release Avidin column (Promega, Madison, Wis.) and eluted with 5 mM biotin. 4 mgs of ACC2 were eluted at a concentration of 0.05 mg/mL (determined by A280) with an estimated purity of 95% (determined by A280). The purified ACC2 was dialyzed in 50 mM Tris, 200 mM NaCl, 4 mM DTT, 2 mM EDTA, and 5% glycerol. The pooled protein was frozen and stored at −80°, with no loss of activity upon thawing. For measurement of ACC2 activity and assessment of ACC2 inhibition, test compounds were dissolved in DMSO and added to the rhACC2 enzyme as a 5× stock with a final DMSO concentration of 1%. rhACC2 was assayed in a Costar #3767 (Costar, Canbridge, Mass.) 384-well plate using the Transcreener ADP detection FP assay kit (Bellbrook Labs, Madison, Wis.) using the manufactures' conditions for a 50 uM ATP reaction. The final conditions for the assay were 50 mM HEPES, pH7.5, 5 mM $MgCl_2$, 5 mM tripotassium citrate, 2 mM DTT, 0.5 mg/mL BSA, 30 μM acetyl-CoA, 50 μM ATP, and 8 mM $KHCO_3$. Typically, a 10 μl reaction was run for 1 hour at room temperature, and 10 μl of Transcreener stop and detect buffer was added and incubated for an additional 1 hour. The data was acquired on a Envision Fluorescence reader (Perkinelmer) using a 620 excitation Cy5 FP general dual mirror, 620 ecxitation Cy5 FP filter, 688 emission (S) and a 688 (P) emission filter.

The results using the rat liver ACC radio enzymatic and recombinant hACC2 transcreener assays described above are summarized in the table below for the Compounds of Formula (I) exemplified in the Examples above.

| Ex. | Compound Name | Rat liver ACC $IC_{50}$ (nM) | Rat liver ACC n* | rhACC2 $IC_{50}$ (nM) | rhACC2 n* |
|---|---|---|---|---|---|
| 1.001 | 1-[(3,7-Dimethyl-1H-indazol-5-yl)carbonyl]-2'-ethyl-3'-methyl-2'H-spiro[piperidine-4,5'-pyrano[3,2-c]pyrazol]-7'(6'H)-one | 9 | 12 | 11 | 9 |
| 1.002 | 1-[(3,7-Dimethyl-1H-indazol-5-yl)carbonyl]-2'-isopropyl-2'H-spiro[piperidine-4,5'-pyrano[3,2-c]pyrazol]-7'(6'H)-one | 11 | 4 | 8 | 3 |
| 1.003 | 1-[(3,7-Dimethyl-1H-indazol-5-yl)carbonyl]-2'-ethyl-2'H-spiro[piperidine-4,5'-pyrano[3,2-c]pyrazol]-7'(6'H)-one | 21 | 10 | 11 | 4 |
| 1.004 | 1-[(3,7-Dimethyl-1H-indazol-5-yl)carbonyl]-2'-propyl-2'H-spiro[piperidine-4,5'-pyrano[3,2-c]pyrazol]-7'(6'H)-one | 26 | 5 | 20 | 3 |
| 1.005 | 1-[(3,7-Dimethyl-1H-indazol-5-yl)carbonyl]-2',3'-dimethyl-2'H-spiro[piperidine-4,5'-pyrano[3,2-c]pyrazol]-7'(6'H)-one | 103 | 3 | 117 | 2 |
| 1.006 | 1-[(3,7-Dimethyl-1H-indazol-5-yl)carbonyl]-2'-methyl-2'H-spiro[piperidine-4,5'-pyrano[3,2-c]pyrazol]-7'(6'H)-one | 132 | 3 | 80 | 2 |
| 1.007 | 1-(3,7-dimethyl-1H-indazole-5-carbonyl)-3'-ethyl-2'-methyl-2'H-spiro[piperidine-4,5'-pyrano[3,2-c]pyrazol]-7'(6'H)-one | 182 | 3 | 189 | 4 |
| 1.008 | 2'-Cyclohexyl-1-[(3,7-dimethyl-1H-indazol-5-yl)carbonyl]-2'H-spiro[piperidine-4,5'-pyrano[3,2-c]pyrazol]-7'(6'H)-one | 19 | 4 | 21 | 3 |
| 1.009 | 2'-Cyclopentyl-1-[(3,7-dimethyl-1H-indazol-5-yl)carbonyl]-2'H-spiro[piperidine-4,5'-pyrano[3,2-c]pyrazol]-7'(6'H)-one | 8 | 3 | 4 | 3 |
| 1.010 | 2'-Cyclobutyl-1-[(3,7-dimethyl-1H-indazol-5-yl)carbonyl]-2'H- | 8 | 6 | 4 | 4 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | spiro[piperidine-4,5'-pyrano[3,2-c]pyrazol]-7'(6'H)-one | | | | |
| 1.011 | 2'-tert-Butyl-1-[(3,7-dimethyl-1H-indazol-5-yl)carbonyl]-3'-methyl-2'H-spiro[piperidine-4,5'-pyrano[3,2-c]pyrazol]-7'(6'H)-one | 16 | 3 | 15 | 3 |
| 1.012 | 2'-tert-Butyl-1-[(3,7-dimethyl-1H-indazol-5-yl)carbonyl]-2'H-spiro[piperidine-4,5'-pyrano[3,2-c]pyrazol]-7'(6'H)-one | 6 | 6 | 2 | 3 |
| 1.013 | 1-[(3,7-Dimethyl-1H-indazol-5-yl)carbonyl]-2'-isopropyl-3'-methyl-2'H-spiro[piperidine-4,5'-pyrano[3,2-c]pyrazol]-7'(6'H)-one | 8 | 4 | 8 | 3 |
| 1.014 | 2'-Cyclopropyl-1-[(3,7-dimethyl-1H-indazol-5-yl)carbonyl]-3'-methyl-2'H-spiro[piperidine-4,5'-pyrano[3,2-c]pyrazol]-7'(6'H)-one | 12 | 1 | 9 | 2 |
| 1.015 | 1-[(3,7-Dimethyl-1H-indazol-5-yl)carbonyl]-3'-methyl-2'-(tetrahydrofuran-3-yl)-2'H-spiro[piperidine-4,5'-pyrano[3,2-c]pyrazol]-7'(6'H)-one | 21 | 3 | 20 | 2 |
| 1.016 | 1-[(3,7-Dimethyl-1H-indazol-5-yl)carbonyl]-2'-(tetrahydrofuran-3-yl)-2'H-spiro[piperidine-4,5'-pyrano[3,2-c]pyrazol]-7'(6'H)-one | 31 | 2 | 22 | 2 |
| 1.017 | 1-[(3-Ethyl-7-methyl-1H-indazol-5-yl)carbonyl]-2'-isopropyl-2'H-spiro[piperidine-4,5'-pyrano[3,2-c]pyrazol]-7'(6'H)-one | 15 | 2 | 3 | 1 |
| 1.018 | 1-[(7-Ethoxy-3-ethyl-1H-indazol-5-yl)carbonyl]-2'-ethyl-2'H-spiro[piperidine-4,5'-pyrano[3,2-c]pyrazol]-7'(6'H)-one | 22 | 2 | 34 | 1 |
| 1.019 | 2'-Ethyl-1-[(3-ethyl-7-methyl-1H-indazol-5-yl)carbonyl]-2'H-spiro[piperidine-4,5'-pyrano[3,2-c]pyrazol]-7'(6'H)-one | 36 | 2 | 18 | 1 |
| 1.020 | 2'-tert-Butyl-1-[(3-ethyl-7-methyl-1H-indazol-5-yl)carbonyl]-2'H-spiro[piperidine-4,5'-pyrano[3,2-c]pyrazol]-7'(6'H)-one | 7 | 1 | 3 | 1 |
| 1.021 | 2'-(3-methoxyphenyl)-1-(7-methyl-1H-indazole-5-carbonyl)-2'H-spiro[piperidine 4,5'-pyrano[3,2-c]pyrazol]-7'(6'H)-one | 16 | 1 | na | Na |
| 1.022 | 2'-Isopropyl-1-[(7-methyl-1H-indazol-5-yl)carbonyl]-2'H-pyrano[3,2-c]pyrazol]-7'(6'H) one | 22 | 4 | 28 | 3 |
| 1.023 | 2'-Ethyl-3'-methyl-1-[(7-methyl-1H-indazol-5-yl)carbonyl]-2'H-spiro[piperidine-4,5'- | 28 | 4 | 31 | 3 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | pyrano[3,2-c]pyrazol]-7'(6'H)one | | | | |
| 1.024 | 1-(7-methyl-1H-indazole-5-carbonyl)-2'-phenyl-2'H-spiro[piperidine-4,5'-pyrano[3,2-c]pyrazol]-7'(6'H)one | 37 | 3 | na | na |
| 1.025 | 2'-Ethyl-1-[(7-methyl-1H-indazol-5-yl)carbonyl]-2'H-spiro[piperidine-4,5'-pyrano[3,2-c]pyrazol]-7'(6'H)one | 57 | 3 | 54 | 3 |
| 1.026 | 3'-methyl-1-(7-methyl-1H-indazole-5-carbonyl)-2'-(2,2,2-trifluoroethyl)-2'H-spiro[piperidine-4,5'-pyrano[3,2-c]pyrazol]-7'(6'H)one | 44 | 3 | na | na |
| 1.027 | 1-[(7-Methyl-1H-indazol-5-yl)carbonyl]-2'-propyl-2'H-spiro[piperidine-4,5'-pyrano[3,2-c]pyrazol]-7'(6'H)one | 48 | 3 | 43 | 3 |
| 1.028 | 2-methoxy-4-(3'-methyl-1-(7-methyl-1H-indazole-5-carbonyl)-7'-oxo-6',7'-dihydro-2'H-spiro[piperidine-4,5'-pyrano[3,2-c]pyrazole]-2'-yl)benzonitrile | 76 | 2 | 127 | 1 |
| 1.029 | 2'-Methyl-1-[(7-methyl-1H-indazol-5-yl)carbonyl]-2'H-spiro[piperidine-4,5'-pyrano[3,2-c]pyrazol]-7'(6'H)one | 341 | 3 | 629 | 2 |
| 1.030 | 2',3'-Dimethyl-1-[(7-methyl-1 indazol-5-yl)carbonyl]-2'H-spiro[piperidine-4,5'-pyrano[3,2-c]pyrazol]-7'(6'H)one | 271 | 3 | 376 | 4 |
| 1.031 | 1-(7-methyl-1H-indazole-5-carbonyl)-2'-(pyridin-2-yl)-2'H-spiro[piperidine-4,5'-pyrano[3,2-c]pyrazol]-7'(6'H)one | 226 | 2 | na | na |
| 1.032 | 2'-benzyl-1-(7-methyl-1H-indazole-5-carbonyl)-2'H-spiro[piperidine-4,5'-pyrano[3,2-c]pyrazol]-7'(6'H)one | 243 | 3 | na | na |
| 1.033 | 2'-Benzyl-3'-methyl-1-[(7-methyl-1H-indazol-5-yl)carbonyl]-2'H-spiro[piperidine-4,5'-pyrano[3,2-c]pyrazol]-7'(6'H)one | 251 | 1 | 487 | 3 |
| 1.034 | 3'-methyl-1-(7-methyl-1H-indazole-5-carbonyl)-2'-(pyridin-2-yl)-2'H-spiro[piperidine-4,5'-pyrano[3,2-c]pyrazol]-7'(6'H)one | 257 | 2 | na | na |
| 1.035 | 3'-Ethyl-2'-methyl-1-[(7-methyl-1H-indazol-5-yl)carbonyl]-2'H-spiro[piperidine-4,5'-pyrano[3,2-c]pyrazol]-7'(6'H)one | 559 | 2 | 367 | 4 |
| 1.036 | 2'-(3-methoxyphenyl)-3'-methyl-1-(7-methyl-1H-indazole-5-carbonyl)-2'H-spiro[piperidine-4,5'-pyrano[3,2-c]pyrazol]-7'(6'H)one | 171 | 2 | na | na |
| 1.037 | 2'-cyclohexyl-1-(7-methyl-1H-indazole-5-carbonyl)- | 45 | 4 | 60 | 3 |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | 2'H-spiro[piperidine-4,5'-pyrano[3,2-c]pyrazol]-7'(6'H)-one | | | | |
| 1.038 | 2'-Cyclopentyl-1-[(7-methyl-1H-indazol-5-yl)carbonyl]-2'H-spiro[piperidine-4,5'-pyrano[3,2-c]pyrazol]-7'(6'H)one | 14 | 4 | 9 | 3 |
| 1.039 | 2'-Cyclobutyl-1-[(7-methyl-1H-indazol-5-yl)carbonyl]-2'H-spiro[piperidine-4,5'-pyrano[3,2-c]pyrazol]-7'(6'H)one | 15 | 6 | 13 | 3 |
| 1.040 | 2'-Isopropyl-3'-methyl-1-[(7-methyl-1H-indazol-5-yl)carbonyl]-2'H-spiro[piperidine-4,5'-pyrano[3,2-c]pyrazol]-7'(6'H)one | 15 | 3 | 15 | 3 |
| 1.041 | 3'-Methyl-1-[(7-methyl-1H-indazol-5-yl)carbonyl]-2'-(tetrahydrofuran-3-yl)-2'H-spiro[piperidine-4,5'-pyrano[3,2-c]pyrazol]-7'(6'H)one | 39 | 3 | 46 | 2 |
| 1.042 | 2'-tert-Butyl-1-[(7-methyl-1H-indazol-5-yl)carbonyl]-2'H-spiro[piperidine-4,5'-pyrano[3,2-c]pyrazol]-7'(6'H)one | 5 | 30 | 4 | 29 |
| 1.043 | 2'-tert-Butyl-3'-methyl-1-[(7-methyl-1H-indazol-5-yl)carbonyl]-2'H-spiro[piperidine-4,5'-pyrano[3,2-c]pyrazol]-7'(6'H)one | 20 | 3 | 43 | 2 |
| 1.044 | 1-[(3-Ethyl-7-methoxy-1H-indazol-5-yl)carbonyl]-2'-isopropyl-2'H-spiro[piperidine-4,5'-pyrano[3,2-c]pyrazol]-7'(6'H)-one | 15 | 3 | 5 | 3 |
| 1.045 | 2'-Ethyl-1-[(3-ethyl-7-methoxy-1H-indazol-5-yl)carbonyl]-3'-methyl-2'H-spiro[piperidine-4,5'-pyrano[3,2-c]pyrazol]-7'(6'H)-one | 20 | 3 | 22 | 2 |
| 1.046 | 2'-Ethyl-1-[(3-ethyl-7-methoxy-1H-indazol-5-yl)carbonyl]-2'H-spiro[piperidine-4,5'-pyrano[3,2-c]pyrazol]-7'(6'H)-one | 31 | 3 | 29 | 3 |
| 1.047 | 2'-tert-Butyl-1-[(3-ethyl-7-methoxy-1H-indazol-5-yl)carbonyl]-2'H-spiro[piperidine-4,5'-pyrano[3,2-c]pyrazol]-7'(6'H)-one | 7 | 4 | 2 | 3 |
| 1.048 | 2'-Cyclohexyl-1-[(3-ethyl-7-methoxy-1H-indazol-5-yl)carbonyl]-2'H-spiro[piperidine-4,5'-pyrano[3,2-c]pyrazol]-7'(6'H)-one | 27 | 4 | 18 | 2 |
| 1.049 | 2'-Cyclopentyl-1-[(3-ethyl-7-methoxy-1H-indazol-5-yl)carbonyl]-2'H-spiro[piperidine-4,5'-pyrano[3,2-c]pyrazol]-7'(6'H)-one | 9 | 4 | 7 | 4 |
| 1.050 | 2'-Cyclobutyl-1-[(3-ethyl-7-methoxy-1H-indazol-5-yl)carbonyl]-2'H-spiro[piperidine-4,5'- | 10 | 3 | 5 | 4 |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | pyrano[3,2-c]pyrazol]-7'(6'H)-one | | | | |
| 1.051 | 2'-Isopropyl-1-[(7-methoxy-1H-indazol-5-yl)carbonyl]-2'H-spiro[piperidine-4,5'-pyrano[3,2-c]pyrazol]-7'(6'H)-one | 28 | 3 | 17 | 3 |
| 1.052 | 2'Ethyl-1-[(7-methoxy-1H-indazol-5-yl)carbonyl]-3'-methyl-2'H-spiro[piperidine-4,5'-pyrano[3,2-c]pyrazol]-7'(6'H)-one | 54 | 3 | 33 | 3 |
| 1.053 | 2'-Ethyl-1-[(7-methoxy-1H-indazol-5-yl)carbonyl]-2'H-spiro[piperidine-4,5'-pyrano[3,2-c]pyrazol]-7'(6'H)-one | 80 | 3 | 62 | 3 |
| 1.054 | 2'-tert-Butyl-1-[(7-methoxy-1H-indazol-5-yl)carbonyl]-3'-methyl-2'H-spiro[piperidine-4,5'-pyrano[3,2-c]pyrazol]-7'(6'H)-one | 27 | 3 | 29 | 2 |
| 1.055 | 2'-Isopropyl-1-[(7-methoxy-1H-indazol-5-yl)carbonyl]-3'-methyl-2'H-spiro[piperidine-4,5'-pyrano[3,2-c]pyrazol]-7'(6'H)-one | 20 | 3 | 10 | 4 |
| 1.056 | 2'-Ethyl-1-[(7-ethyl-1H-indazol-5-yl)carbonyl]-3'-methyl-2'H-spiro[piperidine-4,5'-pyrano[3,2-c]pyrazol]-7'(6'H)-one | 30 | 7 | 35 | 3 |
| 1.057 | 2'-Ethyl-1-[(7-ethyl-1H-indazol-5-yl)carbonyl]-2'H-spiro[piperidine-4,5'-pyrano[3,2-c]pyrazol]-7'(6'H)-one | 50 | 3 | 40 | 2 |
| 1.058 | 1-[(7-Ethyl-1H-indazol-5-yl)carbonyl]-2',3'-dimethyl-2'H-spiro[piperidine-4,5'-pyrano[3,2-c]pyrazol]-7'(6'H)-one | 154 | 4 | na | na |
| 1.059 | 1[(7-Ethyl-1H-indazol-5-yl)carbonyl]-2'-methyl-2'H-spiro[piperidine-4,5'-pyrano[3,2-c]pyrazol]-7'(6'H)-one | 210 | 3 | 210 | 3 |
| 1.060 | 2'-tert-Butyl-1-[(7-ethyl-1H-indazol-5-yl)carbonyl]-2'H-spiro[piperidine-4,5'-pyrano[3,2-c]pyrazol]-7'(6'H)-one | 10 | 3 | 6 | 3 |
| 1.061 | 1-[(7-Chloro-1H-indazol-5-yl)carbonyl]-2'-ethyl-3'-methyl-2'H-spiro[piperidine-4,5'-pyrano[3,2-c]pyrazol]-7'(6'H)-one | 42 | 3 | 54 | 3 |
| 1.062 | 1-[(7-Chloro-1H-indazol-5-yl)carbonyl]-2'-ethyl-2'H-spiro[piperidine-4,5'-pyrano[3,2-c]pyrazol]-7'(6'H)-one | 69 | 3 | 43 | 3 |
| 1.063 | 1-[(7-Chloro-1H-indazol-5-yl)carbonyl]-2',3'-dimethyl-2'H-spiro[piperidine-4,5'-pyrano[3,2-c]pyrazol]-7'(6'H)-one | 193 | 2 | 137 | 1 |
| 1.064 | 1-[(7-Chloro-1H-indazol-5-yl)carbonyl]-2'-methyl-2'H- | 266 | 1 | na | na |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | spiro[piperidine-4,5'-pyrano[3,2-c]pyrazol]-7'(6'H)-one | | | | |
| 1.065 | 2'-tert-Butyl-1-[(7-chloro-1H-indazol-5-yl)carbonyl]-2'H-spiro[piperidine-4,5'-pyrano[3,2-c]pyrazol]-7'(6'H)-one | 12 | 2 | 8 | 2 |
| 1.066 | 1-[(7-Chloro-1H-indazol-5-yl)carbonyl]-2'-isopropyl-2'H-spiro[piperidine-4,5'-pyrano[3,2-c]pyrazol]-7'(6'H)-one | 21 | 3 | 26 | 4 |
| 1.067 | 1-(1H-Indazol-5-ylcarbonyl)-2'-isopropyl-2'H-spiro[piperidine-4,5'-pyrano[3,2-c]pyrazol]-7'(6'H)-one | 73 | 6 | 50 | 4 |
| 1.068 | 2'-Ethyl-1-(1H-indazol-5-ylcarbonyl)-3'-methyl-2'H-spiro[piperidine-4,5'-pyrano[3,2-c]pyrazol]-7'(6'H)-one | 94 | 4 | 84 | 3 |
| 1.069 | 2'-Ethyl-1-(1H-indazol-5-ylcarbonyl)-2'H-spiro[piperidine-4,5'-pyrano[3,2-c]pyrazol]-7'(6'H)-one | 176 | 3 | 197 | 4 |
| 1.070 | 1-(1H-Indazol-5-ylcarbonyl)-2',3'-dimethyl-2'H-spiro[piperidine-4,5'-pyrano[3,2-c]pyrazol]-7'(6'H)-one | 668 | 3 | 713 | 2 |
| 1.071 | 1-(1H-Indazol-5-ylcarbonyl)-2'-methyl-2'H-spiro[piperidine-4,5'-pyrano[3,2-c]pyrazol]-7'(6'H)-one | 570 | 22 | 773 | 27 |
| 1.072 | 2'-tert-Butyl-1-(1H-indazol-5-ylcarbonyl)-3'-methyl-2'H-spiro[piperidine-4,5'-pyrano[3,2-c]pyrazol]-7'(6'H)-one | 60 | 3 | 61 | 3 |
| 1.073 | 1-(1H-Indazol-5-ylcarbonyl)-2'-isopropyl-3'-methyl-2'H-spiro[piperidine-4,5'-pyrano[3,2-c]pyrazol]-7'(6'H)-one | 43 | 3 | 35 | 3 |
| 1.074 | 2'-tert-Butyl-1-(1H-indazol-5-ylcarbonyl)-2'H-spiro[piperidine-4,5'-pyrano[3,2-c]pyrazol]-7'(6'H)-one | 17 | 8 | 7 | 7 |
| 1.075 | 2'-Isopropyl-1-[(7-methoxy-3-methyl-1H-indazol-5-yl)carbonyl]-2'H-spiro[piperidine-4,5'-pyrano[3,2-c]pyrazol]-7'(6'H)-one | 24 | 3 | 6 | 3 |
| 1.076 | 2'-tert-Butyl-1-[(7-methoxy-3-methyl-1H-indazol-5-yl)carbonyl]-2'H-spiro[piperidine-4,5'-pyrano[3,2-c]pyrazol]-7'(6'H)-one | 10 | 3 | 2 | 4 |
| 1.077 | 2'-Ethyl-1-[(7-methoxy-3-methyl-1-indazol-5-yl)carbonyl]-3'-methyl-2'H-spiro[piperidine-4,5'-pyrano[3,2-c]pyrazol]-7'(6'H)-one | 19 | 3 | 15 | 3 |
| 1.078 | 2'-Isopropyl-1-[(7-methoxy-3-methyl-1H-indazol-5-yl)carbonyl]-3'-methyl-2'H-spiro[piperidine-4,5'- | 10 | 3 | 4 | 3 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | pyrano[3,2-c]pyrazol]-7'(6'H)-one | | | | |
| 1.079 | 2'-Ethyl-1-[(7-methoxy-3-methyl-1H-indazol-5-yl)carbonyl]-2'H-spiro[piperidine-4,5'-pyrano[3,2-c]pyrazol]-7'(6'H)-one | 31 | 3 | 12 | 3 |
| 1.080 | 2'-Ethyl-3'-methyl-1-[(3-methyl-1H-indazol-5-yl)carbonyl]-2'H-spiro[piperidine-4,5'-pyrano[3,2-c]pyrazol]-7'(6'H)-one | 23 | 7 | 36 | 4 |
| 1.081 | 2'-Isopropyl-1-[(3-methyl-1H-indazol-5-yl)carbonyl]-2'H-spiro[piperidine-4,5'-pyrano[3,2-c]pyrazol]-7'(6'H)-one | 30 | 3 | 10 | 3 |
| 1.082 | 1-[(3-Methyl-1H-indazol-5-yl)carbonyl]-2'-propyl-2'H-spiro[piperidine-4,5'-pyrano[3,2-c]pyrazol]-7'(6'H)-one | 73 | 3 | 53 | 3 |
| 1.083 | 2'-Ethyl-1-[(3-methyl-1H-indazol-5-yl)carbonyl]-2'H-spiro[piperidine-4,5'-pyrano[3,2-c]pyrazol]-7'(6'H)-one | 73 | 3 | 43 | 3 |
| 1.084 | 2',3'-Dimethyl-1-[(3-methyl-1H-indazol-5-yl)carbonyl]-2'H-spiro[piperidine-4,5'-pyrano[3,2-c]pyrazol]-7'(6'H)-one | 335 | 2 | na | na |
| 1.085 | 2'-Methyl-1-[(3-methyl-1H-indazol-5-yl)carbonyl]-2'H-spiro[piperidine-4,5'-pyrano[3,2-c]pyrazol]-7'(6'H)-one | 424 | 3 | 403 | 3 |
| 1.086 | 2'-tert-Butyl-1-[(3-methyl-1H-indazol-5-yl)carbonyl]-2'H-spiro[piperidine-4,5'-pyrano[3,2-c]pyrazol]-7'(6'H)-one | 10 | 4 | 3 | 4 |
| 1.087 | 2'-Cyclohexyl-1-[(3-methyl-1H-indazol-5-yl)carbonyl]-2'H-spiro[piperidine-4,5'-pyrano[3,2-c]pyrazol]-7'(6'H)-one | 79 | 4 | 135 | 3 |
| 1.088 | 2'-Cyclopentyl-1-[(3-methyl-1H-indazol-5-yl)carbonyl]-2'H-spiro[piperidine-4,5'-pyrano[3,2-c]pyrazol]-7'(6'H)-one | 25 | 4 | 16 | 3 |
| 1.089 | 2'-Cyclobutyl-1-[(3-methyl-1H-indazol-5-yl)carbonyl]-2'H-spiro[piperidine-4,5'-pyrano[3,2-c]pyrazol]-7'(6'H)-one | 19 | 4 | 22 | 3 |
| 1.090 | 2'-tert-Butyl-3'-methyl-1-[(3-methyl-1H-indazol-5-yl)carbonyl]-2'H-spiro[piperidine-4,5'-pyrano[3,2-c]pyrazol]-7'(6'H)-one | 28 | 3 | 23 | 3 |
| 1.091 | 2'-Isopropyl-3'-methyl-1-[(3-methyl-1H-indazol-5-yl)carbonyl]-2'H-spiro[piperidine-4,5'-pyrano[3,2-c]pyrazol]-7'(6'H)-one | 16 | 3 | 15 | 3 |
| 1.092 | 2'-Ethyl-1-[(3-ethyl-1H-indazol-5-yl)carbonyl]-3'-methyl-2'H-spiro[piperidine-4,5'- | 35 | 5 | na | na |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | pyrano[3,2-c]pyrazol]-7'(6'H)-one | | | | |
| 1.093 | 2'-Ethyl-1-[(3-ethyl-1H-indazol-5-yl)carbonyl]-2'H-spiro[piperidine-4,5'-pyrano[3,2-c]pyrazol]-7'(6'H)-one | 59 | 2 | 18 | 1 |
| 1.094 | 1-[(3-Ethyl-1H-indazol-5-yl)carbonyl]-2',3'-dimethyl-2'H-spiro[piperidine-4,5'-pyrano[3,2-c]pyrazol]-7'(6'H)-one | 189 | 5 | na | na |
| 1.095 | 1-[(3-Ethyl-1H-indazol-5-yl)carbonyl]-2'-methyl-2'H-spiro[piperidine-4,5'-pyrano[3,2-c]pyrazol]-7'(6'H)-one | 204 | 2 | 397 | 1 |
| 1.096 | 2'-tert-butyl-1-[(3-ethyl-1H-indazol-5-yl)carbonyl]-2'H-spiro[piperidine-4,5'-pyrano[3,2-c]pyrazol]-7'(6'H)-one | 21 | 2 | 12 | 1 |
| 1.097 | 2'-Ethyl-3'-methyl-1-[(3-propyl-1H-indazol-5-yl)carbonyl]-2'H-spiro[piperidine-4,5'-pyrano[3,2-c]pyrazol]-7'(6'H)-one | 39 | 5 | na | Na |
| 1.098 | 2',3'-Dimethyl-1-[(3-propyl-1H-indazol-5-yl)carbonyl]-2'H-spiro[piperidine-4,5'-pyrano[3,2-c]pyrazol]-7'(6'H)-one | 181 | 5 | na | Na |
| 1.099 | 2'-Ethyl-1-[(3-ethyl-7-methoxy-1-methyl-1H-indazol-5-yl)carbonyl]-2'H-spiro[piperidine-4,5'-pyrano[3,2-c]pyrazol]-7'(6'H)-one | 21 | 2 | 20 | 1 |
| 1.100 | 2'-Ethyl-1-[(7-ethyl-3-methyl-1H-indazol-5-yl)carbonyl]-2'H-spiro[piperidine-4,5'-pyrano[3,2-c]pyrazol]-7'(6'H)-one | 23 | 2 | 36 | 1 |
| 1.101 | 1-[(7-Chloro-3-ethyl-1H-indazol-5-yl)carbonyl]-2'-ethyl-2'H-spiro[piperidine-4,5'-pyrano[3,2-c]pyrazol]-7'(6'H)-one | 89 | 1 | 45 | 1 |
| 1.102 | 1-[(7-Chloro-3-methyl-1H-indazol-5-yl)carbonyl]-2'-isopropyl-2'H-spiro[piperidine-4,5'-pyrano[3,2-c]pyrazol]-7'(6'H)-one | 12 | 3 | 5 | 3 |
| 1.103 | 2'-tert-Butyl-1-[(3-chloro-1H-indazol-5-yl)carbonyl]-2'H-spiro[piperidine-4,5'-pyrano[3,2-c]pyrazol]-7'(6'H)-one | 7 | 2 | 5 | 2 |
| 1.104 | 1-[(3-Chloro-7-methyl-1H-indazol-5-yl)carbonyl]-2'-isopropyl-2'H-spiro[piperidine-4,5'-pyrano[3,2-c]pyrazol]-7'(6'H)-one | 7 | 2 | 4 | 2 |
| 1.105 | 2'-tert-Butyl-1-[(3-chloro-7-methyl-1H-indazol-5-yl)carbonyl]-2'H-spiro[piperidine-4,5'-pyrano[3,2-c]pyrazol]-7'(6'H)-one | 5 | 2 | 2 | 2 |
| 1.106 | 1-[(3-Chloro-7-methyl-1H-indazol-5-yl)carbonyl]-2'-cyclobutyl-2'H- | 8 | 4 | 8 | 2 |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | spiro[piperidine-4,5'-pyrano[3,2-c]pyrazol]-7'(6'H)-one | | | | |
| 1.107 | 1-[(3-Chloro-7-methyl-1H-indazol-5-yl)carbonyl]-2'-cyclopentyl-2'H-spiro[piperidine-4,5'-pyrano[3,2-c]pyrazol]-7'(6'H)-one | 6 | 2 | 3 | 1 |
| 1.108 | 1-[(3-Chloro-7-methyl-1H-indazol-5-yl)carbonyl]-2'-ethyl-2'H-spiro[piperidine-4,5'-pyrano[3,2-c]pyrazol]-7'(6'H)-one | 10 | 3 | 19 | 3 |
| 1.109 | 1-[(3-Chloro-7-methyl-1H-indazol-5-yl)carbonyl]-2'-propyl-2'H-spiro[piperidine-4,5'-pyrano[3,2-c]pyrazol]-7'(6'H)-one | 11 | 2 | 12 | 2 |
| 1.110 | 2'-tert-Butyl-1-[(7-chloro-3-methyl-1H-indazol-5-yl)carbonyl]-2'H-spiro[piperidine-4,5'-pyrano[3,2-c]pyrazol]-7'(6'H)-one | 8 | 3 | 3 | 3 |
| 1.111 | 1-[(7-Chloro-3-methyl-1H-indazol-5-yl)carbonyl]-2'-ethyl-3'-methyl-2'H-spiro[piperidine-4,5'-pyrano[3,2-c]pyrazol]-7'(6'H)-one | 27 | 1 | 12 | 1 |
| 1.112 | 2'-Ethyl-3'-methyl-1-[(1-methyl-1H-indazol-5-yl)carbonyl]-2'H-spiro[piperidine-4,5'-pyrano[3,2-c]pyrazol]-7'(6'H)-one | 217 | 2 | 79 | 1 |
| 1.113 | 2'-ethyl-1-(7-ethyl-3-methyl-1H-indazole-5-carbonyl)-3'-methyl-2'H-spiro[piperidine-4,5'-pyrano[3,2-c]pyrazol]-7'(6'H)-one | 20 | 2 | 10 | 1 |
| 1.114 | 1-[(3-chloro-7-methyl-1H-indazol-5-yl)carbonyl]-2'-ethyl-3'-methyl-2'H-spiro[piperidine-4,5'-pyrano[3,2-c]pyrazol]-7'(6'H)-one | 9 | 2 | na | Na |
| 1.115 | 1-[(7-Ethoxy-3-ethyl-1H-indazol-5-yl)carbonyl]-2'-ethyl-2'H-spiro[piperidine-4,5'-pyrano[3,2-c]pyrazol]-7'(6'H)-one | 26 | 2 | 12 | 1 |
| 1.116 | 2'-tert-Butyl-1-[(7-ethoxy-3-methyl-1H-indazol-5-yl)carbonyl]-2'H-spiro[piperidine-4,5'-pyrano[3,2-c]pyrazol]-7'(6'H)-one | 5 | 1 | 5 | 1 |
| 1.117 | 2'-tert-Butyl-1-[(7-ethoxy-3-ethyl-1H-indazol-5-yl)carbonyl]-2'H-spiro[piperidine-4,5'-pyrano[3,2-c]pyrazol]-7'(6'H)-one | 5 | 1 | 4 | 1 |
| 1.118 | 1-[(7-Ethoxy-3-methyl-1H-indazol-5-yl)carbonyl]-2'-ethyl-3'-methyl-2'H-spiro[piperidine-4,5'-pyrano[3,2-c]pyrazol]-7'(6'H)-one | 11 | 2 | 27 | 1 |
| 1.119 | 1-[(7-Ethoxy-3-ethyl-1H-indazol-5-yl)carbonyl]-2'-ethyl-3'-methyl-2'H-spiro[piperidine-4,5'- | 13 | 2 | 18 | 1 |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | pyrano[3,2-c]pyrazol]-7'(6'H)-one | | | | |
| 1.120 | 1-[(7-Ethoxy-3-methyl-1H-indazol-5-yl)carbonyl]-2'-isopropyl-2'H-spiro[piperidine-4,5'-pyrano[3,2-c]pyrazol]-7'(6'H)-one | 9 | 2 | 6 | 2 |
| 1.121 | 1-[(7-Ethoxy-3-ethyl-1H-indazol-5-yl)carbonyl]-2'-isopropyl-2'H-spiro[piperidine-4,5'-pyrano[3,2-c]pyrazol]-7'(6'H)-one | 7 | 2 | 6 | 2 |
| 1.122 | 1-[(7-Ethoxy-1H-indazol-5-yl)carbonyl]-2'-isopropyl-3'-methyl-2'H-spiro[piperidine-4,5'-pyrano[3,2-c]pyrazol]-7'(6'H)-one | 11 | 2 | 5 | 2 |
| 1.123 | 1-[(7-Ethoxy-1H-indazol-5-yl)carbonyl]-2'-isopropyl-2'H-spiro[piperidine-4,5'-pyrano[3,2-c]pyrazol]-7'(6'H)-one | 16 | 2 | 14 | 2 |
| 1.124 | 2',3'-dimethyl-1-(1-methyl-1H-indazole-5-carbonyl)-2'H-spiro[piperidine-4,5'-pyrano[3,2-c]pyrazol]-7'(6'H)-one | 1460 | 2 | >3000 | 1 |
| 1.125 | 2'-ethyl-1-(3-ethyl-7-methyl-1H-indazole-5-carbonyl)-3'-methyl-2'H-spiro[piperidine-4,5'-pyrano[3,2-c]pyrazol]-7'(6'H)-one | 22 | 2 | 7 | 1 |
| 1.126 | 2'-cyclobutyl-1-(3,7-dimethyl-1H-indazole-5-carbonyl)-3'-methyl-2'H-spiro[piperidine-4,5'-pyrano[3,2-c]pyrazol]-7'(6'H)-one | 6 | 3 | 3 | 4 |
| 1.127 | 2'-cyclobutyl-1-(7-methoxy-1H-indazole-5-carbonyl)-3'-methyl-2'H-spiro[piperidine-4,5'-pyrano[3,2-c]pyrazol]-7'(6'H)-one | 12 | 2 | 20 | 2 |
| 1.128 | 2'-cyclobutyl-3'-methyl-1-(7-methyl-1H-indazole-5-carbonyl)-2'H-spiro[piperidine-4,5'-pyrano[3,2-c]pyrazol]-7'(6'H)-one | 12 | 3 | 8 | 4 |
| 1.129 | 1-(3,7-dimethyl-1H-indazole-5-carbonyl)-2'-isobutyl-3'-methyl-2'H-spiro[piperidine-4,5'-pyrano[3,2-c]pyrazol]-7'(6'H)-one | 10 | 3 | 5 | 3 |
| 1.130 | 2'-isobutyl-3'-methyl-1-(7-methyl-1H-indazole-5-carbonyl)-2'H-spiro[piperidine-4,5'-pyrano[3,2-c]pyrazol]-7'(6'H)-one | 29 | 3 | 13 | 4 |
| 1.131 | 2'-isobutyl-1-(7-methoxy-1H-indazole-5-carbonyl)-3'-methyl-2'H-spiro[piperidine-4,5'-pyrano[3,2-c]pyrazol]-7'(6'H)-one | 31 | 2 | 19 | 2 |
| 1.132 | 2'-isobutyl-1-(7-methoxy-3-methyl-1H-indazole-5-carbonyl)-3'-methyl-2'H-spiro[piperidine-4,5'- | 13 | 2 | 13 | 2 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | pyrano[3,2-c]pyrazol]-7'(6'H)-one | | | | |
| 1.133 | 1-(7-chloro-1H-indazole-5-carbonyl)-2'-isopropyl-3'-methyl-2'H-spiro[pipedine-4,5'-pyrano[3,2-c]pyrazol]-7'(6'H)-one | 15 | 4 | 4 | 3 |
| 1.134 | 1-(3,7-dimethyl-1H-indazole-5-carbonyl)-2'-isobutyl-2'H-spiro[piperidine-4,5'-pyrano[3,2-c]pyrazol]-7'(6'H)-one | 18 | 4 | 10 | 3 |
| 1.135 | 2'-isobutyl-1-(7-methyl-1H-indazole-5-carbonyl)-2'H-spiro[piperidine-4,5'-pyrano[3,2-c]pyrazol]-7'(6'H)-one | 27 | 3 | 32 | 3 |
| 1.135 | 2'-sec-butyl-1-(3,7-dimethyl-1H-indazole-5-carbonyl)-3'-methyl-2'H-spiro[piperidine-4,5'-pyrano[3,2-c]pyrazol]-7'(6'H)-one | 9 | 3 | 4 | 4 |
| 1.137 | 2'-sec-butyl-3'-methyl-1-(3-methyl-1H-indazole-5-carbonyl)-2'H-spiro[piperidine-4,5'-pyrano[3,2-c]pyrazol]-7'(6'H)-one | 17 | 3 | 9 | 4 |
| 1.138 | 2'-sec-butyl-3'-methyl-1-(3-methyl-1H-indazole-5-carbonyl)-2'H-spiro[piperidine-4,5'-pyrano[3,2-c]pyrazol]-7'(6'H)-one | 20 | 4 | 14 | 2 |
| 1.138 | 2'-sec-butyl-1-(1H-indazole-5-carbonyl)-3'-methyl-2'H-spiro[piperidine-4,5'-pyrano[3,2-c]pyrazol]-7'(6'H)-one | 36 | 3 | 20 | 3 |
| 1.140 | 2'-sec-butyl-1-(3,7-dimethyl-1H-indazole-5-carbonyl)-2'H-spiro[piperidine-4,5'-pyrano[3,2-c]pyrazol]-7'(6'H)-one | 13 | 3 | 2 | 2 |
| 1.141 | 2'-sec-butyl-1-(3-methyl-1H-indazole-5-carbonyl)-2'H-spiro[piperidine-4,5'-pyrano[3,2-c]pyrazol]-7'(6'H)-one | 32 | 3 | 19 | 4 |
| 1.142 | 2'-sec-butyl-1-(1H-indazole-5-carbonyl)-2'H-spiro[piperidine-4,5'-pyrano[3,2-c]pyrazol]-7'(6'H)-one | 73 | 3 | 20 | 2 |
| 1.143 | 2'-cyclopropyl-1-(3,7-dimethyl-1H-indazole-5-carbonyl)-2'H-spiro[piperidine-4,5'-pyrano[3,2-c]pyrazol]-7'(6'H)-one | 20 | 3 | 7 | 3 |
| 1.144 | 2'-cyclopropyl-1-(7-methyl-1H-indazole-5-carbonyl)-2'H-spiro[piperidine-4,5'-pyrano[3,2-c]pyrazol]-7'(6'H)-one | 37 | 3 | 19 | 3 |
| 1.145 | 2'-tert-butyl-1-(1-methyl-1H-indazole-5-carbonyl)-2'H-spiro[piperidine-4,5'-pyrano[3,2-c]pyrazol]-7'(6'H)-one | 18 | 8 | 26 | 6 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| 1.146 | 2'-tert-butyl-1-(6-methyl-1H-indazole-5-carbonyl)-2'H-spiro[piperidine-4,5'-pyrano[3,2-c]pyrazol]-7'(6'H)-one | 7 | 2 | 27 | 3 |
| 1.147 | 2'-tert-butyl-1-(4-methyl-1H-indazole-5-carbonyl)-2'H-spiro[piperidine-4,5'-pyrano[3,2-c]pyrazol]-7'(6'H)-one | 15 | 2 | 49 | 3 |
| 2.001 | 2'-Ethyl-3'-methyl-1-[(3-methyl-1H-indazol-6-yl)carbonyl]-2'H-spiro[piperidine-4,5'-pyrano[3,2-c]pyrazol]-7'(6'H)-one | 131 | 4 | 161 | 3 |
| 2.002 | 1-(3-methyl-1H-indazole-6-carbonyl)-2'-phenyl-2'H-spiro[piperidine-4,5'-pyrano[3,2-c]pyrazol]-7'(6'H)-one | 92 | 4 | na | na |
| 2.003 | 2'-Ethyl-1-[(3-methyl-1H-indazol-6-yl)carbonyl]-2'H-spiro[piperidine-4,5'-pyrano[3,2-c]pyrazol]-7'(6'H)-one | 263 | 2 | 113 | 1 |
| 2.004 | 2'-Ethyl-3'-methyl-1-[(1-methyl-1H-indazol-6-yl)carbonyl]-2'H-spiro[piperidine-4,5'-pyrano[3,2-c]pyrazol]-7'(6'H)-one | 236 | 2 | 229 | 2 |
| 2.005 | 2'-Isopropyl-1-[(3-methyl-1H-indazol-6-yl)carbonyl]-2'H-spiro[piperidine-4,5'-pyrano[3,2-c]pyrazol]-7'(6'H)-one | 35 | 2 | 33 | 1 |
| 2.006 | 1-[(4-chloro-1H-indazol-6-yl)carbonyl]-2'-isopropyl-2'H-spiro[piperidine-4,5'-pyrano[3,2-c]pyrazol]-7'(6'H)-one | 25 | 2 | 13 | 1 |
| 2.007 | 1-[(3-ethyl-1-methyl-1H-indazol-6-yl)carbonyl]-2'-isopropyl-2'H-spiro[piperidine-4,5'-pyrano[3,2-c]pyrazol]-7'(6'H)-one | 21 | 2 | 14 | 1 |
| 2.008 | 2'-Ethyl-1-[(3-ethyl-1-methyl-1H-indazol-6-yl)carbonyl]-2'H-spiro[piperidine-4,5'-pyrano[3,2-c]pyrazol]-7'(6'H)-one | 73 | 2 | 81 | 1 |
| 2.009 | 2'-tert-butyl-1-(4-chloro-1H-indazole-6-carbonyl)-2'H-spiro[piperidine-4,5'-pyrano[3,2-c]pyrazol]-7'(6'H)-one | 11 | 3 | 7 | 3 |
| 2.010 | 1-[(2,4-Dimethyl-1H-benzimidazol-6-yl)carbonyl]-2'-isopropyl-2'H-spiro[piperidine-4,5'-pyrano[3,2-c]pyrazol]-7'(6'H)-one | 27 | 4 | 28 | 3 |
| 2.011 | 2'-ethyl-1-(1H-indazole-6-carbonyl)-3'-methyl-2'H-spiro[piperidine-4,5'-pyrano[3,2-c]pyrazol]-7'(6'H)-one | 102 | 2 | 82 | 3 |
| 2.012 | 2'-tert-butyl-1-(1H-indazole-6-carbonyl)-2'H-spiro[piperidine-4,5'-pyrano[3,2-c]pyrazol]-7'(6'H)-one | 13 | 8 | 7 | 8 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| 2.013 | 2'-tert-butyl-1-(1-methyl-1H-indazole-6-carbonyl)-2'H-spiro[piperidine-4,5'-pyrano[3,2-c]pyrazol]-7'(6'H)-one | 8 | 4 | 19 | 6 |
| 2.014 | 2'-tert-butyl-1-(4-fluoro-1H-indazole-6-carbonyl)-2'H-spiro[piperidine-4,5'-pyrano[3,2-c]pyrazol]-7'(6'H)-one | 39 | 3 | 28 | 3 |
| 2.015 | 1-(4-fluoro-1H-indazole-6-carbonyl)-2'-isopropyl-2'H-spiro[piperidine-4,5'-pyrano[3,2-c]pyrazol]-7'(6'H)-one | 145 | 2 | 136 | 3 |
| 2.016 | 2'-ethyl-1-(4-fluoro-1H-indazole-6-carbonyl)-3'-methyl-2'H-spiro[piperidine-4,5'-pyrano[3,2-c]pyrazol]-7'(6'H)-one | 231 | 2 | 200 | 3 |
| 2.017 | 2'-tert-butyl-1-(7-fluoro-1H-indazole-6-carbonyl)-2'H-spiro[piperidine-4,5'-pyrano[3,2-c]pyrazol]-7'(6'H)-one | 44 | 3 | 52 | 3 |
| 2.018 | 2'-tert-butyl-1-(4-methyl-1H-indazole-6-carbonyl)-2'H-spiro[piperidine-4,5'-pyrano[3,2-c]pyrazol]-7'(6'H)-one | 16 | 4 | 33 | 6 |
| 2.019 | 2'-tert-butyl-1-(4-methyl-1H-indazole-6-carbonyl)-2'H-spiro[piperidine-4,5'-pyrano[3,2-c]pyrazol]-7'(6'H)-one | 109 | 4 | 138 | 4 |
| 2.020 | 2'-tert-butyl-1-(7-methoxy-1H-indazole-6-carbonyl)-2'H-spiro[piperidine-4,5'-pyrano[3,2-c]pyrazol]-7'(6'H)-one | 15 | 3 | 27 | 3 |
| 2.021 | 2'-ethyl-1-(7-methoxy-1H-indazole-6-carbonyl)-3'-methyl-2'H-spiro[piperidine-4,5'-pyrano[3,2-c]pyrazol]-7'(6'H)-one | 118 | 2 | 70 | 2 |
| 2.022 | 2'-isopropyl-1-(7-methoxy-1H-indazole-6-carbonyl)-2'H-spiro[piperidine-4,5'-pyrano[3,2-c]pyrazol]-7'(6'H)-one | 93 | 2 | 47 | 2 |
| 2.023 | 2'-tert-butyl-1-(4-methoxy-1H-indazole-6-carbonyl)-2'H-spiro[piperidine-4,5'-pyrano[3,2-c]pyrazol]-7'(6'H)-one | 2 | 4 | 3 | 6 |
| 2.024 | 2'-ethyl-1-(3-methyl-1H-indazole-6-carbonyl)-2'H-spiro[piperidine-4,5'-pyrano[3,2-c]pyrazol]-7'(6'H)-one | 113 | 2 | 60 | 1 |
| 2.025 | 2'-ethyl-3'-methyl-1-(3-methyl-1H-indazole-6-carbonyl)-2'H-spiro[piperidine-4,5'-pyrano[3,2-c]pyrazol]-7'(6'H)-one | 68 | 4 | 44 | 3 |
| 3.001 | 1-(2,4-dimethyl-1H-benzo[d]imidazole-6-carbonyl)-2'-isopropyl-2'H-spiro[piperidine-4,5'-pyrano[3,2-c]pyrazol]-7'(6'H)-one | 27 | 4 | 28 | 3 |
| 3.002 | 1-(2,4-dimethyl-1H-benzo[d]imidazole-6- | 33 | 2 | 54 | 2 |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | carbonyl)-2'-ethyl-3'-methyl-2'H-spiro[piperidine-4,5'-pyrano[3,2-c]pyrazol]-7'(6'H)-one | | | | |
| 3.003 | 2'-tert-butyl-1-(2,4-dimethyl-1H-benzo[d]imidazole-6-carbonyl)-2'H-spiro[piperidine-4,5'-pyrano[3,2-c]pyrazol]-7'(6'H)-one | 10 | 6 | 4 | 3 |
| 3.004 | 1-(2,4-dimethyl-1H-benzo[d]imidazole-6-carbonyl)-2'-ethyl-2'H-spiro[piperidine-4,5'-pyrano[3,2-c]pyrazol]-7'(6'H)-one | 113 | 2 | 111 | 2 |
| 3.005 | 2'-ethyl-3'-methyl-1-(4-methyl-1H-benzo[d]imidazole-6-carbonyl)-2'H-spiro[piperidine-4,5'-pyrano[3,2-c]pyrazol]-7'(6'H)-one | 48 | 2 | 79 | 2 |
| 3.006 | 2'-cyclobutyl-1-(4-methyl-1H-benzo[d]imidazole-6-carbonyl)-2'H-spiro[piperidine-4,5'-pyrano[3,2-c]pyrazol]-7'(6'H)-one | 20 | 2 | 55 | 1 |
| 3.007 | 2'-isopropyl-1-(4-methyl-1H-benzo[d]imidazole-6-carbonyl)-2'H-spiro[piperidine-4,5'-pyrano[3,2-c]pyrazol]-7'(6'H)-one | 27 | 2 | 24 | 2 |
| 3.008 | 2'-tert-butyl-1-(4-methyl-1H-benzo[d]imidazole-6-carbonyl)-2'H-spiro[piperidine-4,5'-pyrano[3,2-c]pyrazol]-7'(6'H)-one | 9 | 4 | 6 | 4 |
| 3.009 | 1-(1,4-dimethyl-1H-benzo[d]imidazole-6-carbonyl)-2'-isopropyl-2'H-spiro[piperidine-4,5'-pyrano[3,2-c]pyrazol]-7'(6'H)-one | 50 | 2 | 22 | 2 |
| 3.010 | 1-(1H-benzo[d]imidazole-5-carbonyl)-2'-tert-butyl-2'H-spiro[piperidine-4,5'-pyrano[3,2-c]pyrazol]-7'(6'H)-one | 19 | 5 | 12 | 5 |
| 3.011 | 2'-tert-butyl-1-(2-methyl-1H-benzo[d]imidazole-5-carbonyl)-2'H-spiro[piperidine-4,5'-pyrano[3,2-c]pyrazol]-7'(6'H)-one | 42 | 3 | 15 | 4 |
| 3.012 | 2'-isopropyl-1-(2-methyl-1H-benzo[d]imidazole-5-carbonyl)-2'H-spiro[piperidine-4,5'-pyrano[3,2-c]pyrazol]-7'(6'H)-one | 130 | 2 | 129 | 2 |
| 3.013 | 2'-ethyl-3'-methyl-1-(2-methyl-1H-benzo[d]imidazole-5-carbonyl)-2'H-spiro[piperidine-4,5'-pyrano[3,2-c]pyrazol]-7'(6'H)-one | 256 | 4 | 211 | 2 |
| 3.014 | 2'-tert-butyl-1-(1-methyl-1H-benzo[d]imidazole-6-carbonyl)-2'H- | 48 | 2 | 21 | 2 |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| 3.015 | spiro[piperidine-4,5'-pyrano[3,2-c]pyrazol]-7'(6'H)-one 2'-isopropyl-1-(1-methyl-1H-benzo[d]imidazole-6-carbonyl)-2'H-spiro[piperidine-4,5'-pyrano[3,2-c]pyrazol]-7'(6'H)-one | 205 | 2 | 153 | 2 |
| 3.016 | 2'-ethyl-3'-methyl-1-(1-methyl-1H-benzo[d]imidazole-6-carbonyl)-2'H-spiro[piperidine-4,5'-pyrano[3,2-c]pyrazol]-7'(6'H)-one | 364 | 2 | 271 | 2 |
| 3.017 | 2'-isopropyl-3'-methyl-1-(4-methyl-1H-benzo[d]imidazole-6-carbonyl)-2'H-spiro[piperidine-4,5'-pyrano[3,2-c]pyrazol]-7'(6'H)-one | 23 | 2 | 14 | 1 |
| 3.018 | 2'-ethyl-1-(4-fluoro-2-methyl-1H-benzo[d]imidazole-6-carbonyl)-3'-methyl-2'H-spiro[piperidine-4,5'-pyrano[3,2-c]pyrazol]-7'(6'H)-one | 233 | 2 | 105 | 1 |
| 3.019 | 2'-tert-butyl-1-(4-fluoro-2-methyl-1H-benzo[d]imidazole-6-carbonyl)-2'H-spiro[piperidine-4,5'-pyrano[3,2-c]pyrazol]-7'(6'H)-one | 35 | 3 | 17 | 2 |
| 3.020 | 2'-ethyl-1-(4-fluoro-1H-benzo[d]imidazole-6-carbonyl)-3'-methyl-2'H-spiro[piperidine-4,5'-pyrano[3,2-c]pyrazol]-7'(6'H)-one | 149 | 2 | 139 | 1 |
| 3.021 | 1-(4-fluoro-1H-benzo[d]imidazole-6-carbonyl)-2'-isopropyl-2'H-spiro[piperidine-4,5'-pyrano[3,2-c]pyrazol]-7'(6'H)-one | 82 | 2 | 39 | 1 |
| 3.022 | 2'-tert-butyl-1-(4-fluoro-1H-benzo[d]imidazole-6-carbonyl)-2'H-spiro[piperidine-4,5'-pyrano[3,2-c]pyrazol]-7'(6'H)-one | 34 | 3 | 14 | 3 |
| 3.023 | 2'-tert-butyl-1-(1,4-dimethyl-1H-benzo[d]imidazole-6-carbonyl)-2'H-spiro[piperidine-4,5'-pyrano[3,2-c]pyrazol]-7'(6'H)-one | 16 | 2 | 15 | 1 |
| 3.024 | 1-(4-fluoro-2-methyl-1H-benzo[d]imidazole-6-carbonyl)-2'-isopropyl-2'H-spiro[piperidine-4,5'-pyrano[3,2-c]pyrazol]-7'(6'H)-one | 113 | 2 | 70 | 1 |
| 3.025 | 1-(1,4-dimethyl-1H-benzo[d]imidazole-6-carbonyl)-2'-ethyl-3'-methyl-2'H-spiro[piperidine-4,5'-pyrano[3,2-c]pyrazol]-7'(6'H)-one | 89 | 2 | 49 | 2 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| 3.026 | 1-(1H-benzo[d]imidazole-5-carbonyl)-2'-ethyl-3'-methyl-2'H-spiro[piperidine-4,5'-pyrano[3,2-c]pyrazol]-7'(6'H)-one | 162 | 2 | 168 | 3 |
| 3.027 | 2'-tert-butyl-1-(1,2-dimethyl-1H-benzo[d]imidazole-6-carbonyl)-2'H-spiro[piperidine-4,5'-pyrano[3,2-c]pyrazol]-7'(6'H)-one | 52 | 6 | 42 | 4 |
| 4.001 | 1-(3,7-dimethyl-1H-indole-5-carbonyl)-2'-ethyl-3'-methyl-2'H-spiro[piperidine-4,5'-pyrano[3,2-c]pyrazol]-7'(6'H)-one | 9 | 2 | 29 | 1 |
| 5.001 | 2'-ethyl-1-(2-methyl-2H-indazole-6-carbonyl)-2'H-spiro[piperidine-4,5'-pyrano[3,2-c]pyrazol]-7'(6'H)-one | 901 | 2 | 675 | 1 |
| 5.002 | 2'-isopropyl-1-(2-methyl-2H-indazole-6-carbonyl)-2'H-spiro[piperidine-4,5'-pyrano[3,2-c]pyrazol]-7'(6'H)-one | 201 | 2 | 147 | 1 |
| 6.001 | 2'-ethyl-1-(7-methoxy-2-naphthoyl)-3'-methyl-2'H-spiro[piperidine-4,5'-pyrano[3,2-c]pyrazol]-7'(6'H)-one | 17 | 2 | 13 | 2 |
| 6.002 | 2'-ethyl-3'-methyl-1-(6-methyl-2-naphthoyl)-2'H-spiro[piperidine-4,5'-pyrano[3,2-c]pyrazol]-7'(6'H)-one | 198 | 2 | 207 | 1 |
| 6.003 | 2'-tert-butyl-1-(7-methoxy-2-naphthoyl)-2'H-spiro[piperidine-4,5'-pyrano[3,2-c]pyrazol]-7'(6'H)-one | 3 | 5 | 2 | 4 |
| 6.004 | 2'-tert-butyl-1-(6-methoxy-2-naphthoyl)-2'H-spiro[piperidine-4,5'-pyrano[3,2-c]pyrazol]-7'(6'H)-one | 77 | 2 | 38 | 2 |
| 6.005 | 2'-tert-butyl-1-(6-methyl-2-naphthoyl)-2'H-spiro[piperidine-4,5'-pyrano[3,2-c]pyrazol]-7'(6'H)-one | 43 | 2 | 48 | 2 |
| 6.006 | 2'-tert-butyl-1-(5-methoxy-2-naphthoyl)-2'H-spiro[piperidine-4,5'-pyrano[3,2-c]pyrazol]-7'(6'H)-one | 14 | 2 | 7 | 2 |
| 6.007 | 1-(2-naphthoyl)-2'-ethyl-3'-methyl-2'H-spiro[piperidine-4,5'-pyrano[3,2-c]pyrazol]-7'(6'H)-one | 29 | 4 | 40 | 2 |
| 6.008 | 2'-ethyl-1-(5-methoxy-2-naphthoyl)-3'-methyl-2'H-spiro[piperidine-4,5'-pyrano[3,2-c]pyrazol]-7'(6'H)-one | 26 | 2 | 35 | 2 |
| 7.001 | 1-(3-aminobenzo-[d]isothiazole-5-carbonyl)-2'-isopropyl-2'H-spiro[piperidine-4,5'-pyrano[3,2-c]pyrazol]-7'(6'H)-one | 72 | 2 | 16 | 2 |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| 7.002 | 1-(3-aminobenzo-[d]isothiazole-5-carbonyl)-2'-tert-butyl-2'H-spiro[piperidine-4,5'-pyrano[3,2-c]pyrazol]-7'(6'H)-one | 11 | 3 | 3 | 3 |
| 7.003 | 1-(3-aminobenzo-[d]isothiazole-5-carbonyl)-2'-ethyl-3'-methyl-2'H-spiro[piperidine-4,5'-pyrano[3,2-c]pyrazol]-7'(6'H)-one | 57 | 2 | 19 | 2 |
| 7.004 | 1-(benzo[d]isothiazole-5-carbonyl)-2'-tert-butyl-2'H-spiro[piperidine-4,5'-pyrano[3,2-c]pyrazol]-7'(6'H)-one | 26 | 2 | 23 | 2 |
| 7.005 | 1-(benzo[d]isothiazole-5-carbonyl)-2'-ethyl-3'-methyl-2'H-spiro[piperidine-4,5'-pyrano[3,2-c]pyrazol]-7'(6'H)-one | 184 | 2 | 36 | 1 |
| 7.006 | 1-(benzo[d]isothiazole-5-carbonyl)-2'-isopropyl-2'H-spiro[piperidine-4,5'-pyrano[3,2-c]pyrazol]-7'(6'H)-one | 117 | 2 | 92 | 2 |
| 7.007 | 2'-tert-butyl-1-(7-methylbenzo[d]isothiazole-5-carbonyl)-2'H-spiro[piperidine-4,5'-pyrano[3,2-c]pyrazol]-7'(6'H)-one | 10 | 2 | 5 | 2 |
| 7.008 | 2'-ethyl-3'-methyl-1-(7-methylbenzo[d]isothiazole-5-carbonyl)-2'H-spiro[piperidine-4,5'-pyrano[3,2-c]pyrazol]-7'(6'H)-one | 40 | 2 | 93 | 2 |
| 7.009 | 2'-isopropyl-1-(7-methylbenzo[d]isothiazole-5-carbonyl)-2'H-spiro[piperidine-4,5'-pyrano[3,2-c]pyrazol]-7'(6'H)-one | 27 | 2 | 18 | 2 |
| 8.001 | 2'-tert-butyl-1-(1,7-dimethyl-1H-benzo[d]imidazole-5-carbonyl)-2'H-spiro[piperidine-4,5'-pyrano[3,2-c]pyrazol]-7'(6'H)-one | 50 | 2 | 36 | 1 |
| 8.002 | 1-(1,7-dimethyl-1H-benzo[d]imidazole-5-carbonyl)-2'-isopropyl-2'H-spiro[piperidine-4,5'-pyrano[3,2-c]pyrazol]-7'(6'H)-one | 198 | 2 | 59 | 1 |
| 8.003 | 1-(1,7-dimethyl-1H-benzo[d]imidazole-5-carbonyl)-2'-ethyl-3'-methyl-2'H-spiro[piperidine-4,5'-pyrano[3,2-c]pyrazol]-7'(6'H)-one | 217 | 2 | 87 | 1 |
| 8.004 | 2'-ethyl-1-(1-ethyl-2-methyl-1H-benzo[d]imidazole-5-carbonyl)-3'-methyl-2'H-spiro[piperidine-4,5'-pyrano[3,2-c]pyrazol]-7'(6'H)-one | 1150 | 2 | 481 | 1 |
| 8.005 | 2'-ethyl-3'-methyl-1-(1-methyl-1H-benzo[d]imidazole-5- | 713 | 4 | 159 | 2 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | carbonyl)-2'H-spiro[piperidine-4,5'-pyrano[3,2-c]pyrazol]-7'(6'H)-one | | | | |
| 8.006 | 1-(1,2-dimethyl-1H-benzo[d]imidazole-5-carbonyl)-2'-ethyl-3'-methyl-2'H-spiro[piperidine-4,5'-pyrano[3,2-c]pyrazol]-7'(6'H)-one | na | na | 266 | 1 |
| 8.007 | 2'-tert-butyl-1-(1-methyl-1H-benzo[d]imidazole-5-carbonyl)-2'H-spiro[piperidine-4,5'-pyrano[3,2-c]pyrazol]-7'(6'H)-one | 102 | 4 | 58 | 2 |
| 8.008 | 2'-tert-butyl-1-(1-ethyl-2-methyl-1H-benzo[d]imidazole-5-carbonyl)-2'H-spiro[piperidine-4,5'-pyrano[3,2-c]pyrazol]-7'(6'H)-one | 166 | 4 | 52 | 2 |
| 8.009 | 2'-tert-butyl-1-(1,2-dimethyl-1H-benzo[d]imidazole-5-carbonyl)-2'H-spiro[piperidine-4,5'-pyrano[3,2-c]pyrazol]-7'(6'H)-one | 64 | 6 | 47 | 4 |
| 8.010 | 2'-tert-butyl-1-(2-hydroxy-1-methyl-1H-benzo[d]imidazole-5-carbonyl)-2'H-spiro[piperidine-4,5'-pyrano[3,2-c]pyrazol]-7'(6'H)-one | 12 | 4 | 18 | 3 |
| 8.011 | 2'-ethyl-1-(2-hydroxy-1-methyl-1H-benzo[d]imidazole-5-carbonyl)-3'-methyl-2'H-spiro[piperidine-4,5'-pyrano[3,2-c]pyrazol]-7'(6'H)-one | 217 | 2 | 186 | 1 |
| 9.001 | 1-(benzo[d]oxazole-5-carbonyl)-2'-isopropyl-2'H-spiro[piperidine-4,5'-pyrano[3,2-c]pyrazol]-7'(6'H)-one | 1220 | 2 | 300 | 2 |
| 9.002 | 1-(benzo[d]oxazole-5-carbonyl)-2'-tert-butyl-2'H-spiro[piperidine-4,5'-pyrano[3,2-c]pyrazol]-7'(6'H)-one | 327 | 3 | 291 | 3 |
| 9.003 | 2'-tert-butyl-1-(7-methoxy-2-methylbenzo[d]oxazole-5-carbonyl)-2'H-spiro[piperidine-4,5'-pyrano[3,2-c]pyrazol]-7'(6'H)-one | 38 | 3 | 29 | 3 |
| 9.004 | 2'-isopropyl-1-(7-methoxy-2-methylbenzo[d]oxazole-5-carbonyl)-2'H-spiro[piperidine-4,5'-pyrano[3,2-c]pyrazol]-7'(6'H)-one | 100 | 2 | 83 | 2 |
| 9.005 | 2'-ethyl-1-(7-methoxy-2-methylbenzo[d]oxazole-5-carbonyl)-3'-methyl-2'H-spiro[piperidine-4,5'-pyrano[3,2-c]pyrazol]-7'(6'H)-one | 153 | 2 | 179 | 2 |
| 10.001 | 1-(benzo[d]thiazole-6-carbonyl)-2'-ethyl-3'-methyl-2'H- | na | na | 285 | 3 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | spiro[piperidine-4,5'-pyrano[3,2-c]pyrazol]-7'(6'H)-one | | | | |
| 10.002 | 1-(benzo[d]thiazole-6-carbonyl)-2'-tert-butyl-2'H-spiro[piperidine-4,5'-pyrano[3,2-c]pyrazol]-7'(6'H)-one | 46 | 3 | 25 | 3 |
| 11.001 | 2'-ethyl-3'-methyl-1-(8-methyl-2-oxo-1,2-dihydroquinoline-6-carbonyl)-2'H-spiro[piperidine-4,5'-pyrano[3,2-c]pyrazol]-7'(6'H)-one | 220 | 4 | 33 | 1 |
| 11.002 | 2'-tert-butyl-1-(8-methyl-2-oxo-1,2-dihydroquinoline-6-carbonyl)-2'H-spiro[piperidine-4,5'-pyrano[3,2-c]pyrazol]-7'(6'H)-one | 14 | 6 | 11 | 5 |
| 12.001 | 2'-ethyl-3'-methyl-1-(1-methyl-2-oxo-1,2,3,4-tetrahydroquinoline-7-carbonyl)-2'H-spiro[piperidine-4,5'-pyrano[3,2-c]pyrazol]-7'(6'H)-one | 589 | 2 | 299 | 1 |
| 12.002 | 2'-ethyl-3'-methyl-1-(2-oxo-1,2,3,4-tetrahydroquinoline-7-carbonyl)-2'H-spiro[piperidine-4,5'-pyrano[3,2-c]pyrazol]-7'(6'H)-one | 245 | 4 | 36 | 1 |
| 12.003 | 2'-tert-butyl-1-(1-methyl-2-oxo-1,2,3,4-tetrahydroquinoline-7-carbonyl)-2'H-spiro[piperidine-4,5'-pyrano[3,2-c]pyrazol]-7'(6'H)-one | 81 | 4 | 52 | 2 |
| 12.004 | 2'-tert-butyl-1-(2-oxo-1,2,3,4-tetrahydroquinoline-7-carbonyl)-2'H-spiro[piperidine-4,5'-pyrano[3,2-c]pyrazol]-7'(6'H)-one | 20 | 8 | 14 | 8 |
| 12.005 | 6-(2'-tert-butyl-7'-oxo-6',7'-dihydro-2'H-spiro[piperidine-4,5'-pyrano[3,2-c]pyrazole]-1-ylcarbonyl)-2H-benzo[b][1,4]oxazin-3(4H)-one | 20 | 4 | 45 | 4 |
| 13.001 | 2'-ethyl-3'-methyl-1-(2-oxo-1,2,3,4-tetrahydroquinoline-6-carbonyl)-2'H-spiro[piperidine-4,5'-pyrano[3,2-c]pyrazol]-7'(6'H)-one | 522 | 2 | 421 | 1 |
| 13.002 | 7-(2'-ethyl-3'-methyl-7'-oxo-6',7'-dihydro-2'H-spiro[piperidine-4,5'-pyrano[3,2-c]pyrazole]-1-ylcarbonyl)-2H-benzo[b][1,4]oxazin-3(4H)-one | na | na | 861 | 1 |
| 13.003 | 7-(2'-tert-butyl-7'-oxo-6',7'-dihydro-2'H-spiro[piperidine-4,5'-pyrano[3,2-c]pyrazole]-1- | 64 | 6 | 49 | 5 |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | ylcarbonyl)-2H-benzo[b][1,4]oxazin-3(4H)-one | | | | |
| 13.004 | 2'-tert-butyl-1-(2-oxo-1,2,3,4-tetrahydroquinoline-6-carbonyl)-2'H-spiro[piperidine-4,5'-pyrano[3,2-c]pyrazol]-7'(6'H)-one | 41 | 6 | 33 | 5 |
| 14.001 | 2'-tert-butyl-1-(2-methylbenzo[d]thiazole-5-carbonyl)-2'H-spiro[piperidine-4,5'-pyrano[3,2-c]pyrazol]-7'(6'H)-one | 22 | 6 | 7 | 4 |
| 14.002 | 2'-ethyl-3'-methyl-1-(2-methylbenzo[d]thiazole-5-carbonyl)-2'H-spiro[piperidine-4,5'-pyrano[3,2-c]pyrazol]-7'(6'H)-one | 206 | 2 | 176 | 2 |
| 15.001 | 2'-tert-butyl-1-(2-methylquinoline-6-carbonyl)-2'H-spiro[piperidine-4,5'-pyrano[3,2-c]pyrazol]-7'(6'H)-one trifluoroacetate salt | 53 | 2 | 26 | 2 |
| 15.002 | 2'-tert-butyl-1-(quinoline-6-carbonyl)-2'H-spiro[piperidine-4,5'-pyrano[3,2-c]pyrazol]-7'(6'H)-one trifluoroacetate salt | 10 | 3 | 11 | 5 |
| 15.003 | 2'-ethyl-3'-methyl-1-(quinoline-6-carbonyl)-2'H-spiro[piperidine-4,5'-pyrano[3,2-c]pyrazol]-7'(6'H)-one | 131 | 2 | 179 | 2 |
| 16.001 | 2'-tert-butyl-1-(quinoline-7-carbonyl)-2'H-spiro[piperidine-4,5'-pyrano[3,2-c]pyrazol]-7'(6'H)-one trifluoroacetate salt | 42 | 2 | 12 | 2 |
| 16.002 | 2'-ethyl-3'-methyl-1-(quinoline-7-carbonyl)-2'H-spiro[piperidine-4,5'-pyrano[3,2-c]pyrazol]-7'(6'H)-one trifluoroacetate salt | 204 | 2 | 250 | 1 |
| 17.001 | 1-(benzofuran-5-carbonyl)-2'-tert-butyl-2'H-spiro[piperidine-4,5'-pyrano[3,2-c]pyrazol]-7'(6'H)-one | 38 | 2 | 33 | 2 |
| 17.002 | 1-(benzofuran-5-carbonyl)-2'-ethyl-3'-methyl-2'H-spiro[piperidine-4,5'-pyrano[3,2-c]pyrazol]-7'(6'H)-one | 256 | 2 | 283 | 2 |
| 18.001 | 2'-tert-butyl-1-(1-methyl-1H-indole-6-carbonyl)-2'H-spiro[piperidine-4,5'-pyrano[3,2-c]pyrazol]-7'(6'H)-one | 11 | 2 | 3 | 3 |
| 18.002 | 2'-ethyl-3'-methyl-1-(1-methyl-1H-indole-6-carbonyl)-2'H-spiro[piperidine-4,5'-pyrano[3,2-c]pyrazol]-7'(6'H)-one | 11 | 4 | 33 | 5 |
| 19.001 | 2'-tert-butyl-1-(1-oxo-1,2-dihydroisoquinoline-6-carbonyl)-2'H- | 5 | 2 | 9 | 3 |

-continued

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| | spiro[piperidine-4,5'-pyrano[3,2-c]pyrazol]-7'(6'H)-one | | | | |
| 20.001 | 2'-tert-butyl-1-(2-oxo-2,3-dihydrobenzo[d]oxazole-6-carbonyl)-2'H-spiro[piperidine-4,5'-pyrano[3,2-c]pyrazol]-7'(6'H)-one | 14 | 2 | 28 | 3 |
| 21.001 | 2'-tert-butyl-1-(1-oxo-1,2-dihydroisoquinoline-7-carbonyl)-2'H-spiro[piperidine-4,5'-pyrano[3,2-c]pyrazol]-7'(6'H)-one | 5 | 2 | 16 | 3 |
| 22.001 | 1-(benzo[d]isoxazole-5-carbonyl)-2'-isopropyl-2'H-spiro[piperidine-4,5'-pyrano[3,2-c]pyrazol]-7'(6'H)-one | 2588 | 2 | >1000 | 1 |
| 22.002 | 1-(benzo[d]isoxazole-5-carbonyl)-2'-tert-butyl-2'H-spiro[piperidine-4,5'-pyrano[3,2-c]pyrazol]-7'(6'H)-one | 196 | 2 | 518 | 1 |
| 22.003 | 1-(benzo[d]isoxazole-5-carbonyl)-2'-ethyl-3'-methyl-2'H-spiro[piperidine-4,5'-pyrano[3,2-c]pyrazol]-7'(6'H)-one | 3261 | 2 | >1000 | 1 |
| 23.001 | 2'-isopropyl-1-(3-methylbenzo[d]isoxazole-6-carbonyl)-2'H-spiro[piperidine-4,5'-pyrano[3,2-c]pyrazol]-7'(6'H)-one | 463 | 2 | 585 | 2 |
| 23.002 | 2'-tert-butyl-1-(3-methylbenzo[d]isoxazole-6-carbonyl)-2'H-spiro[piperidine-4,5'-pyrano[3,2-c]pyrazol]-7'(6'H)-one | 190 | 3 | 55 | 3 |
| 23.003 | 2'-ethyl-3'-methyl-1-(3-methylbenzo[d]isoxazole-6-carbonyl)-2'H-spiro[piperidine-4,5'-pyrano[3,2-c]pyrazol]-7'(6'H)-one | 957 | 2 | 335 | 3 |
| 23.004 | 1-(benzo[d]isoxazole-6-carbonyl)-2'-isopropyl-2'H-spiro[piperidine-4,5'-pyrano[3,2-c]pyrazol]-7'(6'H)-one | 2745 | 2 | >1000 | 2 |
| 23.005 | 1-(benzo[d]isoxazole-6-carbonyl)-2'-tert-butyl-2'H-spiro[piperidine-4,5'-pyrano[3,2-c]pyrazol]-7'(6'H)-one | 567 | 3 | 158 | 2 |
| 24.001 | 1-(benzo[d]isothiazole-6-carbonyl)-2'-tert-butyl-2'H-spiro[piperidine-4,5'-pyrano[3,2-c]pyrazol]-7'(6'H)-one | 66 | 4 | 23 | 3 |
| 24.002 | 1-(benzo[d]isothiazole-6-carbonyl)-2'-isopropyl-2'H-spiro[piperidine-4,5'-pyrano[3,2-c]pyrazol]-7'(6'H)-one | 255 | 2 | 198 | 3 |
| 24.003 | 1-(benzo[d]isothiazole-6-carbonyl)-2'-ethyl-3'-methyl-2'H-spiro[piperidine-4,5'-pyrano[3,2-c]pyrazol]-7'(6'H)-one | 433 | 2 | 411 | 3 |

| Ex. | Compound Name | Rat liver ACC IC$_{50}$ (nM) | Rat liver ACC n* | rhACC2 IC$_{50}$ (nM) | rhACC2 n* |
|---|---|---|---|---|---|
| 25.001 | 1-(2,7-dimethyl-2H-indazole-5-carbonyl)-2'-ethyl-3'-methyl-2'H-spiro[piperidine-4,5'-pyrano[3,2-c]pyrazol]-7'(6'H)-one | 194 | 2 | na | na |
| 25.002 | 1-(2,7-dimethyl-2H-indazole-5-carbonyl)-2',3'-dimethyl-2'H-spiro[piperidine-4,5'-pyrano[3,2-c]pyrazol]-7'(6'H)-one | 953 | 2 | na | na |
| 25.003 | 1-(2,7-dimethyl-2H-indazole-5-carbonyl)-2'-methyl-2'H-spiro[piperidine-4,5'-pyrano[3,2-c]pyrazol]-7'(6'H)-one | 1016 | 3 | na | na |
| 25.004 | 2'-ethyl-3'-methyl-1-(2-methyl-2H-indazole-5-carbonyl)-2'H-spiro[piperidine-4,5'-pyrano[3,2-c]pyrazol]-7'(6'H)-one | 327 | 2 | 122 | 1 |
| 25.005 | 2',3'-dimethyl-1-(2-methyl-2H-indazole-5-carbonyl)-2'H-spiro[piperidine-4,5'-pyrano[3,2-c]pyrazol]-7'(6'H)-one | 1706 | 2 | 1535 | 1 |

Acute in vivo Assessment of ACC Inhibition in Experimental Animals

The ACC inhibitory activity of the compound of the present invention can be confirmed in vivo by evaluation of their ability to reduce malonyl-CoA levels in liver and muscle tissue from treated animals.

Measurement of malonyl-CoA production inhibition in experimental animals. In this method, male Sprague-Dawley Rats, maintained on standard chow and water ad libitum (225-275 g), were randomized prior to the study. Animals were either fed, or fasted for 18 hours prior to the beginning of the experiment. Two hours into the light cycle the animals were orally dosed with a volume of 5 mL/kg, (0.5% methyl cellulose; vehicle) or with the appropriate compound (prepared in vehicle). Fed vehicle controls were included to determine baseline tissue malonyl-CoA levels while fasted animals were included to determine the effect fasting had on malonyl-CoA levels. One hour after compound administration the animals were asphyxiated with $CO_2$ and the tissues were removed. Specifically, blood was collected by cardiac puncture and placed into BD Microtainer tubes containing EDTA (BD Biosciences, NJ), mixed, and placed on ice. Plasma was used to determine drug exposure. Liver and quadriceps were removed, immediately freeze-clamped, wrapped in foil and stored in liquid nitrogen.

Tissues were pulverized under liquid $N_2$ to ensure uniformity in sampling. Malonyl-CoA was extracted from the tissue (150-200 mg) with 5 volumes 10% tricarboxylic acid in Lysing Matrix A (MP Biomedicals, PN 6910) in a FastPrep FP120 (Thermo Scientific, speed=5.5; for 45 seconds). The supernatant containing malonyl-CoA was removed from the cell debris after centrifugation at 15000×g for 30 minutes (Eppendorf Centrifuge 5402). Samples were stably frozen at −80 C until analysis is completed.

Analysis of malonyl CoA levels in liver and muscle tissue can be evaluated using the following methodology.

The method utilizes the following materials: Malonyl-CoA tetralithium salt and malonyl-$^{13}C_3$-CoA trilithium salt which were purchased from Isotec (Miamisburg, Ohio, USA), sodium perchlorate (Sigma, cat no. 410241), trichloroacetic acid (ACROS, cat no. 42145), phosphoric acid (J. T. Baker, cat no. 0260-01), ammonium formate (Fluke, cat no. 17843), methanol (HPLC grade, J. T. Baker, cat no. 9093-33), and water (HPLC grade, J. T. Baker, 4218-03) were used to make the necessary mobile phases. Strata-X on-line solid phase extraction columns, 25 µm, 20 mm×2.0 mm I.D (cat no. 00M-S033-B0-CB) were obtained from Phenomenex (Torrance, Calif., USA). SunFire C18 reversed-phase columns, 3.5 µm, 100 mm×3.0 mm I.D. (cat no. 186002543) were purchased from Waters Corporation (Milford, Mass., USA).

This method may be performed utilizing the following equipment. Two-dimensional chromatography using an Agilent 1100 binary pump, an Agilent 1100 quaternary pump and two Valco Cheminert 6-port two position valves. Samples were introduced via a LEAP HTC PAL auto sampler with Peltier cooled stack maintained at 10° C. and a 20 µL sampling loop. The needle wash solutions for the autosampler are 10% trichloroacetic acid in water (w/v) for Wash 1 and 90:10 methanol:water for Wash 2. The analytical column (Sunfire) was maintained at 35° C. using a MicroTech Scientific Micro-LC Column Oven. The eluant was analyzed on an ABI Sciex API3000 triple quadrupole mass spectrometer with Turbo Ion Spray.

Two-dimensional chromatography was performed in parallel using distinct gradient elution conditions for on-line solid phase extraction and reversed-phase chromatography. The general design of the method was such that the first dimension was utilized for sample clean-up and capture of the analyte of interest followed by a brief coupling of both dimensions for elution from the first dimension onto the second dimension. The dimensions were subsequently uncoupled allowing for gradient elution of the analyte from the second dimension for quantification while simultaneously preparing the first dimension for the next sample in the sequence. When both dimensions were briefly coupled together, the flow of the mobile phase in the first dimension was reversed for analyte elution on to the second dimension, allowing for optimal peak width, peak shape, and elution time.

The first dimension of the HPLC system utilized the Phenomenex strata-X on-line solid phase extraction column and the mobile phase consisted of 100 mM sodium perchlorate/0.1% (v/v) phosphoric acid for solvent A and methanol for solvent B.

The second dimension of the HPLC system utilized the Waters SunFire C18 reversed-phase column and the mobile phase consisted of 100 mM ammonium formate for solvent A and methanol for solvent B. The initial condition of the gradient was maintained for 2 minutes and during this time the analyte was transferred to the analytical column. It was important that the initial condition was at a sufficient strength to elute the analyte from the on-line SPE column while retaining it on the analytical. Afterwards, the gradient rose linearly to 74.5% A in 4.5 minutes before a wash and re-equilibration step.

Mass spectrometry when coupled with HPLC can be a highly selective and sensitive method for quantitatively measuring analytes in complex matrices but is still subject to interferences and suppression. By coupling a two dimensional HPLC to the mass spectrometer, these interferences were significantly reduced. Additionally, by utilizing the Multiple Reaction Monitoring (MRM) feature of the triple quadrupole mass spectrometer, the signal-to-noise ratio was significantly improved.

For this assay, the mass spectrometer was operated in positive ion mode with a TurboIonSpray voltage of 2250V. The nebulizing gas was heated to 450° C. The Declustering Potential (DP), Focusing Potential (FP), and Collision Energy (CE) were set to 60, 340, and 42 V, respectively. Quadrupole 1 (Q1) resolution was set to unit resolution with Quadrupole 3 (Q3) set to low. The CAD gas was set to 8. The MRM transitions monitored were for malonyl CoA: 854.1→347.0 m/z (L. Gao et al. (2007) *J. Chromatogr. B* 853, 303-313); and for malonyl-$^{13}C_3$-CoA: 857.1→350.0 m/z with dwell times of 200 ms. The eluant was diverted to the mass spectrometer near the expected elution time for the analyte, otherwise it was diverted to waste to help preserve the source and improve robustness of the instrumentation. The resulting chromatograms were integrated using Analyst software (Applied Biosystems). Tissue concentrations for malonyl CoA were calculated from a standard curve prepared in a 10% solution of trichloroacetic acid in water.

Samples comprising the standard curve for the quantification of malonyl-CoA in tissue extracts were prepared in 10% (w/v) trichloroacetic acid (TCA) and ranged from 0.01 to 1 pmol/μL. Malonyl-$^{13}C_3$-CoA (final concentration of 0.4 pmol/μL) was added to each standard curve component and sample as an internal standard.

Six intra-assay quality controls were prepared; three from a pooled extract prepared from fasted animals and three from a pool made from fed animals. These were run as independent samples spiked with 0, 0.1 or 0.3 pmol/μL $^{12}$C-malonyl-CoA as well as malonyl-$^{13}C_3$-CoA (0.4 pmol/μL). Each intra-assay quality control contained 85% of aqueous tissue extract with the remaining portion contributed by internal standard (0.4 pmol/μL) and $^{12}$C-malonyl-CoA. Inter assay controls were included in each run; they consist of one fasted and one fed pooled sample of quadriceps and/or one fasted and one fed pooled sample of liver. All such controls are spiked with malonyl-$^{13}C_3$-CoA (0.4 pmol/μL).

The certain Compounds of Formula (I) indicated below were used in the in vivo test described above to determine their effect upon malonyl CoA levels in liver and muscle tissue. The results are provided in the following table.

| Compound | Dose | Muscle Malonyl-CoA (quadriceps)[a] | Liver Malonyl-CoA[a] |
|---|---|---|---|
| 1.001 | 1 mg/kg | 5.69 (8.73) | 28.29 (8.40) |
| | 3 mg/kg | 2.90 (4.29) | 30.37 (11.50) |
| | 10 mg/kg | 22.83 (5.72) | 45.45 (3.51) |
| | 30 mg/kg | 48.03 (2.63) | 54.31 (7.63) |
| 1.003 | 1 mg/kg | -3.72 (8.87) | 31.45 (4.12) |
| | 3 mg/kg | 21.23 (8.81) | 47.61 (4.70) |
| | 10 mg/kg | 33.30 (4.83) | 67.40 (5.67) |
| | 30 mg/kg | 48.81 (3.51) | 70.47 (2.48) |
| 1.042 | 1 mg/kg | 29.90 (5.21) | 41.87 (2.70) |
| | 3 mg/kg | 27.60 (5.87) | 48.07 (8.08) |
| | 10 mg/kg | 61.60 (5.38) | 71.81 (2.36) |
| | 30 mg/kg | 74.70 (1.37) | 86.50 (0.72) |
| 1.012 | 1 mg/kg | 31.53 (3.58) | 40.32 (6.24) |
| | 3 mg/kg | 43.01 (4.24) | 54.87 (3.22) |
| | 10 mg/kg | 59.48 (5.28) | 75.72 (2.47) |
| | 30 mg/kg | 71.08 (2.18) | 86.52 (1.49) |
| 1.074 | 1 mg/kg | 2.34 (5.44) | 34.97 (2.59) |
| | 3 mg/kg | 24.42 (6.83) | 53.97 (1.19) |
| | 10 mg/kg | 49.00 (2.40) | 70.74 (3.49) |
| | 30 mg/kg | 57.06 (2.04) | 63.60 (3.57) |

[a]percent decrease in tissue malonyl-CoA relative to chow-fed vehicle control group (% decrease +/− SEM)

What is claimed is:

1. A compound of Formula (I)

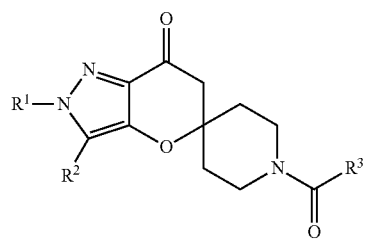

wherein
R$^1$ is (C$_1$-C$_4$)alkyl, (C$_3$-C$_6$)cycloalkyl, tetrahydrofuranyl, benzyl, pyridyl, or phenyl optionally substituted with 1 to 2 substituents independently selected from cyano and methoxy;
R$^2$ is hydrogen, methyl or ethyl;
R$^3$ is a chemical moiety selected from the group consisting of

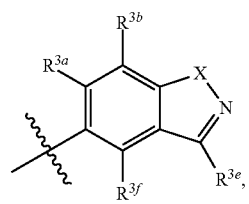

(1a)

-continued
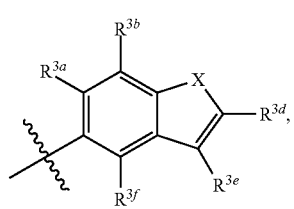 (1b)
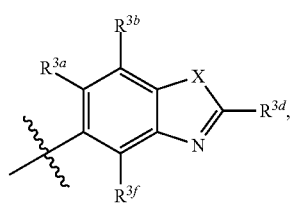 (1c)
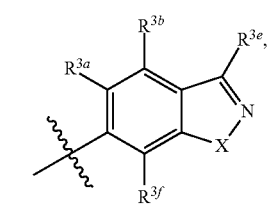 (1d)
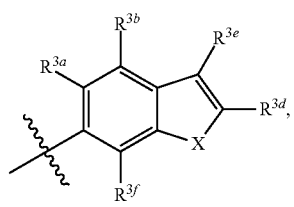 (1e)
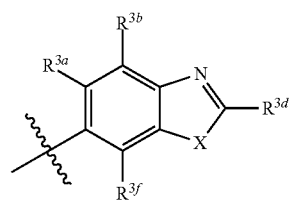 (1f)
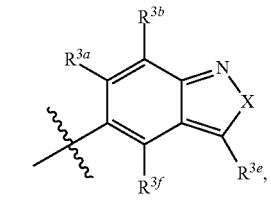 (1g)
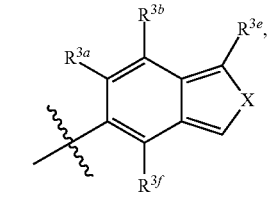 (1h)
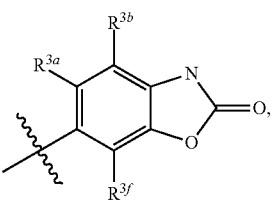 (1i)
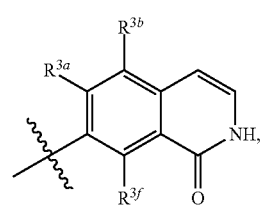 (1j)
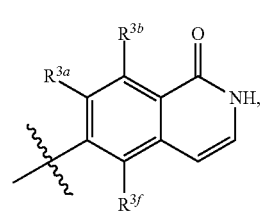 (1k)
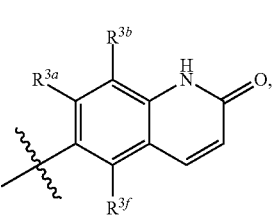 (1l)
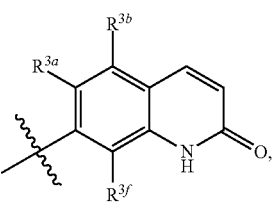 (1m)
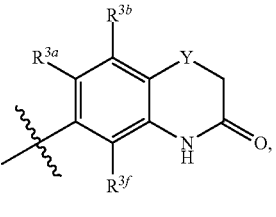 (1n)
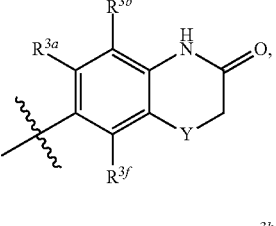 (1o)
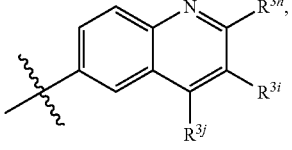 (1p)

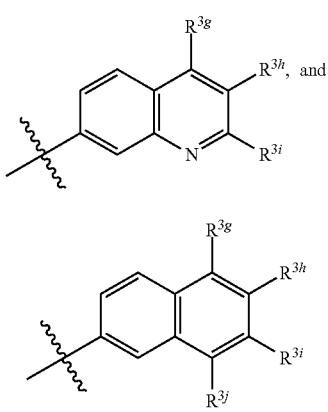

where X is O, S, or N—$R^{3c}$;
Y is $CH_2$ or O;
$R^{3a}$ is hydrogen or methyl;
$R^{3b}$ is hydrogen, methyl, ethyl, halo, methoxy, or ethoxy;
$R^{3c}$ is hydrogen, methyl, ethyl, or 3- to 6-membered cycloalkyl;
$R^{3d}$ is hydrogen, methyl, or hydroxyl;
$R^{3e}$ is hydrogen, methyl, ethyl, halo, or amino;
$R^{3f}$ is hydrogen, methyl, or methoxy;
$R^{3g}$ is hydrogen, or methoxy;
$R^{3h}$ is hydrogen, methyl, methoxy, or halo;
$R^{3i}$ is hydrogen, methyl, or methoxy; or
$R^{3j}$ is hydrogen, or methoxy;
or a pharmaceutically acceptable salt thereof.

2. The compound of claim 1 wherein $R^1$ is ($C_1$-$C_4$)alkyl, ($C_3$-$C_6$)cycloalkyl, tetrahydrofuranyl; and $R^2$ is hydrogen or methyl; or a pharmaceutically acceptable salt thereof.

3. The compound of claim 1 or 2 wherein $R^1$ is ethyl, isopropyl or t-butyl; and $R^3$ is a chemical moiety of Formula (1a), (1c), (1d), (1f), (1i), (1j), (1k), (1l), (1m), (1n), (1o), (1p), or (1q), where X is O or N—$R^{3c}$; Y is $CH_2$; $R^{3a}$, is hydrogen; $R^{3b}$ is hydrogen, methyl, methoxy, chloro or fluoro; $R^{3c}$ and $R^{3e}$ are each independently hydrogen or methyl; and $R^{3f}$, $R^{3g}$, $R^{3h}$, $R^{3i}$ and $R^{3j}$ are hydrogen; or a pharmaceutically acceptable salt thereof.

4. The compound of claim 3 wherein $R^1$ is t-butyl; $R^2$ is hydrogen; and $R^3$ is a chemical moiety of Formula (1a), (1c), (1d), (1f), (1j), or (1k), where X is N—$R^{3c}$; and $R^{3d}$ is hydrogen;
or a pharmaceutically acceptable salt thereof.

5. A pharmaceutical composition comprising (i) a compound according to claim 1; and (ii) a pharmaceutically acceptable excipient, diluent, or carrier.

6. The composition of claim 5 further comprising at least one additional pharmaceutical agent selected from the group consisting of an anti-obesity agent and an anti-diabetic agent.

7. The composition of claim 6 wherein said anti-obesity agent is selected from the group consisting of dirlotapide, mitratapide, implitapide, lorcaserin, cetilistat, naltrexone, oleoyl-estrone, obinepitide, pramlintide, tesofensine, leptin, liraglutide, bromocriptine, orlistat, exenatide, and sibutramine.

8. The composition of claim 6 wherein said anti-diabetic agent is selected from the group consisting of metformin, acetohexamide, chlorpropamide, diabinese, glibenclamide, glipizide, glyburide, glimepiride, gliclazide, glipentide, gliquidone, glisolamide, tolazamide, tolbutamide, tendamistat, trestatin, acarbose, adiposine, camiglibose, emiglitate, miglitol, voglibose, pradimicin-Q, salbostatin, balaglitazone, ciglitazone, darglitazone, englitazone, isaglitazone, pioglitazone, rosiglitazone, troglitazone, exendin-3, exendin-4, trodusquemine, reservatrol, hyrtiosal extract, sitagliptin, vildagliptin, alogliptin and saxagliptin.

9. A method for treating obesity in a human comprising the step of administering to the human in need of such treatment a therapeutically effective amount of a compound according to claim 1.

10. A method for treating Type 2 diabetes in a human comprising the step of administering to the human in need of such treatment a therapeutically effective amount of a compound according to claim 1.

11. A method for treating obesity in a human comprising the step of administering to the human in need of such treatment a pharmaceutical composition according to claim 5.

12. A method for treating Type 2 diabetes in a human comprising the step of administering to the human in need of such treatment a pharmaceutical composition according to claim 5.

* * * * *